US009669055B1

(12) United States Patent
Blough et al.

(10) Patent No.: US 9,669,055 B1
(45) Date of Patent: Jun. 6, 2017

(54) METHODS FOR TREATING SEPSIS

(71) Applicant: Marshall University Research Corporation, Huntington, WV (US)

(72) Inventors: Eric Blough, Huntington, WV (US); Nandini Manne, Huntington, WV (US); Selvaraj Vellaisamy, Huntington, WV (US)

(73) Assignee: Marshall University Research Corporation, Huntington, WV (US)

( * ) Notice: Subject to any disclaimer, the term of this patent is extended or adjusted under 35 U.S.C. 154(b) by 0 days.

(21) Appl. No.: 14/685,426

(22) Filed: Apr. 13, 2015

Related U.S. Application Data

(60) Provisional application No. 61/978,337, filed on Apr. 11, 2014.

(51) Int. Cl.
*A61K 33/24* (2006.01)
*B01J 23/10* (2006.01)
*A61P 29/00* (2006.01)

(52) U.S. Cl.
CPC ............ *A61K 33/24* (2013.01); *B01J 23/10* (2013.01)

(58) Field of Classification Search
CPC ................................ A61K 33/24; B01J 23/10
See application file for complete search history.

(56) References Cited

U.S. PATENT DOCUMENTS

| | | | |
|---|---|---|---|
| 7,347,987 B2 | 3/2008 | McGinnis et al. | |
| 7,504,356 B1 | 3/2009 | Self et al. | |
| 7,534,453 B1 | 5/2009 | Rzigalinski et al. | |
| 7,727,559 B2 | 6/2010 | McGinnis et al. | |
| 2010/0166821 A1* | 7/2010 | Rzigalinski | A61K 9/14 424/423 |
| 2013/0251756 A1* | 9/2013 | Self | A61K 33/24 424/400 |
| 2014/0227368 A1* | 8/2014 | Self | B01J 23/10 424/617 |

OTHER PUBLICATIONS

Akcay et al, Mediators of Inflammation in Acute Kdney Injury, review Article, Hindawi Publishing Corporation. 2009.*
Reed, H.L., Renton, S.D. and Hines, M.D. Dependence of All-Cause Standardized In-Hospital Mortality on Sepsis Mortality Between 2005 and 2010. Am J Med Qual, 2013.
Mayr FB, Yende S, Angus DC. Epidemiology of severe sepsis. Virulence. 2014;5:4-11.
Kishta OA, Goldberg P, Husain SN. Gadolinium chloride attenuates sepsis-induced pulmonary apoptosis and acute lung injury. ISRN inflammation. 2012;2012:393481.
Kono H, Fujii H, Tsuchiya M, Hirai Y, Ishii K, Hosomura N, et al. Inhibition of the Kupffer cell and neutralization of IL-10 increase the expression of chemokines in the lung in a rat peritonitis model. J Surg Res. 2008;150:169-82.
Kono H, Fujii H, Hirai Y, Tsuchiya M, Amemiya H, Asakawa M, et al. The Kupffer cell protects against acute lung injury in a rat peritonitis model: role of IL-10. J Leukoc Biol. 2006;79:809-17.
Wunsch H. Untangling the healthcare use patterns of severe sepsis survivors. American journal of respiratory and critical care medicine. 2014;190:7-8.
Hofhuis JG, Spronk PE, Van Stel HF, Schrijvers AJ, Rommes JH, Bakker J. The impact of severe sepsis on health-related quality of life: a long-term follow-up study. Anesthesia and analgesia. 2008;107:1957-64.
Hirst SM, Karakoti AS, Tyler RD, Sriranganathan N, Seal S, Reilly CM. Anti-inflammatory properties of cerium oxide nanoparticles. Small. 2009;5:2848-56.
Wason MS, Colon J, Das S, Seal S, Turkson J, Zhao J, et al. Sensitization of pancreatic cancer cells to radiation by cerium oxide nanoparticle-induced ROS production. Nanomedicine. 2013;9:558-69.
Heckert EG, Karakoti AS, Seal S, Self WT. The role of cerium redox state in the SOD mimetic activity of nanoceria. Biomaterials. 2008;29:2705-9.
Dowding JM, Dosani T, Kumar A, Seal S, Self WT. Cerium oxide nanoparticles scavenge nitric oxide radical ( NO). Chemical communications. 2012;48:4896-8.
Chen S, Hou Y, Cheng G, Zhang C, Wang S, Zhang J. Cerium oxide nanoparticles protect endothelial cells from apoptosis induced by oxidative stress. Biological trace element research. 2013;154:156-66.
Niu J, Wang K, Kolattukudy PE. Cerium oxide nanoparticles inhibit oxidative stress and nuclear factorkappaB activation in H9c2 cardiomyocytes exposed to cigarette smoke extract. The Journal of pharmacology and experimental therapeutics. 2011;338:53-61.
Niu J, Azfer A, Rogers LM, Wang X, Kolattukudy PE. Cardioprotective effects of cerium oxide nanoparticles in a transgenic murine model of cardiomyopathy. Cardiovascular research. 2007;73:549-59.
Hirst SM, Karakoti A, Singh S, Self W, Tyler R, Seal S, et al. Bio-distribution and in vivo antioxidant effects of cerium oxide nanoparticles in mice. Environmental toxicology. 2013;28:107-18.
Amin KA, Hassan MS, Awad EL ST, Hashem KS. The protective effects of cerium oxide nanoparticles against hepatic oxidative damage induced by monocrotaline. International journal of nanomedicine. 2011;6:143-9.
Kolli MB, Manne ND, Para R, Nalabotu SK, Nandyala G, Shokuhfar T, et al. Cerium oxide nanoparticles attenuate monocrotaline induced right ventricular hypertrophy following pulmonary arterial hypertension. Biomaterials. 2014.
Dejager L, Pinheiro I, Dejonckheere E, Libert C. Cecal ligation and puncture: the gold standard model for polymicrobial sepsis? Trends in microbiology. 2011;19:198-208.

(Continued)

*Primary Examiner* — Mina Haghighatian
(74) *Attorney, Agent, or Firm* — Stites & Harbison, PLLC; Terry L. Wright

(57) ABSTRACT

Methods for treating sepsis are provided and include the administration an effective amount of cerium oxide nanoparticles to a subject in need thereof. The sepsis being treated can include polymicrobial sepsis and can include the administration of about 0.1 mg/kg to about 1.0 mg/kg of the cerium oxide nanoparticles. The administration of the cerium oxide nanoparticles further allows one or more of the symptoms of sepsis to be treated. Methods of treating an inflammatory disorder that make use of cerium oxide nanoparticles are further provided.

20 Claims, 83 Drawing Sheets

(56) References Cited

OTHER PUBLICATIONS

Neunaber C, Oestern S, Andruszkow H, Zeckey C, Mommsen P, Kutter D, et al. Cytokine productive capacity of alveolar macrophages and Kupffer cells after femoral fracture and blunt chest trauma in a murine trauma model. Immunology letters. 2013;152:159-66.

Seitz DH, Perl M, Liener UC, Tauchmann B, Braumuller ST, Bruckner UB, et al. Inflammatory alterations in a novel combination model of blunt chest trauma and hemorrhagic shock. The Journal of trauma. 2011;70:189-96.

Lee SH, Clemens MG, Lee SM. Role of Kupffer cells in vascular stress genes during trauma and sepsis. The Journal of surgical research. 2010;158:104-11.

Campbell SJ, Zahid I, Losey P, Law S, Jiang Y, Bilgen M, et al. Liver Kupffer cells control the magnitude of the inflammatory response in the injured brain and spinal cord. Neuropharmacology. 2008;55:780-7.

Gong JP, Wu CX, Liu CA, Li SW, Shi YJ, Yang K, et al. Intestinal damage mediated by Kupffer cells in rats with endotoxemia. World journal of gastroenterology : WJG. 2002;8:923-7.

Koo DJ, Chaudry IH, Wang P. Kupffer cells are responsible for producing inflammatory cytokines and hepatocellular dysfunction during early sepsis. The Journal of surgical research. 1999;83:151-7.

Kim TH, Yoon SJ, Lee SM. Genipin attenuates sepsis by inhibiting Toll-like receptor signaling. Molecular medicine. 2012;18:455-65.

Chopra M, Golden HB, Mullapudi S, Dowhan W, Dostal DE, Sharma AC. Modulation of myocardial mitochondrial mechanisms during severe polymicrobial sepsis in the rat. PloS one. 2011;6:e21285.

Dowding JM, Das S, Kumar A, Dosani T, McCormack R, Gupta A, et al. Cellular interaction and toxicity depend on physicochemical properties and surface modification of redox-active nanomaterials. ACS nano. 2013;7:4855-68.

Celardo I, Pedersen JZ, Traversa E, Ghibelli L. Pharmacological potential of cerium oxide nanoparticles. Nanoscale. 2011;3:1411-20.

Das S, Dowding JM, Klump KE, McGinnis JF, Self W, Seal S. Cerium oxide nanoparticles: applications and prospects in nanomedicine. Nanomedicine. 2013;8:1483-508.

Assaly RA, Habib RH, Azizi M, Shapiro JI, Dignam JD. Use of multiple fluorophores for evaluating microvascular permeability in control rats and rats with sepsis. Clinical science. 2008;114:123-30.

Assaly RA, Azizi M, Kennedy DJ, Amauro C, Zaher A, Houts FW, et al. Plasma expansion by polyethylene-glycol-modified albumin. Clinical science. 2004;107:263-72.

Montravers P, Mohler J, Saint Julien L, Carbon C. Evidence of the proinflammatory role of Enterococcus faecalis in polymicrobial peritonitis in rats. Infection and immunity. 1997;65:144-9.

Hu MD, Yang Y, Zhou CX, Li Q, Yi W, Qian GS, et al. Pretreatment with anti-flagellin serum delays acute lung injury in rats with sepsis. Inflammation research : official journal of the European Histamine Research Society [et al]. 2012;61:837-44.

Weber GF, Schlautkotter S, Kaiser-Moore S, Altmayr F, Holzmann B, Weighardt H. Inhibition of interleukin-22 attenuates bacterial load and organ failure during acute polymicrobial sepsis. Infection and immunity. 2007;75:1690-7.

Gloire G, Legrand-Poels S, Piette J. NF-kappaB activation by reactive oxygen species: fifteen years later. Biochemical pharmacology. 2006;72:1493-505.

Schortgen, F, Asfar, P. Update in Sepsis and Acute Kidney Injury 2014. American Journal of Respiratory and Critical Care Medicine. 2015; 191:1226-1231.

\* cited by examiner

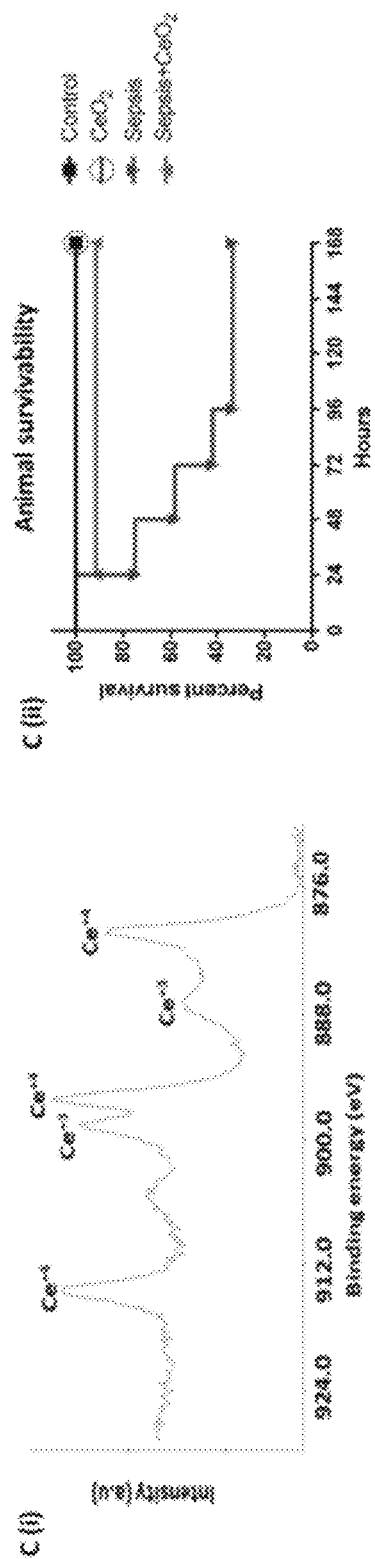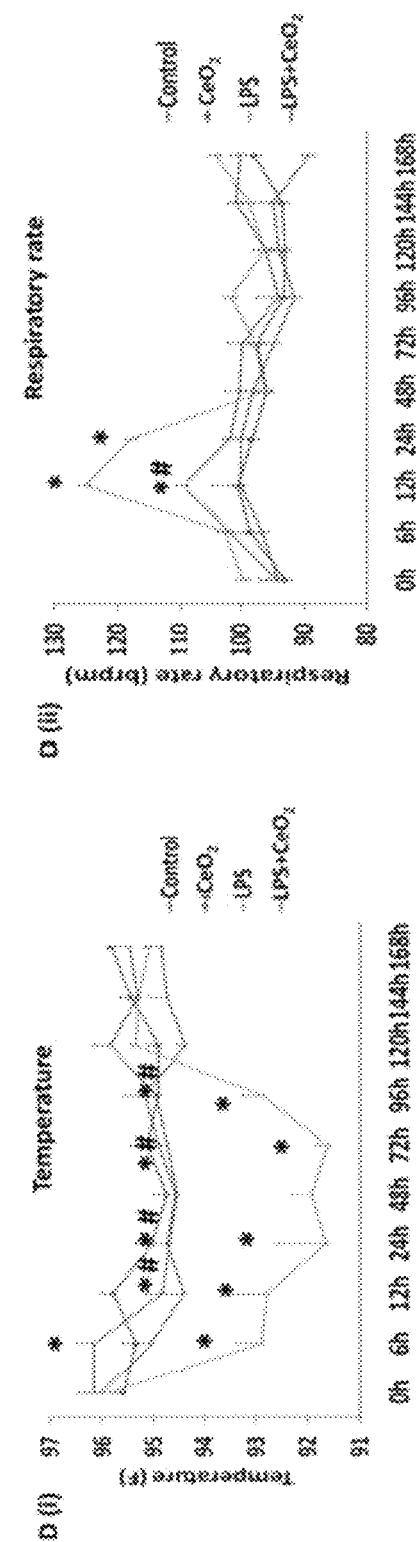
FIG. 35C
FIG. 35D

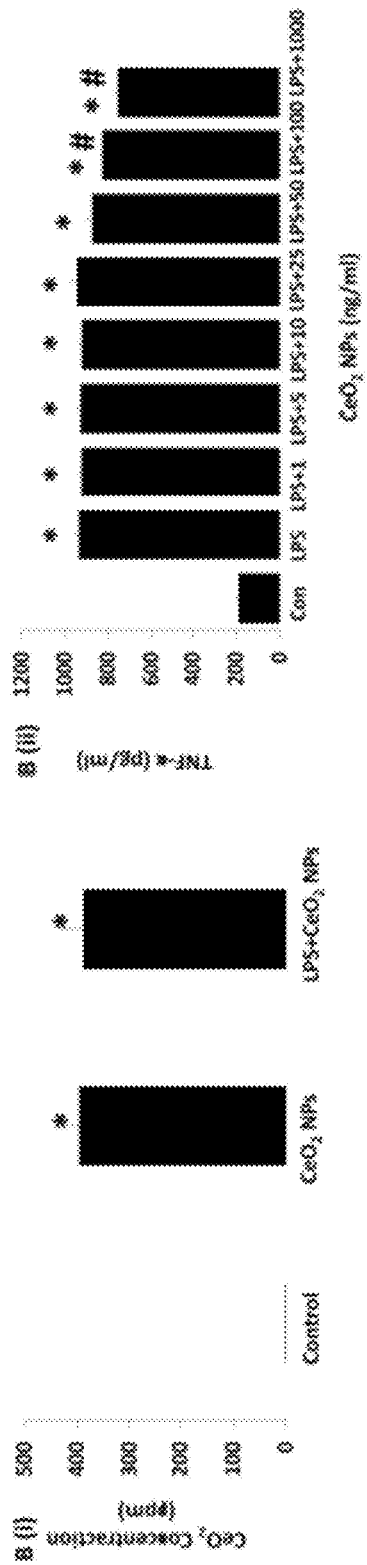
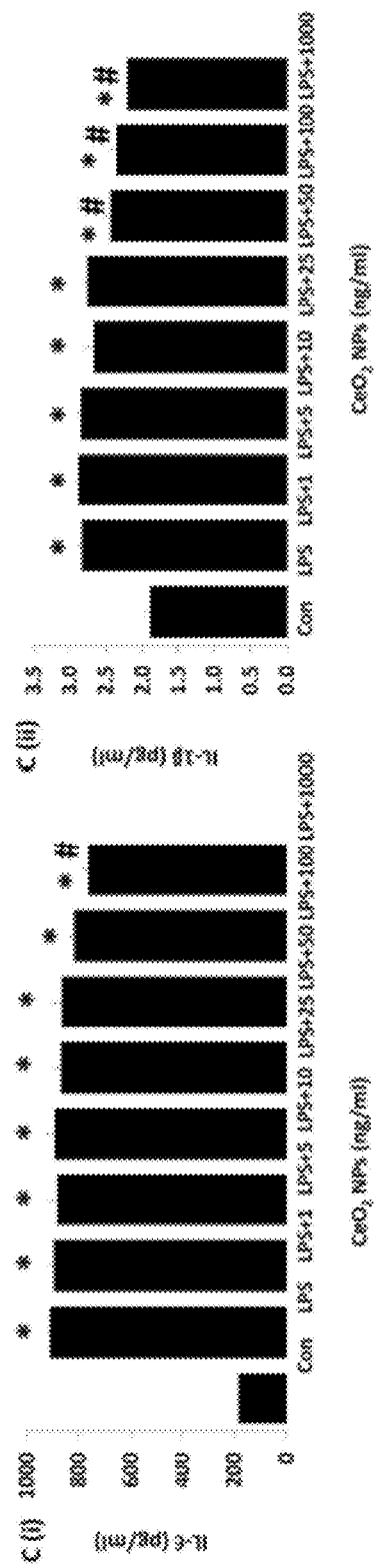
FIG. 39B
FIG. 39C

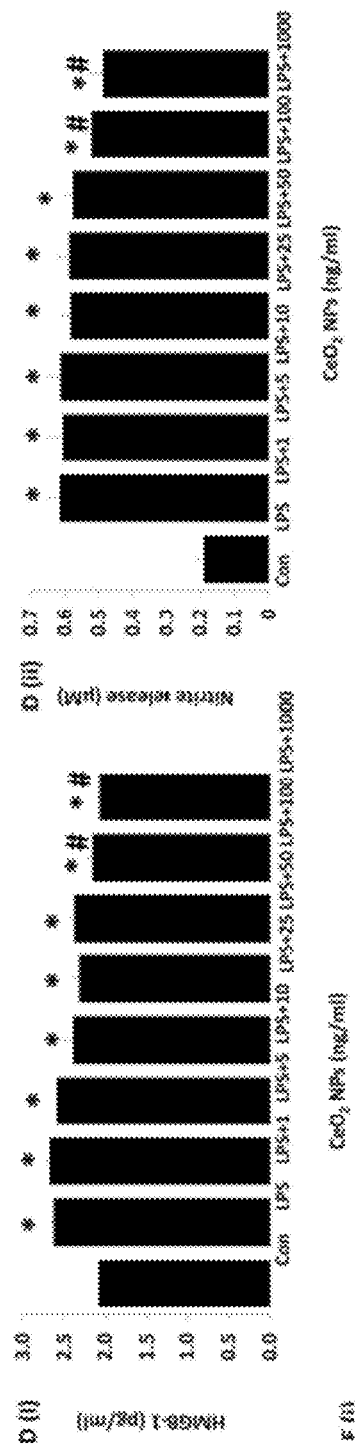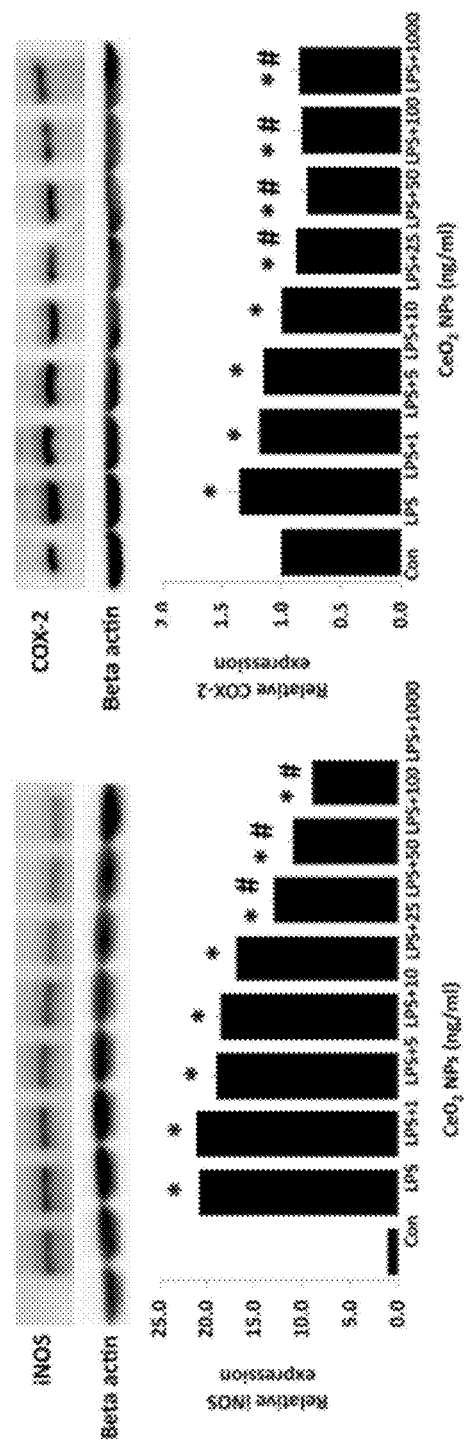
FIG. 39D
FIG. 39E

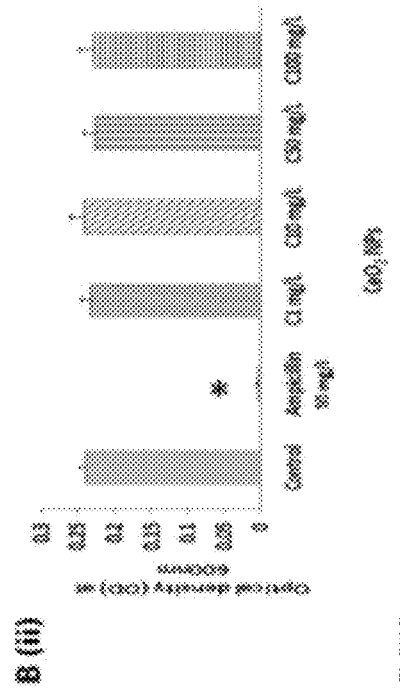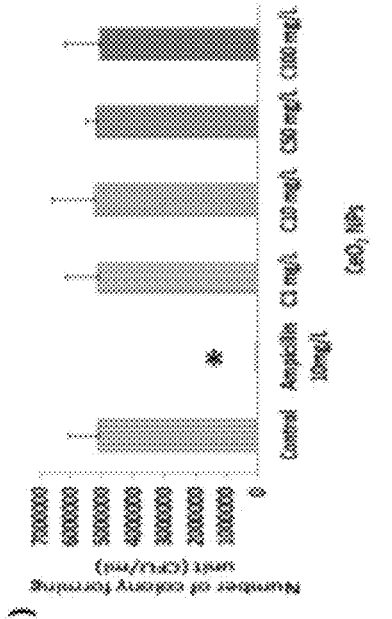
FIG. 48B
FIG. 48C
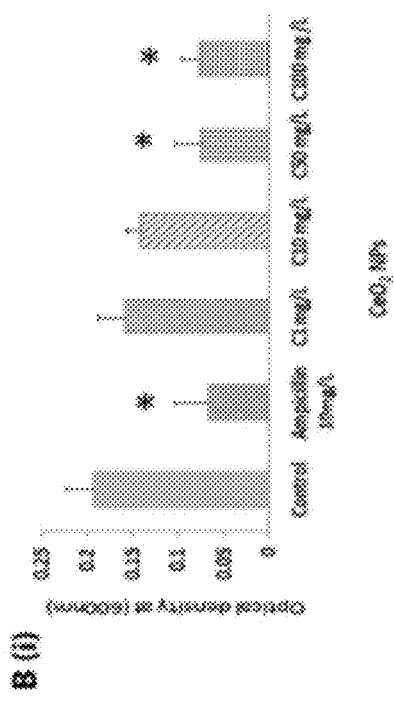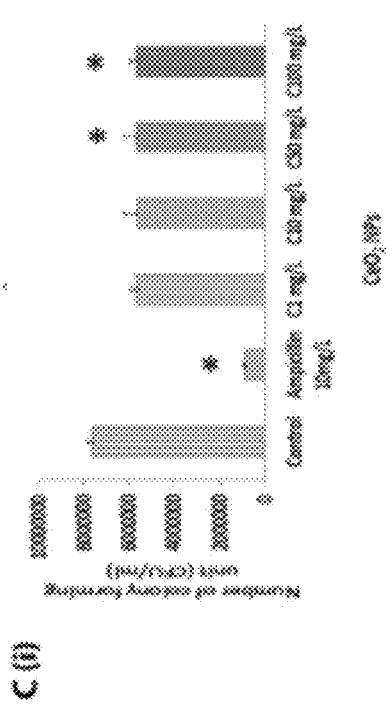

METHODS FOR TREATING SEPSIS

RELATED APPLICATIONS

This application claims priority from U.S. Provisional Application Ser. No. 61/978,337, filed Apr. 11, 2014, the entire disclosure of which is incorporated herein by this reference.

TECHNICAL FIELD

The presently-disclosed subject matter relates to methods for treating sepsis. In particular, the presently-disclosed subject matter relates to methods for treating sepsis that make use of cerium oxide nanoparticles.

BACKGROUND

Severe sepsis is a medical emergency that is characterized by systemic inflammatory response syndrome that progresses to multi-organ dysfunction and death if left untreated. Indeed, sepsis is the leading cause of death in non-coronary intensive care units and ranks among the top fifteen causes of mortality in the United States. Current treatment for sepsis typically involves the use of antibiotics, fluid resuscitation, vasopressors, non-steroidal anti-inflammatory drugs (NSAIDS), and mechanical ventilator support. Recent trials using anti-tumor necrosis factor-alpha (TNF-α) antibodies, activated Protein C, and antioxidants have also been employed in animal models and have been shown to improve survivability by 30-40%. However, although promising in animals, similar results in humans have yet to be realized, and there is currently no FDA-approved agent that is capable of treating severe sepsis. Accordingly, a therapeutic agent and/or method that is capable of treating sepsis, including the underlying symptoms and causes of sepsis, would be both highly desirable and beneficial.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter, methods for treating sepsis are provided. In some embodiments, a method for treating sepsis is provided that comprises administering to a subject in need thereof an effective amount of cerium oxide nanoparticles. In some embodiments, administering an effective amount of cerium oxide nanoparticles comprises administering about 0.1 mg/kg to about 1.0 mg/kg of the cerium oxide nanoparticles. In some embodiments, the cerium oxide nanoparticles can be administered intravenously to treat the sepsis, including, in some embodiments, polymicrobial sepsis.

By administering an effective amount of cerium oxide nanoparticles to a subject in need thereof, in some embodiments, one or more symptoms of the sepsis can be treated. For instance, in some embodiments, administering the cerium oxide nanoparticles normalizes a body temperature of the subject, reduces an amount of blood urea nitrogen in the subject, increases arterial oxygen levels in the subject, improves diaphragm contractility in the subject, or a combination thereof. In further embodiments, administering the cerium oxide nanoparticles decreases an amount of mitogen activated protein kinase (MAPK) signaling in a cell of the subject, decreases an amount of signal transducer and activation of transcription (stat) signaling in a cell of the subject, decreases an amount of NF-κB activation in a cell of the subject, or a combination thereof. In yet further embodiments, administering the nanoparticles reduces an amount of an inflammatory marker in the subject, such as, in some embodiments, an amount of glutathione S-transferase, myeloperoxidase, leukemia inhibitory factor, interferon gamma, interleukin 6, macrophage inflammatory protein, monocyte chemotactic protein, and tumor necrosis factor alpha. In some embodiments, administering the nanoparticles increases an amount of P-selectin and/or vascular cell adhesion molecule (VCAM) expression in a cell of the subject.

Further provided, in some embodiments of the presently-disclosed subject matter, are methods for treating an inflammatory disorder. In some embodiments, a method for treating an inflammatory disorder is provided that comprises administering to a subject in need thereof an effective amount of cerium oxide nanoparticles. In some embodiments, the inflammatory disorder is selected from the group consisting of acute kidney injury, acute lung injury, systemic inflammatory response syndrome, multiple organ dysfunction syndrome, and polymicrobial sepsis. In some embodiments, administering an effective amount of cerium oxide nanoparticles to treat the inflammatory disorder comprises administering about 0.1 mg/kg to about 1.0 mg/kg of the cerium oxide nanoparticles.

Similar to the treatment of sepsis described herein above, in some embodiments of the presently-disclosed methods for treating an inflammatory disorder, the administration of the cerium oxide nanoparticles ameliorates one or more of the symptoms associated with the inflammatory disorder. For example, in some embodiments, administering the cerium oxide nanoparticles normalizes a body temperature of the subject, reduces an amount of blood urea nitrogen in the subject, increases arterial oxygen levels in the subject, improves diaphragm contractility in the subject, or a combination thereof. In other embodiments, administering the cerium oxide nanoparticles reduces an amount of an inflammatory marker in the subject, such as glutathione S-transferase, myeloperoxidase, leukemia inhibitory factor, or an inflammatory cytokine (e.g., tumor necrosis factor α, interleukin 6, and interferon gamma). As another example, in some embodiments, administering the cerium oxide nanoparticles decreases an amount of mitogen activated protein kinase (MAPK) signaling in a cell of the subject, decreases an amount of signal transducer and activation of transcription (stat) signaling in a cell of the subject, decreases an amount of NF-κB activation in a cell of the subject, or a combination thereof.

Further features and advantages of the present invention will become evident to those of ordinary skill in the art after a study of the description, figures, and non-limiting examples in this document.

BRIEF DESCRIPTION OF THE DRAWINGS

FIGS. 35A-35E include images and graphs showing additional characterization of $CeO_2$ nanoparticles, animal survivability and physiological changes, including a scanning electron microscopy (SEM) image of $CeO_2$ nanoparticles (FIG. 35A, A(i)) and a transmission electron microscopy (TEM) image of $CeO_2$ nanoparticles (FIG. 35A, A (ii)), a dynamic light scattering (DLS) image of $CeO_2$ nanoparticles (FIG. 35B, B(i)), an X-ray diffraction graph of $CeO_2$ nanoparticles (FIG. 35B, B(ii)), an X-ray photoelectron spectroscopy image of $CeO_2$ nanoparticles (FIG. 35C, C(i)), a graph showing animal survivability of control (vehicle only), $CeO_2$ nanoparticle treated (0.5 mg/kg), sepsis (40 mg/kg of LPS), and sepsis+$CeO_2$ nanoparticle treatment (40 mg/kg of LPS+0.5 mg/kg of $CeO_2$ nanoparticles) (FIG. 35C, C (ii)), and graphs showing the temperature (FIG. 35D, D(i)), respiratory rate (FIG. 35D, D(i)) and blood pressure (FIG. 35E) in the various experimental groups (*P<0.05 compared to control group, #<0.05 compared to LPS group);

FIGS. 39A-39E include graphs and images showing the effect of $CeO_2$ nanoparticles on survival, ROS, Δψm, and cytokines production induced by LPS in RAW cells where cells were exposed to LPS in the presence and absence of $CeO_2$ nanoparticles for 24 h, including: graphs (FIG. 39A) showing the A (i) protective effect of $CeO_2$ nanoparticles against LPS insult and showing that A (ii) $CeO_2$ nanoparticles do not have any tendency to bind with LPS and neutralize the functionality of LPS; graphs (FIG. 38B) showing B (i) the amount of cerium oxide uptake by macrophage confirmed by ICP-MS analysis, B (ii) tumor necrosis factor alpha (TNF-α) levels; graphs (FIG. 39C) showing C (i) interleukin-6 (IL-6) and C (ii) interleukin-1 beta (IL-1β) levels; graphs (FIG. 39D) showing D (i) high mobility box group protein-1 (HMGB1) and (ii) measurement of nitrite in the medium as determined by ELISA; and images and graphs showing E (i) and E (ii) expression of iNOS and COX-2 by western blot analysis;

(FIG. 43A) a transmission electron microscopy image of $CeO_2$ nanoparticles (A (i)), a graph showing particle size as determined by dynamic light scattering (A (ii)), and an atomic force microscopy images (A (iii)); graphs (FIGS. 43B-43C) showing animal survivability of control, $CeO_2$ nanoparticle treated, sepsis, and sepsis+$CeO_2$ nanoparticle treatment (400 mg/kg of cecal inoculate+3.5 mg/kg of $CeO_2$ nanoparticles (B (i)), showing the effect of $CeO_2$ nanoparticle treatment on serum IL-6 at 6 and 24 hour after sepsis insult (*significantly different from controls ($P<0.05$), significantly different from septic animals ($P<0.05$)) B (ii)), and the effect of $CeO_2$ nanoparticle treatment on serum biomarkers (B (iii), C (i), C (ii), and C (iiii));

FIGS. 48A-48C include images and graphs showing the antibacterial activities of $CeO_2$ nanoparticles, where Muller Hatton agar plates containing *E. coli* and *S. aureus* were impregnated with Whatman filter paper discs (6 mm) containing various concentrations of $CeO_2$ nanoparticles (Control: no particles, C1: 1 mg $CeO_2$, C10: 10 mg $CeO_2$, C50: 50 mg $CeO_2$ and C100: 100 mg $CeO_2$) or ampicillin (A 10 mg) and incubated at 37° C. for 6 h, where, after 6 h, the zone clearance around the bacterial colony was observed and recorded, where the zone of inhibition (FIG. 48A) against *E. coli* (A (i)) and *S. aureus* (A (ii)) was then determined, where the effect of exposure to $CeO_2$ on microbial growth (FIG. 48B) as determined by the measurement of optical density at 600 nm for *E. coli* (B (i)) and *S. aureus* (B (ii)) was determined, and where the effect of $CeO_2$ treatment on colony forming unit (CFU) (FIG. 48C) was determined for *E. coli* (C (i)) and *S. aureus* (C (ii));

DESCRIPTION OF EXEMPLARY EMBODIMENTS

Figure 1A:
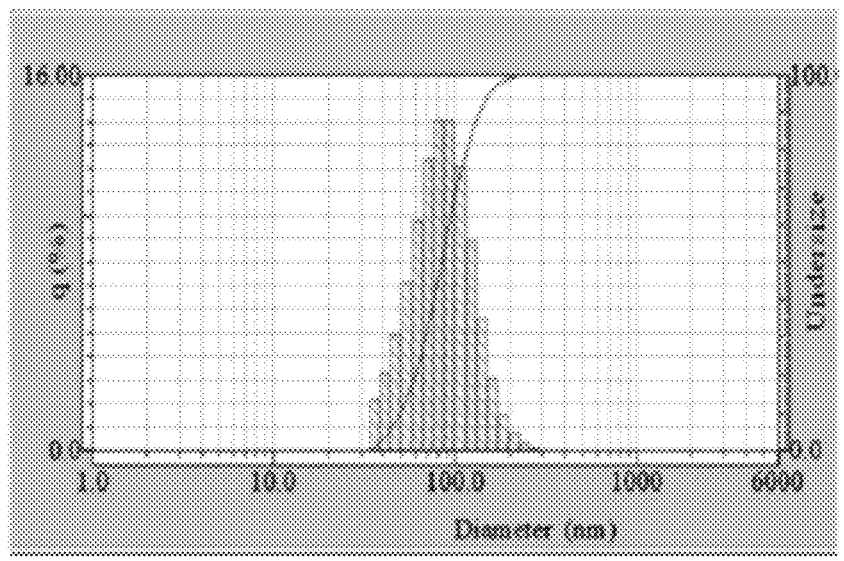
FIGS. 1A-1E include graphs and images showing the characterization (shape, size and composition) of cerium oxide nanoparticles (round in shape and 10-30 nm in diameter in size) by scanning electron microscopy (FIG. 1A), transmission electron microscopy (FIG. 1B), dynamic light scattering (FIG. 1C), atomic force microscopy (FIG. 1D), and energy dispersive x-ray spectroscopy (FIG. 1E)
Figure 1B:
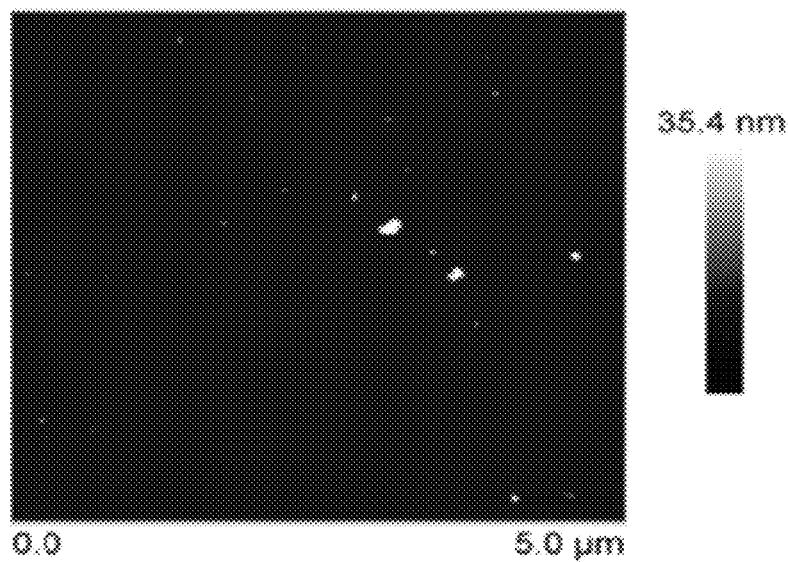
Figure 1C:
Figure 1D:
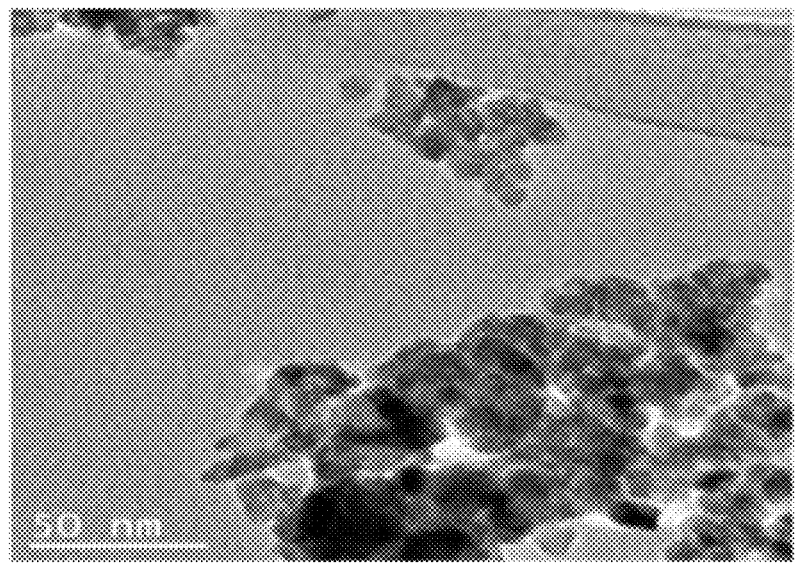

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Cerium oxide nanoparticles are potent antioxidants as such nanoparticles are capable of either donating or receiving electrons by virtue of their ability to alternate between the +3 and +4 valence states. That dual oxidation state has made cerium oxide nanoparticles an ideal catalyst in industrial applications, and more recently, cerium oxide nanoparticles have also proven to be useful in neutralizing free radicals in a number of biological applications. It has now been determined, however, that cerium oxide nanoparticles can be used to significantly improve survivability in subjects with severe sepsis. In particular, it has been surprisingly determined that the administration of cerium oxide nanoparticles to severely septic subjects improves the survivability of such subjects in manner that is not only associated with a normalization of body temperature in the subjects, but is also associated with significant decreases in the levels of blood urea nitrogen and the expression of inflammatory markers, without any evidence of organ or systemic toxicity at the dose utilized.

In this regard, the presently-disclosed subject matter thus includes methods for treating sepsis that make use of cerium oxide nanoparticles. In some embodiments of the presently-disclosed subject matter, a method of treating sepsis is provided that comprises administering an effective amount of cerium nanoparticles to a subject in need thereof. In some embodiments, the cerium oxide nanoparticles used in accordance with the presently-disclosed subject matter are commercially-available cerium oxide nanoparticles, such as those manufactured by U.S. Research Nanomaterials, Inc. (Stock#3036). In some embodiments, the cerium oxide nanoparticles are suspended in deionized water and sonicated for a period of time (e.g., 2 minutes at 600 W followed by 30 second interval and subsequent 2 minute sonication on ice) to disperse them evenly in the solution prior to administration.

As used herein, the terms "treatment" or "treating" relate to any treatment of a condition of interest (e.g., sepsis), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

For administration of a therapeutic composition as disclosed herein (e.g., cerium oxide nanoparticles), conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate kg factor. In an adult human, 100 mg/kg is equivalent to 100 mg/kg×37 kg/sq m=3700 mg/m$^2$. In some embodiments, administering an effective amount of cerium oxide nanoparticles comprises administering about 0.1 mg/kg to about 0.5 mg/kg to about 1.0 mg/kg of the cerium oxide nanoparticles.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, dermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, the therapeutic compositions are administered intravenously to treat a disease or disorder, such as sepsis.

Regardless of the route of administration, the cerium oxide nanoparticles used in accordance with the presently-disclosed subject matter are typically administered in an amount effective to achieve the desired response. As such, the term "effective amount" is used herein to refer to an amount of the therapeutic composition (e.g., cerium oxide nanoparticles and a pharmaceutically vehicle, carrier, or excipient) sufficient to produce a measurable biological response (e.g., a decrease in inflammation). Actual dosage levels of active ingredients in a therapeutic composition used in accordance with the presently-disclosed subject matter can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) Toxicol. Lett. 100-101:255-263.

With further respect to the therapeutic methods described herein, in some embodiments, administering the cerium oxide nanoparticles reduces one or more of the symptoms associated with or the causes of severe sepsis. For example, in some embodiments of the presently-disclosed subject matter, administering the cerium oxide nanoparticles normalizes a body temperature of the subject, reduces an amount of blood urea nitrogen in the subject, increases arterial oxygen levels in the subject, improves diaphragm contractility in the subject, or a combination thereof. In further embodiments, administering the cerium oxide nanoparticles decreases an amount of mitogen activated protein kinase (MAPK) signaling in a cell of the subject, decreases an amount of signal transducer and activation of transcription (stat) signaling in a cell of the subject, decreases an amount of NF-κB activation in a cell of the subject, or a combination thereof. In still further embodiments, administering the cerium oxide nanoparticles reduces an amount of an inflammatory marker in the subject, including, in some embodiments, a reduction in the amount of protein nitrosylation, glutathione S-transferase, myeloperoxidase, leukemia inhibitory factor, interferon gamma, interleukin 6, macrophage inflammatory protein, monocyte chemotactic protein, and tumor necrosis factor alpha, or combinations thereof. In some embodiments, administering the nanoparticles increases an amount of P-selectin and/or vascular cell adhesion molecule (VCAM) expression in a cell of the subject Various methods known to those skilled in the art can be used to determine a reduction in the amount of a marker or symptom associated with sepsis, or other disease or disorder, in a subject. For example, in some embodiments, the amounts of expression of an inflammatory marker in a subject can be determined by probing for mRNA of the gene encoding the inflammatory marker in a biological sample obtained from the subject (e.g., a tissue sample, a urine sample, a saliva sample, a blood sample, a serum sample, a plasma sample, or sub-fractions thereof) using any RNA identification assay known to those skilled in the art. Briefly, RNA can be extracted from the sample, amplified, converted to cDNA, labeled, and allowed to hybridize with probes of a known sequence, such as known RNA hybridization probes immobilized on a substrate, e.g., array, or microarray, or quantitated by real time PCR (e.g., quantitative real-time PCR, such as available from Bio-Rad Laboratories, Hercules, Calif.). Because the probes to which the nucleic acid molecules of the sample are bound are known, the molecules in the sample can be identified. In this regard, DNA probes for one or more of the mRNAs encoded by the inflammatory genes can be immobilized on a substrate and provided for use in practicing a method in accordance with the presently-disclosed subject matter.

With further regard to determining levels of inflammatory markers in samples, mass spectrometry and/or immunoassay devices and methods can also be used to measure the inflammatory cytokines in samples, although other methods can also be used and are well known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Any suitable immunoassay can be utilized, for example, enzyme-linked immunoassays (ELISA), radioimmunoassays (RIAs), competitive binding assays, and the like. Specific immunological binding of the antibody to the inflammatory molecule can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

The use of immobilized antibodies or fragments thereof specific for the inflammatory molecules is also contemplated by the present invention. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

Mass spectrometry (MS) analysis can be used, either alone or in combination with other methods (e.g., immunoassays), to determine the presence and/or quantity of an inflammatory molecule in a subject. Exemplary MS analyses that can be used in accordance with the present invention include, but are not limited to: liquid chromatography-mass spectrometry (LC-MS); matrix-assisted laser desorption/ionization time-of-flight MS analysis (MALDI-TOF-MS), such as for example direct-spot MALDI-TOF or liquid chromatography MALDI-TOF mass spectrometry analysis; electrospray ionization MS (ESI-MS), such as for example liquid chromatography (LC) ESI-MS; and surface enhanced laser desorption/ionization time-of-flight mass spectrometry analysis (SELDI-TOF-MS). Each of these types of MS analysis can be accomplished using commercially-available spectrometers, such as, for example, triple quadropole mass spectrometers. Methods for utilizing MS analysis to detect the presence and quantity of peptides, such as inflammatory cytokines, in biological samples are known in the art. See, e.g., U.S. Pat. Nos. 6,925,389; 6,989,100; and 6,890,763 for further guidance, each of which are incorporated herein by this reference.

With still further regard to the various therapeutic methods described herein, although certain embodiments of the methods disclosed herein only call for a qualitative assessment (e.g., the presence or absence of the expression of an inflammatory marker in a subject), other embodiments of the methods call for a quantitative assessment (e.g., an amount of decrease in the level of an inflammatory marker in a subject). Such quantitative assessments can be made, for example, using one of the above mentioned methods, as will be understood by those skilled in the art.

The skilled artisan will also understand that measuring a reduction in the amount of a certain feature (e.g., cytokine levels) or an improvement in a certain feature (e.g., inflammation) in a subject is a statistical analysis. For example, a reduction in an amount of inflammatory markers in a subject can be compared to control level of inflammatory markers, and an amount of inflammatory markers of less than or equal to the control level can be indicative of a reduction in the amount of inflammatory markers, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

By making use of cerium oxide nanoparticles for the treatment of sepsis, it has been observed that the survivability of subjects after septic insult increases from less than 10% to greater than 80%. Moreover, the administration of cerium oxide nanoparticles diminishes systemic capillary permeability, protein leakage into the interstitial space, generalized edema, development of hypovolemic shock, and cardiac dysfunction, while also improving pulmonary structure and preventing renal and hepatic failure. The administration of the cerium oxide nanoparticles was additionally observed to prevent the development of systemic inflammatory response syndrome (SIRS) and multiple organ dysfunction syndrome, and to improve and/or modulate AST, BUN, creatinine, monocytes, MIP-2, MDC, CGP-2, Eotaxin, VEGF-A and other systemic modulators of inflammation. In this regard, further provided, in some embodiments of the presently-disclosed subject matter, are methods for treating an inflammatory disorder. In some embodiments, a method for treating an inflammatory disorder is provided that comprises administering to a subject in need thereof an effective amount of cerium oxide nanoparticles.

As used herein, the term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cancer, or other agents or conditions.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders capable of being treated in accordance with the presently-disclosed subject matter include, but are not limited to, acute kidney injury, acute lung injury, acute liver failure, acute drug toxicity, acetaminophen-induced acute liver failure, alcoholic pancreatitis, pancreatitis, alcoholic liver disease, nonalcoholic steatohepatitis, liver obesity induced hyperglycemia, obesity induced insulin resistance, central nervous system inflammation such as that seen following brain or spinal cord injury, systemic inflammatory response syndrome, multiple organ dysfunction syndrome, and polymicrobial sepsis.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Example 1—Characterization of Cerium Oxide Nanoparticles $CeO_2$ nanoparticles were characterized using the following methods:

Aqueous $CeO_2$ NPs Preparation and Evaluation of Nanoparticle Size:

Previously characterized NanoActive $CeO_2$ (99.9% purity as determined by ICP-MS; Lot #06-0118) was purchased from NanoScale corporation (Manhattan, Kans., USA). The stock suspensions (3.5 mg/ml) were prepared in dd$H_2$O by sonication using a Vibra Cell Sonicator (Sonics & Materials, Inc.) at 600 W for 2 min at room temperature.

Field Emission Scanning Electron Microscopy:

The surface morphology of nanoparticles was observed by field emission scanning electron microscopy FE-SEM, Hitachi S-4800 (Hitachi High Technologies, Inc., Dallas, Tex., USA) using an accelerating voltage of 3 kV.

Transmission Electron Microscopy:

Particles were imaged using a Hitachi-H-7000 electron microscope at 75 keV and a magnification of 50,000×. ImageJ software was used to calculate particle size.

Dynamic Light Scattering:

The hydrodynamic size and size distribution of CeO2 nanoparticles were evaluated in dd$H_2$O using a Particle Size Analyzer (HORIBA, Model-LB-550) equipped with a He—Ne laser (633 nm) using back scattered light. Experiments were performed utilizing triplicate runs performed on three different days with freshly prepared samples.

Atomic Force Microscopy:

Particles were imaged in their native state using a MultiMode-8, Atomic Force Microscope (Bruker, Ewing, N.J.) in the tapping mode. Briefly, a few drops of $CeO_2$ nanoparticles were placed on freshly pealed mica substrate and allowed to dry in a petri dish floating in a sonicator water bath (VWR, 50D, Radnor, Pa.) for 30 min at 240 W. Images were recorded in topography mode. Width and height measurements of adsorbed NPs were made using the microscope's section analysis software. For each set of solutions conditions, at least 100 particle measurements were performed.

Using the foregoing methods for $CeO_2$ nanoparticle characterization, CeO2 nanoparticle agglomerate size was determined by TEM to be 143.3±49 nm (FIG. 1). The mean hydrodynamic diameter of the $CeO_2$ nanoparticles as measured by dynamic light scattering (DLS) was 140±52.9 nm (FIG. 1). AFM analysis indicated an agglomerate size of 37.75±3.8 nm width and 1.38±0.28 nm height respectively (FIG. 1).

With respect to the states of the $CeO_2$ nanoparticles, other data have shown that changing the ratio of Ce 3+ to Ce 4+ can function to change the enzymatic properties of the $CeO_2$ nanoparticles. For example, a reduced level of cerium in the +3 state is correlated with catalase mimetic activity and the ability to scavenge nitric oxide radicals, while an increase in the amount of cerium in the +3 state is associated superoxide dismutase ((SOD) activity (PMID reference numbers: 22498787, 18395249, 20369466). As such, and without wishing to be bound by any particular theory or mechanism, it was believed that it may be desirable to use $CeO_2$ nanoparticles with an increased amount of cerium in the +3 state during the initial and middle stages of sepsis. Conversely, when nitric oxide levels are high such as that seen in the latter stages of the septic continuum, it was believed that it may be advantages to use $CeO_2$ nanoparticles with a low amount of cerium in the +3 state. In addition to the ratio of Ce+3 to Ce+4 it may also be desirable to use different sizes of $CeO_2$ nanoparticles to target different cell types. As an example, SIRS is thought to be caused by the release of cytokines from the Kuppfer cells in the liver and the macrophage cells located in the spleen and periphery (PMID 9191670, 12516206, 21492870). To target these cells, it is believed that it is likely that the cerium oxide particle size should range between 80 and 200 nm to optimize nanoparticle uptake (PMID: 22841920). Conversely, to target other areas of the body, it may be advantageous to reduce the size of the $CeO_2$ particles.

Example 2—Administration of Cerium Oxide Nanoparticles to Septic Subjects

To preliminarily assess the administration of $CeO_2$ nanoparticles to septic subjects, 12 week old male Sprague Dawley rats were used. Animals were randomly assigned to one of the four groups—a) Sham control group, b) $CeO_2$ control group, c) Sepsis group, and d) Sepsis and treatment group. Animals were anesthetized under isoflurane to perform the experiments. Sham control group animals underwent an abdominal incision of approximately 0.25 cm followed by an intraperitoneal injection of 5% sterile dextrose at 5 ml/kg body weight. Immediately, 0.2 ml of deionized water was administrated by tail vein injection as a vehicle control. Cerium oxide group animals also underwent an abdominal incision of approximately 0.25 cm followed by injection of 5% sterile dextrose at 5 ml/kg body weight. Simultaneously, 0.5 mg/kg of $CeO_2$ nanoparticles in 0.2 ml of deionized water was administrated intravenously via tail vein. Sepsis group animals also underwent an abdominal incision of approximately 0.25 cm followed by injection of 5% sterile dextrose at 5 ml/kg body weight containing 600 mg/kg body weight of cecal material obtained from caecum of healthy donor animal. Immediately, 0.2 ml of deionized water was injected intravenously via tail vein. Animals from the sepsis+cerium oxide nanoparticles treatment group underwent an abdominal incision of approximately 0.25 cm followed by injection of 5% sterile dextrose at 5 ml/kg body weight containing 600 mg/kg body weight of cecal material obtained from caecum of healthy donor animal. Immediately after cecal material inoculation, 0.5 mg/kg of $CeO_2$ nanoparticles in 0.2 ml of deionized water was administered intravenously via tail vein. All rats were given free access to food and water after recovery from anesthesia.

After the procedure, animals were monitored under the experimental conditions for survivability for a period of 72 hrs. Any surviving animals were sacrificed humanely under anesthesia thereafter. During the survival period, animals' temperature was recorded at regular intervals using a rectal probe attached to mouseox plus instrument (Starr Life Sciences Corp.,) at regular intervals.

In other experiments, animals were randomly assigned to one of the four groups as detailed in the preceding section. At 3 or 18 h after study initiation, animals were sacrificed and their blood was collected by cardiac puncture. Serum was separated and used for measuring various serum protein markers.

Upon the analysis of the results from these experiments, and as shown in FIGS. 2-5, it was observed that the one time, intravenous dosing tested in the rat polymicrobial and LPS-sepsis models improved animal survivability after septic insult from <10% to >80%. Nanoparticle intervention appeared to diminish systemic capillary permeability, protein leakage into the interstitial space, generalized edema, development of hypovolemic shock and cardiac dysfunction. Intervention also improved pulmonary structure, prevented renal and hepatic failure, and prevented the development of SIRS and MODS. Further administration of the $CeO_2$ particles appeared to improve/modulate, BUN, creatinine, monocytes, MIP-2, MDC, CGP-2, Eotaxin, VEGF-A and other systemic modulators. Similar in vitro experimentation using RAW 264.7 cells suggest that the $CeO_2$ particles were functioning by diminishing cellular superoxide (ROS)→iNOS/COX-2/nitric oxide→p38-MAPK/NF-κB→NF-κB binding to DNA. The $CeO_2$ particles also appeared to possess anti-bacterial (gram negative), anti-inflammatory and anti-oxidative properties.

Example 3—Therapeutic Potential of Cerium Oxide Nanoparticles for the Treatment of Severe Inflammation by Polymicrobial Insult Additional experiments were undertaken to further evaluate whether $CeO_2$ nanoparticles can improve survival rate in Sprague Dawley rats with severe intra-abdominal infection and to investigate whether the treatment associated changes in systemic inflammatory response attenuate hepatic and cardiac inflammation.

Materials and Methods for Example 3
Characterization of Cerium Oxide Nanoparticles.
Cerium oxide nanoparticles were purchased from US Research Nanomaterials Inc. (Houston, Tex.). Dynamic light scattering (DLS) was performed to estimate the mean size of $CeO_2$ nanoparticles in suspension using LB-550 DLS particle size analyzer (Horiba Scientific, Edison, N.J.). Size of the $CeO_2$ nanoparticles was characterized by transmission electron microscopy using a JEOL JEM-2010 transmission electron microscope (TEM). X-ray diffraction (XRD) was performed by Scintag XDS 2000 powder diffractometer. Scanning transmission electron microscopy (STEM) images were acquired by the Aberration Corrected Analytical Electron Microscope (TEM/STEM JEOL J EM-ARM200CF, Japan) operated at 200 keV. Electron energy loss spectroscopy (EELS) data for $CeO_2$ nanoparticles were collected by Gatan Enfina.

Induction of Intra-Abdominal Infection and Therapeutic Intervention.

Male Sprague Dawley rats aged 10 weeks were purchased from Hill-Top Laboratories and housed in two-per cage at 22±2° C. with a 12:12 light-dark cycle for 2 weeks prior to experimentation. Animals were fed with standard rodent chow and had access to food and water ad libitum. All experiments that necessitate the use of animals were approved by the institutional review board of Marshall University. All surgical procedures were performed in accordance with the guidelines provided by Marshall University Institutional Animal Care and Use Committee (IACUC), and the Association for Assessment and Accreditation of Laboratory Animal Care (AAALAC). Briefly, animals were anesthetized under isoflurane and a small mid ventral incision of 0.5 cm was made. Sham controls and $CeO_2$ only groups were injected with 5 ml/kg of 5% sterile dextrose solution intraperitoneally and the incision was closed with 3-0 silk sutures. For the peritonitis and peritonitis+$CeO_2$ groups, animals received a cecal inoculum of 600 mg/kg BW in 5 ml/kg BW of 5% sterile dextrose solution intraperitoneally. Cecal material was obtained from healthy rats and the material from each donor was used to induce peritonitis in 4-5 rats. Sham control and peritonitis groups received 200 µl of sterile distilled water intravenously via tail vein while the $CeO_2$ and peritonitis+$CeO_2$ groups received $CeO_2$ nanoparticles (0.5 mg/kg) in 200 µl of sterile distilled water intravenously at the same time of polymicrobial injection. Rectal temperature was recorded at 0, 3, 6, 12, 18, 24, and 48 h after sham surgery or injection of cecal inoculum. Animals were observed for mortality for a period of 14 days.

Sample Collection and Estimation of Ceria Content.
Whole blood was collected by cardiac puncture and centrifuged at 5,000×g for 10 min to collect serum. The heart and liver were excised and washed in Krebs-Ringer bicarbonate buffer (KRB) to remove any blood, blotted to remove excess moisture, snap frozen in liquid nitrogen, and stored at −80° C. for further analysis. Frozen hearts, livers, lungs, spleens and kidneys were sent to Elemental Analysis Inc. (Lexington, Ky.) for estimation of ceria content by induction coupled plasma-mass spectrometry (ICP-MS) as described elsewhere.

Estimation of Immune Cell Number and Serum Markers of Inflammation.

The number of white blood cells (WBC), neutrophils, monocytes and lymphocytes were estimated in peritoneal fluid using an Abaxis VetScan HM2 hematology analyzer (Abaxis, Union city, CA). Total serum ROS/RNS was measured using OxiSelect™ in vitro ROS/RNS assay kit (Cell Biolabs, Inc., San Diego, Calif.) as outlined by the manufacturer. Serum samples from each of the different groups (n=6/group) were pooled and sent to Myriad RBM (Austin, Tex.) for the analysis of inflammatory markers using rodent MAP® V. 3.0. Samples were run in triplicate for statistical analysis.

Liver Histology and Superoxide Levels.
Liver tissue was sectioned (4 µm) using Leica CM1950 cryostat onto poly-L-lysine coated slides. Visualization of hematoxylin and eosin staining was performed to evaluate liver morphology using Evos XL microscope (Life Technologies, Grand Island, N.Y.). Levels of hepatic superoxide were estimated using dihydroethidium stain (Life Technologies, Grand Island, N.Y.) as described previously. Briefly, liver sections were washed with PBS for 5 min and stained with a 5 µM solution of dihydroethidium for 1 h at room temperature in the dark. Tissue sections were imaged using Evos FL microscope (Life Technologies, Grand Island, N.Y.) after PBS washing (3×5 min) and the levels of superoxide were estimated by image analysis using image J analysis software. Four random areas per section were evaluated with n=4/group for histology and determination of superoxide levels.

Immunohistochemistry.

Immunohistochemistry was performed in liver tissue sections for ED1 molecule to determine the number of monocytes/macrophages. Briefly, frozen liver sections were fixed with formalin for 15 min, washed with PBS (3×5 min) and incubated with 0.25% Triton X 100 in PBS for 20 min. After washing with PBS (3×5 min) the sections were blocked with 1% bovine serum albumin in PBS for 30 min and then incubated for 1 h with primary ED1 antibody (1:250 in 1% BSA in PBS) (Abcam, Cat no: ab31630). The primary antibody was removed by PBS wash (3×5 min) and the sections were incubated in the dark for 1 h with secondary Alexa Fluor 594 goat anti-mouse antibody (1:1000). After incubation with the secondary antibody, the sections were washed with PBS (3×5 min), and mounted. Image J software was used for determination of ratio of ED1 positive cells to total number of cells in each field. Seven different fields per section were imaged to determine the number of macrophages from four animals in each group.

SDS-PAGE and Immunoblotting.

Approximately 100 mg of frozen tissue was pulverized in liquid nitrogen and added to 900 µl of T-PER (Pierce, Rockford, Ill., USA) containing 1% protease and phosphatase inhibitors (P8340 and P5726, Sigma-Aldrich, St. Louis, Mo., USA). Samples were homogenized for 30 sec using Tissuemiser homogenizer (Fisher Scientific, Pittsburgh, Pa.) and centrifuged at 10,000×g for 10 min at 4° C. to collect the supernatant. Amount of protein in the samples was estimated using the 660 nm assay (Pierce, Rockford, Ill., USA). Forty microgram of total protein from each sample was loaded in 10% PAGE Gold Precast gel (Lonza, Rockland, Me.), subjected to electrophoresis and transferred to nitrocellulose membranes using standard protocol as detailed elsewhere. Membranes were blocked with 5% milk in TBST for 1 h at room temperature, washed with TBST (3×5 min) and incubated with the appropriate primary antibody (ERK 1/2 MAPK (1:1000), p-ERK 1/2 MAPK (Thr202/Tyr204) (1:500), Stat-3 (1:1000), p-Stat-3 (Tyr705) (1:500), GAPDH (1:10,000) (Cell Signaling Technology, Danvers, Mass.), P-selectin (1:250), VCAM-1 (1:250), nitrotyrosine (1:1000) (Abcam, Cambridge, Mass.) and iNOS (1:500) (Santa Cruz, Dallas, Tex.)) overnight at 4° C. After the primary antibody incubation, membranes were washed with TBST (3×5 min), and incubated with secondary anti-rabbit (Cell Signaling Technology, Danvers, Mass.) or anti-mouse antibody (Santa Cruz, Dallas, Tex.) for 1 h at room temperature. Immunoreactive signal was visualized using Supersignal West Pico Chemiluminiscent substrate (Pierce, Rockford, Ill., USA) and quantified using Fluorchem 9900 software (Protein Simple, Santa Clara, Calif.). Protein expression was normalized to glyceraldehyde 3-phosphate dehydrogenase (GAPDH).

Cell Culture and MTT Cell Proliferation Assay.

Cell culture studies were performed using murine RAW 264.7 macrophage cell line (ATCC, Manassas, Va.) that were grown in Dulbecco's modified Eagle medium supplemented with 5% fetal bovine serum (Hyclone), 1% penicillin and streptomycin at 37° C. with 95% air and 5% CO2. For determination of toxicity of $CeO_2$ nanoparticles to macrophages (immune cells), MTT assay was performed to evaluate cell viability with different doses of $CeO_2$ nanoparticles. The MTT assay is based on the principle that living cells reduce the tetrazolium salt 3-(4,5-dimethylthiazol-2-yl)-2,5-diphenyltetrazolium bromide to formazan. Briefly, cells were seeded in 48 well microplate at the rate of $5 \times 10^4$ cells/ml and incubated overnight and then treated with 1 µg/ml, 10 µg/ml, 25 µg/ml, 50 µg/ml and 100 µg/ml of $CeO_2$ nanoparticles in cell culture media for 48 h. MTT assay was performed as described elsewhere and the optical density of each well was determined at a wavelength of 570 nm. Experiments were performed in triplicate for statistical analysis.

Estimation of Serum Creatine Kinase Activity.

Creatine kinase activity was measured in serum samples of 18 h time point using creatine kinase fluorometric assay kit (Cayman Chemical Company, Ann Arbor, Mich.) as directed by the kit instructions.

Statistical Analysis.

Results are presented as mean±SEM. Sample size was determined using power analysis to achieve >25% difference/benefit in most of the examined endpoints with a power of 0.80 and probability of Type I error of 0.05. The log-rank test (Mantel-Cox) was performed using Prism 5.0 software (GraphPad Software, La Jolla, Calif.) to determine differences in animal survivability between groups. A two way analysis of variance using Tukey's multiple comparison was performed where appropriate to evaluate differences in core temperature amongst the different groups. Differences in groups with equal sample size was evaluated by one way analysis of variance using Student Newman Keuls or Dunn's post hoc analysis for samples with unequal size. Kruskal Wallis one way ANOVA by ranks was used for samples with non-normal distribution and a simple t-test was performed where appropriate using Sigmaplot 12 statistical software (Systat software Inc., San Jose, Calif.) to test for the presence of significant differences between groups. A probability value of P<0.05 was considered to be statistically significant.

Results for Example 3

Characterization of $CeO_2$ Nanoparticles.

Figure 6A:
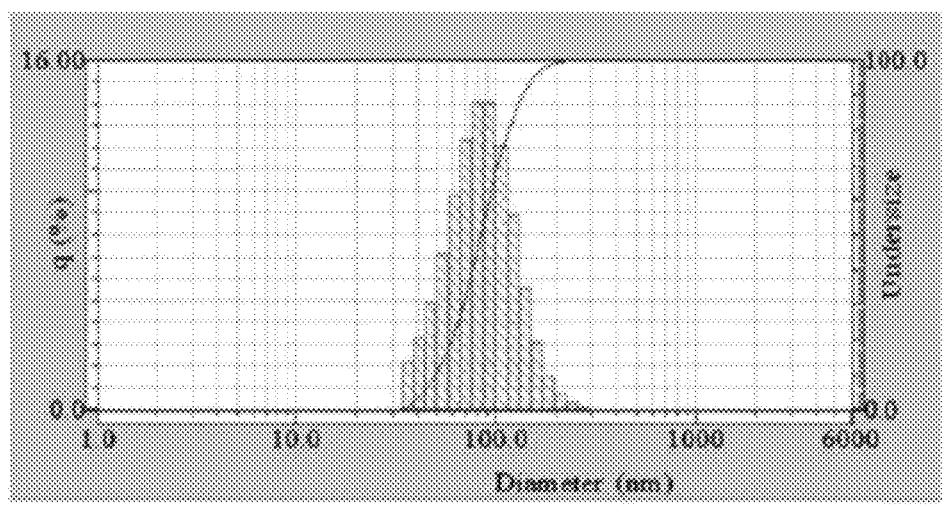
FIGS. 6A-6G include graphs and images showing the characterization of further $CeO_2$ nanoparticles.
Figure 6B:
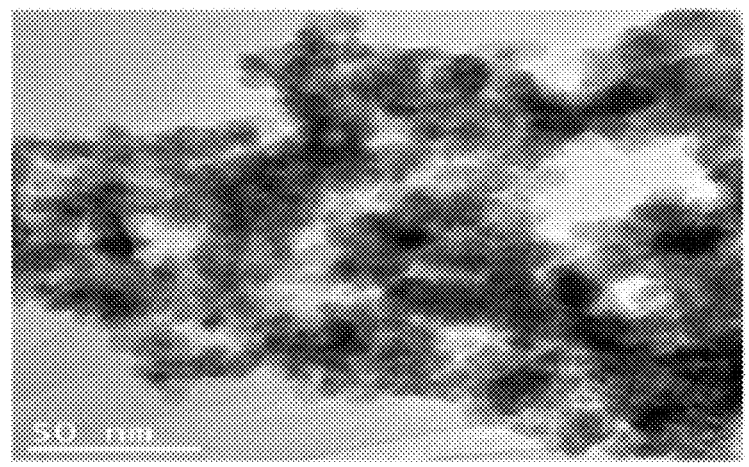
Figure 6C:
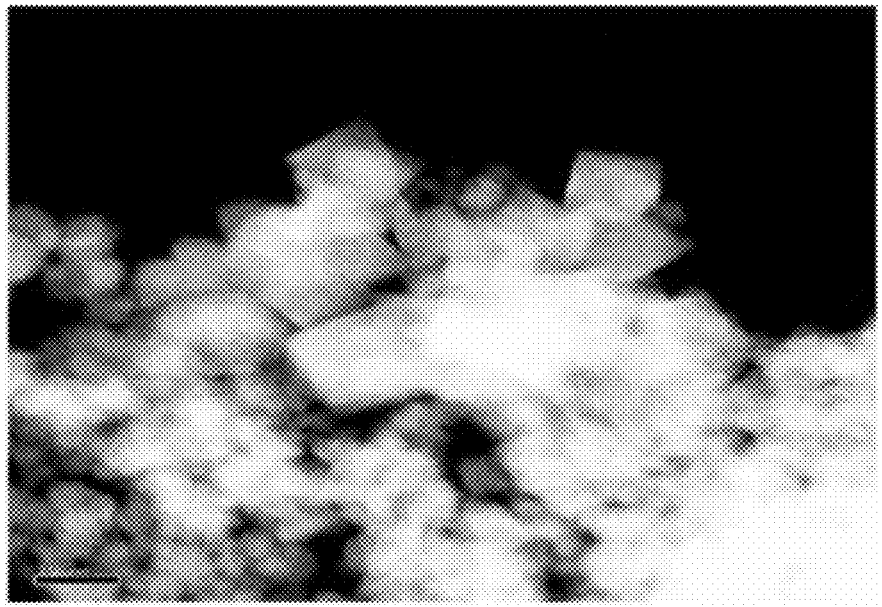
Figure 6D:
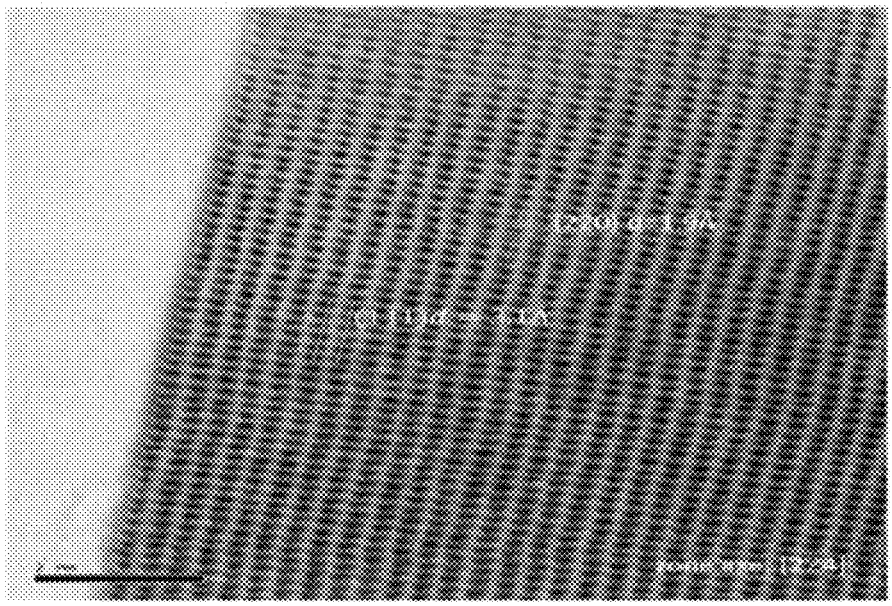
Figure 6E:
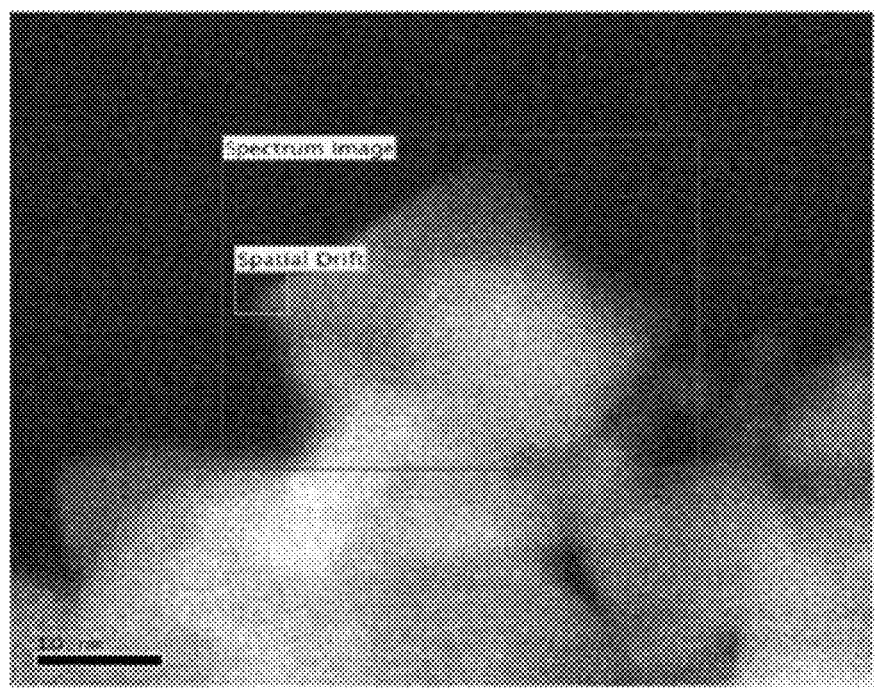
Figure 6F:
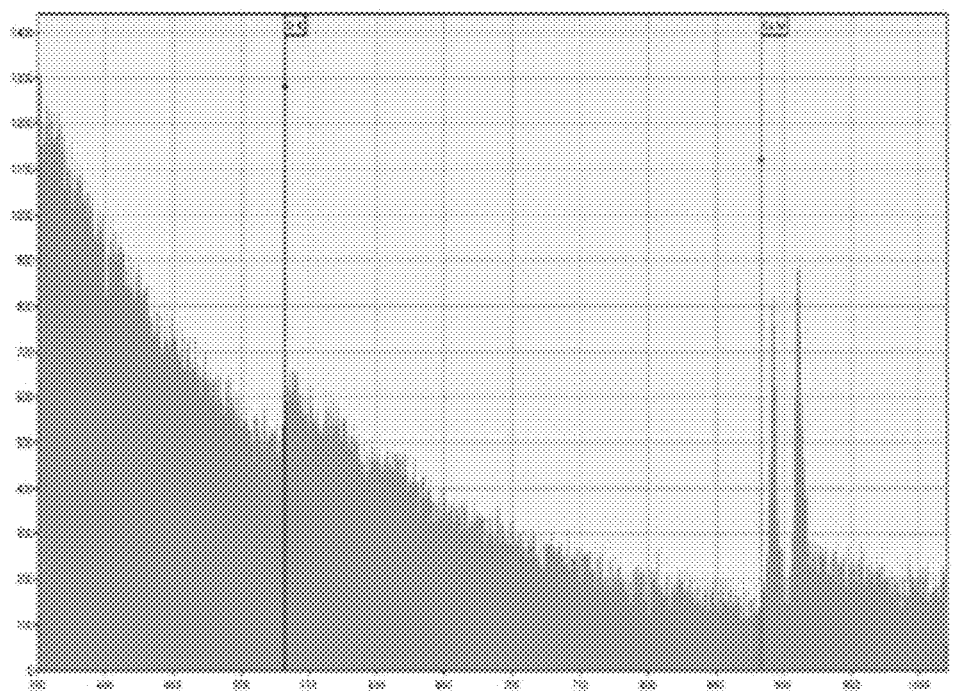
Figure 6G:
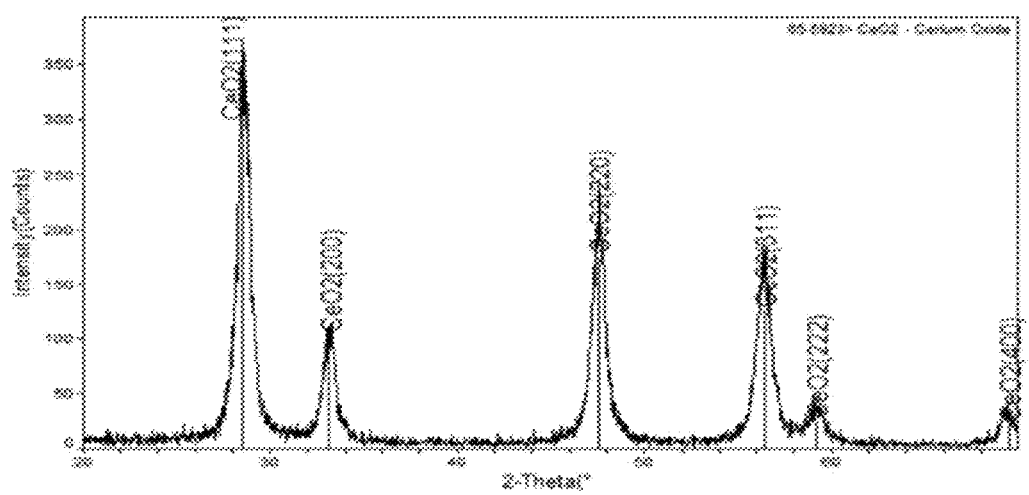

The mean hydrodynamic diameter of $CeO_2$ nanoparticles as estimated through dynamic light scattering experiments was found to be approximately 90 nm (FIG. 6A). Transmission electron microscopy (TEM) and scanning transmission electron microscopy-High angle annular dark field (STEM-HAAF) analysis determined the size of individual nanoparticle to be approximately in between 10-30 nm (FIGS. 6B-6C). The high resolution image of the $CeO_2$ nanoparticle showed that the atoms of $CeO_2$ were highly ordered (FIG. 6D) and the electron energy loss spectroscopy (EELS) data (FIG. 6F) confirmed the existence of the Ce and O element. X-ray diffraction (XRD) was used to demonstrate cubic fluorite structure of $CeO_2$ nanoparticles as seen through typical peaks (FIG. 6G).

Effect of $CeO_2$ Nanoparticles on Severe Peritonitis-Induced Mortality, Hypothermia and Systemic ROS Levels.

Figure 7:
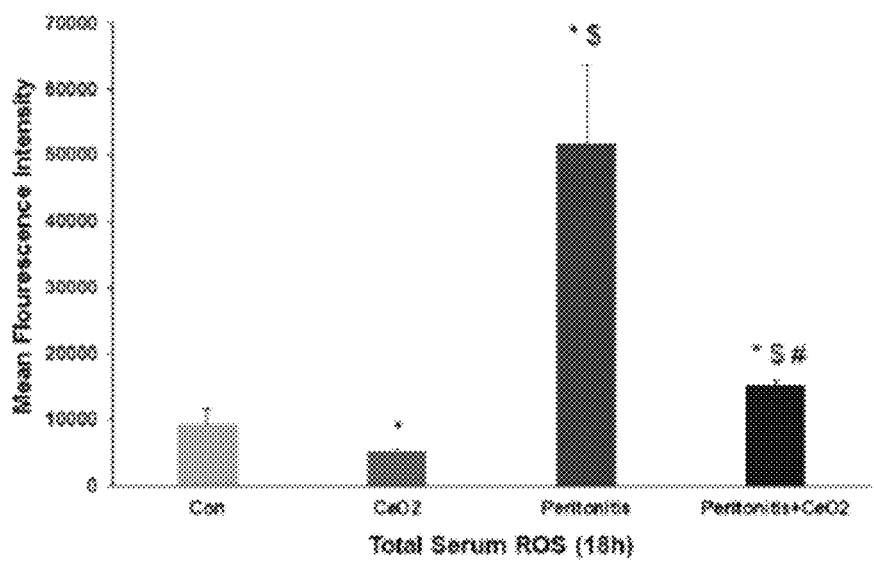
FIG. 7 is a graph showing the effect of nanoparticle treatment on total serum ROS levels at 3 h and 18 h (where *$P<0.05$ compared to control group, \$ $P<0.05$ compared to $CeO_2$ group, and # $P<0.05$ compared to peritonitis group)

In an effort to determine the appropriate $CeO_2$ dosage, experiments employing different nanoparticle concentrations (0.25 mg/kg, 0.5 mg/kg or 1 mg/kg) were performed (n=4 animals/group). No mortality was seen in control or $CeO_2$ nanoparticle only groups. Conversely, the untreated animals with peritonitis exhibited a 100% mortality rate while the animals treated with $CeO_2$ nanoparticles at 0.25, 0.5, or 1 mg/kg (n=4/group) demonstrated survival rates of 75%, 100% and 50%, respectively. On the basis of these data, and previous showing that indicating that a dose of 0.5 mg/kg is non-toxic and associated with the attenuation of oxidative stress (20), the 0.5 mg/kg dosage was selected for further investigation. Using this dosage, it was found that the nanoparticle treatment decreased peritonitis-induced mortality from 100% to ~25%. Improvements in animal survivability were associated with a significant increases in core body temperature and diminished total serum ROS levels at 18 h (FIG. 7, P<0.05).

Tissue Distribution of Cerium Oxide Nanoparticles Upon Intravenous Injection.

Induction coupled plasma mass spectroscopy (ICP-MS) demonstrated that the deposition of ceria in the nanoparticle injected animals was highest in the liver followed by the lungs and spleen while it was not detectable in the heart or kidneys (Table 1).

TABLE 1

Levels of ceria content in various organs as determined through ICP-MS.

| Organ | Control 3 h | CeO₂ 3 h | Peritonitis 3 h | Peritonitis + CeO₂ 3 h | Control 18 h | CeO₂ 18 h | Peritonitis 18 h | Peritonitis + CeO₂ 18 h |
|---|---|---|---|---|---|---|---|---|
| Heart | <LLOQ | <LLOQ | <LLOQ | <LLOQ | <LLOQ | <LLOQ | <LLOQ | <LLOQ |
| Liver | <LLOQ | 12.00 ± 0.76 ppm | <LLOQ | 0.07 ± 0.08 ppm | <LLOQ | 10.67 ± 0.17 ppm | <LLOQ | 12.00 ± 0.28 ppm |
| Spleen | <LLOQ | 1.37 ± 0.00 ppm | <LLOQ | 1.47 ± 0.20 ppm | <LLOQ | 1.87 ± 0.24 ppm | <LLOQ | 2.00 ± 0.20 ppm |
| Kidney | <LLOQ | <LLOQ | <LLOQ | <LLOQ | <LLOQ | <LLOQ | <LLOQ | <LLOQ |
| Lungs | <LLOQ | 1.95 ± 0.93 ppm | <LLOQ | 1.77 ± 1.00 ppm | <LLOQ | 0.71 ± 0.27 ppm | <LLOQ | 4.47 ± 0.38 ppm |

Nanoparticle Treatment Decreases Peritonitis-Induced Hepatic Damage, Tissue Superoxide and iNOS Levels.

Figure 8A:
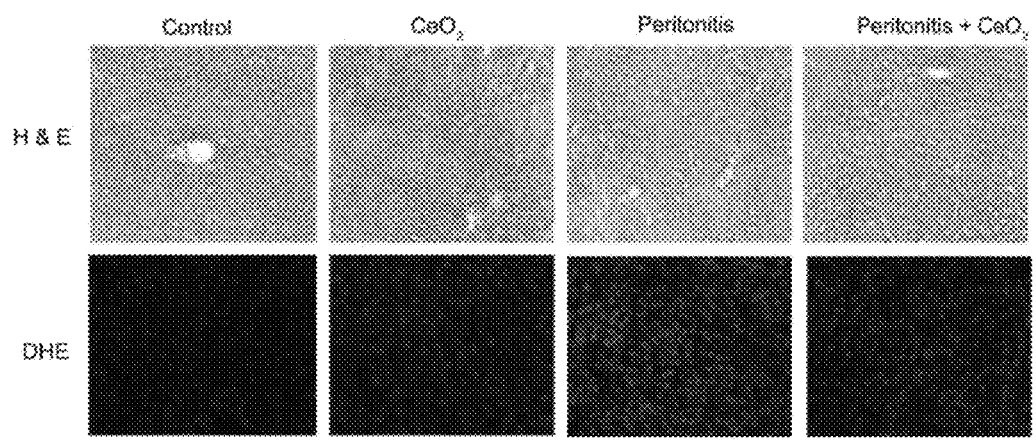
FIGS. 8A-8B are images and a graph showing the effect of $CeO_2$ nanoparticles on severe peritonitis-induced hepatic inflammatory damage, including images showing hematoxylin and eosin staining of 18 h time point liver sections imaged at 200× magnification of control, $CeO_2$, peritonitis, and peritonitis+$CeO_2$ animals (FIG. 8A, top images), images showing dihydroethidium staining of 18 h time point liver sections imaged at 200× magnification of control, $CeO_2$, peritonitis and peritonitis+$CeO_2$ animals (FIG. 8A, bottom images), and a graph showing quantification of superoxide levels in the different groups at the 18 h time point, where *$P<0.05$ compared to control group, \$ $P<0.05$ compared to $CeO_2$ group and # $P<0.05$ compared to peritonitis group.
Figure 8B:
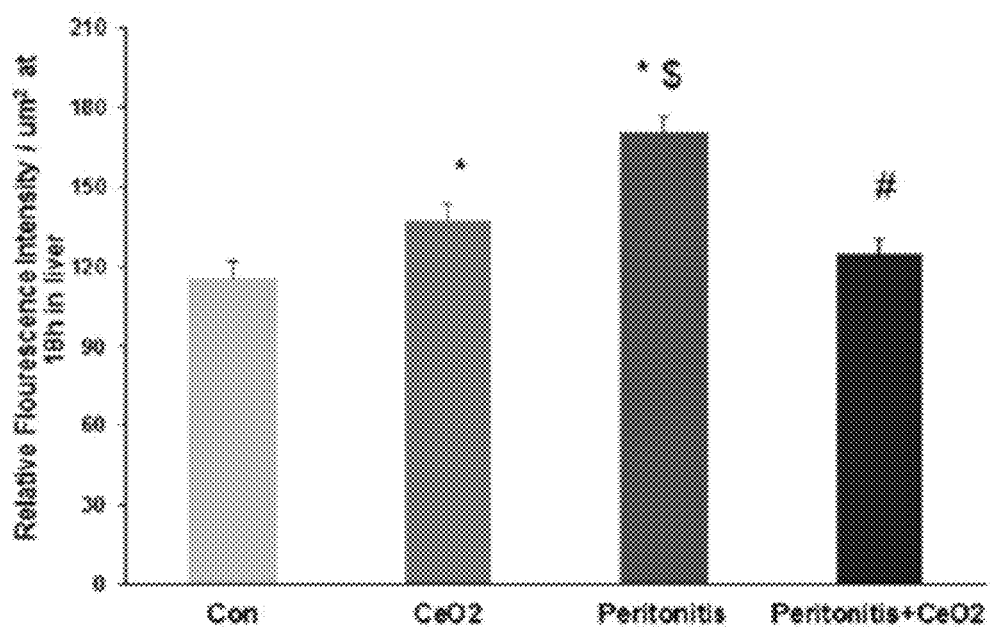
Figure 9A:
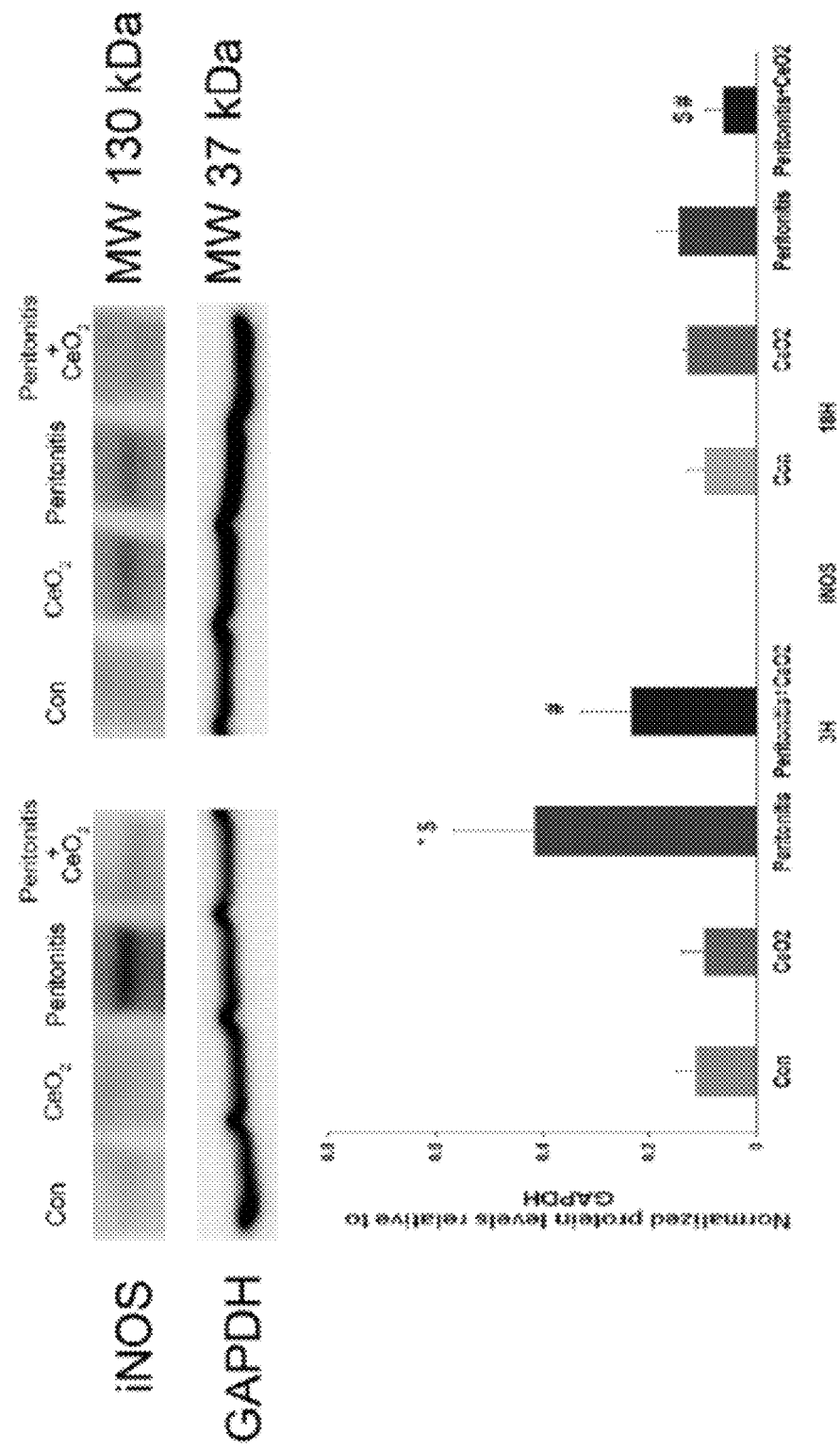
FIGS. 9A-9B include images and graphs showing the effect of $CeO_2$ nanoparticles on severe peritonitis-induced hepatic nitrosative stress, including images and a graph showing levels of iNOS as determined by western blotting and normalized to GAPDH (FIG. 9A), and images and a graph showing levels of nitrotyrosine as determined by western blotting and normalized to GAPDH (FIG. 9B), where *$P<0.05$ compared to control group, \$ $P<0.05$ compared to $CeO_2$ group and # $P<0.05$ compared to peritonitis group.
Figure 9B:
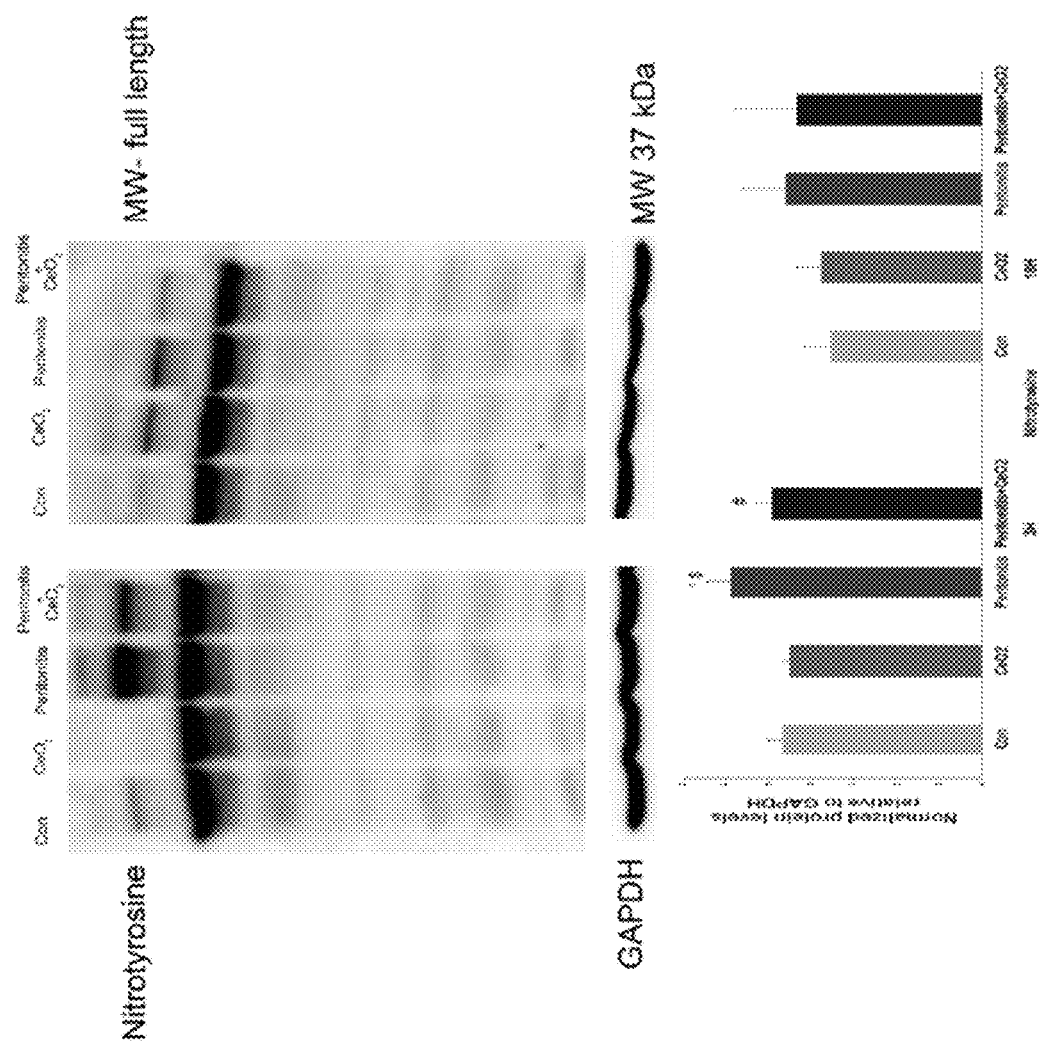

Histological analysis of the livers obtained from control animals revealed normal hepatic and sinusoidal morphology. Nanoparticle treatment diminished severe peritonitis-induced sinusoidal dilatation and hepatocyte congestion (FIG. 8A, upper images). Consistent with the histological findings, peritonitis associated increase in hepatic superoxide (FIG. 8B, lower images, FIG. 8C, P<0.05), iNOS, and protein nitrosylation levels were also decreased with nanoparticle treatment (FIGS. 9A-9B, P<0.05).

Nanoparticle Treatment Modulates Severe Peritonitis Related Inflammatory Proteins in the Serum and Peritoneal Fluid.

Nanoparticle treatment reversed peritonitis-induced changes in serum inflammatory chemokines, cytokines and other inflammation related proteins at both 3 h and 18 h (Table 2, Table 3, P<0.05). Similarly, nanoparticle treatment also attenuated the peritonitis-induced increase in peritoneal fluid inflammatory biomarkers (Table 4, P<0.05). Importantly, $CeO_2$ nanoparticle treatment also attenuated peritonitis-induced increase in the major inflammatory cytokines interferon gamma (IFN-γ), tumor necrosis factor alpha (TNF-α) and interleukin-6 (IL-6) (Table 2, Table 3, P<0.05) and in the hepatic damage markers GST-α and GST-Mu by 15- and 19-fold (Table 3, P<0.05).

TABLE 2

Effect of $CeO_2$ nanoparticles on severe peritonitis induced inflammatory biomarkers at 3 h after polymicrobial injection.

| Analyte | Control 3 h | CeO₂ 3 h | Peritonitis 3 h | Peritonitis + CeO₂ 3 h |
|---|---|---|---|---|
| Eotaxin (pg/mL) | 362.33 ± 1.76 | 354.67 ± 8.29 | 1273.33 ± 28.46*$ | 856.00 ± 14.47*$# |
| Macrophage-Derived Chemokine (pg/mL) | 938.00 ± 18.56 | 995.67 ± 27.42 | 1483.33 ± 26.03*$ | 1553.33 ± 31.80*$ |
| Macrophage Inflammatory Protein-1α(ng/mL) | Below LLOQ | Below LLOQ | 4.20 ± 0.20 | 6.37 ± 0.17# |
| Macrophage Inflammatory Protein-2 (pg/mL) | 25.67 ± 1.20 | 20.67 ± 1.33* | 318.33 ± 7.26*$ | 215.00 ± 2.65*$# |
| Monocyte Chemotactic Protein 1 (pg/mL) | 897.33 ± 16.50 | 848.00 ± 17.95 | 2270.00 ± 85.06*$ | 2240.00 ± 75.06*$ |
| Monocyte Chemotactic Protein-5 (pg/mL) | Below LLOQ | Below LLOQ | 3.70 ± 0.17 | 1.98 ± 0.42# |
| T-Cell-Specific Protein RANTES (pg/mL) | 1.10 ± 0.00 | 1.04 ± 0.06 | 2.50 ± 0.06*$ | 2.10 ± 0.06# |
| Interferon gamma (pg/mL) | Below LLOQ | Below LLOQ | 102.33 ± 5.78 | 67.00 ± 8.00# |
| Interleukin-6 (pg/mL) | Below LLOQ | Below LLOQ | 7.50 ± 1.00 | 4.97 ± 0.27 |
| Tumor Necrosis Factor alpha (ng/mL) | 0.10 ± 0.02 | Below LLOQ | 0.22 ± 0.01* | 0.13 ± 0.01$# |
| Leptin (ng/mL) | 0.44 ± 0.02 | 0.43 ± 0.02 | 0.75 ± 0.01*$ | 0.68 ± 0.02*$# |
| Myeloperoxidase (ng/mL) | 11.00 ± 0.58 | 11.33 ± 0.33 | 30.67 ± 0.88*$ | 24.00 ± 0.58*$# |
| Myoglobin (ng/mL) | 1153.33 ± 12.02 | 1373.33 ± 31.80* | 3083.33 ± 23.33*$ | 1546.67 ± 20.28*$# |
| Glutathione S-Transferase alpha (ng/mL) | 54.00 ± 2.00 | 30.33 ± 1.67* | 69.33 ± 2.19*$ | 42.67 ± 3.93*$# |
| Glutathione S-Transferase Mu (ng/mL) | 376.33 ± 20.20 | Below LLOQ | 228.33 ± 37.44* | 173.33 ± 25.43* |

TABLE 3

Effect of $CeO_2$ nanoparticles on severe peritonitis induced inflammatory biomarkers at 18 h after polymicrobial injection.

| Analyte | Control 18 h | CeO₂ 18 h | Peritonitis 18 h | Peritonitis + CeO₂ 18 h |
|---|---|---|---|---|
| Eotaxin (pg/mL) | 806.33 ± 41.79 | 349.33 ± 5.55* | 1866.67 ± 26.03*$ | 1020.00 ± 5.77*$# |
| Macrophage-Derived Chemokine (pg/mL) | 1039.67 ± 32.46 | 711.00 ± 5.20* | 4410.00 ± 55.68*$ | 2500.00 ± 60.00*$# |
| Macrophage Inflammatory Protein-1α (ng/mL) | Below LLOQ | Below LLOQ | 20.67 ± 0.67 | 6.70 ± 0.29# |
| Macrophage Inflammatory Protein-2 (pg/mL) | 23.33 ± 2.33 | Below LLOQ | 654.33 ± 10.71* | 257.00 ± 6.08*# |
| Monocyte Chemotactic Protein 1 (pg/mL) | 1483.33 ± 42.56 | 973.00 ± 19.66* | 2903.33 ± 121.70*$ | 2650.00 ± 45.09*$# |
| T-Cell-Specific Protein RANTES (pg/mL) | 1.43 ± 0.03 | 0.74 ± 0.01* | 2.30 ± 0.00*$ | 1.60 ± 0.00*$# |
| Interferon gamma (pg/mL) | 36.67 ± 9.21 | Below LLOQ | 46.67 ± 14.33 | 38.33 ± 9.74 |
| Interleukin-6 (pg/mL) | Below LLOQ | Below LLOQ | 5.27 ± 0.67 | Below LLOQ |
| Leukemia Inhibitory Factor (pg/mL) | Below LLOQ | Below LLOQ | 1520.00 ± 30.00 | Below LLOQ |
| Tumor Necrosis Factor alpha (ng/mL) | Below LLOQ | Below LLOQ | 0.14 ± 0.01 | 0.14 ± 0.01 |
| Leptin (ng/mL) | 0.27 ± 0.01 | 0.25 ± 0.01 | 2.97 ± 0.15*$ | 1.83 ± 0.07# |
| Myeloperoxidase (ng/mL) | 25.67 ± 0.33 | 25.00 ± 0.58 | 39.33 ± 0.67*$ | 34.00 ± 0.00*$# |
| Myoglobin (ng/mL) | 1086.67 ± 31.80 | 1186.67 ± 17.64 | 6220.00 ± 200.75*$ | 3246.67 ± 52.39*$# |
| Glutathione S-Transferase alpha (ng/mL) | 62.67 ± 2.60 | 35.00 ± 1.53* | 2126.67 ± 56.67*$ | 147.00 ± 1.53*$# |
| Glutathione S-Transferase Mu (ng/mL) | 232.00 ± 0.00 | Below LLOQ | 14133.33 ± 328.30* | 764.67 ± 40.53# |
| Vascular Endothelial Growth Factor A (pg/mL) | Below LLOQ | Below LLOQ | 459.00 ± 12.70 | 296.67 ± 31.33# |

TABLE 4

Effect of CeO$_2$ nanoparticles on severe peritonitis induced inflammatory biomarkers in peritoneal fluid.

| Analyte | Peritoneal fluid | |
|---|---|---|
| | Peritonitis 18 h | Peritonitis + CeO$_2$ 18 h |
| Macrophage Inflammatory Protein-1 alpha (ng/mL) | 1740.00 ± 17.32 | 1413.33 ± 71.26# |
| Macrophage Inflammatory Protein-2 (pg/mL) | 43933.33 ± 2760.64 | 32533.33 ± 1502.59# |
| T-Cell-Specific Protein RANTES (pg/mL) | 4.37 ± 0.03 | 3.20 ± 0.12# |
| Interferon gamma (IFN-gamma) (pg/mL) | 48.67 ± 2.19 | 15.87 ± 0.67# |
| Interleukin-6 (IL-6) (pg/mL) | 36.33 ± 1.76 | 13.67 ± 0.33# |
| Leukemia Inhibitory Factor (LIF) (pg/mL) | 12000.00 ± 321.46 | 7616.67 ± 141.93# |
| Tumor Necrosis Factor alpha (TNF-alpha) (ng/mL) | 0.39 ± 0.01 | 0.34 ± 0.01# |
| Myeloperoxidase (ng/mL) | 16433.33 ± 970.11 | 11600.00 ± 305.51# |
| Myoglobin (ng/mL) | 1004.33 ± 22.41 | 756.67 ± 15.45# |
| Glutathione S-Transferase alpha (ng/mL) | 213.33 ± 11.78 | 138.00 ± 6.56# |
| Glutathione S-Transferase Mu (ng/mL) | 10666.67 ± 272.84 | 58.30 ± 245.02# |

Cerium Oxide Nanoparticles Modulate the Inflammatory Response in the Liver and Peritoneum by Decreasing the Recruitment of Immune Cells.

Previous studies have shown that septic peritonitis causes the infiltration of neutrophils and macrophages which is associated with organ dysfunction. Consistent with the foregoing cytokine and chemokine findings, it was found that the nanoparticle treatment decreased the effects of peritonitis on liver macrophage number (FIGS. 5A-5B, P<0.05) and the increase in the number of peritoneal lymphocytes and monocytes at 18 h (FIGS. 11A-11D, P<0.05).

CeO$_2$ Nanoparticles Reduce the Phosphorylation of Cardiac ERK 1/2 MAPK-Stat-3 and Endothelial Cell Activation.

Figure 12A:
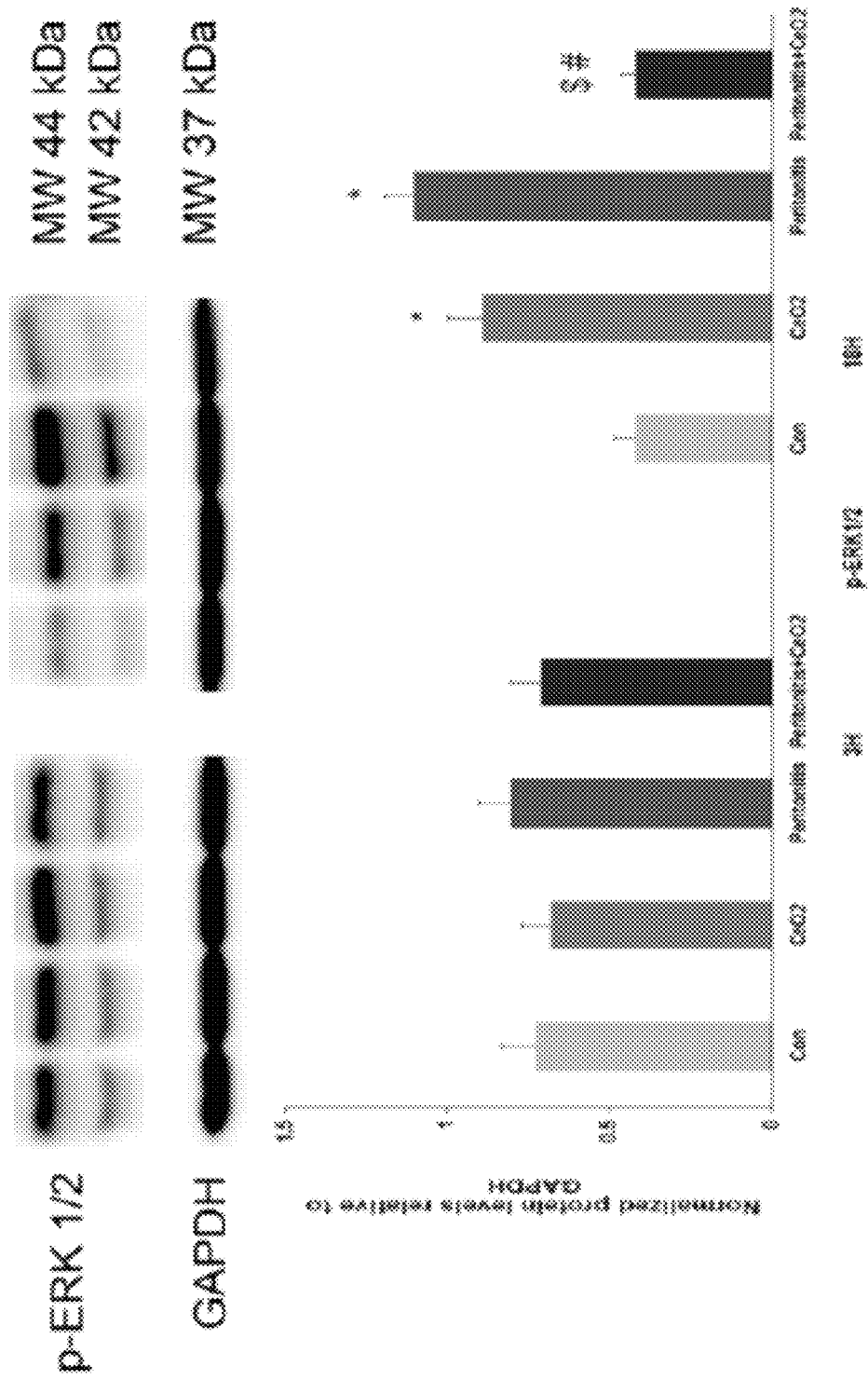
FIGS. 12A-12D include images and graphs showing the effect of $CeO_2$ nanoparticles on severe peritonitis-induced cardiac inflammation, including images and graphs showing levels of phosphorylated and total ERK1/2 (FIGS. 12A-12B) as determined by western blotting and normalized to GAPDH respectively, and images and graphs showing levels of phosphorylated (Tyr 705) and total Stat-3 (FIGS. 12C-12D) as determined by western blotting and normalized to GAPDH respectively, where *$P<0.05$ compared to control group, \$ $P<0.05$ compared to $CeO_2$ group and # $P<0.05$ compared to peritonitis group.
Figure 12B:
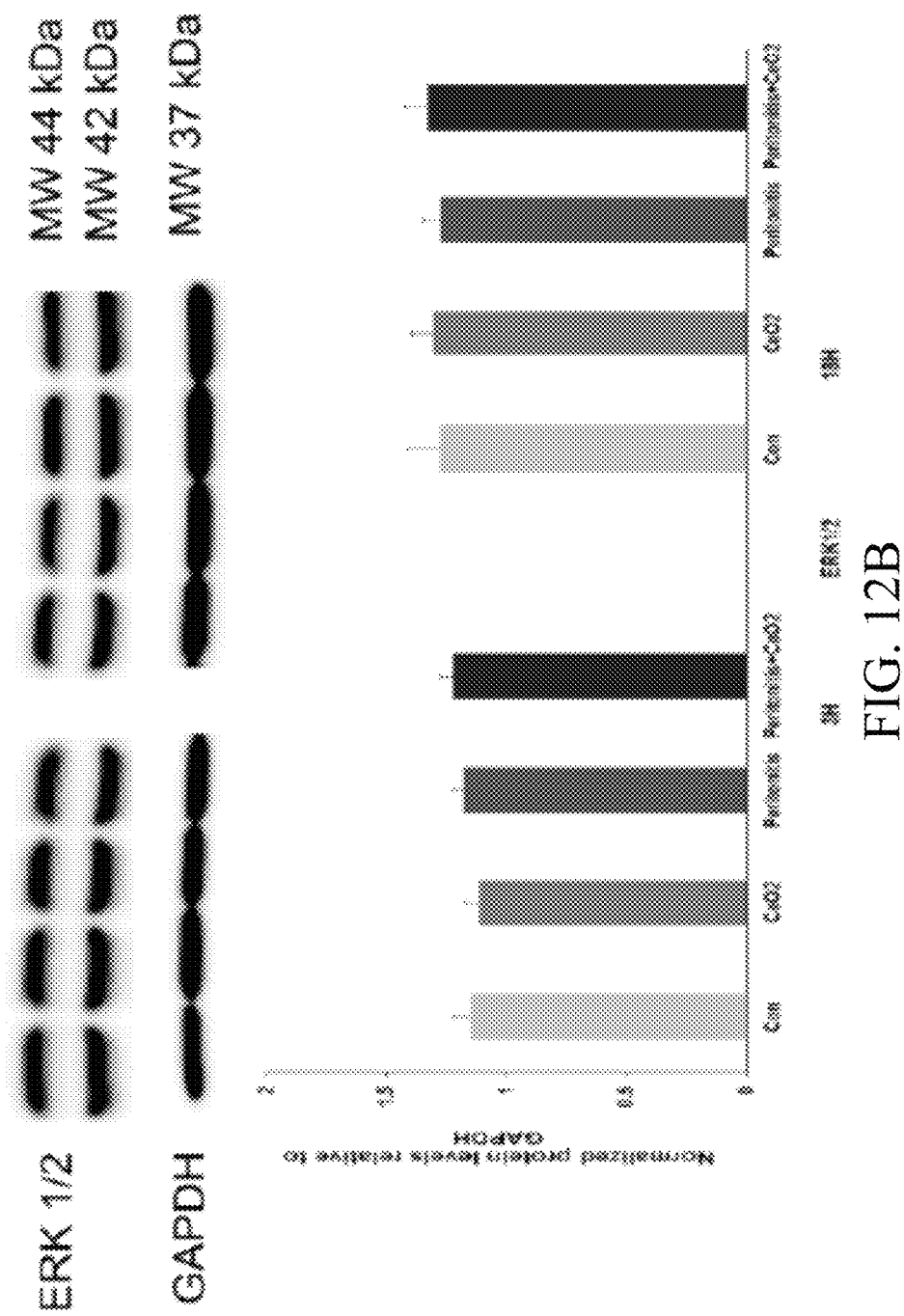
Figure 12C:
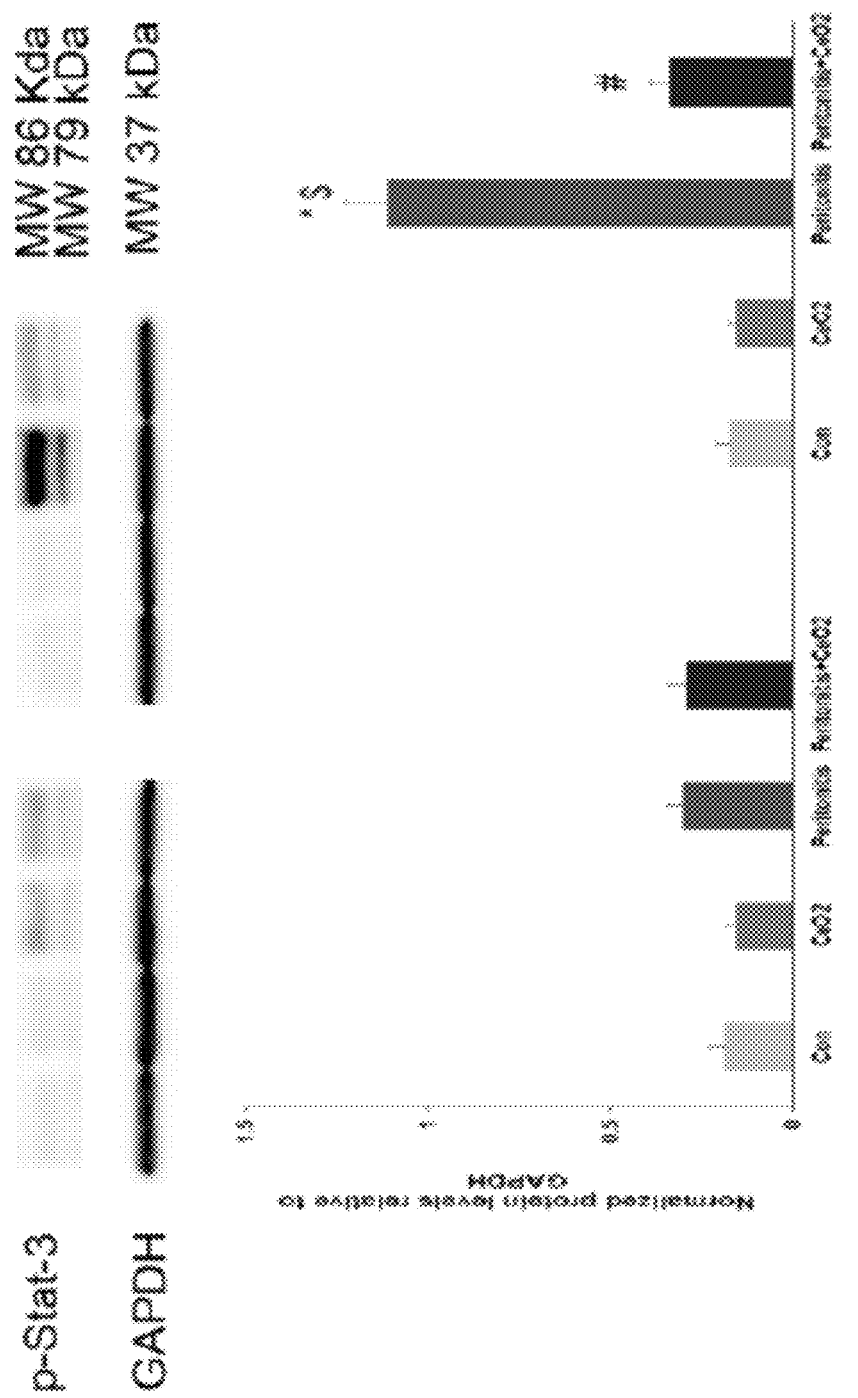
Figure 12D:
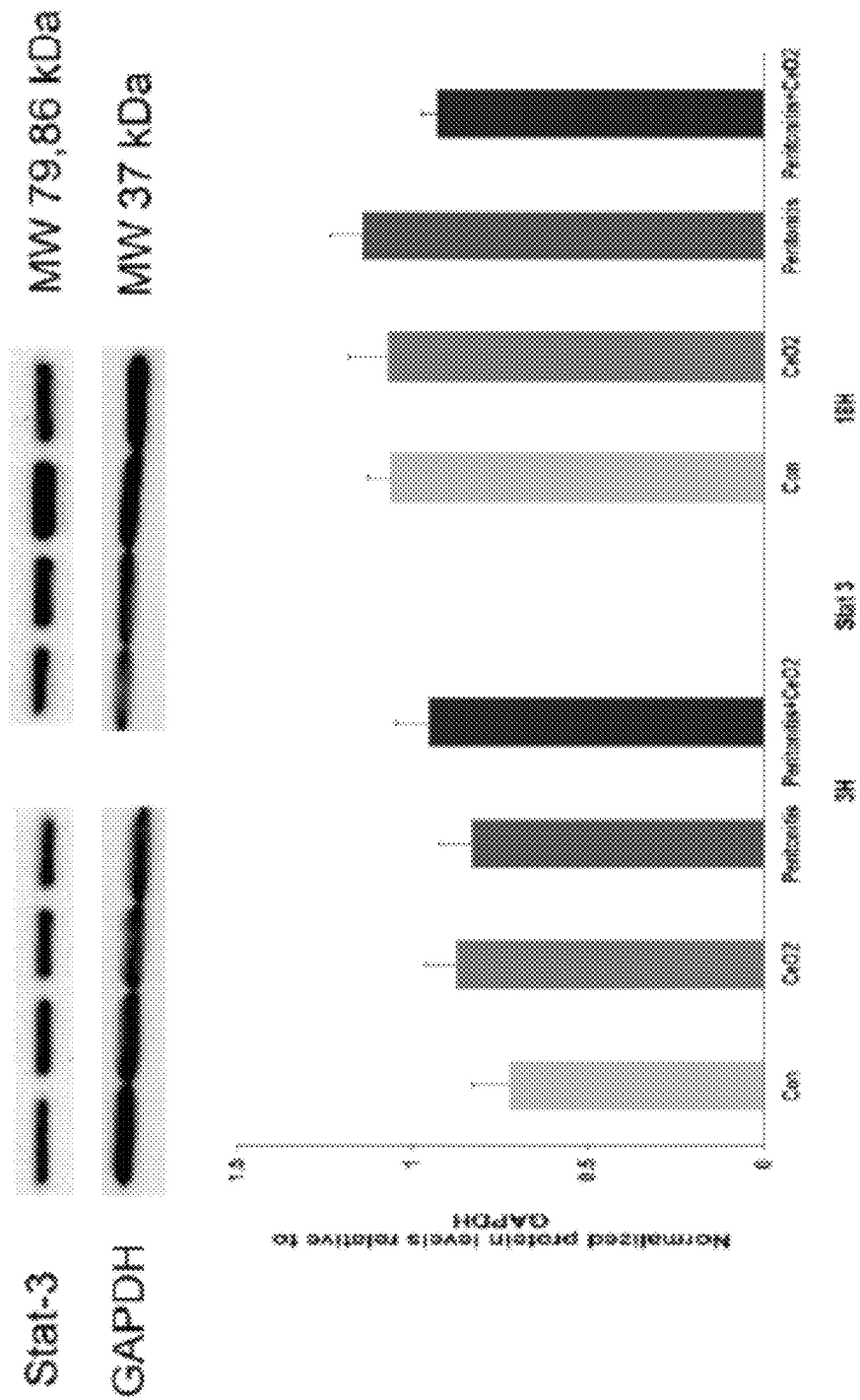
Figure 13A:
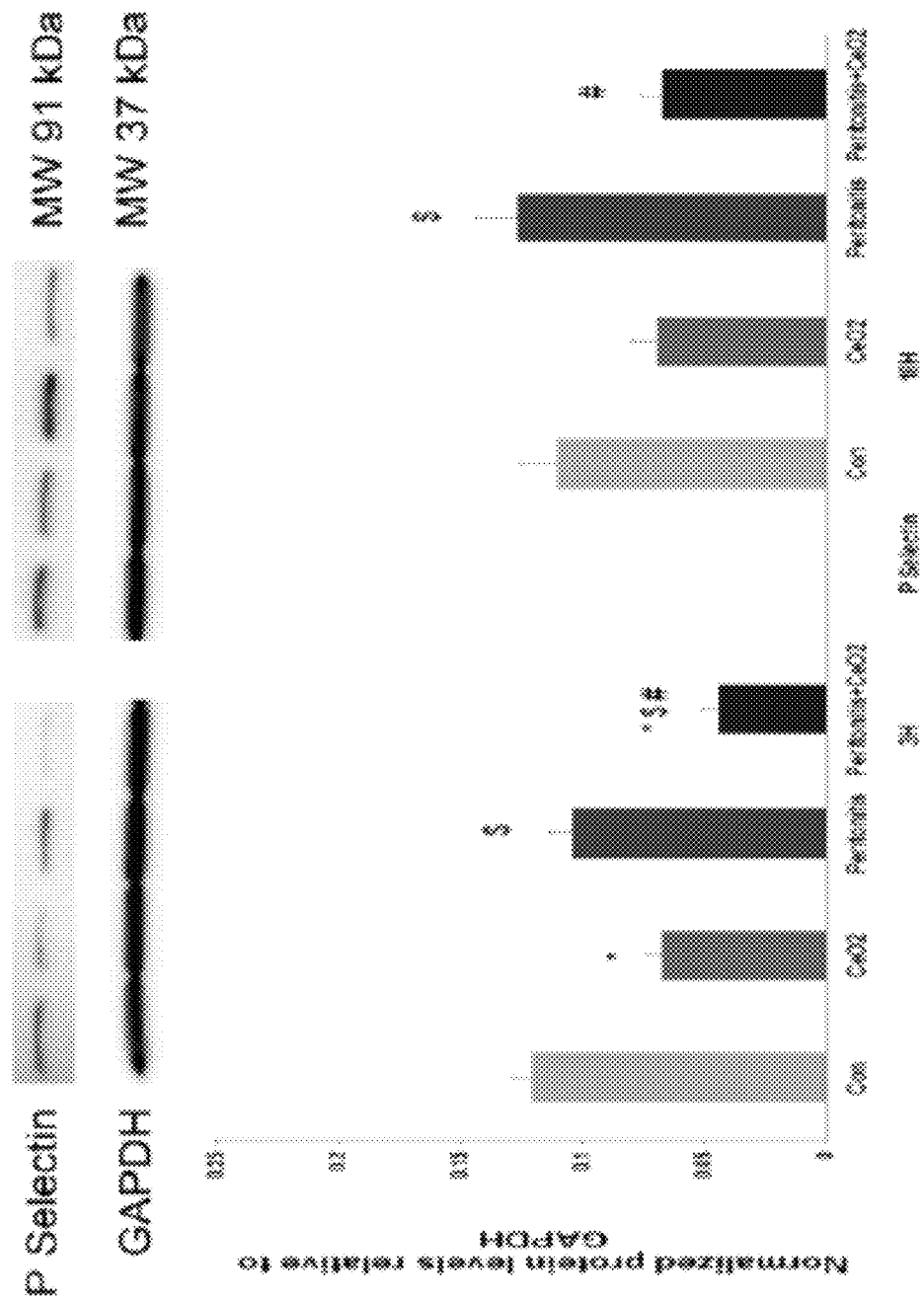
FIGS. 13A-13B include images and graphs showing the effect of $CeO_2$ nanoparticles on peritonitis-induced cardiac permeability, including images and graphs showing levels of P Selectin (FIG. 13A) and VCAM-1 (FIG. 13B) as determined by western blotting and normalized to GAPDH respectively, where *$P<0.05$ compared to control group, \$ $P<0.05$ compared to $CeO_2$ group and # $P<0.05$ compared to peritonitis group.
Figure 13B:
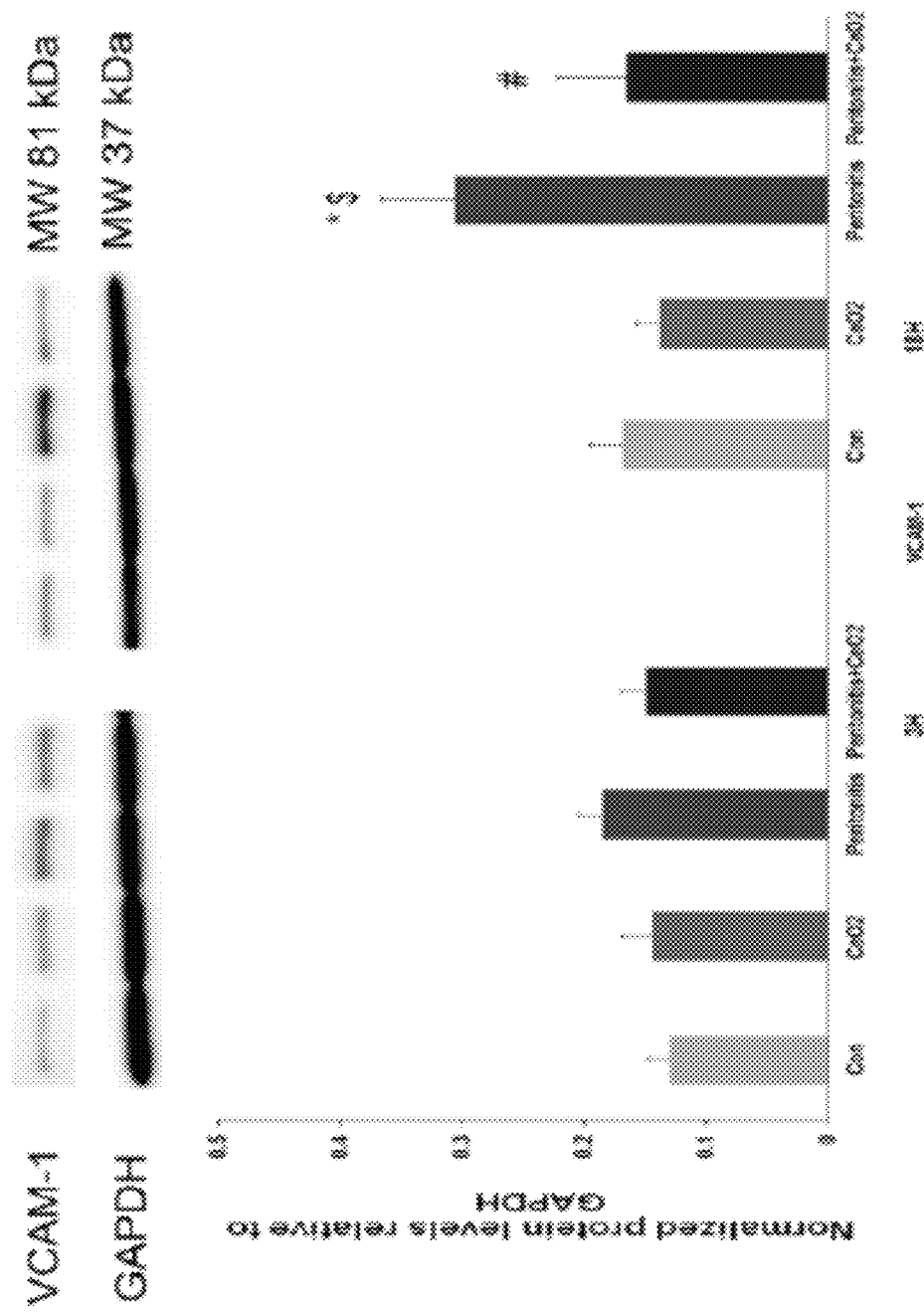

Studies have shown that peritonitis is associated with activation of mitogen activated protein kinases (MAPK) and Stat signaling. Severe peritonitis increased and nanoparticle treatment decreased the phosphorylation of ERK 1/2 (FIGS. 12A-12B, P<0.05) and Stat-3 at the 18 h time point in the heart (FIGS. 12C-12D, P<0.05). These changes in protein phosphorylation were accompanied by treatment associated decreases in P-Selectin (FIG. 13A, P<0.05) and VCAM-1 in the animals with peritonitis at 3- and 18 h respectively (FIG. 13B, P<0.05).

CeO2 Nanoparticles do not Affect RAW 264.7 Macrophage Cell Viability.

Figure 14:
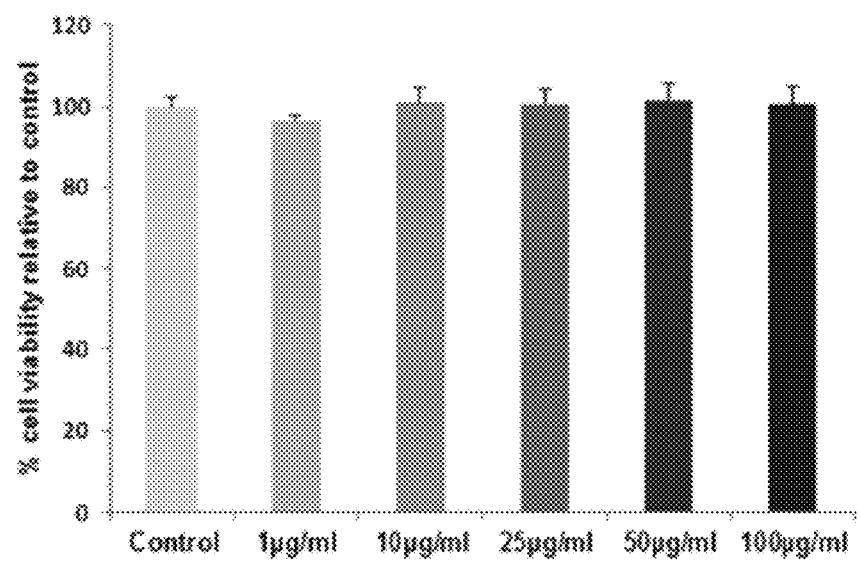
FIG. 14 is a graph showing the results of an MTT cell viability assay, where doses of $CeO_2$ nanoparticles ranging from 1 µg/ml to 100 µg/ml were non-toxic to RAW 264.7 macrophages, and where absorbance values are shown relative to control.

An MTT assay was further performed to determine the cytotoxic potential of CeO2 nanoparticles to macrophages. Doses of CeO2 nanoparticles ranging from 1 μg/ml to 100 μg/ml did not affect the cell viability of RAW 264.7 macrophages at least until 48 h which indicates that CeO2 nanoparticles can attenuate SIRS by attenuation of macrophage activation rather than increasing macrophage cell death (FIG. 14).

Effect of CeO2 Nanoparticles Treatment on Serum Creatine Kinase Activity

Studies have shown that septic peritonitis causes an increase in creatine kinase activity which is a marker for cardiac muscle damage.

Figure 15:
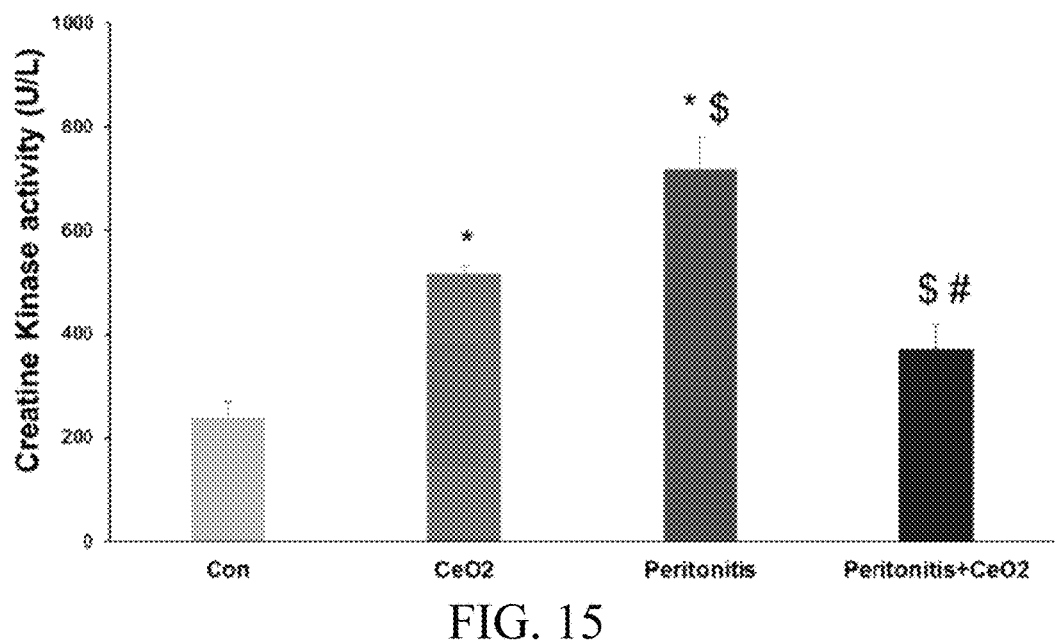
FIG. 15 is a graph showing the ability of cerium oxide nanoparticles to attenuate severe peritonitis induced serum creatine kinase activity, where *$P≤0.05$ compared to control group, \$ $P≤0.05$ compared to $CeO_2$ group, and # $P≤0.05$ compared to peritonitis group.

It was found that peritonitis increased and nanoparticle treatment decreased serum creatine kinase activity at 18 h (FIG. 15, P<0.05).

Discussion of Example 3

Despite decades of extensive research, the mortality rate associated with severe sepsis remains unacceptably high. The aim of the foregoing studies was to evaluate whether CeO$_2$ nanoparticles can be used to diminish intra-abdominal infection/peritonitis-induced mortality in the laboratory rat. To test this possibility, a polymicrobial model of peritonitis was utilized that is characterized by severe mortality. The animal model used in the foregoing study substantially differed from the conventional cecal ligation puncture (CLP) model or the endotoxemic model in that a single bolus of cecal material was injected into the peritoneal cavity to induce intra-abdominal infection or peritonitis. The bolus of cecal material resulted in an initial inflammatory response from peritoneal macrophages and lymphocytes which in turn attracted immune cells from the circulation. The circulating immune cells responded to the peritoneal inflammatory signals and secreted inflammatory mediators that disrupted the endothelial barrier and resulted in microvascular leakiness, hypovolemia, hypotension and systemic shock. In addition, this model clearly depicted the clinical scenario of acute appendicitis or trauma to the intestinal tract unlike in CLP where it depicted the slow and sustained progression of generalized sepsis. In the current study, compared to the untreated animals, it was found that a one-time CeO$_2$ nanoparticle intervention with 0.5 mg/kg was able to decrease animal mortality rates by approximately 1400%. However, it is worthwhile to note that a dose of 1 mg/kg body weight did not result in increased therapeutic effect and might be due to the initial inflammatory response to nanoparticles that are foreign to the body as seen through rise in body temperature and circulating levels of MIP-1α and MDC (Table 2). As such, one alternative would be to increase the size of nanoparticles but effectively maintaining the same dose that results in decreased particle number and greater margin of safety.

Figure 10A:
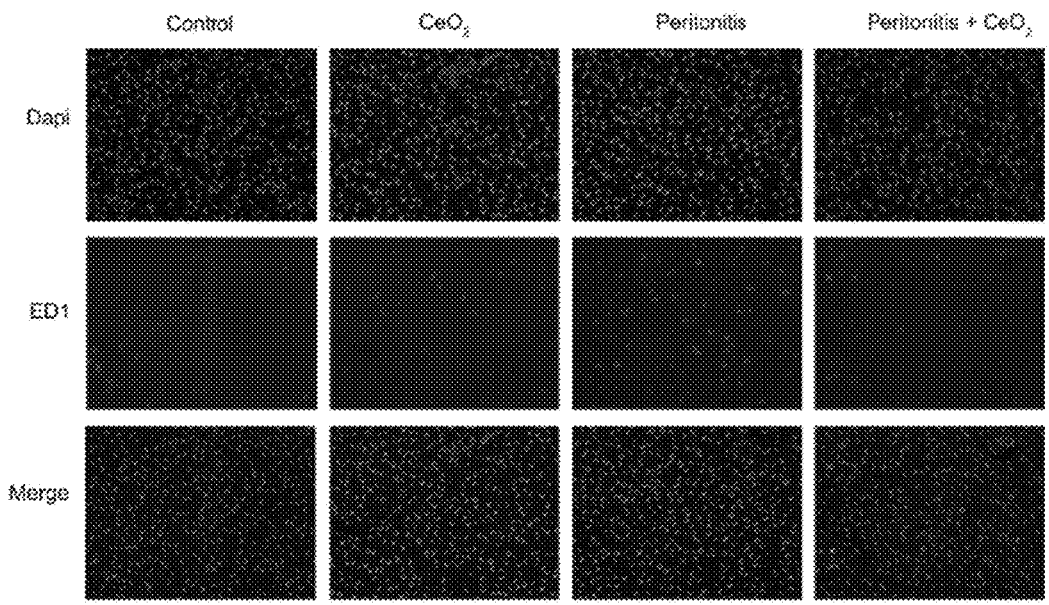
FIGS. 10A-10B include images and a graphs showing the ability of cerium oxide nanoparticles to attenuate severe peritonitis-induced monocyte/macrophage infiltration into liver, including images showing infiltration of macrophages into liver as detected by immunofluorescence using ED1 antibody across different groups (FIG. 10A) and a graph showing the quantification of number of percent ED1 positive cells to the total number of cells (Dapi staining for nuclei) to determine macrophage infiltration (FIG. 10B), where data are presented as mean±SEM. *$P<0.05$ compared to control group, \$ $P<0.05$ compared to CeO.
Figure 10B:
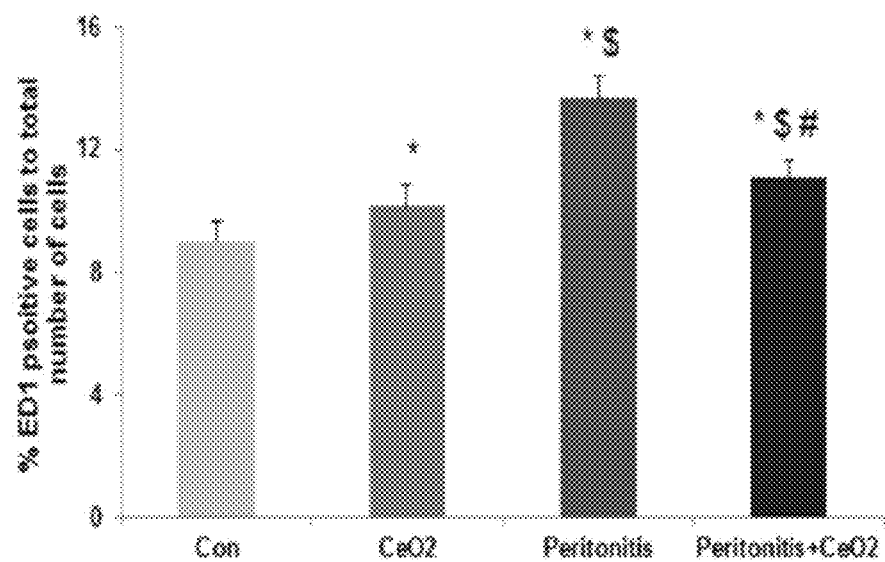
Figure 11A:
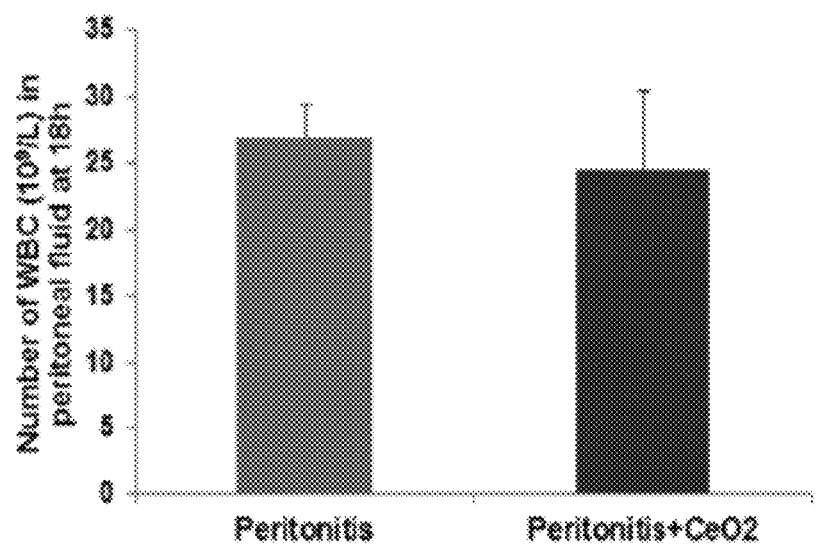
FIGS. 11A-11D include graphs showing the ability of $CeO_2$ nanoparticles to attenuate peritonitis-induced infiltration of inflammatory cells into peritoneal cavity, including a graph showing the number of WBC (FIG. 11A), a graph showing the number of lymphocytes (FIG. 11B); a graph showing the number of monocytes (FIG. 11C), and a graph showing the number of granulocytes in peritoneal fluid of peritonitis and peritonitis+$CeO_2$ nanoparticle groups (FIG. 11D), where # $P<0.05$ compared to peritonitis group.
Figure 11B:
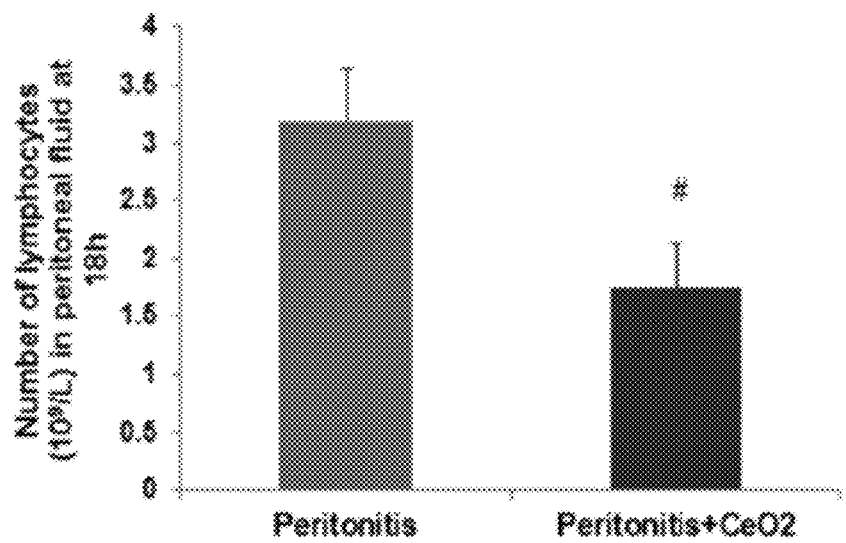
Figure 11C:
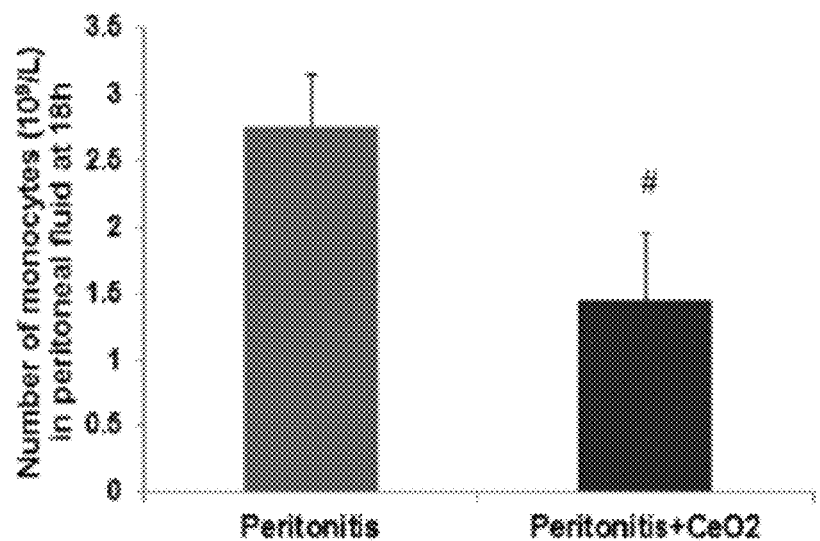
Figure 11D:
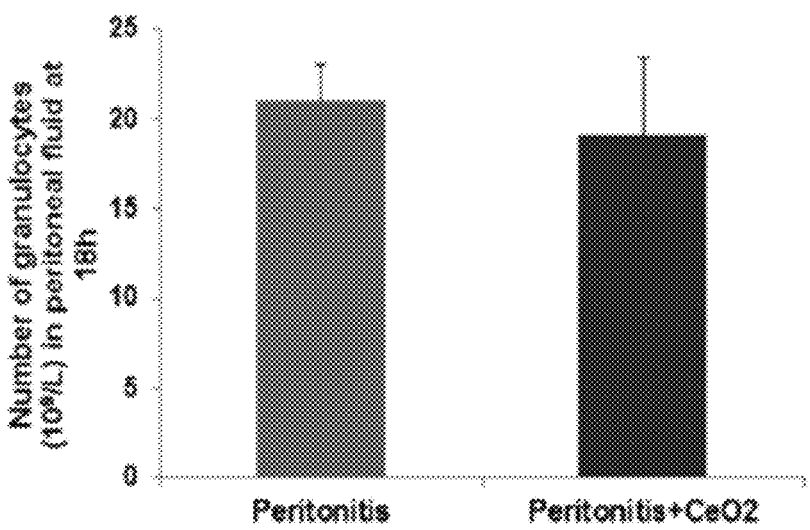

To explore the mechanistic basis of this therapeutic effect, it was first determined where the injected CeO$_2$ nanoparticles might accumulate. Previous work had shown that injected CeO$_2$ nanoparticles exhibited a proclivity to preferentially deposit in the liver, lungs and spleen. Consistent with these data, significantly higher amounts of ceria were found in the liver compared to that observed in other organs (Table 1). To examine if the CeO$_2$ nanoparticles were able to protect the liver against a polymicrobial insult, it was next examined if treatment was associated with improvements in liver morphology. Histological studies demonstrated that severe peritonitis caused hepatic sinusoidal dilatation and hepatocyte congestion which appeared to be decreased with CeO$_2$ nanoparticle treatment (FIGS. 8A-8B). At the cellular level, sepsis is characterized by increases in ROS and NO levels which can cause increased damage to cellular structures and proteins. Recent data has suggested that CeO$_2$ nanoparticles can function to scavenge free radicals and accelerate the decay of peroxynitrite in cultured cells. In the foregoing studies, it was found that severe peritonitis increased hepatic superoxide production, iNOS expression, systemic ROS levels and importantly, that these in vivo alterations were attenuated with nanoparticle treatment (FIGS. 7, 8A-8B, and 9A-9B). Similarly, other work has shown that bacterially derived LPS can stimulate the release of TNF-α, IL-1 and IL-6 from macrophages which is associated with increased tissue/organ dysfunction and the attraction of polymorphonuclear cells (PMN) to the site of infection. Supporting this contention, it was found that the $CeO_2$ nanoparticle treatment decreased the levels of TNF-α and IL-6 which were, in turn, associated with decreased infiltration of macrophages into the liver (FIGS. 10A-10B).

Given that the liver is thought to be the primary source for the excessive inflammatory state seen with severe sepsis, it was next sought to determine if the morphological changes that were observed were also associated with modulation of the hepatic inflammatory response. Consistent with the histological data, it was found that the $CeO_2$ nanoparticle treatment attenuated severe peritonitis-induced alterations in several different types of chemokines, cytokines, growth factors and inflammatory proteins in the serum and peritoneal fluid (Tables 2-4). Of particular note with respect to the assessment of liver damage, it was found that the $CeO_2$ nanoparticle treatment functioned to significantly attenuate peritonitis-induced increase in serum GST-α and GST-mu (Tables 2-3).

In addition to TNF-α, it is thought that IL-6 also plays a key role in mediating the organ damage seen during SIRS. As expected from data examining the effects of treatment on GST-α and GST-mu levels, it was also found that the levels of the inflammatory cytokine IL-6 and LIF were also reduced with treatment (Tables 2-3). These decreases in IL-6 and LIF were also associated with diminished serum levels of creatine kinase activity and myoglobin which have been linked to cardiac damage (FIG. 15, Tables 2-3).

Studies have shown that IL-6 and LIF can bind to gp130 to cause activation of the Jak-Stat pathway. Other work has shown that the phosphorylation of ERK 1/2 can lead to activation of Stat-3 that can cause increased transcription of several inflammatory mediators. In the foregoing studies, it was shown that severe peritonitis leads to activation of Jak-Stat pathway in the heart and that treatment with $CeO_2$ nanoparticles attenuated this activation (FIGS. 12A-12D). Moreover, studies have shown that Stat-3 signaling in the heart can cause increased microvascular permeability by increasing the expression of ICAM-1 and VCAM-1. It is thought that the increased expression of ICAM-1 and VCAM-1 on the endothelium is one of the priming events for recruitment of macrophages and neutrophils into myocardium which can lead to increased microvascular permeability. Consistent with our finding of decreased ERK 1/2-Stat activation, it was found that nanoparticle treatment attenuated severe peritonitis induced increases in VCAM-1 expression (FIGS. 13A-13B). To explore the possibility that this treatment-induced decrease in endothelial activation was associated with diminished vascular leakiness, the effect of the nanoparticle intervention on the accumulation of inflammatory cells in the peritoneal cavity was next examined. Consistent with the VCAM-1 findings, it was found that treatment was associated with decreases in the number of peritoneal monocytes and lymphocytes (FIGS. 11A-11D). Whether this finding was directly due to decreases in VCAM-1 expression was unclear, although it was interesting that it was also found that nanoparticle treatment decreased circulating VEGF levels (Table 3). It was thought that sepsis-associated increases in circulating VEGF were associated with the activation of endothelial MAPK, PI3K and src signaling which resulted in increased microvascular permeability. As such, it was thought that the decreased extravasation observed in the treated animals could be related to changes both in the expression of cellular adhesion molecules and circulating VEGF levels. To investigate the possibility of whether the therapeutic effect of the $CeO_2$ nanoparticles was due to decrease in immune cell number, the MTT cell proliferation assay was performed using RAW 264.7 macrophage cells that had been treated with different concentrations of $CeO_2$ nanoparticles (FIG. 14). It was found that nanoparticle exposure, at least at the tested concentrations, was not associated with diminished cellular viability which suggested that it was likely that the beneficial effects of the nanoparticle treatment on animal survivability were not due to increases in immune cell death.

The foregoing data thus indicated that a single dose of $CeO_2$ nanoparticles in the absence of antibiotics, fluid resuscitation, or other supportive treatment can significantly decrease animal mortality in a severe intra-abdominal sepsis model. This increase in animal survivability was associated with modulation of the hepatic inflammatory response.

Example 4—Cerium Oxide Nanoparticle Attenuation of Polymicrobial Sepsis Induced Kidney Injury In the following studies, the therapeutic efficacy of $CeO_2$ nanoparticles was evaluated in the treatment of sepsis induced acute kidney injury (AKI). More specifically, whether $CeO_2$ nanoparticles could attenuate sepsis induced histological damage, increases in oxidative stress, inflammation, apoptosis and changes in biomarkers of AKI was investigated.

Materials and Methods for Example 4

Characterization of $CeO_2$ Nanoparticles.

$CeO_2$ nanoparticles were commercially purchased from US Research Nanomaterials Inc. (Houston, Tex.). Atomic force microscopy (AFM) was performed to estimate the mean particle size. Briefly 20 µl of $CeO_2$ nanoparticles was placed on freshly cleaved mica (V1 mica, SPI Inc., West Chester, Pa.) incubated for 15 minutes, rinsed with deionized water and dried under nitrogen. Nanoparticles were imaged in noncontact mode at a frequency of 319 kHz and a scan speed of 0.5 Hz using a Nano-R microscope (Pacific Nanotechnology Inc., Santa Clara, Calif.) equipped with a TM300A noncontact probe (SensaProbes Inc., Santa Clara, Calif.). Scanning transmission electron microscopy (STEM) images were obtained by using Aberration Corrected Analytical Electron Microscope (TEM/STEM JEOL JEM-ARM200CF, Japan) operated at 200 keV as described previously (reference from 600 ci paper 1). Size of nanoparticles were obtained using JEOL JEM-2010 transmission electron microscope (TEM). Purity of the sample was estimated by energy dispersive X-ray spectroscopy using Noran Voyager EDX software.

Polymicrobial Sepsis Induction and $CeO_2$ Nanoparticle Treatment.

Male Sprague Dawley rats aged 10 weeks were purchased from Hill-Top Laboratories and allowed to acclimatize for 2 weeks prior to experimentation. All surgical procedures were performed in accordance with the guidelines provided by Marshall University Institutional Animal Care and Use Committee (IACUC), and Association for Assessment and Accreditation of Laboratory Animal Care (AAALAC). Briefly, animals were anesthetized under isoflurane and a small mid ventral incision of 0.5 cm was made. Sham controls and $CeO_2$ only groups were injected with 5 ml/kg of 5% sterile dextrose solution intraperitoneally (i.p) while sepsis and sepsis+$CeO_2$ groups received cecal inoculum of 600 mg/kg BW in 5 ml/kg BW of 5% sterile dextrose solution i.p as described previously. Cecal material was obtained from healthy rats that served as donors. Sham control and sepsis groups were injected with 200 µl of sterile distilled water intravenously (i.v) while the $CeO_2$ and sepsis+$CeO_2$ groups received $CeO_2$ nanoparticles (0.5 mg/kg) in 200 µl of sterile distilled water i.v via tail vein.

Tissue Collection.

Animals were humanely sacrificed under anesthesia and the kidneys were excised, capsule removed and washed in Krebs-Ringer bicarbonate buffer (KRB) to remove any blood. Kidneys were frozen in liquid nitrogen and store at −80° C. for further analysis. Serum was obtained from whole blood through centrifugation at 5,000×g for 10 min at room temperature.

Renal Histology and Staining for F-Actin.

Frozen kidneys were sectioned (4 μm) with Leica CM1950 cryostat and transferred to poly-L-lysine coated slides. Hematoxylin and eosin staining was performed using Histoperfect kit (BBC biochemical, Seattle Wash.) to assess kidney morphology and imaged using Evos XL microscope (Life technologies, Grand Island, N.Y.). Renal sections were stained for F-actin using rhodamine phalloidin (Life Technologies, Grand Island, N.Y.). Briefly frozen sections were washed with PBS and fixed in 4% methanol free formaldehyde for 10 min and washed thrice again with PBS. Sections were then permeabilized with 0.3% triton x in PBS for 20 min and washed thrice with PBS. Sections were then blocked with 1% BSA for 30 min and then incubated with 0.165 μM rhodamine phalloidin for 20 minutes in dark. Finally, sections were washed thrice again with PBS, mounted with cover slip and imaged with Evos FL microscope (Life Technologies, Grand Island, N.Y.). Four images per section were evaluated with a number of three animals per group. Fluorescence intensity across various groups was measured using image J analysis software.

Estimation of Renal Superoxide Levels.

Levels of superoxide in renal sections were estimated using dihydroethidium staining Briefly section were washed with PBS and incubated with 5 mM dihydroethidium for 1 h at room temperature in dark. Sections were washed thrice with PBS for 5 min each and imaged with Evos FL microscope (Life technologies, Grand Island, N.Y.). Four images per section were evaluated n=4 per group. Mean fluorescence intensity was determined across various groups using image J analysis software as a measure for superoxide levels.

SDS-PAGE and Immunoblotting.

Approximately 100 mg of frozen kidney was taken and pulverized to fine powder, added to 900 μl of T-PER (Pierce, Rockford, Ill., USA) with 1% protease and phosphatase inhibitors, homogenized and centrifuged at 13,000 rpm for 10 min at 4° C. to collect the supernatant. 660 nm assay (Pierce, Rockford, Ill., USA) was used to determine the amount of protein in each sample and normalized to a final equal concentration using T-PER. Samples were equally diluted with 4× Laemilli buffer and were subjected to electrophoresis in 10% PAGEr Gold Precast gel (Lonza, Rockland, Me.) and transferred to nitrocellulose membranes as detailed elsewhere. Equal loading of protein was verified by Ponceau S staining of nitrocellulose membranes. Membranes were blocked with 5% milk in TBST for 1 h and later probed with primary antibodies-p-stat-3 (Tyr 705), stat-3, cleaved caspase 3 and caspase 3 (Cell Signaling Technology, Danvers, Mass.). Membranes were washed thrice with TBST and incubated with secondary anti-rabbit (Cell Signaling Technology, Danvers, Mass.) and the chemiluminiscent signal intensity was obtained using Supersignal West Pico Chemiluminiscent substrate (Pierce, Rockford, Ill., USA) and quantified by Fluorchem 9900 software (Protein Simple, Santa Clara, Calif.).

Multiplex Immunoassay and Serum Biochemical Analysis.

Serum samples from different animals in each group were pooled and sent to Myriad RBM (Austin, Tex.) for the analysis of KIM-1, cystatin-C, osteopontin, β-2 microglobulin and VEGF-A using rodent kidney MAP. Samples were run in triplicate for statistical analysis. Levels of glucose, BUN, sodium and potassium were determined in serum using an Abaxis VetScan® analyzer (Abaxis, Union City, Calif., USA).

Statistical Analysis.

Results are presented in the form of mean±standard error of mean. Differences across groups in various parameters were analyzed using one way analysis of variance (ANOVA) with Student Newman Keul's post hoc analysis or ANOVA on ranks with Student Newman Keul's post hoc analysis for non-normally distributed samples. A simple t-test was also used wherever appropriate. A probability value of P<0.05 was accepted to be statistically significant.

Results of Example 4

Characterization of Nanoceria.

Figure 16A:
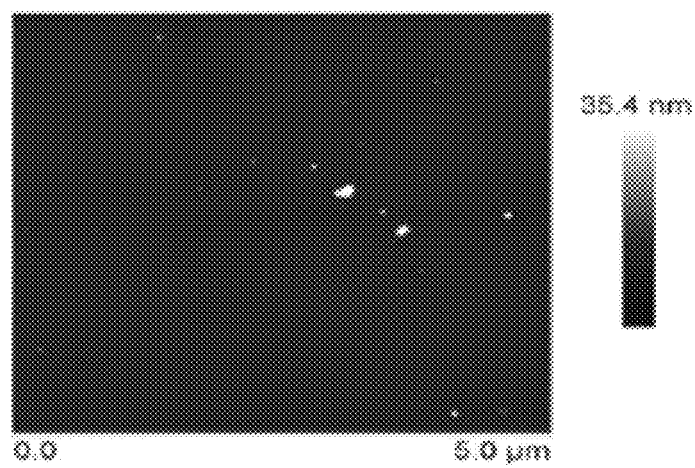
FIGS. 16A-16D are additional images and graphs showing the characterization of $CeO_2$ nanoparticles.
Figure 16B:
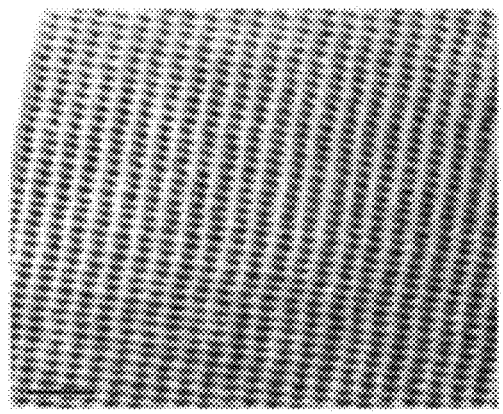
Figure 16C:
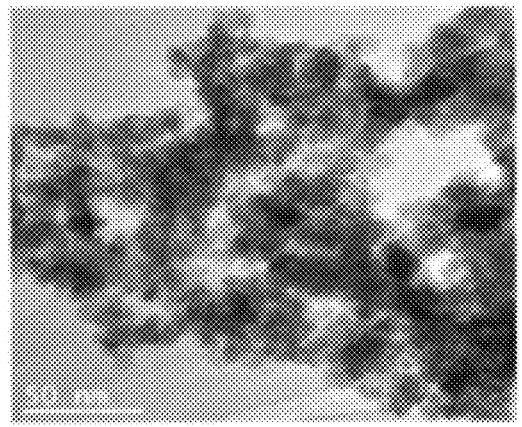
Figure 16D:
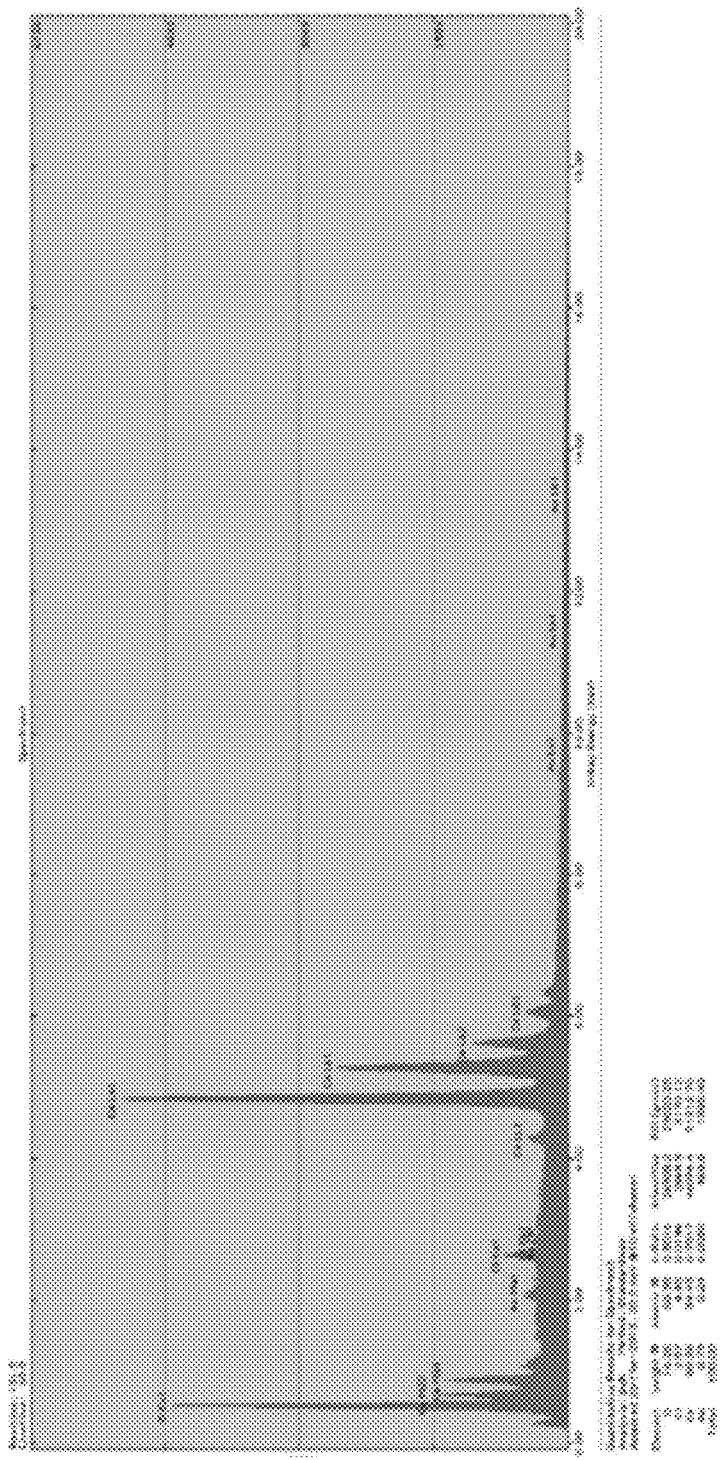

$CeO_2$ nanoparticles characterized using atomic force microscopy (AFM) determined their size to be approximately 30 nm (FIG. 16A). Scanning transmission electron microscopy (STEM) was used to demonstrate the ordered structure of nanoparticles while transmission electron microscopy (TEM) demonstrated the size of $CeO_2$ nanoparticles to be in between 10-40 nm (FIGS. 16B-16C). Energy dispersive X-ray spectroscopy (EDS) was performed to demonstrate the purity of $CeO_2$ nanoparticles and revealed that the content of cerium in the sample to be 80.38% while the content of oxygen was 16.26% (FIG. 16D).

Cerium Oxide Nanoparticles Attenuate Sepsis Induced Renal Damage and Breakdown of Tubular F-Actin.

Figure 17:
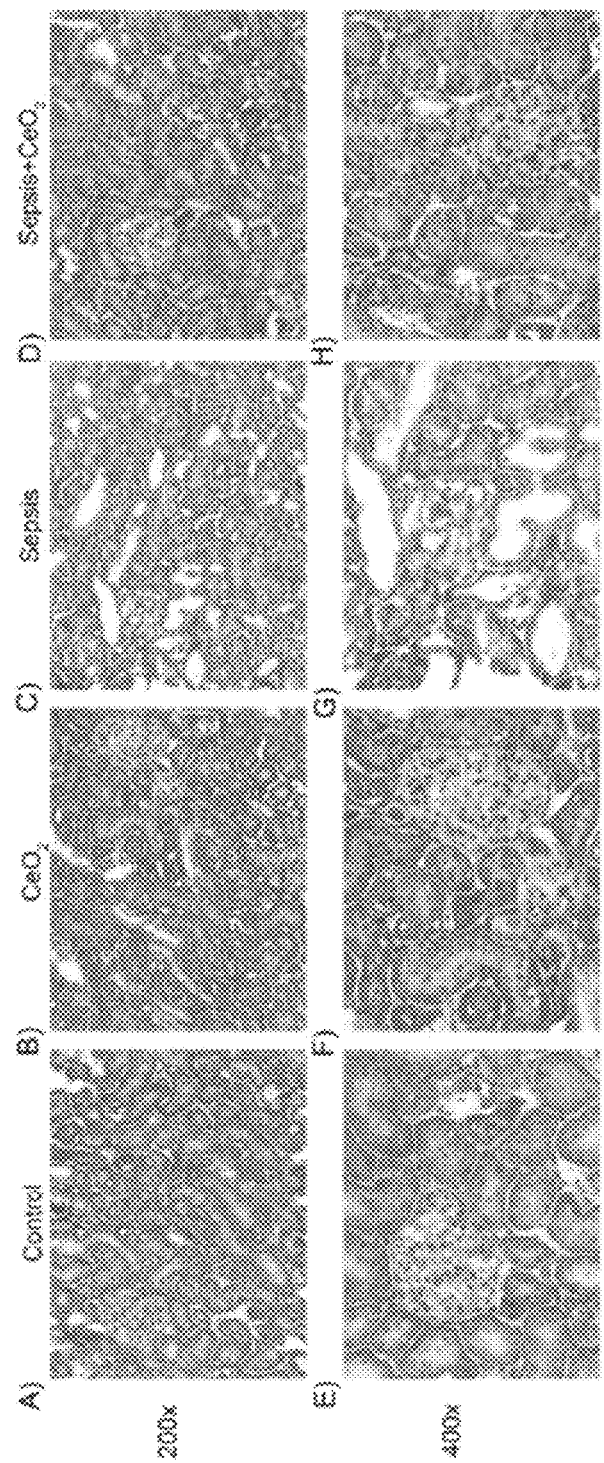
FIG. 17 includes images showing the ability of $CeO_2$ nanoparticles to attenuate sepsis induced renal damage, including hematoxylin and eosin staining of 18 h time point kidney sections in (Panel A) Control, (Panel B) $CeO_2$, (Panel C) Sepsis, (Panel D) Sepsis+$CeO_2$ (imaged at 200× magnification), (Panel E) Control, (Panel F) $CeO_2$, (Panel G) Sepsis, and (Panel H) Sepsis+$CeO_2$ groups.
Figure 18A:
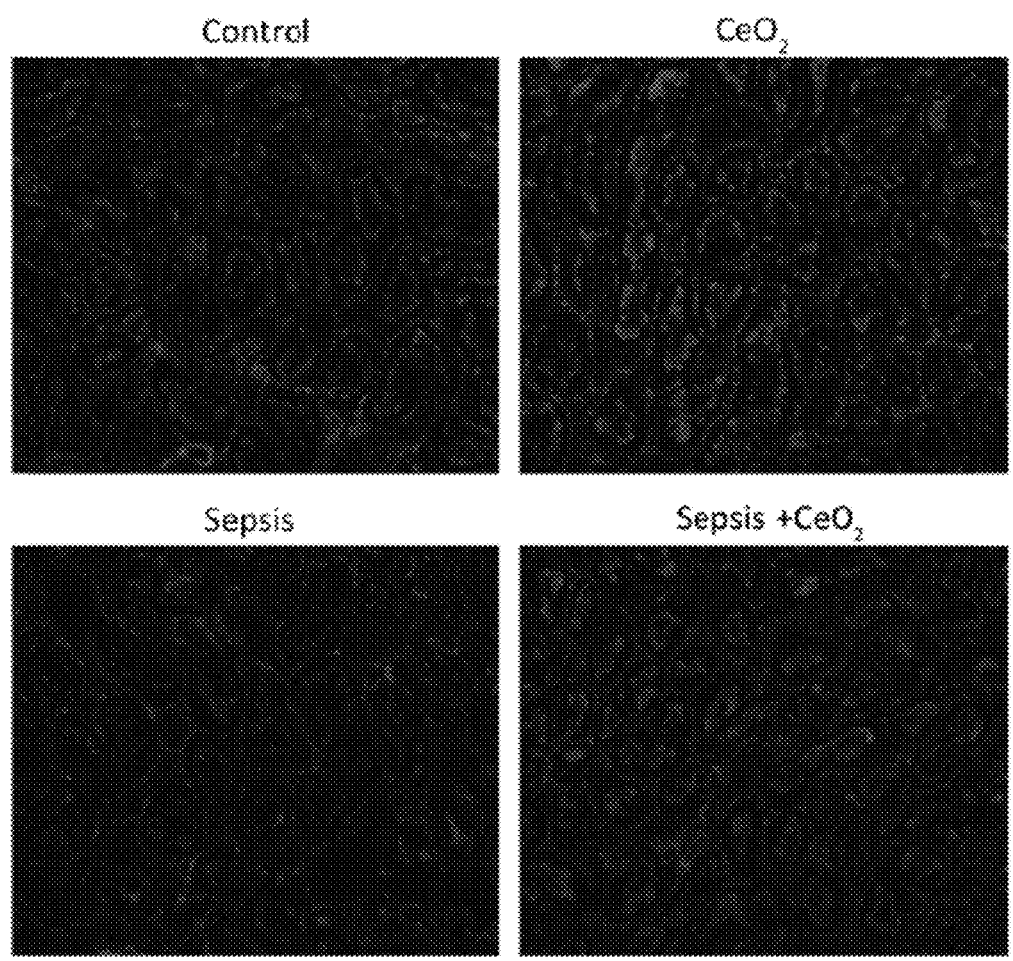
FIGS. 18A-18B include images and a graph showing the ability of $CeO_2$ nanoparticles to attenuate sepsis induced loss of F-actin, including images showing rhodamine phalloidin staining for F-actin of 18 h time point kidney sections imaged at 200× magnification (FIG. 18A), and a graph showing relative fluorescence intensity as a measure of F-actin (FIG. 18B), where *$P<0.05$ compared to control group, \$ $P<0.05$ compared to $CeO_2$ group and # $P<0.05$ compared to sepsis group.

Sepsis induced AKI is marked by renal tubular dilatation and loss of brush border (FIG. 17, panels C and G). Treatment with $CeO_2$ nanoparticles attenuated sepsis induced tubular dilation and loss of brush border (FIG. 17, panels D and H). Furthermore $CeO_2$ nanoparticles appear to attenuate sepsis induced changes in damage to glomerular capillary network (FIG. 17). Renal sections of sepsis induced animals showed marked loss of F-actin in proximal tubular cells (FIG. 18A). In contrast, $CeO_2$ nanoparticles attenuated sepsis induced loss of F-actin and preserved the integrity of cytoskeleton network (FIG. 18A). Mean fluorescence intensity for F-actin was also higher in sepsis+ $CeO_2$ group by 61% when compared to sepsis group alone (FIG. 18B) (P<0.05).

Cerium Oxide Nanoparticles Attenuate Sepsis Induced Oxidative Stress, Prevents Stat-3 Activation and Cleavage of Caspase 3.

Compared to control group, renal sections of sepsis induced animals exhibited an increase in superoxide levels by 71% (FIG. 19A) (P<0.05). In contrast treatment with $CeO_2$ nanoparticles attenuated sepsis induced increases in superoxide levels by 33% when compared to sepsis group alone (FIGS. 19A-19B) (P<0.05).

Similarly, when compared to control group, sepsis increased the ratio of phosphorylated to total levels of stat-3 at 18 h time point by 1300% which was significantly attenuated with $CeO_2$ nanoparticles treatment (FIG. 20A) (P<0.05). Likewise, sepsis increased the cleavage of caspase 3 by 155% and was significantly attenuated with $CeO_2$ nanoparticles treatment at 18 h time point (FIG. 20B) (P<0.05).

Cerium Oxide Nanoparticles Attenuate Sepsis Induced Increases in Biomarkers of Renal Failure.

Compared to control group, sepsis increased the levels of β-2 microglobulin at 3 h and 18 h time points and levels of KIM-1, cystatin-C, osteopontin and VEGF-A at 18 h time point. Treatment with $CeO_2$ nanoparticles attenuated sepsis induced increases in, KIM-1 cystatin-C osteopontin, β-2 microglobulin and VEGF-A at 18 h time point (Table 5) (P<0.05).

Cerium Oxide Nanoparticles Attenuate Sepsis Induced Changes in Serum Biochemical Parameters.

Sepsis caused a decrease in serum levels of sodium at 3 h time point and increase in levels of potassium at 18 h time point when compared to control group (Table 2) (P<0.05). In contrast treatment with $CeO_2$ nanoparticles attenuated sepsis induced changes in serum levels of sodium and potassium (Table 6) (P<0.05). Likewise sepsis induced early hyperglycemia and increases in levels of BUN at 3 h time point were attenuated with $CeO_2$ nanoparticles treatment (Table 6) (P<0.05).

TABLE 5

CeO$_2$ nanoparticles attenuate sepsis induced increases in biomarkers of AKI.

| Analyte | Sham control 3 h | CeO$_2$ 3 h | Sepsis 3 h | Sepsis + CeO$_2$ 3 h | Sham control 18 h | CeO$_2$ 18 h | Sepsis 18 h | Sepsis + CaO$_2$ 18 h |
|---|---|---|---|---|---|---|---|---|
| β2-Microglobulin (μg/mL) | 54.00 ± 3.00 | 49.67 ± 2.40 | 76.00 ± 1.53*$ | 77.33 ± 1.76*# | 52.00 ± 3.51 | 32.67 ± 1.45* | 128.00 ± 5.85*$ | 78.33 ± 7.21*$# |
| Cystatin-C (ng/mL) | 578.67 ± 14.25 | 633.00 ± 30.57 | 686.00 ± 14.47 | 690.33 ± 42.10 | 699.67 ± 52.67 | 555.33 ± 41.63 | 1890.00 ± 62.45*$ | 1093.33 ± 37.56*$# |
| KIM-1 (ng/mL) | Below LLOQ | Below LLOQ | Below LLOQ | Below LLOQ | Below LLOQ | Below LLOQ | 3.27 ± 0.13 | 2.50 ± 0.10# |
| Osteopontin (ng/mL) | 10.80 ± 1.20 | 11.00 ± 0.58 | 11.00 ± 0.58 | 12.33 ± 0.33 | 9.70 ± 0.00 | 7.93 ± 0.23* | 72.33 ± 4.84*$ | 36.33 ± 1.76*$# |
| VEGF-A (pg/mL) | Below LLOQ | Below LLOQ | Below LLOQ | Below LLOQ | Below LLOQ | Below LLOQ | 459.00 ± 12.70 | 296.67 ± 31.33* |

*$p < 0.05$ compared to control group, $$p < 0.05$ compared to CeO$_2$ group and #$p < 0.05$ compared to sepsis group. (n = 6/group).

TABLE 6

CeO$_2$ nanoparticles attenuate sepsis induced alterations in serum biochemical parameters.

| Analyte | Sham control 3 h | CeO$_2$ 3 h | Sepsis 3 h | Sepsis + CeO$_2$ 3 h | Sham control 18 h | CeO$_2$ 18 h | Sepsis 18 h | Sepsis + CeO$_2$ 18 h |
|---|---|---|---|---|---|---|---|---|
| Glucose | 284.00 ± 8.11 | 262.29 ± 10.13 | 426.88 ± 19.74*# | 308.57 ± 22.58* | 245.33 ± 13.25 | 290.63 ± 17.16* | 105.50 ± 8.53*$ | 125.25 ± 5.06*$ |
| Blood urea nitrogen | 22.00 ± 1.10 | 21.00 ± 1.00 | 29.88 ± 1.97*$ | 24.71 ± 1.17* | 19.17 ± 0.54 | 18.50 ± 0.89 | 71.30 ± 7.20*$ | 57.37 ± 3.09$ |
| Sodium | 142.43 ± 0.72 | 142.86 ± 0.88 | 136.75 ± 1.36*$ | 140.14 ± 0.51* | 142.00 ± 1.21 | 141.63 ± 0.91 | 138.80 ± 0.84 | 140.63 ± 0.50 |
| Potassium | 5.91 ± 0.37 | 5.44 ± 0.11 | 6.36 ± 0.27 | 6.30 ± 0.23 | 5.62 ± 0.24 | 5.75 ± 0.33 | 7.83 ± 0.24*$ | 7.06 ± 0.21*$# |

*$p < 0.05$ compared to control group, $$p < 0.05$ compared to CeO$_2$ group and #$p < 0.05$ compared to sepsis group. (n = 6/group).

Discussion of Example 4

Sepsis induced acute kidney injury (AKI) has a poor prognosis despite recent advances in medical care and is largely attributed due its complex pathophysiology. Studies have shown that sepsis induced AKI is associated with increases in oxidative and nitrosative stress which promote inflammation and cause tubular dilatation, vacuolization, sloughing of epithelial cells and loss of brush border leading to severe renal failure. CeO$_2$ nanoparticles have been shown to act as an antioxidant and anti-inflammatory agent in the treatment of several diseases such as cancer and diabetes. With this in mind, it was believed that CeO$_2$ nanoparticles could be used to prevent sepsis induced AKI.

Figure 18B:
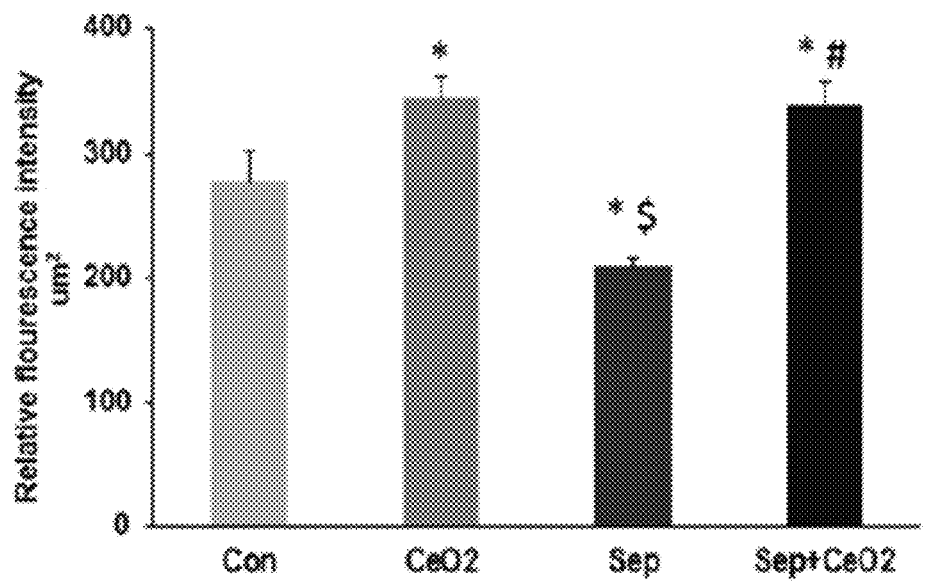

Previous studies have shown that sepsis leads to marked tubular damage along with loss of brush border and derangement in glomerular capillary network. It was found that CeO$_2$ nanoparticles attenuated sepsis induced damage to renal glomeruli and tubules and prevented AKI (FIG. 17). To extend upon these findings, it was next determined whether CeO$_2$ nanoparticles can prevent overall sepsis induced loss of renal structural integrity. AKI is characterized by loss of F-actin that leads to disruption in cytoskeleton network and impairs renal structural and functional integrity. While sepsis caused a significant decrease in loss of F-actin, CeO$_2$ nanoparticles attenuated these changes and protect the kidneys from severe damage (FIGS. 18A-18B).

Figure 19A:
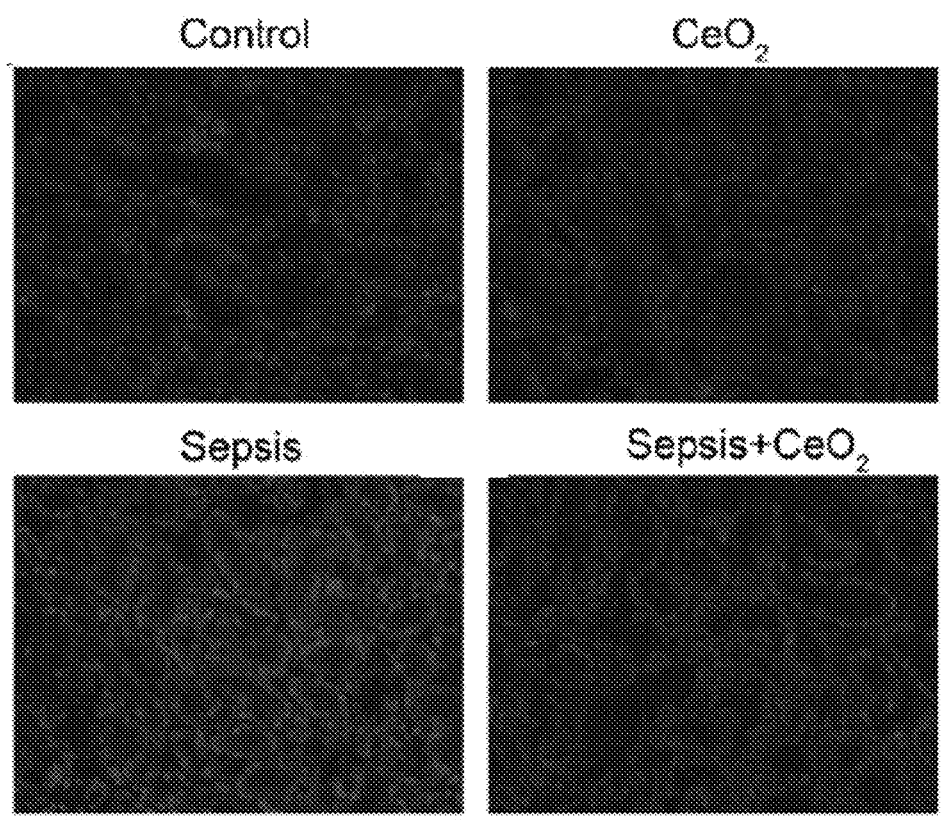
FIGS. 19A-19B include images and a graph showing the ability of $CeO_2$ nanoparticles to attenuate sepsis induced increases in renal superoxide levels, including images showing dihydroethidium staining of 18 h time point kidney sections imaged at 200× magnification (FIG. 19A), and a graph showing quantification of superoxide levels in different groups (FIG. 19B), where *P<0.05 compared to control group, $ P<0.05 compared to $CeO_2$ group and # P<0.05 compared to sepsis group.
Figure 19B:
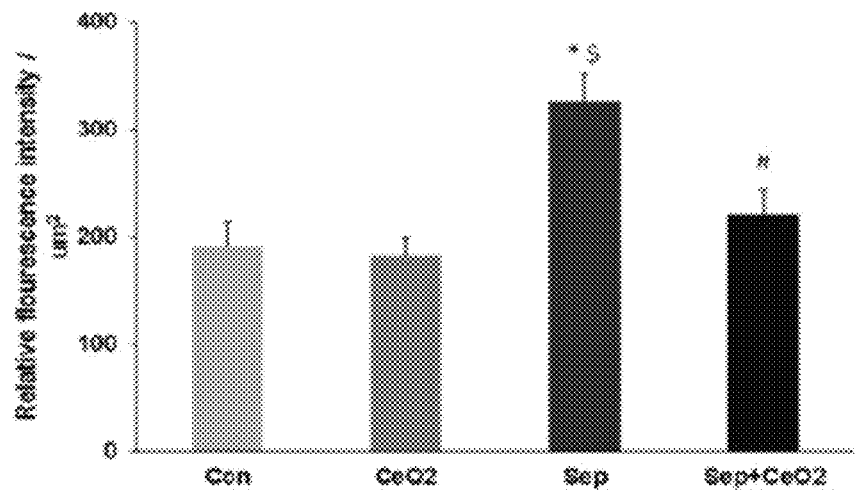

As a next approach, the underlying mechanism of action of CeO$_2$ nanoparticles against severe septic insult was further investigated. Sepsis is characterized by increases in oxidative stress that results in uncontrolled SIRS and multi-organ failure. Studies have shown that CeO$_2$ nanoparticles are potent ROS scavengers and act as a catalase and SOD mimetic. As such, the changes in levels of renal superoxide was evaluated in septic animals with and without nanoparticle treatment. It was found that CeO$_2$ nanoparticles significantly attenuated sepsis induced increases in renal superoxide oxide levels and prevented the development of AKI (FIGS. 19A-19B).

Figure 20A:
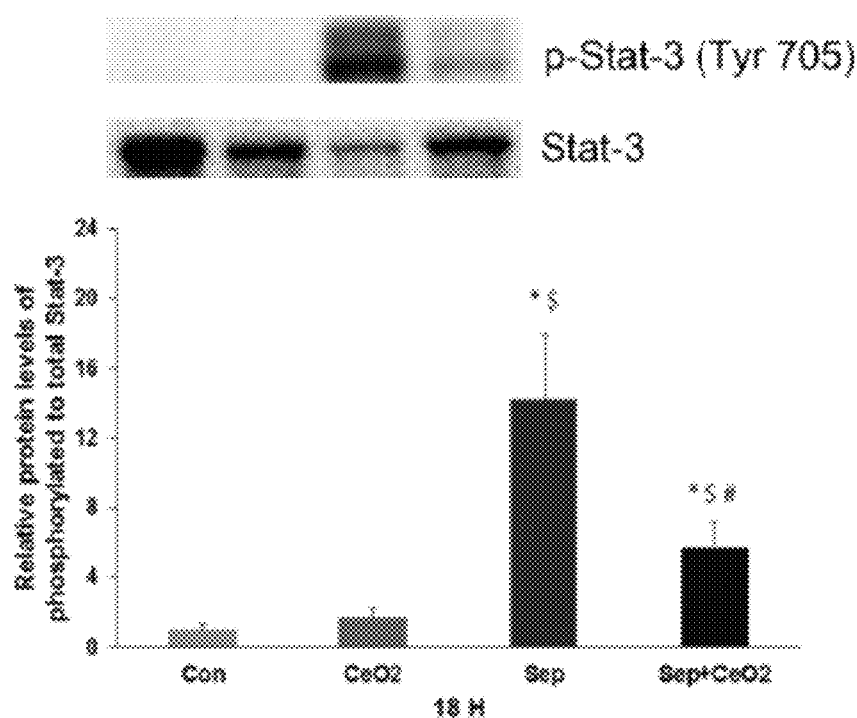
FIGS. 20A-20C include images and graphs showing the ability of $CeO_2$ nanoparticles to attenuate sepsis induced renal inflammation and apoptosis, including images and a graph showing levels of phosphorylated to total Stat-3 as determined by western blotting (FIG. 20A), images and a graph showing levels of cleaved caspase 3 as determined by western blotting (FIG. 20B), and images and a graph showing levels of total caspase 3 as determined by western blotting (FIG. 20C), where *P<0.05 compared to control group, $ P<0.05 compared to $CeO_2$ group and # P<0.05 compared to sepsis group.

To further elucidate the reno-protective effects of CeO$_2$ nanoparticles against sepsis, the Jak-Stat pathway that is associated with inflammation was investigated. Jak-Stat pathway involves multiple downstream targets that are involved in cytokine and growth factor signaling. Studies have shown that action of stat-3 is involved in transcription of VEGF which is synthesized in response to hypoxic state of the organ. Other studies have also shown that Jak-Stat pathway is activated in several diseases such as diabetic nephropathy, renal fibrosis and ischemia reperfusion injury. Here, It was found for the first time that sepsis induced the activation of stat-3 in kidneys, which might have resulted in increased serum levels of VEGF and were attenuated by CeO$_2$ nanoparticle treatment (FIG. 20A, Table 5).

Figure 20B:
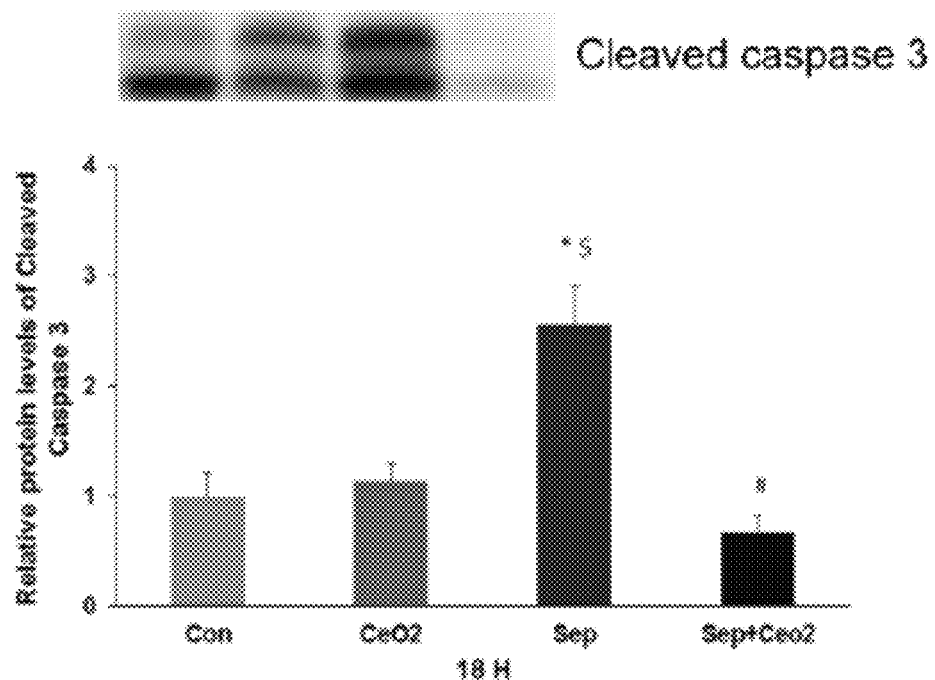
Figure 20C:
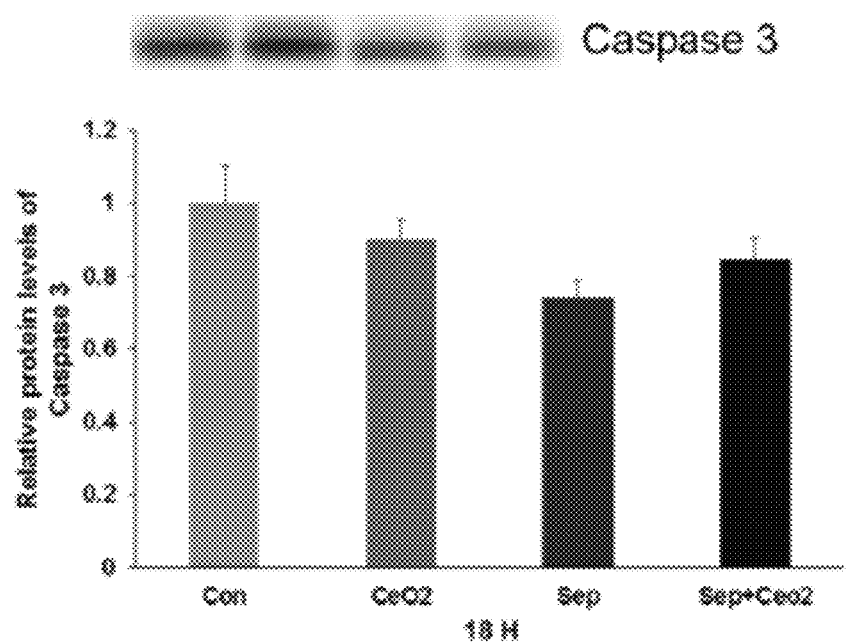
Figure 21A:
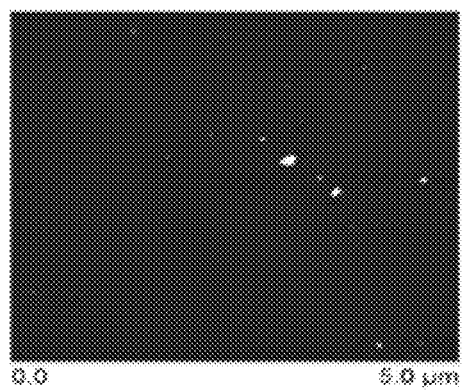
FIGS. 21A-21D are yet further images and graphs showing the characterization of $CeO_2$ nanoparticles.
Figure 21B:
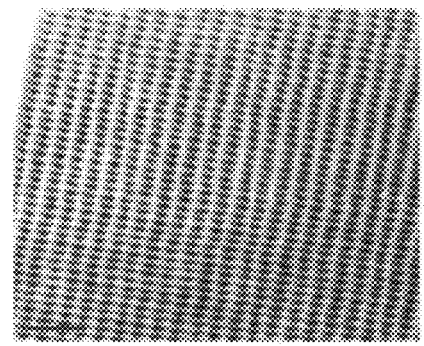
Figure 21C:
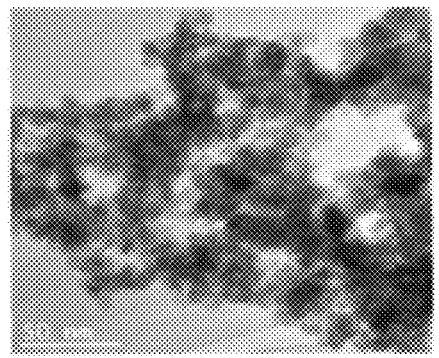
Figure 21D:
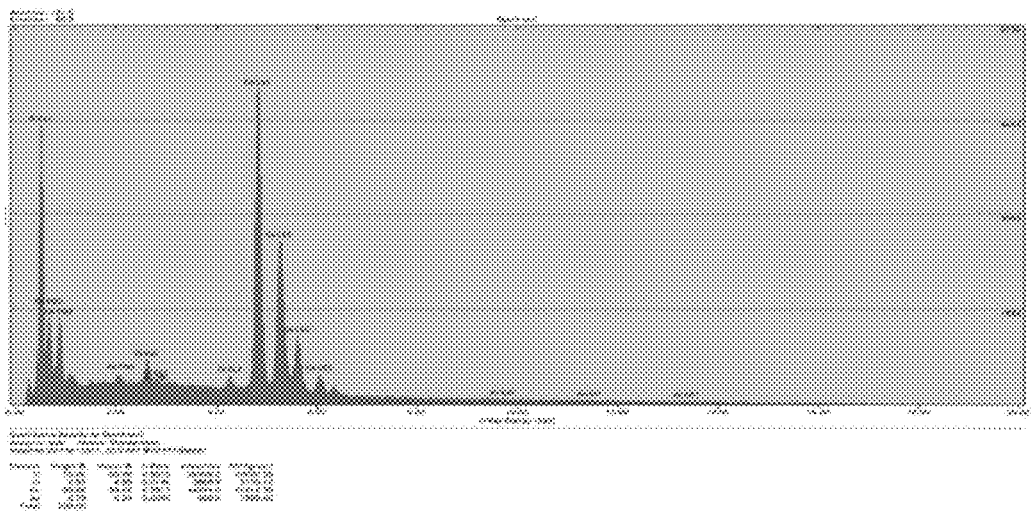

Evidence suggested that apoptosis of renal tubular cells is one of the major causes for AKI in sepsis. Studies have shown that cleavage of caspase 3 is responsible for activation of gelsolin which has F-actin severing properties. Loss of F-actin causes cytoskeletal derangement that leads to apoptotic cell death and development of AKI. Here we found that, sepsis induced cleavage of caspase 3 that is associated with loss of F-actin was significantly attenuated by CeO$_2$ nanoparticle treatment (FIG. 18A, FIGS. 20B-20C).

Increase in serum levels of creatinine is considered to be a traditional biomarker for AKI. However, sepsis induced AKI has a distinct pathophysiology that separates it from non-septic AKI. A recent study has also demonstrated that reduced production of creatinine in sepsis limits its use as a marker for AKI. As such, the changes in novel biomarkers of sepsis induced AKI were evaluated, including: KIM-1-biomarker for proximal tubular injury; β-2 microglobuli, a marker for functional status of proximal tubular cells; cystatin-C, surrogate for glomerular filtration rate; and finally osteopontin, which is associated with increased infiltration of macrophages and neutrophils. It was found that sepsis induced increases in the levels of β-2 microglobulin, KIM-1, cystatin-C and osteopontin were attenuated with $CeO_2$ nanoparticle treatment (Table 5).

Finally, whether $CeO_2$ nanoparticle treatment can attenuate sepsis induced alterations in serum biochemical parameters was investigated. Hyponatremia and hyperkalemia are generally found in acute renal failure with decreased renal tubular flow rate. In the foregoing studies, however, it was found that sepsis caused a decrease in serum levels of sodium and increase in potassium which were attenuated with $CeO_2$ nanoparticle treatment (Table 6). Likewise, $CeO_2$ nanoparticle treatment also attenuated early sepsis induced increases in blood urea nitrogen and glucose thus conferring protection to the kidneys against severe septic insult (Table 6).

The results of the foregoing studies suggested that a single dose of $CeO_2$ nanoparticles confers protection against severe sepsis induced acute kidney injury. $CeO_2$ nanoparticles act by scavenging reactive oxygen species, prevent caspase mediated loss of F-actin and protect the renal tubular cells from severe damage. One advantage of $CeO_2$ nanoparticles in treatment of sepsis induced AKI is the lack of any antibiotic resistance and the unique property of $CeO_2$ nanoparticles to cycle back from $Ce^{+4}$ to $Ce^{+3}$ which can continuously scavenge ROS.

Example 5—Cerium Oxide Nanoparticle Attenuation of Polymicrobial Sepsis Induced Acute Lung Injury Whether $CeO_2$ nanoparticles can help to prevent sepsis induced lung damage has not been investigated. The study described below was thus undertaken to determine if $CeO_2$ nanoparticles could be used as treatment to decrease lung injury in an animal model of severe sepsis and (acute lung injury) ALI. It was believed that cerium oxide nanoparticle treatment could attenuate lung damage due to ALI in sepsis via antioxidant and antibacterial properties.

Materials and Methods for Example 5
Characterization of $CeO_2$ Nanoparticles.

Cerium oxide nanoparticles were purchased from US Research Nanomaterials Inc. (Houston, Tex.). Dynamic light scattering (DLS) was performed to estimate the mean size of $CeO_2$ nanoparticles in suspension using LB-550 DLS particle size analyzer (Horiba Scientific, Edison, N.J.). Naked particle size of the $CeO_2$ nanoparticles was characterized by transmission electron microscopy using JEOL JEM-2010 transmission electron microscope (TEM). X-ray diffraction (XRD) was performed by Scintag XDS 2000 powder diffractometer. Scanning transmission electron microscopy (STEM) images were acquired by the Aberration Corrected Analytical Electron Microscope (TEM/STEM JEOL JEM-ARM200CF, Japan) operated at 200 keV. Electron energy loss spectroscopy (EELS) data for $CeO_2$ nanoparticles were collected by Gatan Enfina.

Induction of Polymicrobial Sepsis and Therapeutic Intervention.

Male Sprague Dawley rats aged 10 weeks were purchased from Hill-Top Laboratories and housed in two-per cage at 22±2° C. with a 12:12 light-dark cycle for two weeks prior to experimentation. Animals were fed with standard rodent chow and had access to food and water ad libitum. All surgical procedures were performed in accordance with the guidelines provided by Marshall University Institutional Animal Care and Use Committee as guided by the Association for Assessment and Accreditation of Laboratory Animal Care. Briefly, animals were anesthetized under isoflurane and a small (0.5 cm) mid-ventral incision was made. Sham controls and $CeO_2$ only groups were injected with 5 ml/kg of 5% sterile dextrose solution intraperitoneally and the incision was closed with 3-0 silk sutures. For the sepsis and sepsis+$CeO_2$ groups, animals received a cecal inoculum of 600 mg/kg BW in 5 ml/kg BW of 5% sterile dextrose solution intraperitoneally. Cecal material was obtained from healthy rats and the material from each donor was used to induce sepsis in 4-5 rats. Sham control and sepsis groups received 200 μl of sterile distilled water intravenously via tail vein while the $CeO_2$ and sepsis+$CeO_2$ groups received $CeO_2$ nanoparticles (0.5 mg/kg) in 200 μl of sterile distilled water intravenously. Rectal temperature was recorded at 0, 3, 6, 12, and 18 h after receiving the cecal inoculum.

Sample Collection and Estimation of Organ Ceria Content.

Whole blood was collected by cardiac puncture and centrifuged at 5,000×g for 10 min to collect serum. The lung was excised and washed in Krebs-Ringer bicarbonate buffer (KRB) to remove any blood, blotted to remove excess moisture, snap frozen in liquid nitrogen, and stored at −80° C. for further analysis. Frozen lung samples were sent to Elemental Analysis Inc. (Lexington, Ky.) for estimation of ceria content by induction coupled plasma-mass spectrometry (ICP-MS) as described elsewhere.

Lung Histology.

Lung tissue was sectioned (4 μm) using Leica CM1950 cryostat onto poly-L-lysine coated slides. Visualization of hematoxylin and eosin staining was performed to evaluate lung morphology using Evos XL microscope (Life Technologies, Grand Island, N.Y.).

Myeloperoxidase (MPO) Activity Assay.

MPO activity was evaluated in the whole lung to assess neutrophil infiltration. Lungs were homogenized in 50 mM sodium phosphate buffer containing 0.5% hexadecyltrimethylammonium bromide, heated for 2 hours at 55° C., centrifuged at 10,000×g for 20 minutes at 4° C., and then supernatants were collected. Following addition of substrate buffer containing 0-dianisidine and 0.0005% hydrogen peroxide, MPO activity was measured at 460 nm wavelength over 6 minutes (Bio-Tek Instruments Microplate Spectrophotometer, Winooski, Vt.). MPO activity was calculated as optical density/minute per mg of lung tissue.

Bacterial Cultures.

Whole blood was collected via cardiac puncture and peritoneal lavage fluid was obtained following peritoneal instillation with 1 ml sterile saline. Blood and lavage samples were serially diluted in sterile saline and plated on sheep's blood agar plates. Plates were incubated overnight at 37° C. and colony counts were determined 24 hours later. Colony counts were expressed as CFU/ml of fluid and then converted to a logarithmic scale for statistical analysis.

SDS-PAGE and Immunoblotting.

Approximately 100 mg of frozen tissue was taken and pulverized in liquid nitrogen and added to 900 μl of T-PER (Pierce, Rockford, Ill., USA) containing 1% protease and phosphatase inhibitors (P8340 and P5726, Sigma-Aldrich, St. Louis, Mo., USA). Samples were homogenized and centrifuged at 13,000 rpm for 10 min at 4° C. to collect the supernatant. Amount of protein in the samples was estimated through 660 nm assay (Pierce, Rockford, Ill., USA) and normalized with T-PER and 4× Laemlli buffer to a final equal concentration across all samples. Equal amount of protein was loaded in 10% PAGEr Gold Precast gel (Lonza, Rockland, Me.) and transferred to nitrocellulose membranes using standard protocol as detailed elsewhere. Membranes were blocked with 5% milk in TBST for 1 h at room temperature, washed thrice with TBST and probed for detection of p38 MAPK, p-p38 MAPK (Thr202/Tyr204), Stat-3, p-Stat-3 (Tyr705), GAPDH (Cell Signaling Technology, Danvers, Mass.). Membranes were incubated with primary antibody overnight at 4° C., washed with TBST (3×5 min), and incubated with secondary anti-rabbit (Cell Signaling Technology, Danvers, Mass.) or anti-mouse antibody (Santa Cruz, Dallas, Tex.) for 1 h at room temperature. Immunoreactive signal was visualized using Supersignal West Pico Chemiluminiscent substrate (Pierce, Rockford, Ill., USA) and quantified using Fluorchem 9900 software (Protein Simple, Santa Clara, Calif.). Protein expression was normalized to glyceraldehyde 3-phosphate dehydrogenase (GAPDH).

Cytokine-Antibody Array.

Cytokine Antibody Array Murine cytokine antibody arrays (M0308003, RayBiotech Inc., Norcross, Ga., USA) were used to determine levels of cytokines in the lung lysates as detailed by the manufacturer. Briefly, the membranes were sequentially incubated with equal volume of blocking solution, lung lysate, primary biotin-conjugated antibodies, and horseradish peroxidase-conjugated streptavidin. Images were collected and quantified using Fluorchem 9900 software (Protein Simple, Santa Clara, Calif.).

Statistical Analysis.

Results are presented as mean±SEM. The log-rank test (Mantel-Cox) was performed using Prism 5.0 software (GraphPad Software, La Jolla, Calif.) to determine differences in animal survivability between groups. A two way analysis of variance using Tukey's multiple comparison was performed where appropriate to evaluate differences in core temperature amongst the different groups. Differences in groups with equal sample size was evaluated by one way analysis of variance using Student Newman Keuls or Dunn's post hoc analysis for samples with unequal size. A one way ANOVA by ranks with Kruskal Wallis post hoc analysis was used for samples with non-normal distribution and a simple t-test was performed where appropriate using Sigmaplot 12 statistical software (Systat software Inc., San Jose, Calif.) to test for the presence of significant differences between groups. A probability value of $P<0.05$ was considered to be statistically significant.

Results of Example 5

Characterization of $CeO_2$ Nanoparticles.

The mean hydrodynamic diameter of $CeO_2$ nanoparticles as estimated through dynamic light scattering experiments has been reported previously (ref) and was found to be approximately 90 nm (FIG. 21). Similarly, TEM and STEM analysis determined the size of individual nanoparticle to be approximately in between 10-30 nm (FIG. 21). The high resolution image of the $CeO_2$ nanoparticle shows that the atoms of $CeO_2$ are highly ordered (FIG. 21) and the EELS data (FIG. 21) confirmed the existence of the Ce and O element. XRD was used to demonstrate cubic fluorite structure of $CeO_2$ nanoparticles as seen through typical peaks as detailed previously (ref), (FIG. 21).

Nanoparticle Treatment Decreased Sepsis-Induced Lung Damage and Myeloperoxidase Activity without Increasing Pulmonary Ceria Content.

Figure 22:
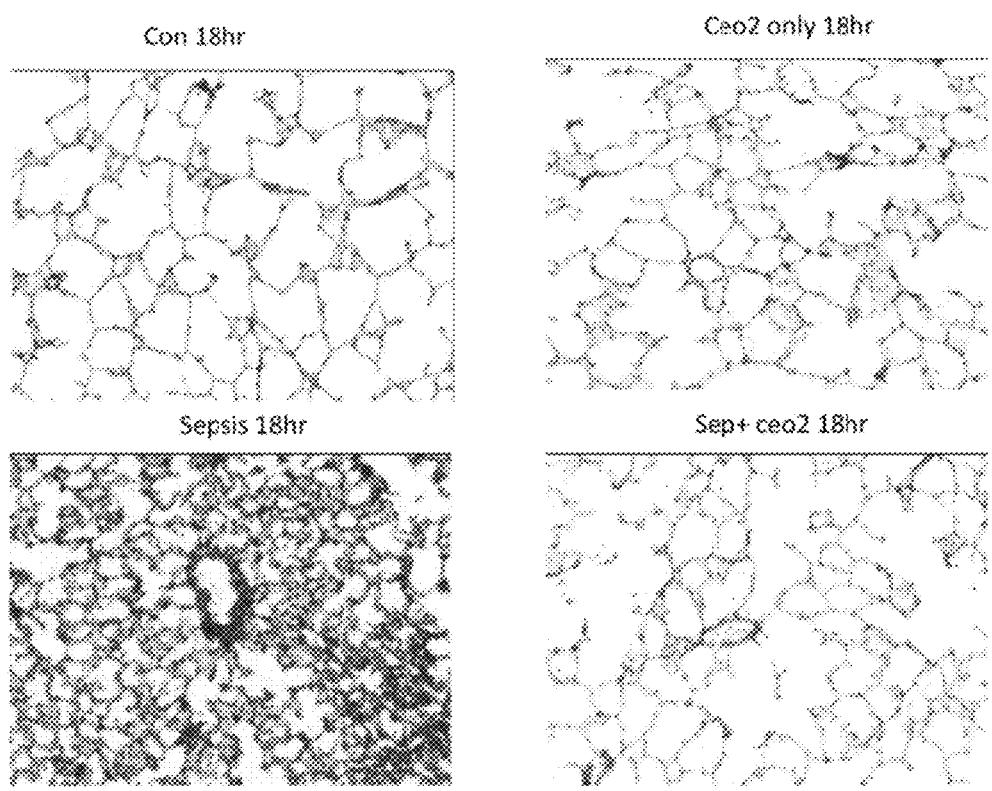
FIG. 22 is a representative micrographs of lung tissue (n=3/group) 18 h after infection as visualized by light microscopy, where infection related changes in the lung included alterations in alveolar structure, evidence of pulmonary inflammation, and a thickening of the alveolar septum.
Figure 23:
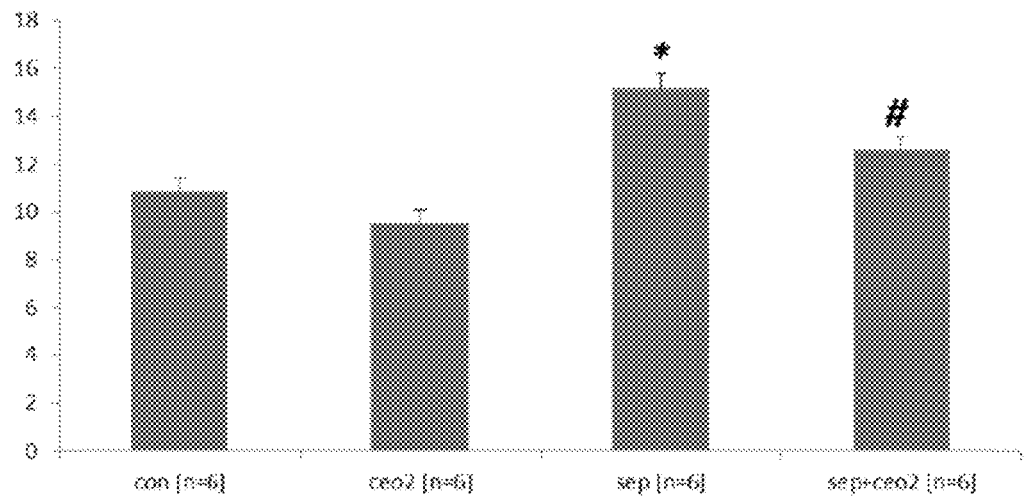
FIG. 23 is a graph showing levels of myeloperoxidase activity in lung homogenate from control (n=6), CeO2 (n=6), Sepsis (n=6), Sepsis+CeO2 (n=6) and analyzed in triplicate, where * indicates significantly different from control (P<0.05), and where # indicates significantly different from infected animals (P<0.05)
Figure 24:
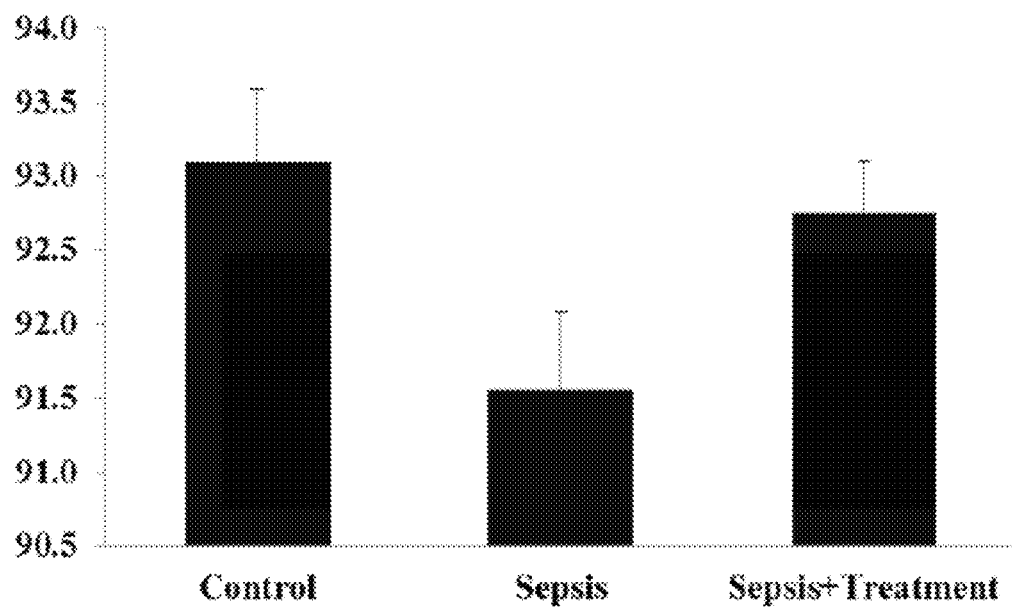
FIG. 24 is a graph showing the effect of infection and treatment on arterial oxygen levels.

Histological analysis of the lungs obtained from control animals revealed normal lung morphology. Nanoparticle treatment appeared to decrease sepsis-induced lung inflammation (FIG. 22). Similarly, sepsis-induced increases in lung MPO activity were decreased in the nanoparticle treated animals (FIG. 23, p<0.05). While arterial oxygen levels decreased in sepsis, the restoration of oxygen level was increased in the nanoparticle treated animals (FIG. 24). Compared to untreated animals, lung ceria content was not different in the animals receiving nanoparticle injections.

Cerium Oxide Nanoparticles Decreases Sepsis Induced Increases in Blood and Peritoneal Cavity Bacterial Load.

Figure 25:
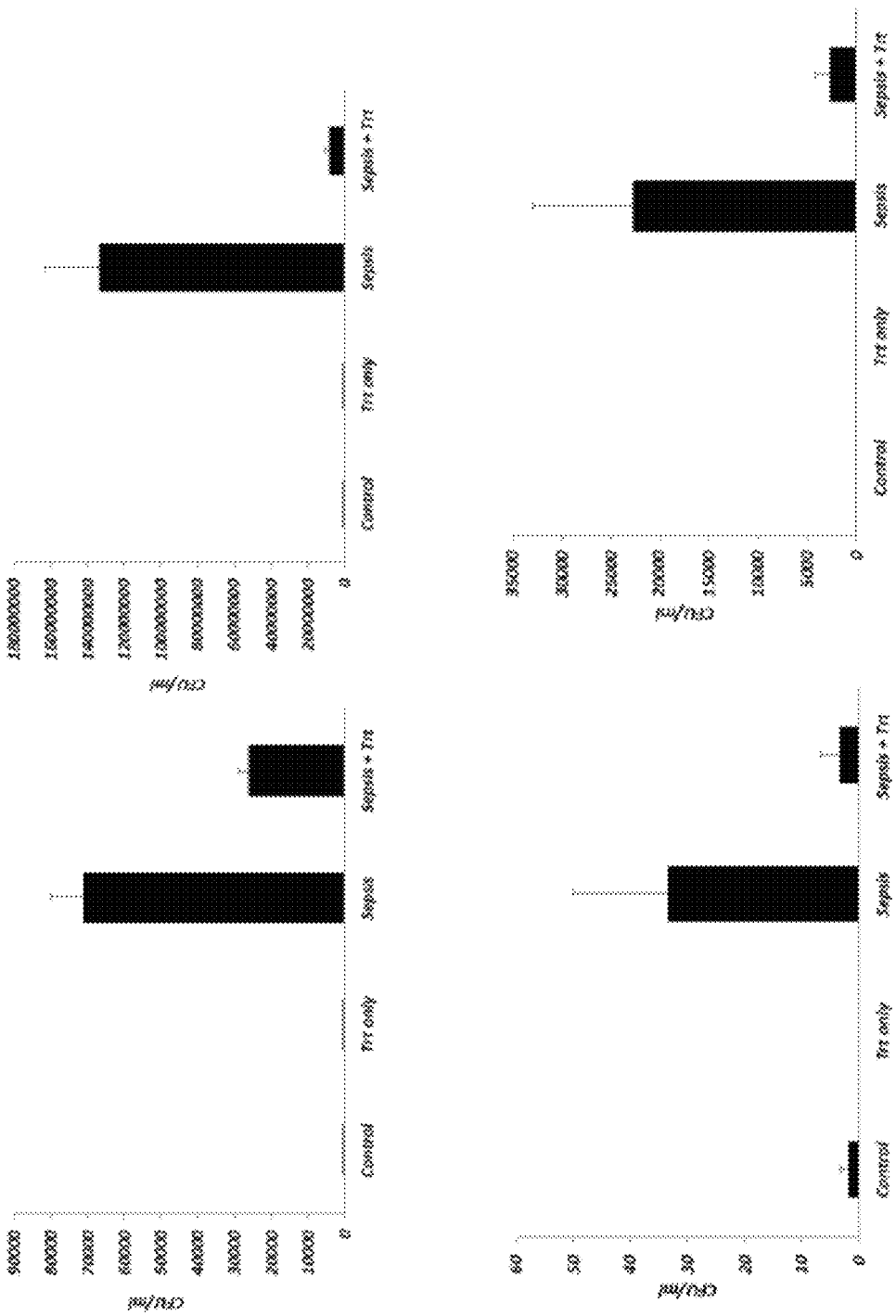
FIG. 25 includes graphs showing the effect of infection and treatment on peritoneal (top row of graphs) and blood (bottom row of graphs) bacterial counts at 3 h (left graphs) and 18 h (right graphs) after infection.

The CFU of samples obtained from the blood and peritoneal cavity were increased with sepsis (FIG. 25). Conversely, nanoparticle treatment reduced sepsis induced increases in the number of bacteria in the blood and peritoneal cavity at 18 h (FIG. 25, P<0.05).

Nanoparticle Treatment Decreases the Activation of Stat-3 and p38-MAPK Signaling in the Septic Lung and Modulates Sepsis Related Cytokines.

Figure 26:
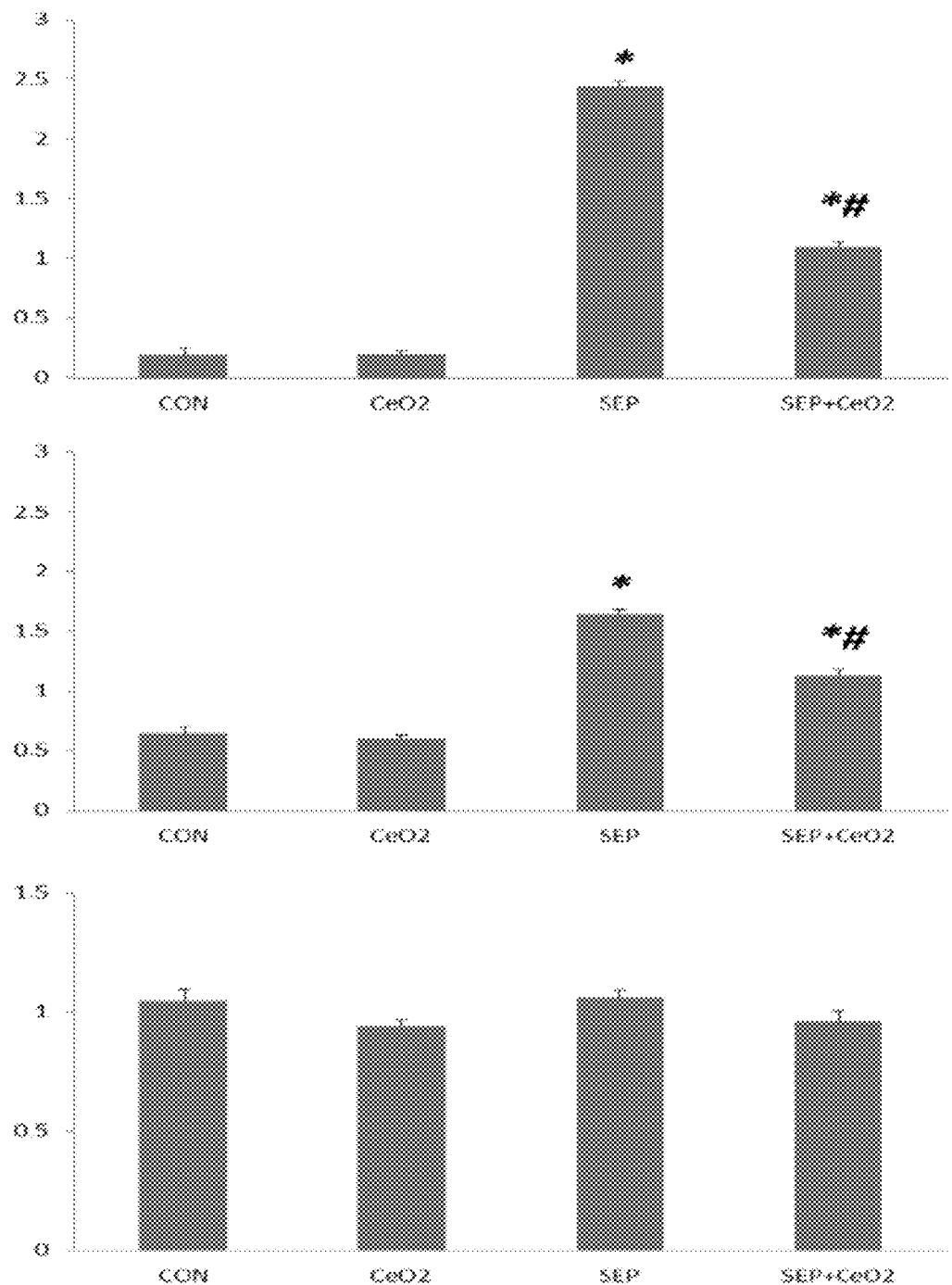
FIG. 26 includes graphs showing the effect of infection and treatment on STAT3 phosphorylation normalized to GAPDH, where values are mean±SEM of at least three independent experiments, where *P<0.05 compared to control group, and where P<0.05 compared to infected animals group.
Figure 27:
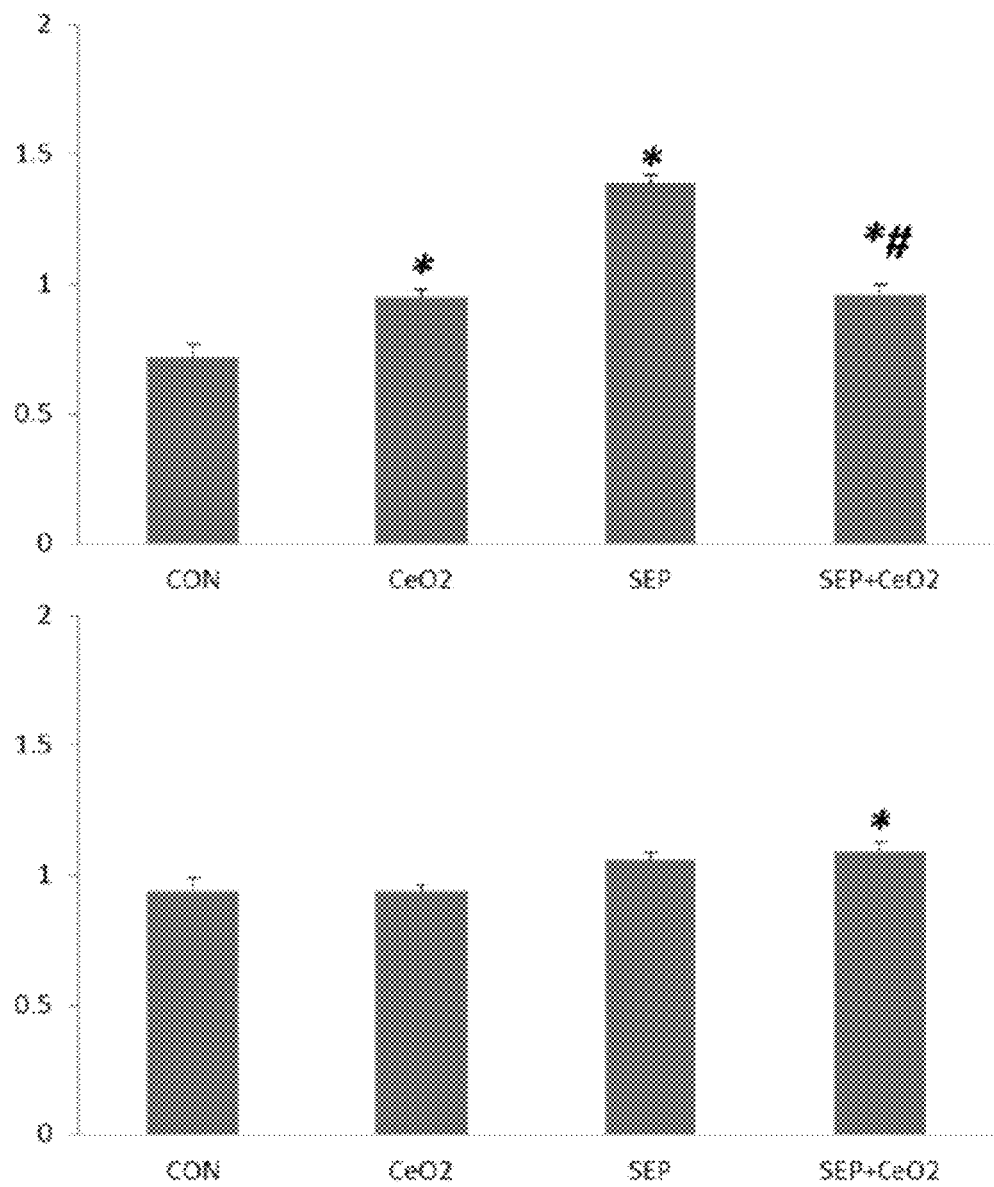
FIG. 27 includes graphs showing the effect of infection and treatment on p38 MAPK phosphorylation normalized to GAPDH, where values are mean±SEM of at least three independent experiments, where *P<0.05 compared to control group, and where P<0.05 compared to infected animals group.
Figure 28:
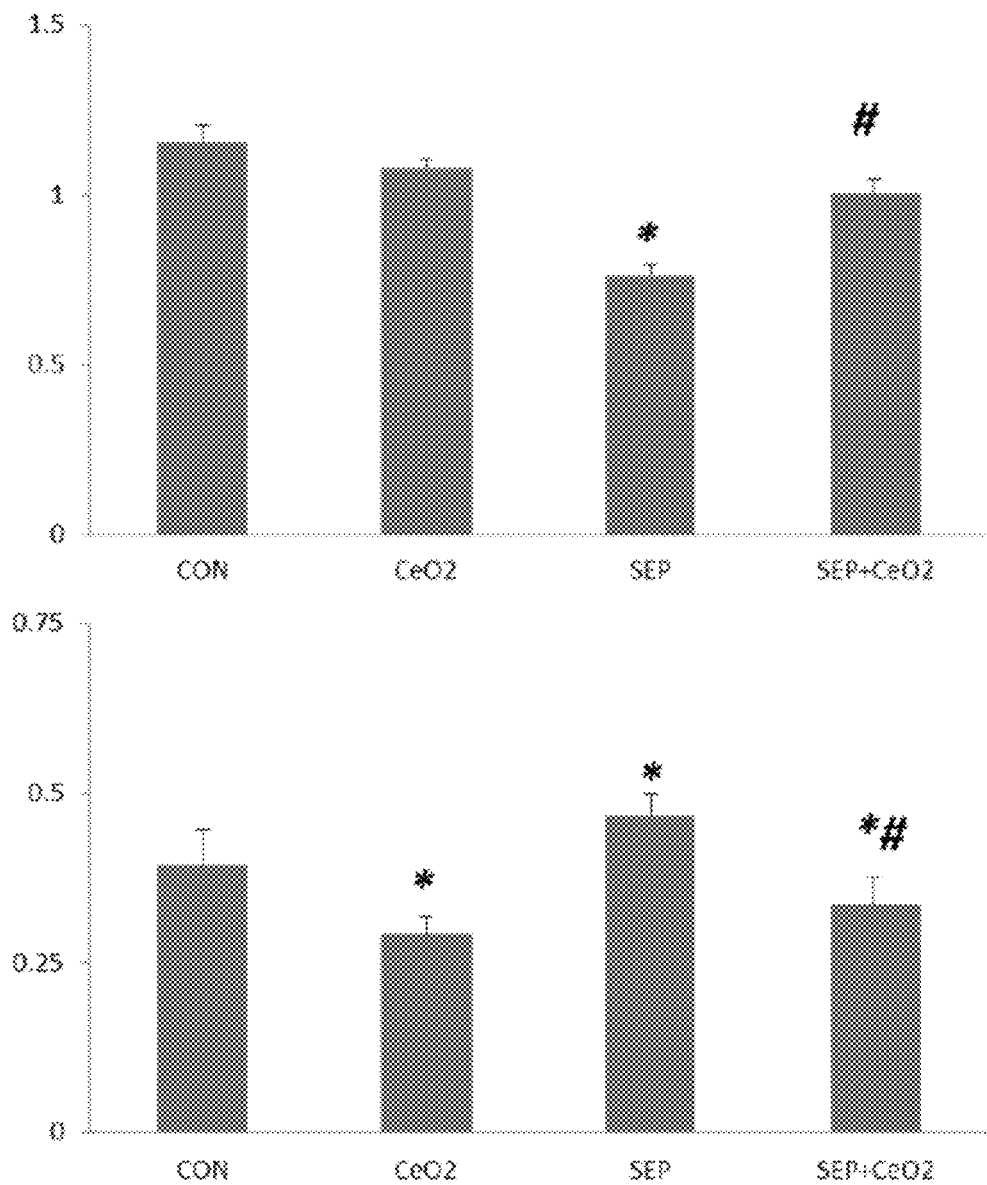
FIG. 28 includes graphs showing the effect of infection and treatment on caspase-3 cleavage normalized to GAPDH, where values are mean±SEM of at least three independent # experiments, where *P<0.05 compared to control group, and where P<0.05 compared to infected animals group.
Figure 29:
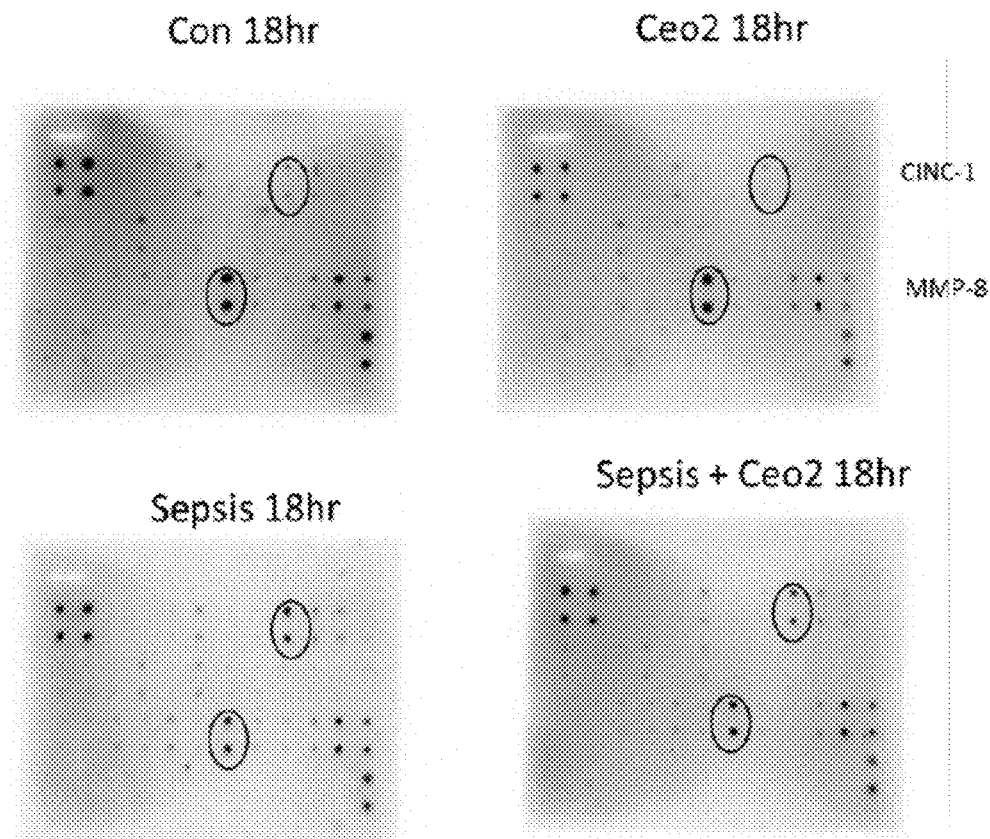
FIG. 29 includes images of a dot blot showing cytokine and chemokine levels in lung homogenates.

Sepsis increased and nanoparticle treatment decreased the phosphorylation of Stat-3 (FIG. 26, P<0.05) and p38-MAPK (FIG. 27, P<0.05). These changes in protein phosphorylation were accompanied by treatment associated decreases in caspase-3 cleavage (FIG. 28, P<0.05). Levels of non-phosphorylated Stat-3 and p38-MAPK remained insignificantly changed. Nanoparticle treatment reversed sepsis-induced changes in several inflammatory chemokines, cytokines including MMP-8 and CINC-1, and other inflammation related proteins (P<0.05).

Discussion of Example 5

Despite decades of research, the sepsis mortality rate remains unacceptably high. The aim of the foregoing studies was to determine whether treatment with $CeO_2$ nanoparticles could decrease lung injury in an animal model of severe sepsis. A finding of this study was the observation that a single injection of $CeO_2$ nanoparticles, in the absence of antibiotic treatment, fluid resuscitation, or other pharmacological intervention, was associated with decreased evidence of sepsis-induced lung damage (FIG. 22). Consistent with these findings, it was also found that the nanoparticle treatment tended to increase arterial oxygen levels suggesting that these improvements in pulmonary morphology may also be associated with improved lung function (FIG. 24).

The factor(s) regulating the development of lung injury during sepsis are not fully understood however, recent data has suggested that bacterial load is likely to play a role given its role in mediating the development of the systemic inflammatory response syndrome. In the present study, it was found that the nanoparticle treatment was associated with a decreased bacterial load in both the peritoneal fluid and the blood (FIG. 25). In this regard, and without wishing to be bound by any particular theory or mechanism, it was believed that it was possible that the nanoparticles may have functioned to have increased the ability of the immune cells to kill bacteria.

Evidence of diminished Stat3 and p38 MAPK activation after treatment indicates interference with cytokine activation. As IL-6 is known to be connected with Stat3 activation, it was thought that $CeO_2$ interfered with its production. The $CeO_2$ likely acted as an inhibitor to lessen the extreme inflammatory response expected in this model of sepsis. Other findings suggested that p38 MAPK inhibitors are effective in decreasing damage due to sepsis. Since p38 MAPK and STAT3 are both activated by cytokine release, it seemed likely that cerium oxide is useful in preventing the upregulation of the 'cytokine storm' seen with sepsis and ALI.

Cleaved caspase-3 levels were significantly reduced in the treated animals, which indicated a decrease in apoptosis. After inflammation and cellular damage, the activated immune response causes the damaged cells to become programmed for cell death as part of a natural cycle of clearing damaged tissue. In a review of caspase involvement, however, others have underscored the role of caspase-3 in promoting cell death in its role promoting damage due to sepsis. With the heightened systemic immune response, the amount of apoptosis increased rapidly, causing a detrimental effect and increased tissue damage that may lead to severe tissue damage and, ultimately, organ failure. This increase in apoptosis is indicated in the septic tissues by the increase in cleaved caspase-3, but with treatment, the levels of cleaved caspase-3 were decreased significantly. This finding goes along with the decreased inflammation seen in the histological sections, as the cerium oxide demonstrates the ability to attenuate the damage via antibacterial affects mentioned above.

Example 6—Cerium Oxide Nanoparticle Amelioration of Peritonitis Induced Diaphragm Dysfunction The foregoing studies indicated that treatment with $CeO_2$ nanoparticles is associated with diminished sepsis-induced mortality and decreased levels of systemic inflammation after polymicrobial insult. However, whether this increase in survivability following $CeO_2$ nanoparticle intervention was also associated with improvements of diaphragm function was unclear. On the basis of previous data demonstrating that rodent diaphragm is particularly susceptible to elevations in oxidative stress and circulating cytokines, it was believed that septic animals that had been treated with $CeO_2$ nanoparticles would exhibit improved diaphragmatic function compared to that observed in the untreated counterparts. The following findings suggest that $CeO_2$ nanoparticle treatment improves diaphragm contractility following a severe polymicrobial insult and that that phenomenon was associated with evidence of diminished muscle damage and inflammation.

Materials and Methods for Example 6

Materials.

All chemicals were purchased from Sigma-Aldrich (St Louis, Mo.), otherwise these chemicals were stated specifically. Following antibodies were purchased from Cell Signaling Technology (Beverly, Mass.): Phospho-Akt (Ser473) (C31E5E) (#4060), Akt (pan) (40D4) (#2920), Phospho-Stat3 (Tyr705) (D3A7) XP (#9145), Stat3 (#9132), α-tubulin (#2144), Bax (#2772), Bcl-2 (#2876), Ubiquitin (p4DI) (#3936), 4EB-1 phos (thr37/46) (#9459) and 4EB-1 Non phos (thr46) (#4923). Horseradish peroxidase conjugated anti-mouse (#7076) and anti-rabbit (#7074) secondary antibodies were also purchased from Cell Signaling Technology. Caspase 8 primary antibody (sc-7890) was obtained from Santa Cruz technology (Santa Cruz, Calif.). iNOS primary antibody (PA1-036) was from Pierce (Rockford, Ill.) and nitrotyrosine antibody (ab7048) was obtained from Abcam (Cambridge, Mass.).

Animals.

Ten-week-old male Sprague Dawley rats were purchased from Hilltop Laboratories (Scottsdale, Pa.) and housed for 1-2 weeks to allow acclimation before the initiation of any experiments. Animals were housed two to a cage with 12-12 dark-light cycles at 25° C. Food and water was provided ad libitum. All animal care and experimental procedures were performed after approval by the Marshall University Institutional Animal Care and Use Committee (IACUC) and in accordance with the Guide for the Care and Use of Laboratory Animals.

Cecal Inoculum (CI) Peritonitis Model.

Animals were anesthetized using isoflurane and fecal peritonitis was induced by making a small abdominal incision followed by the introduction of cecal material and closure of the incision as described previously. The cecal material was prepared by mixing cecal contents obtained from fresh donor rats with 5% dextrose water to yield a concentration of 600 mg cecal material in 5 ml/kg. The CI and CI+ $CeO_2$ nanoparticle treatment animals received fresh inoculum from the same donor animal in each experiment. Sham control animals underwent an identical surgery to induce fecal peritonitis, but received sterile dextrose water (5 ml/kg, i.p.) only. $CeO_2$ nanoparticles (US Research Nanomaterials, Inc. Houston, Tex.) in 200 µL of sterile distilled water were given via the tail vein at the time of peritonitis induction. Sham control and CI group received vehicle (200 µL sterile distilled water). All animals were sacrificed at 3 h and 18 h after the surgery.

Blood Sampling.

Arterial blood sampling was collected via femoral artery catheter at 18 h at the time of sacrifice. Hematocrit was measured from centrifuged arterial blood samples taken in heparinized capillary tubes (Readacrit Centrifuge, Clay Adams, Parsippany, N.J.).

In Vitro Diaphragm Contraction.

Diaphragm contractile function was measured as previously described. Briefly, the entire diaphragm with ribs and the central tendon attached was removed from isoflurane anesthetized animals and quickly placed in ice cold Krebs buffer solution containing (mM) 118 NaCl, 4.7 KCl, 2.5 $CaCl_2$, 1.2 $MgSO_4$, 10 glucose, 1.2 $NaH_2PO_4$ and 25 $NaHCO_3$ oxygenated with 95% $O_2$ plus 5% $CO_2$ to maintain pH 7.4. Two rectangular muscle strips approximately 3-4 mm widths from the costal region of each hemidiaphragm were dissected from the central tendon to the rib along the fiber orientation. The central tendon and ribs were tied with silk sutures with loops to mount the muscle strips in the organ bath. The muscle strips were mounted on the two stainless pins in a glass organ bath and electrical field stimulation (EFS) was delivered using two platinum electrodes along either side of the muscle (Grass Stimulator S88). The Krebs buffer solution in the organ bath contained 10 µM d-tubocurarine chloride (Sigma-Aldrich, St Louis, Mo.) to block nicotinic acetylcholine receptors during electric stimulations and the bath temperature was kept at 25° C. After the 15 min equilibration, EFS with 2 ms single square-wave pulse was delivered at super maximal voltage set at 140 V to contract muscle strips. In order to determine optimal tension ($L_o$), diaphragm muscle strips were stretched in a stepwise manner and the single pulse twitch protocol was repeated to achieve the maximum active tension. Thereafter, tetanic tension was assessed at $L_o$ by measuring active tension developed in response to the sequential stimulation with trains of 1-150 Hz stimuli (train duration 500 ms). An interval of 3 min was used between the muscle contractions. Isometric contraction was recorded using a force displacement transducer (FTD3, Grass Technologies, Warwick, R.I.) to a Grass polygraph and the data were digitized at 5K Hz using storage oscilloscope (DSO-8502, Link Instrument Inc., Fairfield N.J.). Specific tension was normalized to the estimated muscle cross sectional area by the following equation. [CSA=wet weight (g)/length (cm)×1.06 (density g/cm$^3$)] (7)

Immunoblot Analysis.

Semiquantitiative immunodetection was performed as detailed previously. Briefly, diaphragms were pulverized and then homogenized in Tissue Protein Extraction Reagent (Pierce, City, State) supplemented with 1 mM DTT, protease, and phosphatase inhibitor cocktails (Sigma, St. Louis, Mo.). Lysates were sonicated on ice and centrifuged at 10,000×g at 4° C. for 10 min. The supernatant was removed and protein concentration was determined by 660 protein assay reagent (Sigma, St. Louis, Mo.). Samples were diluted in Laemmli sample buffer and equal amounts of protein were separated by SD S-PAGE, followed by electroblotting onto nitrocellulose membranes. Membranes were blocked with 5% milk in TBST for 1 h at room temperature, and washed three times in TBST before incubation overnight at 4° C. with primary antibodies. Membranes were incubated with the secondary antibody conjugated with HRP for 1 h at room temperature. An enhanced ECL was used to detect immunoreactivity using a FluorChem E System (Cell Biosciences, Santa Clara, Calif.).

Histochemical Analysis.

Procion Orange: A bolus administration of 1.5 ml (3% procion orange in 0.9% sterile saline) was infused via femoral vein catheter. After allowing the dye to circulate for 15 min, diaphragm muscle was quickly frozen in liquid nitrogen cooled isopentane. In some animals, muscle strips were immersed in HEPES buffer containing 0.2% Procion orange (Sigma-Aldrich, St Louis, Mo.) for 1 h at room temperature and quickly frozen as described above. Frozen tissues were serially sectioned in 10 µm and placed on poly lysine coated slides. Images were obtained using an inverted fluorescent microscope (EVOS AMG, Bethell, Wash.) using a GFP filter (excitation 450 nm/emission 505 nm)

Hematoxylin and eosin (H & E) staining: Frozen tissues sections from animals without procion orange perfusion were fixed in 4% formalin in PBS, and sections were stained with H & E according to the manufacturer (BBC Biochemical, Mount Vernon, Wash.). Images were obtained using an inverted microscope (EVOS AMG, Bethell, Wash.)

Real Time Polymerase Chain Reaction (PCR).

Real Time PCR was performed for quantification of iNOS and TNF α using a 7500 Real Time PCR system (Applied Biosystems, Foster City, Calif.) as described previously. Briefly, total RNA was extracted using Trizol reagent (Sigma-Aldrich, St Louis) according to the manufacturer's guidelines, and cDNA was synthesized using 1 μg of RNA with the High-Capacity cDNA Reverse Transcription Kit (Applied Biosystems, Foster City, Calif.). SYBR green PCR amplification was performed with SensiMix™ SYBR low-ROX kit (Bioline, London, UK) using the following primers iNOS (NM_012611.3; 5'-GGA AGA GAC GCA CAG GCA GAG-3' and 5'-GCA GGC ACA CGC AAT GAT GG-3'; product size 126 bp), and GAPDH (NM_017008.4; 5'-GTT ACC AGG GCT GCC TTC TC-3' and 5'-GGG TTT CCC GTT GAT GAC C-3'; product size 168 bp) according to the manufacturer's guidelines. Each sample was analyzed in triplicate in 25 μl reactions. For the negative control, a non-template control was included in all PCR reactions. Specific products were determined by the melting curve analysis as well as agarose gel electrophoresis using ethidium bromide. Expression levels between groups were compared using the relative comparison method ($2^{-\Delta\Delta CT}$).

Statistics.

Data are presented as the mean and standard error of the mean as described in the text and figure legends. Statistical comparisons were made using paired-t tests, one- or two-way ANOVA with Bonferroni post hoc tests as appropriate. A $p<0.05$ was considered as significant.

Results of Example 6

$CeO_2$ Nanoparticle Treatment Improves Diaphragmatic Function in the Septic Rat.

Figure 30A:
FIGS. 30A-30B include graphs showing the ability of $CeO_2$ nanoparticle treatment to improve diaphragmatic contractility in the septic rat, including graphs showing representative recording trances of contractile response (FIG. 30A), and a graph showing the ability of nanoparticle treatment to improves diaphragm tension development (FIG. 30B, * vs. Control, † versus CI)
Figure 30B:
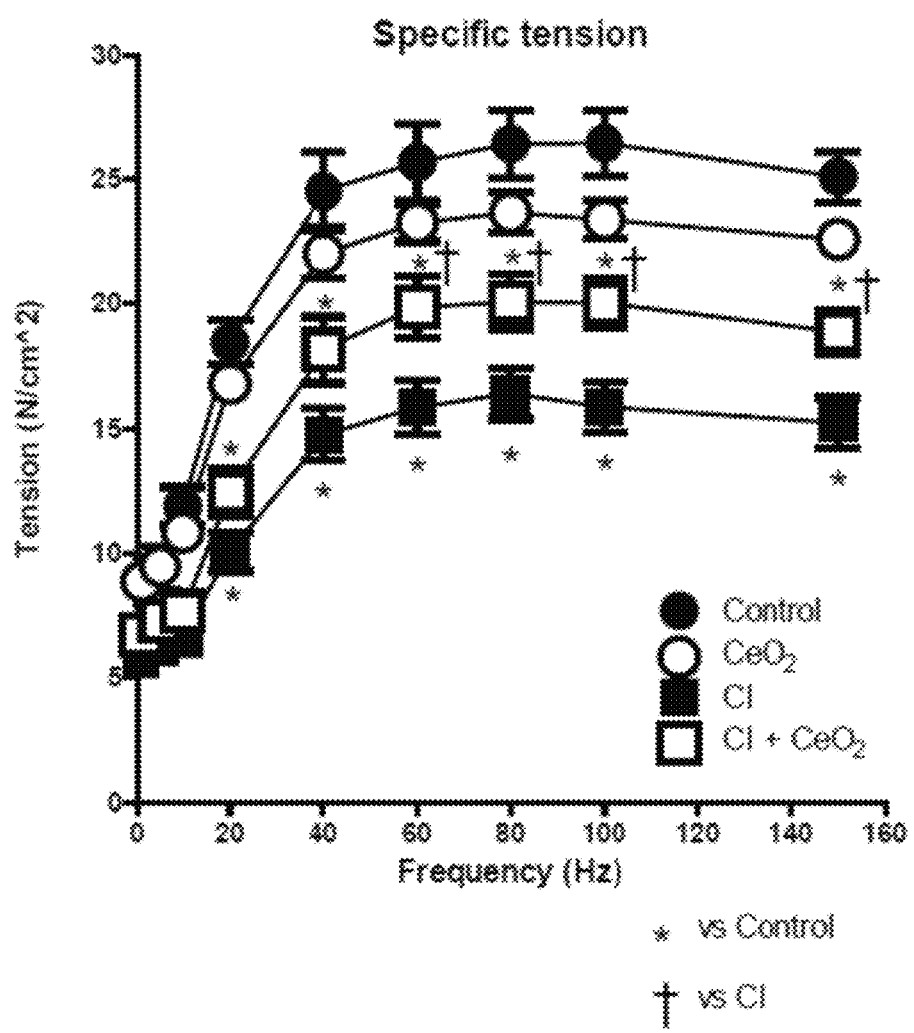
Figure 31A:
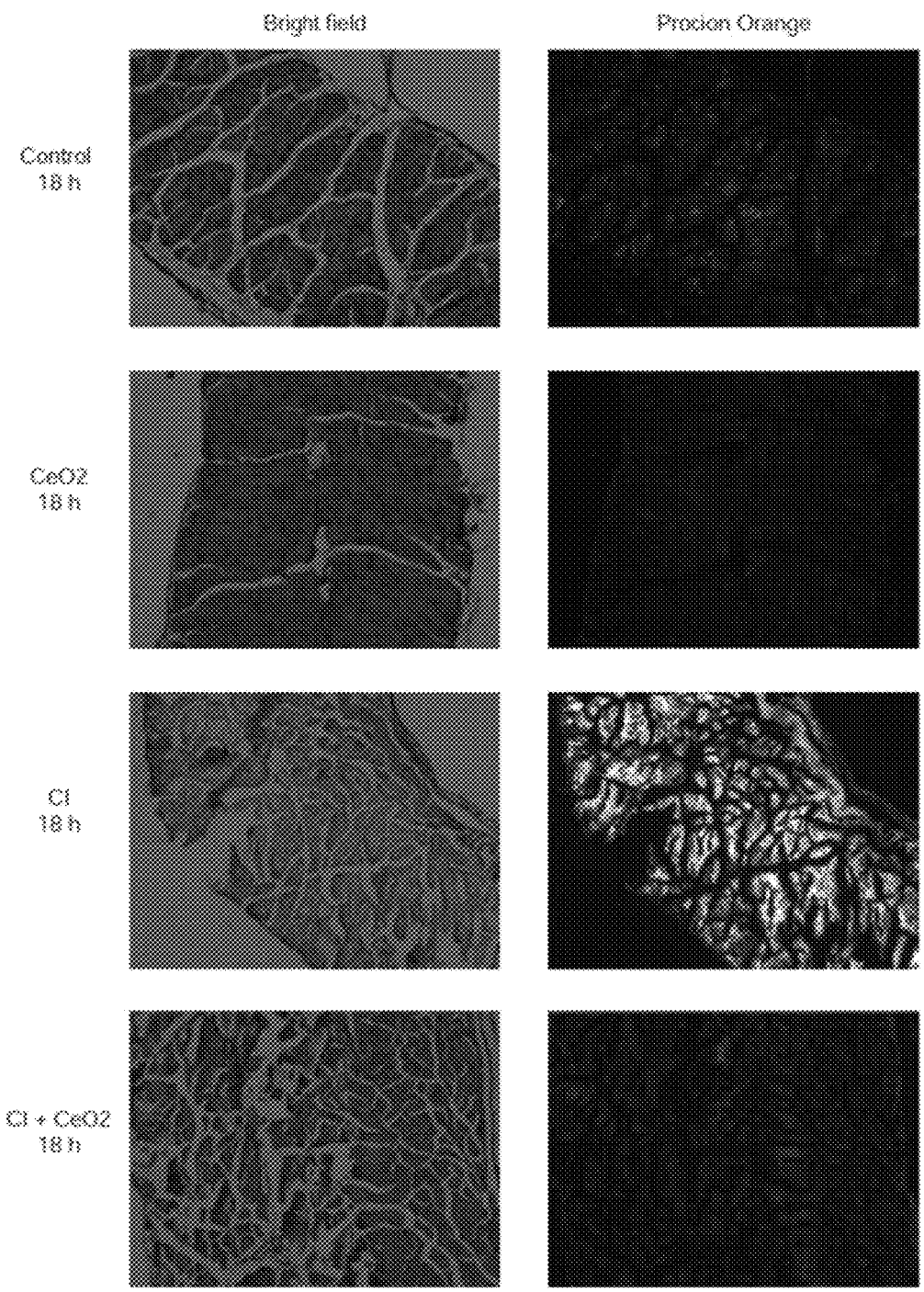
FIGS. 31A-31B include images showing the ability of $CeO_2$ nanoparticle treatment to decrease sepsis induced muscle damage; including images showing that nanoparticle treatment functions to protect the muscle membrane as suggested by diminished Procion orange signal in the treated animals (FIG. 31A), and images showing that sepsis increases and nanoparticle treatment decreases cellular infiltration (FIG. 31B)
Figure 31B:
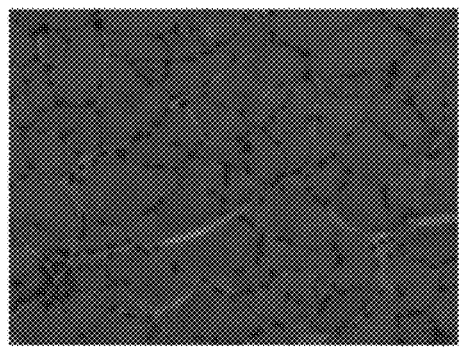
Figure 31B:
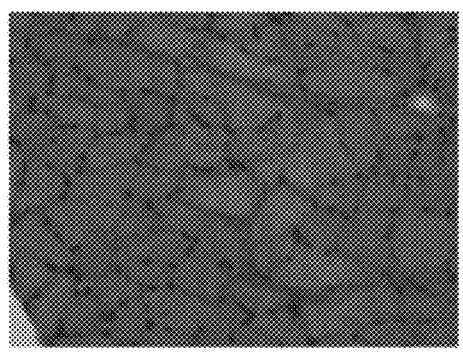
Figure 31B:
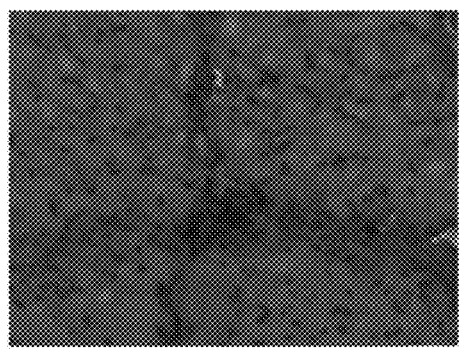
Figure 31B:
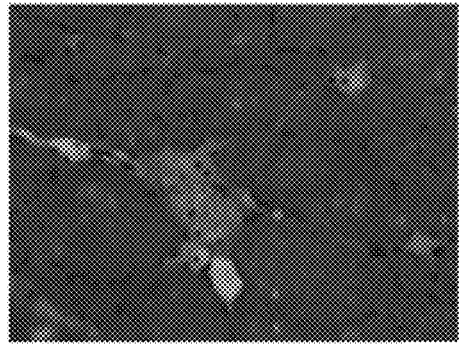

There were significant differences in pre-/post body weight and serum hematocrit levels for the CI and CI+$CeO_2$ groups but not the sham and $CeO_2$ only treated animals (Table 7). The muscle length at which maximal tension was developed ($L_o$) was not different between groups (Table 7). Peak twitch tension was 93±5, 68±4, and 82±5% of sham control for $CeO_2$ only, CI, and CI+$CeO_2$ respectively (Table 7: $p<0.05$). Similarly, peak tetanic tension was 89±3, 62±4, and 78±4% of sham control for $CeO_2$ only, CI, and CI+$CeO_2$, respectively. (FIGS. 30A-30B: $P<0.05$). Consistent with these data, procion orange dye diffusion into the CI diaphragm appeared to be much greater than that observed in the other groups (FIG. 31A). Histological analysis following H & E staining suggested that sepsis was associated with increased cell infiltration that appeared to be diminished with nanoparticle treatment (FIG. 31B).

TABLE 7

Characteristics of diaphragm strip and each animal group at 18 h.

| | Sham Control | $CeO_2$ only | CI | CI + $CeO_2$ |
|---|---|---|---|---|
| Pre-body weight (g) | 419.3 ± 1.9 | 417.9 ± 8.7 | 407.3 ± 5.0 | 409.6 ± 2.8 |
| Post-body weight (g) | 425.3 ± 2.1 | 420.8 ± 8.2 | 396.1 ± 4.5 * | 402.1 ± 3.5 * |
| Delta (g) | 6.1 ± 1.2 | 2.9 ± 1.5 | −10.0 ± 1.3 * | −7.6 ± 2.2 * |
| Hematocrit | 41.3 ± 4.3 | 46.0 ± 4.0 | 61.8 ± 3.3 * | 58.6 ± 1.6 * |
| Strip weight (mg) | 39.7 ± 3.7 | 36.2 ± 2.8 | 39.7 ± 1.7 | 39.3 ± 1.9 |
| Lo (mm) | 20.5 ± 0.4 | 20.4 ± 0.8 | 20.0 ± 0.5 | 19.3 ± 0.3 |
| Pt (N/cm$^2$) | 9.68 ± 0.78 | 9.04 ± 0.49 | 6.56 ± 0.34 * | 7.91 ± 0.48 |
| Po (N/cm$^2$) | 26.45 ± 1.32 | 23.68 ± 0.80 | 16.41 ± 1.03 * | 20.06 ± 1.14 † |
| Contraction time (ms) | 51.28 ± 2.74 | 55.53 ± 3.82 | 49.22 ± 1.74 | 48.19 ± 2.36 |
| Half relaxation time (ms) | 50.45 ± 4.00 | 57.87 ± 4.58 | 58.65 ± 5.27 | 50.00 ± 3.14 |

* $P < 0.05$ compared to control group and
† $P < 0.05$ compared to CI group by One way ANOVA $CeO_2$ Nanoparticle Treatment Attenuates Sepsis Associated Diaphragmatic Inflammation.

Figure 32A:
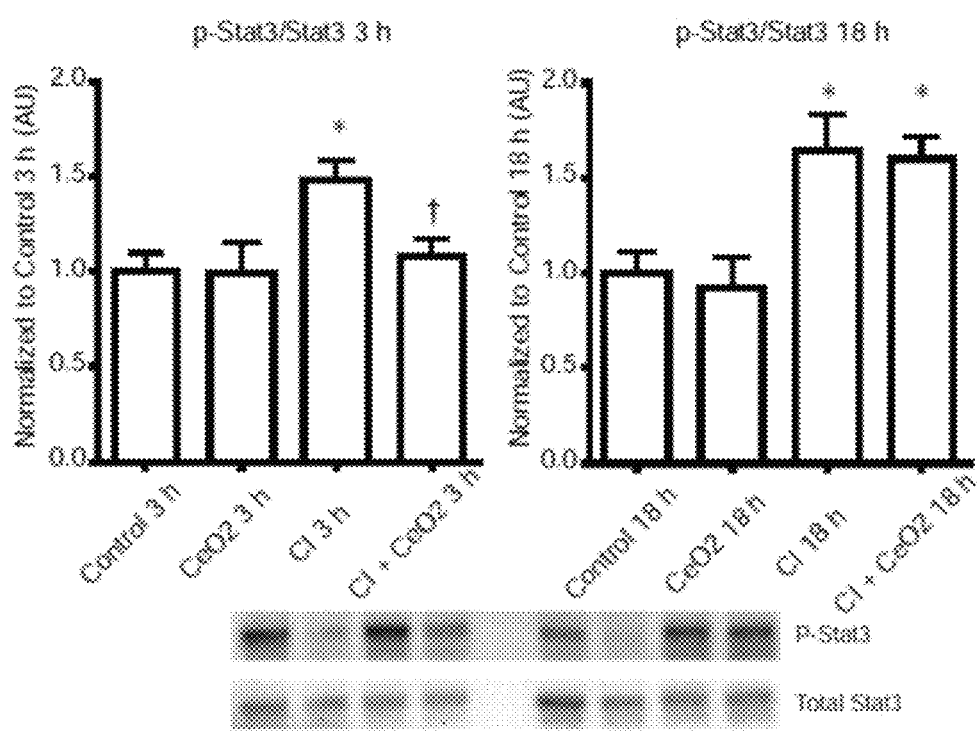
FIGS. 32A-32C include images and a graph showing the ability of $CeO_2$ nanoparticle treatment to attenuate diaphragmatic inflammation after septic insult, including images and a graph showing that sepsis induced increases in stat 3 phosphorylation are diminished with nanoparticle treatment (FIG. 32A), real time PCR amplification curves for iNOS and GAPDH, where iNOS gene expression levels were increased with sepsis and diminished with nanoparticle treatment at 18 h (FIG. 32B), and immunoblot images for iNOS/α-tubulin and nitrotyrosine/α-tubulin are shown (FIG. 32C), * vs. Control, † vs. CI.
Figure 32B:
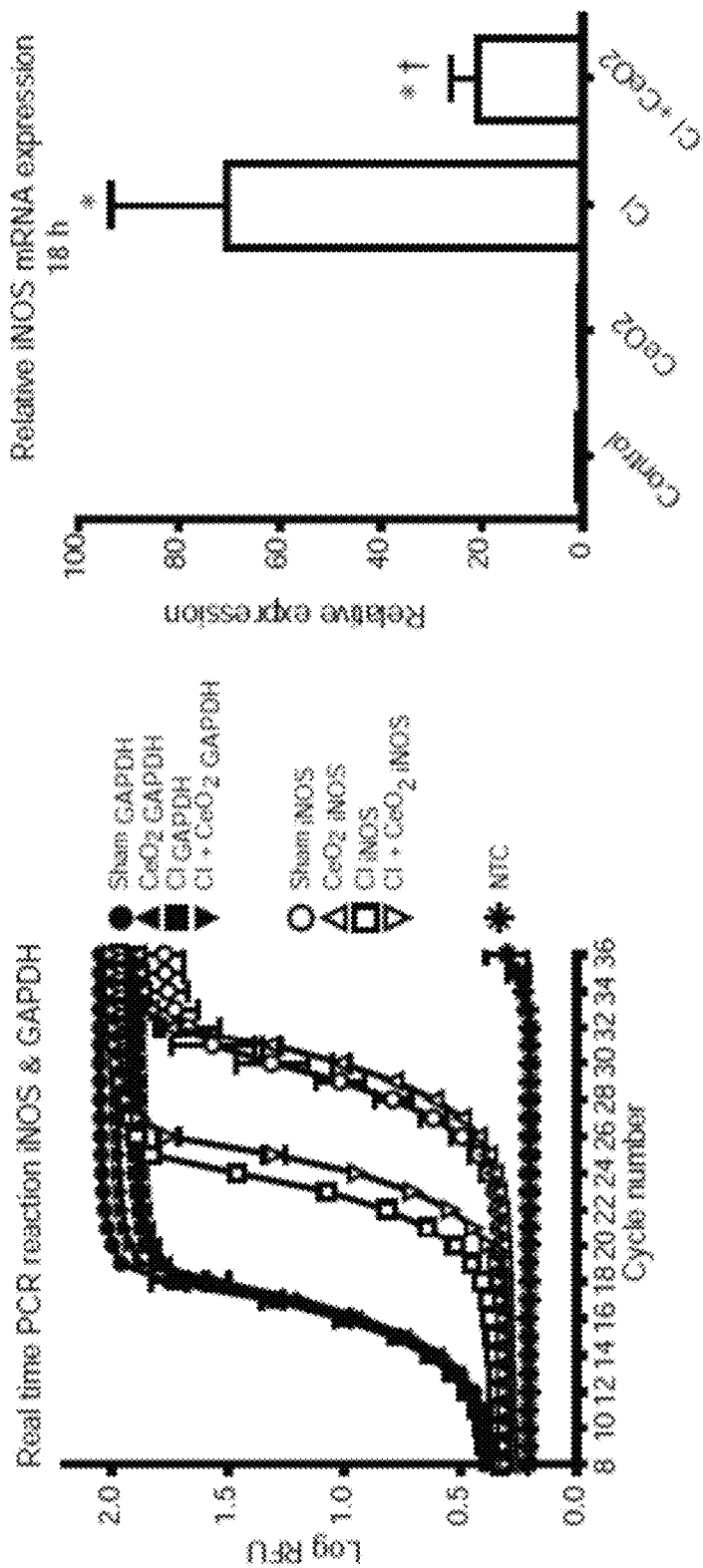
Figure 32C:
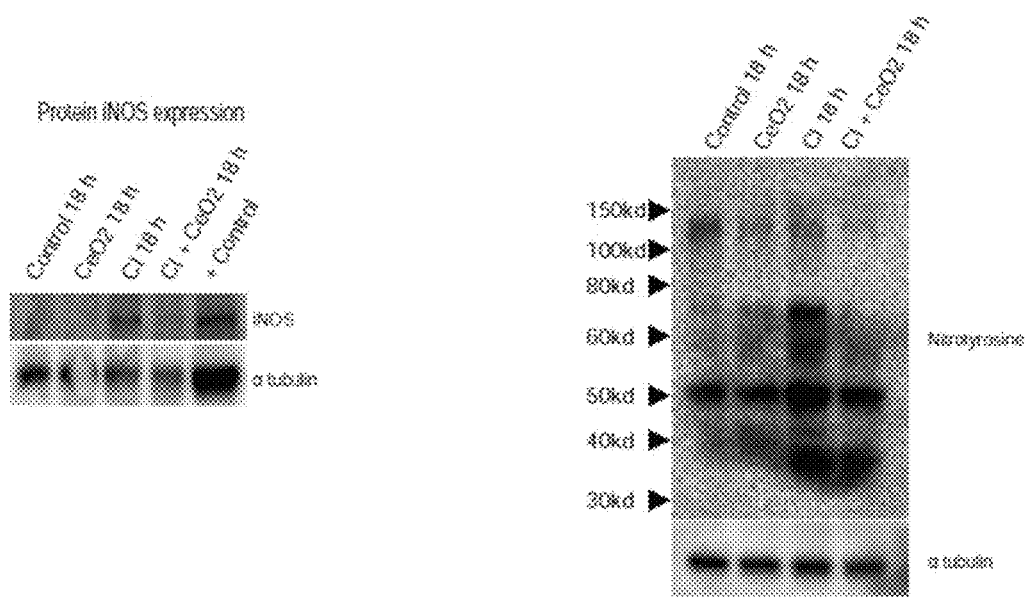

Peritonitis increased the phosphorylation of Stat 3 at 3- and 18 h (FIG. 32A: $P<0.05$). Compared to that seen in the sham animals, CI peritonitis increased iNOS transcript levels at 18 h while nanoparticle treatment significantly decreased iNOS transcript levels compared to CI peritonitis group (FIG. 32B: $P<0.05$). Protein expression of iNOS and nitrotyrosine abundance appeared to be correlated with iNOS qPCR results (FIG. 32C).

$CeO_2$ Nanoparticle Treatment Suppresses Translation Related Signaling, Caspase 8 Cleavage and Protein Ubiquination During Sepsis.

Figure 33A:
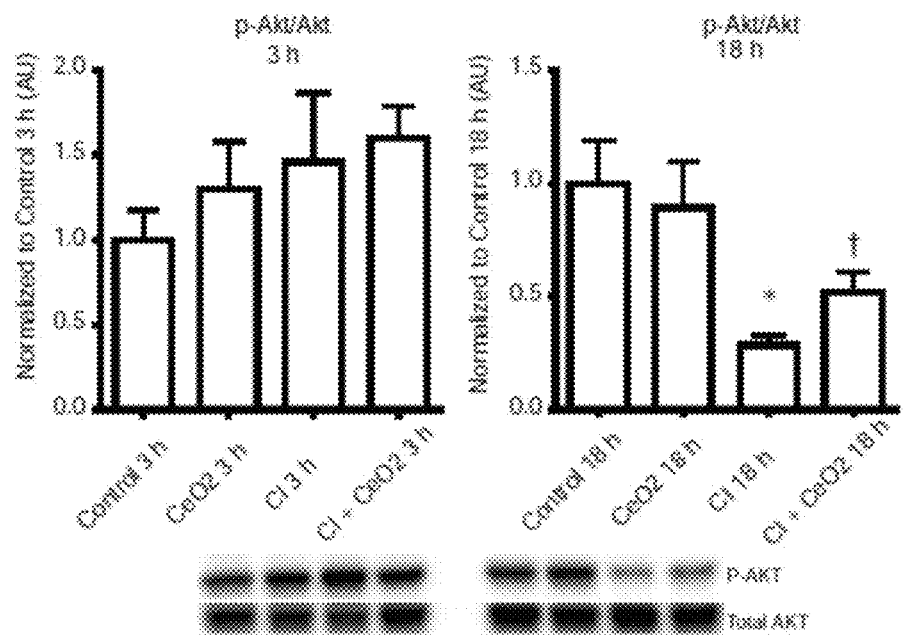
FIGS. 33A-33C include images and graphs showing $CeO_2$ nanoparticle treatment normalizes the disruption of protein synthesis signaling in CI peritonitis diaphragm, including images and graphs showing that nanoparticle treatment increases phospho-Akt (FIG. 33A), phospho-Foxo1 (FIG. 33A), and phospho-4E-BP1 (FIG. 33C) levels in the septic diaphragm (* vs. Control, † vs. CI)
Figure 33B:
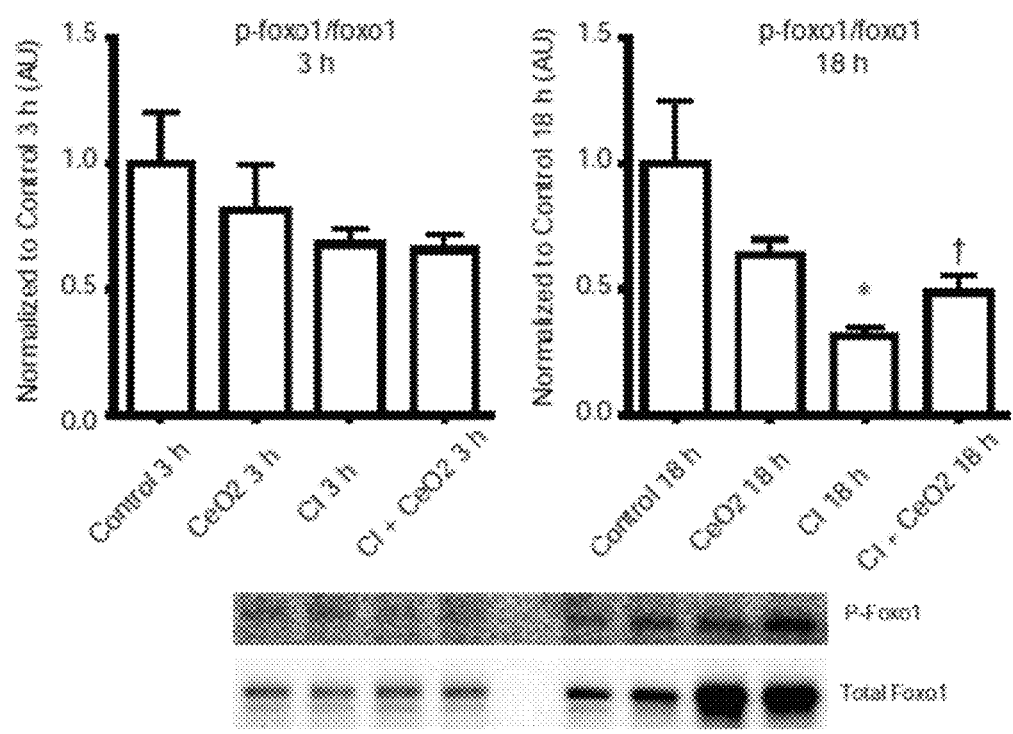
Figure 33C:
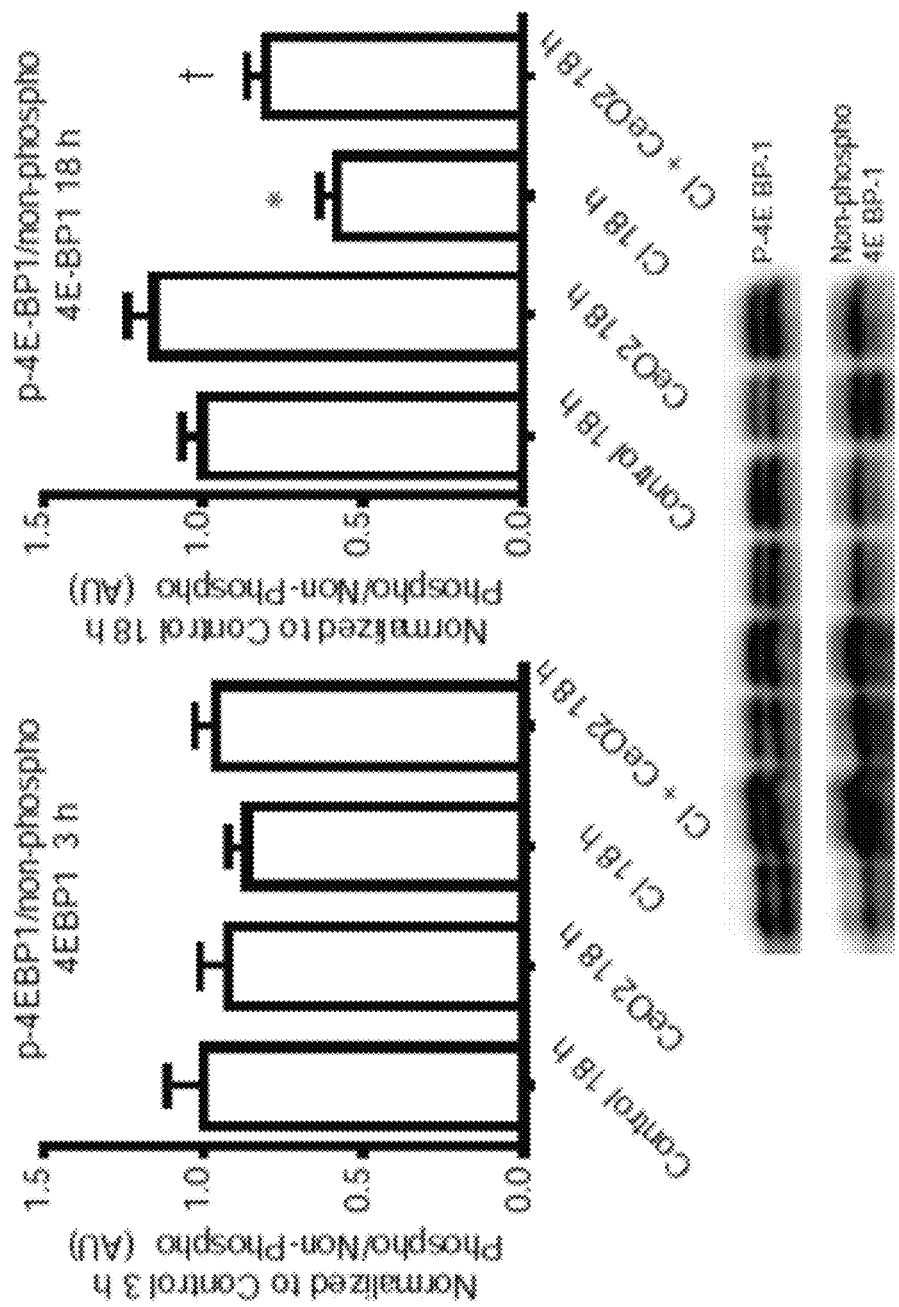

Compared to controls, the phosphorylation of Akt FOXO1 and 4EBP-1 was not changed at 3 h, while CI peritonitis significantly decreased the phosphorylation of Akt, FOXO1 and 4EBP-1 at 18 h (FIGS. 33A-33C: $P<0.05$). $CeO_2$ nanoparticle treatment increased phosphorylation of these molecules to the levels above the sepsis group.

Figure 34A:
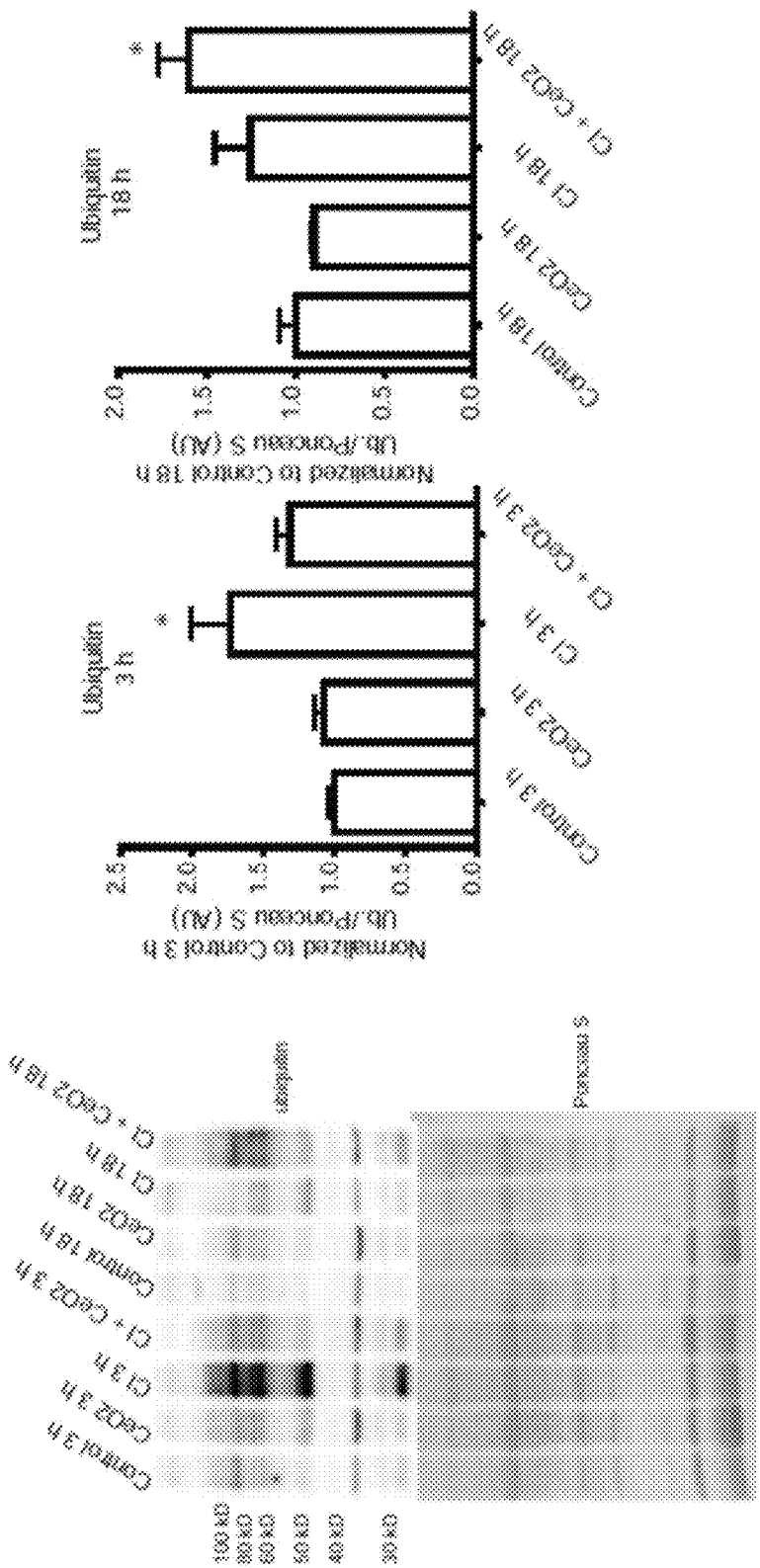
FIGS. 34A-34C includes images and graphs showing that $CeO_2$ nanoparticle treatment decreases protein ubiquination and caspase 8 cleavage during sepsis, including images and graphs showing sepsis and treatment associated changes in protein ubiquination (FIG. 34A), caspase 8 cleavage (FIG. 34B), and apoptotic signaling (FIG. 34C) (* vs. Control, † vs. CI)
Figure 34B:
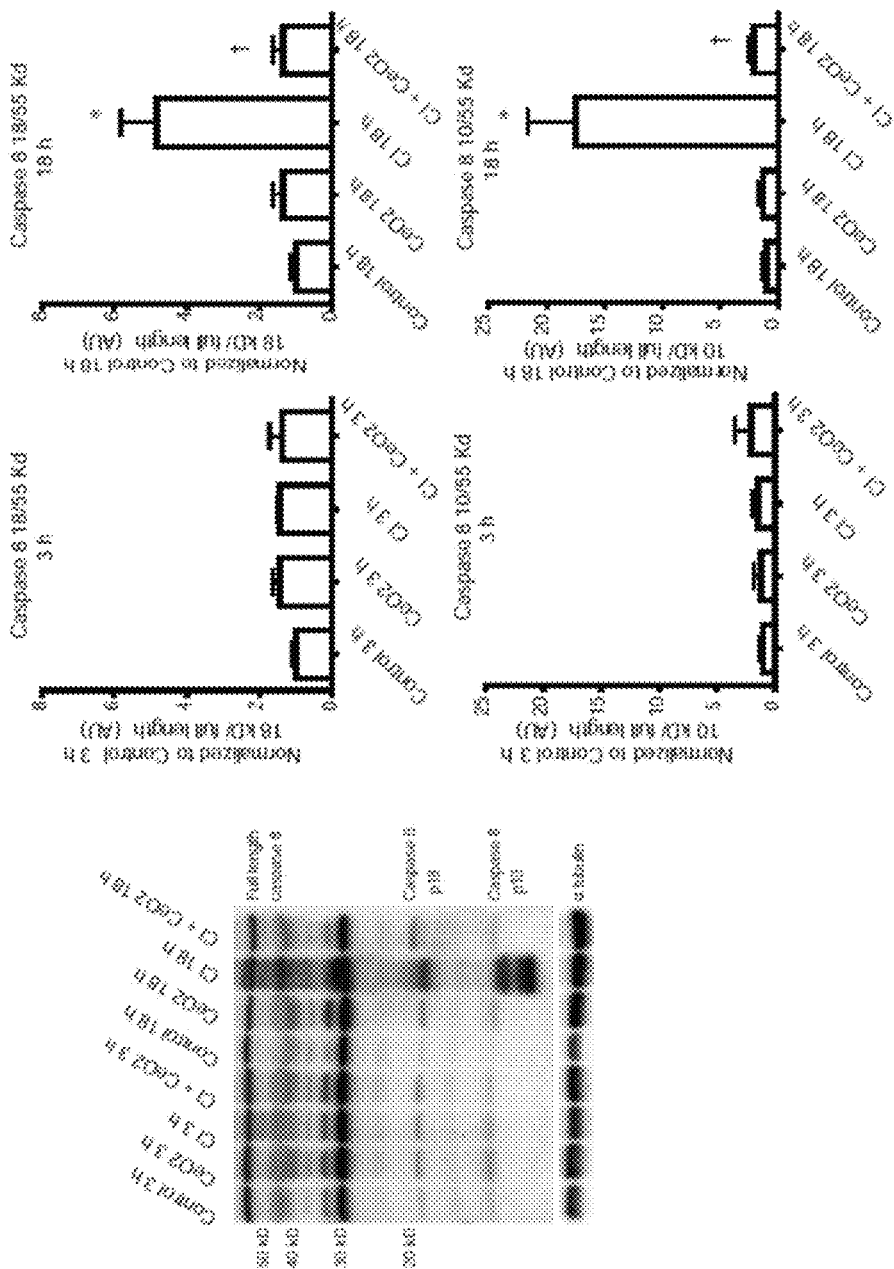
Figure 34C:
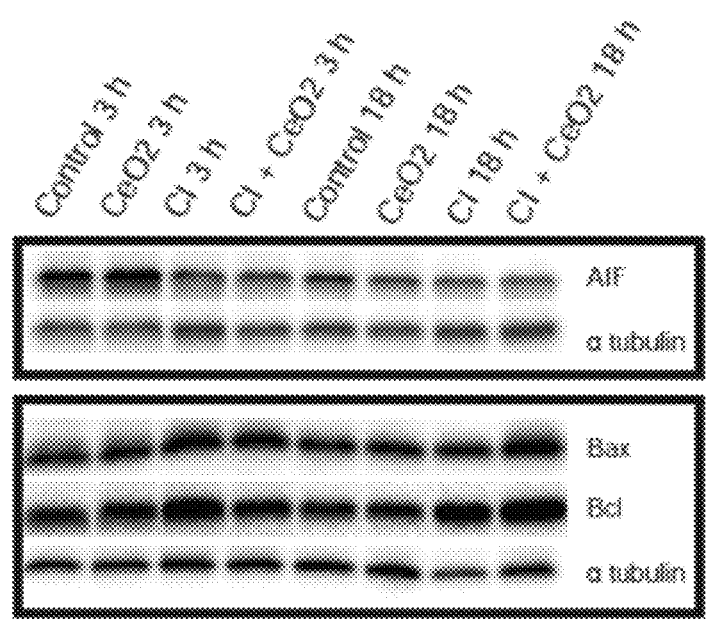

Compared to that observed in the sham animals, CI peritonitis, and nanoparticle treatment increased total protein ubiquination at 3- and 18 h, respectively (FIG. 34A: $P<0.05$). Similarly, CI peritonitis increased the amount of caspase 8 cleavage at 18 h (FIG. 34B: $P<0.05$) which was attenuated with nanoparticle treatment (FIG. 34B: $P<0.05$). Neither CI peritonitis nor nanoparticle treatment was associated with changes in caspase 3 cleavage, apoptosis inducing factor, or the ratio of Bax/Bcl-2 (FIG. 34C).

Discussion of Example 6

Previous work using the CI peritonitis model demonstrated that $CeO_2$ nanoparticle treatment was associated with improved animal survivability and diminished systemic inflammation. Similar to earlier studies employing other sepsis models (5, 11, 20, 36), the above-described studies showed that the CI peritonitis model is also characterized by alterations in diaphragmatic function (FIGS. 30A-30B). Importantly, it was also found that the $CeO_2$ nanoparticle treatment appeared to diminish the effects that the septic condition had on diaphragm tension development. Whether these improvements in diaphragm contractility also reflect an improved pulmonary function in vivo was unclear. Similarly, why muscle function may be decreased with sepsis, or other conditions that are characterized by increased systemic inflammation are not entirely understood; however, it has been suggested that increased cellular infiltration and/or muscle membrane damage may play a role. To investigate this possibility, the effects of CI peritonitis and nanoparticle treatment on muscle histology and membrane permeability were examined following exposure to procion dye. Similar to previous reports, it was found that the diaphragms obtained from septic animals exhibited a marked increase sarcolemma damage and cellular infiltration (FIG. 31A). In addition, and consistent with the findings of improved contractile function with nanoparticle treatment, it was found that these changes in cellular structure appeared to be lessened with nanoparticle treatment (FIG. 31B).

To extend these data, it was next examined if the nanoparticle treatment modulated inflammatory signaling in diaphragm. Several studies have suggested that elevations in the local (muscle) or circulating TNF-alpha may play a key role in regulating diaphragmatic function during infection (6, 16, 20, 23, 34, 37). The above-described data were consistent with this view and previous work that demonstrated elevations in systemic inflammation in the rat CI peritonitis model. How circulating cytokines cause muscle contractile dysfunction remains unclear; however, it has been shown that the activation of Stat3-iNOS signaling by elevations in IL-6 is associated with diminished cardiac contractility. Similar to the mechanisms of the inflammatory response in cardiac muscle, it was found that peritonitis significantly increased Stat3 phosphorylation in diaphragm and importantly, that this increase was attenuated with nanoparticle treatment (FIG. 32A). Likewise, increases in NO have been shown to directly impair contractile function in a number of different skeletal muscles including the diaphragm. Consistent with this premise, it was found that peritonitis significantly increased iNOS gene expression, protein content and protein nitration levels in diaphragm (FIGS. 32B-32C). Similar to the contractile measurements, these alterations in NO signaling were attenuated with nanoparticle treatment. Taken together, these data indicated that nanoparticle treatment attenuated peritonitis-induced diaphragm dysfunction and that this improvement in contractility may be associated with diminished inflammatory signaling.

In addition to muscle damage and increased inflammatory signaling, it was also thought that increases in protein degradation may also be associated with diminished contractile function. Herein, it was found that peritonitis was associated with an increase in the amount of ubiquinated protein at 3 h (FIG. 34A). Why protein ubiquination might be increased during the initial septic response is not yet clear. The coupling of ubiquitin to muscle proteins is thought to be regulated, at least in part by the activity of the muscle E3 ligases MURF-1 and MAFbx which in turn, are thought to be regulated by FOXO-1. The activity of FOXO-1 is controlled by its phosphorylation by Akt, with increased FOXO-1 phosphorylation causing a decrease in its transcriptional activity. Here, it was found that peritonitis was associated with diminished Akt and FOXO phosphorylation (activity) (FIGS. 34A-34B). In addition to its ability to protect the muscle against apoptosis and protein degradation, it is also known that Akt functions in the regulation of protein synthesis. To examine this possibility, the effect of peritonitis and the nanoparticle intervention on the phosphorylation of 4EBP-1 was next determined. It was thought that 4EBP-1 functions to inhibit translation by binding to the translation initiation factor elF4E. It was found that CI peritonitis was associated with decreased phosphorylation of 4EBP-1 (FIG. 34C). This finding was consistent with previous work showing both endotoxemia and polymicrobial sepsis models decrease phosphorylation of 4EBP-1 in rat skeletal muscle. Importantly, it was also found that the nanoparticle treatment normalized this decreased phosphorylation of 4EBP-1 in diaphragm.

Similar to that observed for the effects of protein degradation on muscle function, it was also thought that increased muscle apoptosis can also diminish muscle function. Like previous reports using the LPS endotoxemia model and other work examining the effects of fecal peritonitis on circulating cytokine levels, it was also found that this model was associated with increased caspase-8 cleavage (FIG. 34B). To determine if increases in caspase-8 cleavage led to increased muscle apoptosis, it was next examined if peritonitis was associated with increased cleavage of caspase-3. Unlike previous data showing that LPS challenge increased caspase-3 activity in the rat diaphragm, the above-described studies failed to find any change in caspase-3 cleavage or caspase-3 activity in CI peritonitis model. Supporting these data, the experiments failed to find any change in the ratio of Bax/Bcl-2 or in the amount of AIF protein (FIG. 34C).

In summary, the above-described studies demonstrated that $CeO_2$ nanoparticle treatment improved CI peritonitis-induced diaphragm dysfunction. This improvement was associated with alterations in NO-related signaling and what appeared to be improvements in the balance between protein synthesis and proteolysis. The study demonstrated that the systemic delivery of nanoparticles can be used to improve diaphragm dysfunction in preclinical animal model of sepsis.

Example 7—Inhibition of MAP Kinase/NF-κB Mediated Signaling and Attenuation of Lipopolysaccharide Induced Sever Sepsis by Cerium Oxide Nanoparticles Ceria is a rare earth element of the lanthanide series that is used in automobile catalytic converters to convert carbon monoxide to carbon dioxide. As described above, in its oxide form, ceria can transition between $Ce^{3+}$ and $Ce^{4+}$ oxidative states which can allow for auto regenerative redox cycling and free radical scavenging. Although the use of $CeO_2$ in nanoparticle form for biomedical applications awaits further development, previous studies have indicated that these particles possess anti-oxidative activity and that they tend to accumulate in the Kuppfer cells when injected into the systemic circulation of the laboratory rat. On the basis of these data, it was believed that the systemic administration of $CeO_2$ nanoparticles could be associated with diminished Kupffer cell cytokine/chemokine release and decreased SIRS development which would result in improved animal survival following sepsis insult.

Materials and Methods for Example 7
Cerium Oxide Nanoparticle Preparation and Characterization.

The $CeO_2$ nanoparticles were purchased from Sigma-Aldrich (USA) and characterized as outlined. Stock suspensions (3.5 mg/ml) were prepared in $ddH_2O$ by sonication (600 W for 2 min) using a Vibra Cell Sonicator (Sonics & Materials, Inc.) at room temperature and characterized. Dynamic light scattering (DLS) was performed to estimate the mean size of $CeO_2$ NPs in suspension using LB-550 DLS particle size analyzer (Horiba Scientific, Edison, N.J.). Naked particle size of the $CeO_2$ NPs was characterized by transmission electron microscopy (TEM) using JEOL JEM 1200Ex. X-ray diffraction (XRD) was performed using a Scintag XDS 2000 powder diffractometer. Scanning transmission electron microscopy (STEM) images were acquired using a JEM-ARM200CF (JEOL, Japan) operated at 200 keV. The oxidative state of cerium was analyzed by X-ray photoelectron spectroscopy (XPS) using a PHI ESCA 5400 spectrophotometer.

Animal Preparation and Experimental Design.
Animals were prepared for experiments as detailed in the supplementary methods and were randomly assigned to one of four groups. The control group (n=6) received 1.5 ml of endotoxin free water by i.p. while the $CeO_2$ nanoparticle treated group (n=6) received 1.5 ml of endotoxin free water by i.p. and $CeO_2$ nanoparticles (0.5 mg/kg) in 200 i.tl of sterile distilled water via the tail vein. The LPS treated group (n=12) received LPS (055-B5; 40 mg/kg, Sigma, St. Louis, Mo.) in 1.5 ml of sterile water by i.p. and 200 µl of sterile distilled water via the tail vein while the LPS+CeO$_2$ NPs treatment group received LPS (40 mg/kg) in 1.5 ml of sterile water by i.p. and CeO$_2$ nanoparticles (0.5 mg/kg) in 200 µl of sterile distilled water via the tail vein. The animal survival rate was assessed for a period of 7 days. LPS-induced sepsis symptoms were quantitated by monitoring animal behavior, body temperature and respiratory rate using a Mouse Ox Plus from Star Scientific Corp (Massachusetts, USA), while heart rate and blood pressure were evaluated using a CODA blood pressure system from Kent Scientific (Connecticut, USA).

Sample Collection, Estimation of Blood Cell Number and Quantification of Serum Cytokines.

In an additional set of experiments, blood and livers were collected at 6 or 24 h after study initiation. Differential blood cells were estimated in whole blood using an Abaxis VetScan HM2 hematology analyzer (Abaxis, Union city, CA). Serum TNF-α levels were analyzed by enzyme-linked immunosorbent assay (ELISA) (BD Bioscience, Franklin Lakes, N.J.). Serum samples from each of the different groups (n=6/group) were pooled and sent to Myriad RBM (Austin, Tex.) for the analysis of cytokines, chemokines and markers of inflammation using rodent MAP® V. 3.0 as detailed elsewhere. Nitrite in the serum was assayed using the Griess reaction using a kit from Cayman Chemical Company (Ann Arbor, Mich., USA).

Estimation of CeO$_2$ Nanoparticle Content in the Liver and Analysis of Liver Damage.

Liver ceria content was estimated by induction coupled plasma-mass spectrometry (ICP-MS) as described elsewhere. In other experiments, portions of each liver were formalin fixed, sectioned, and stained with hematoxylin and eosin (H&E) for histopathological examination. Microscopic images were captured using an EVOS XL Core microscope (Fisher Scientific, Pittsburgh, Pa., USA). Liver damage markers in the serum were estimated using an Abaxis VetScan analyzer (Abaxis, Union City, Calif.) and Myriad RBM (Austin, Tex.).

Immunoblotting and TUNEL Staining.

Proteins samples were prepared from the liver for immunoblotting as detailed in the supplementary methods. Liver cell apoptosis was assessed using a transferase-mediated dUTP nick-end labeling (TUNEL) kit (Roche Applied Science, Indianapolis, Ind.) as described previously.

Kupffer Cell Isolation and Assays.

Kupffer cells were isolated from rat liver and purified by differential centrifugation using a Percoll gradient as described previously [17]. The purity of the KCs was determined by ED1 and ED2 staining (immunofluorescence) as described previously. KCs were cultured and treated with LPS in the presence and absence of CeO$_2$ nanoparticles for 24 h and TNF-α release was measured by ELISA. Reactive oxygen species (ROS) levels were determined using the OxiSelect™ kit from Cell Bio Labs (San Diego, Calif.), as outlined by the manufacturer.

Macrophage Uptake of CeO$_2$ Nanoparticles and Effect Against LPS Challenge.

The cytotoxic and protective effect of CeO$_2$ nanoparticles against LPS challenge was determined by the MTT assay as described in the supplementary methods. CeO$_2$ nanoparticle uptake by the macrophage cells was estimated by inductively coupled plasma-mass spectrometry (ICP-MS) at Elementary Analysis Inc. (Lexington, Ky., USA) as described previously. ROS levels were determined using the OxiSelect™ kit from Cell Bio Labs (San Diego, Calif.) while mitochondrial membrane damage was estimated by Δψm using the JC 1 dye (Cell Technology, Mountain View, Calif.) as described elsewhere. Nitrite production was assayed using the Griess reaction kit from Cayman Chemical Company (Ann Arbor, Mich., USA) as described by the manufacturer. The concentration of TNF-α, IL-6, IL-1β and HMGB1 in the media was measured by ELISA reagent kits as described in the supplementary methods.

Electromobility Shift and Luciferase Reporter Assays.

The electromobility shift (EMSA) assay was performed using a commercially available kit (Pierce, Rockford, Ill., USA) as described therein. Luciferase reporter assays were performed using a NF-κB reporter construct from Promega (Madison, Wis., USA).

Statistical Analysis.

Data are presented as mean±standard error of the mean (SEM). Dependent variables were analyzed by one way ANOVA by Holm-Sidak test using SigmaStat (Aspire Software International, Auburn Va.) and post-hoc testing where appropriate. A P<0.05 was considered as significant.

Results of Example 3

Characterization of CeO$_2$ Nanoparticle.

Figure 35A:
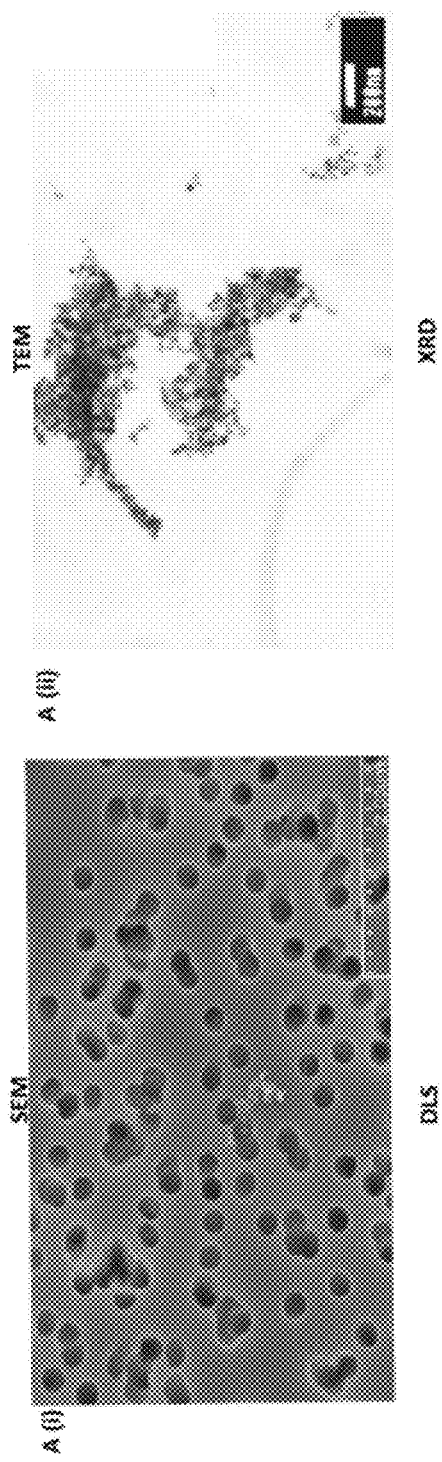
Figure 35B:
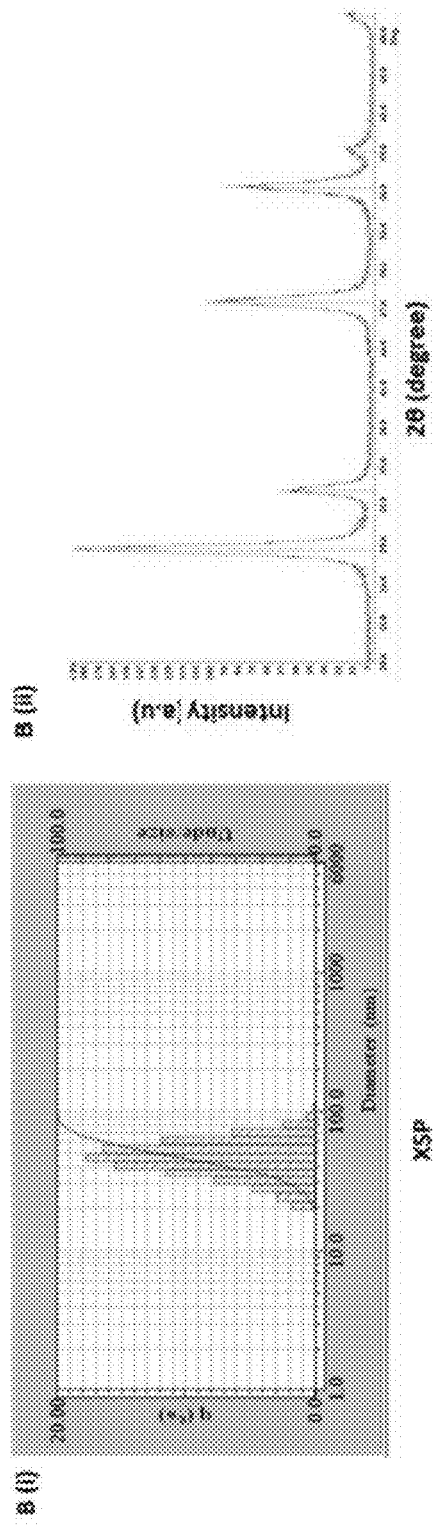
Figure 35E:
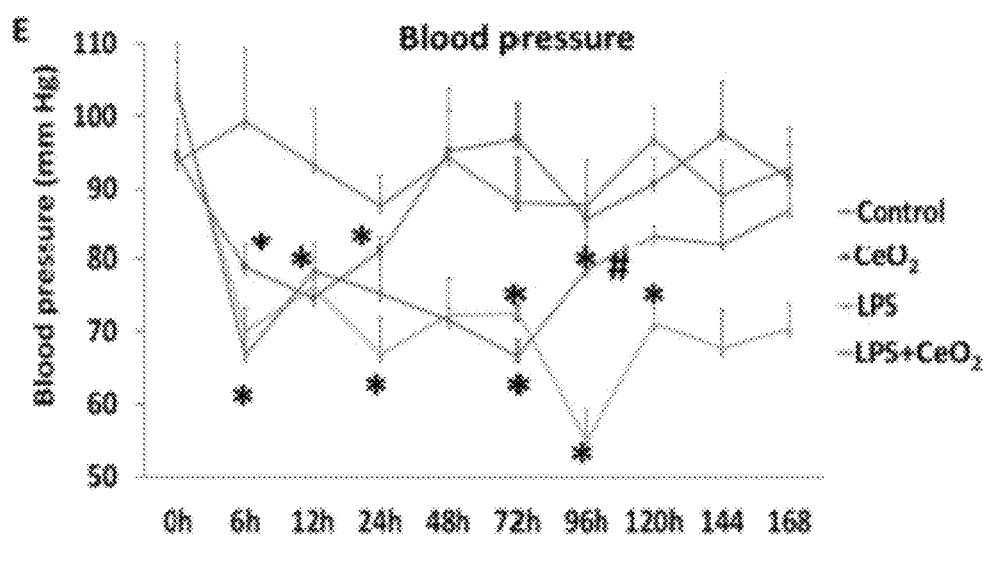

SEM and TEM analysis determined the size of individual nanoparticles to be between 20-40 nm (FIG. 35 A, A(i, ii)). The mean hydrodynamic diameter of CeO$_2$ nanoparticles as estimated by dynamic light scattering was 53.36±7.04 nm (FIG. 35B, B(i)). XRD spectral analysis confirmed the purity of CeO$_2$ nanoparticles preparation and demonstrated well defined peaks 2θ=28.5, 33.1, 47.5, 56.2, 59.0 and 69.2. No other peaks related to impurities were detected (FIG. 35B, B(ii)). XSP spectral analysis indicated a higher concentration of Ce$^{4+}$ than Ce$^{3+}$ in the CeO$_2$ nanoparticles (FIG. 35C, C(i)).

Effect of CeO$_2$ Nanoparticle Treatment on Animal Mortality and Physiological Function.

Figure 1E:
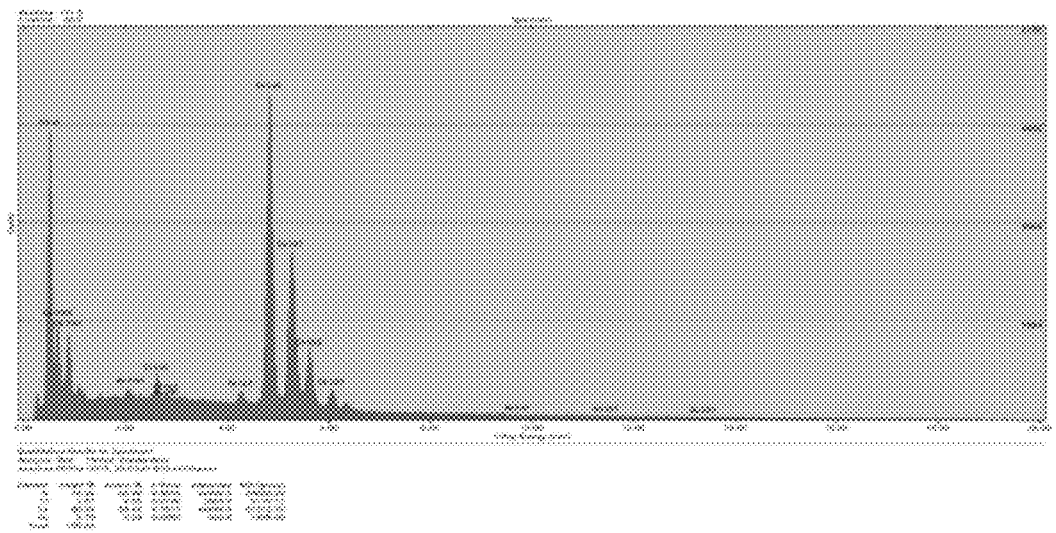
Figure 2:
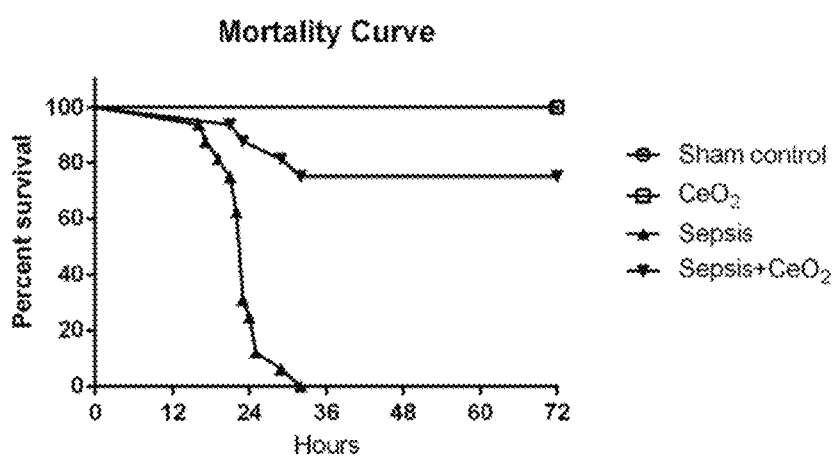
FIG. 2 is a graph showing the ability of cerium oxide nanoparticles to significantly improve survivability in septic animals ($p<0.001$)
Figure 3:
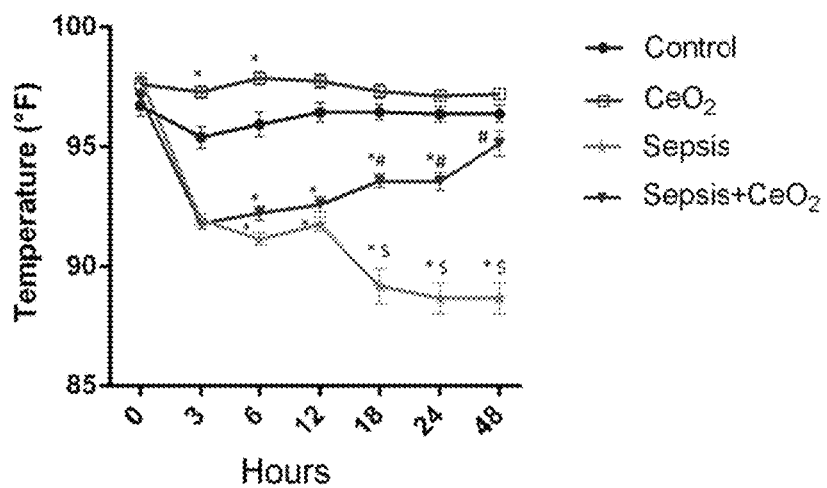
FIG. 3 is a graph showing the ability of cerium oxide nanoparticles to significantly improve survivability in septic animals, where "*" indicates a significant difference from control animals, "#" indicates a significant difference from sepsis animals, and "$" indicates temperature of animals that have died in previous time points and have be used for later time points for running a two way ANOVA of repeated measures ($p<0.05$).
Figure 4:
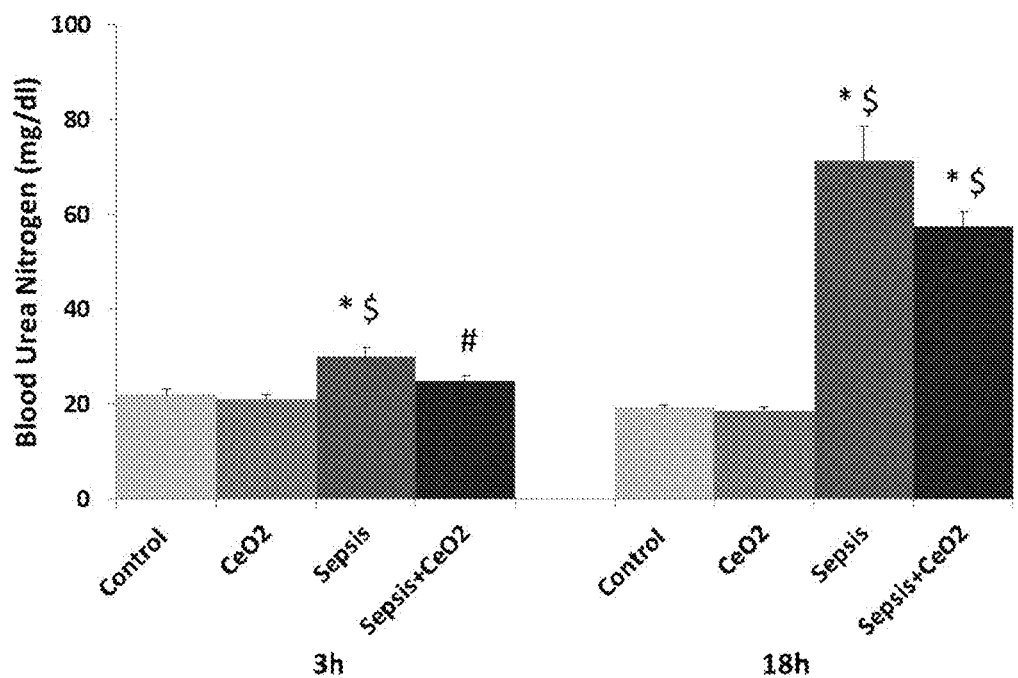
FIG. 4 is a graph showing the ability of cerium oxide nanoparticles to significantly decrease blood urea nitrogen in septic animals at 3 hrs and 18 hrs after of induction of sepsis, where "*" indicates a significant difference from control animals, and "#" indicates a significant difference from sepsis animals ($p<0.05$)
Figure 5:
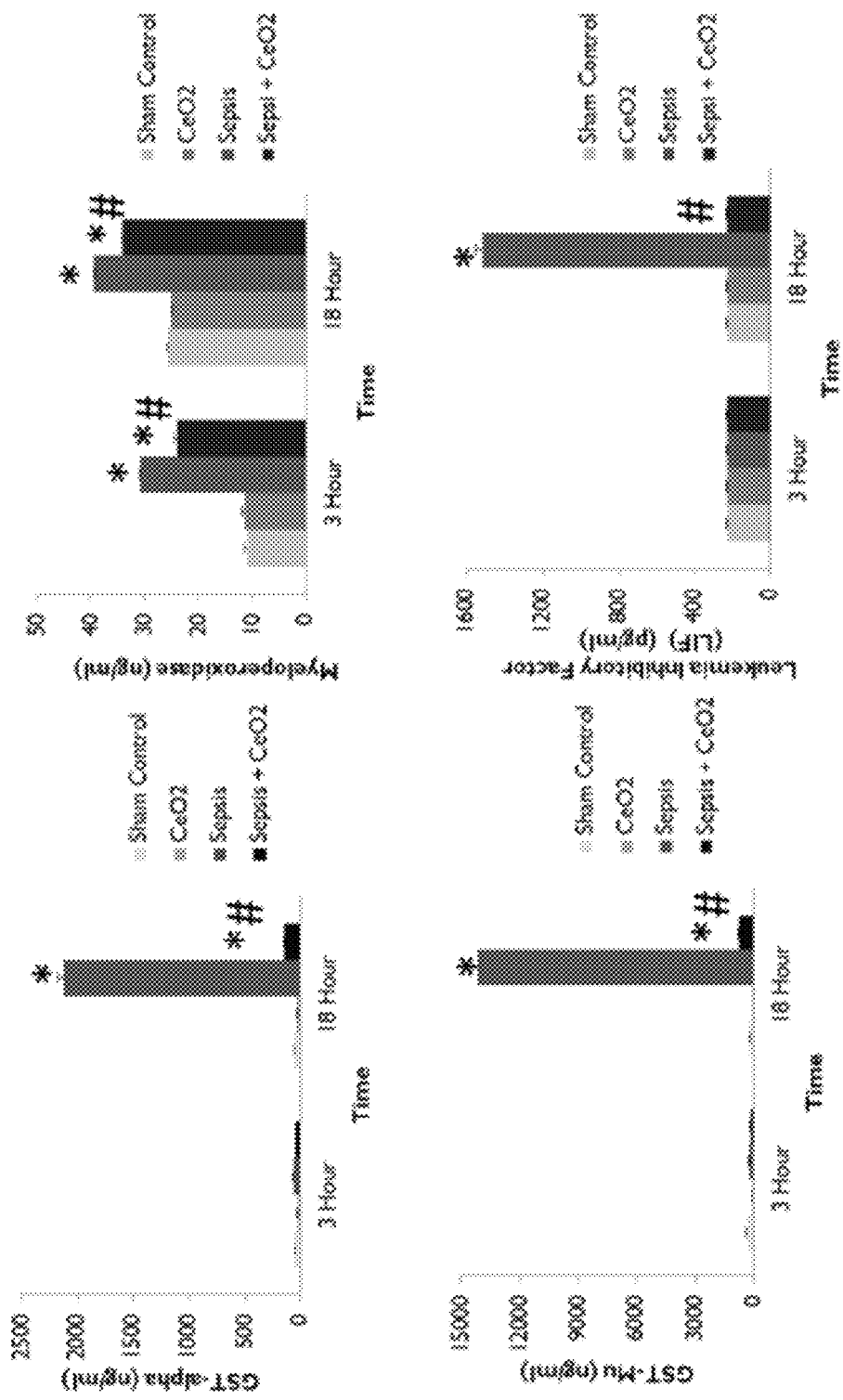
FIG. 5 includes graphs showing the ability of cerium oxide nanoparticles to significantly decrease inflammatory markers in serum of septic animals, where "*" indicates a significant difference from control animals, and "#" indicates a significant difference from sepsis animals ($p<0.05$)

Nanoparticle treatment decreased LPS induced mortality from 70% to 10% (FIG. 35C, C(ii), P<0.05). Increases in animal survivability were associated with improvements in animal behavior (Table 8), core body temperature (FIG. 35D, D(i), P<0.05), decreased respiratory rate (FIG. 35D, D(ii)), and increases in blood pressure (FIG. 1E). Sepsis decreased the percentage of lymphocytes and increased the percentage of granulocytes at 6 and 24 h. Nanoparticle treatment reversed these changes at the 6 h time point (Table 9, P<0.05).

TABLE 8

Effect of CeO$_2$ nanoparticles on septic symptoms (physical behavior and morphological changes).

| Physical behavior | External symptoms/sign | score | Control & CeO$_2$ | | | | | | | | | |
|---|---|---|---|---|---|---|---|---|---|---|---|---|
| | | | 0 h | 6 h | 22 h | 24 h | 48 h | 72 h | 96 h | 120 h | 144 h | 168 h |
| Appearance | Normal, Smooth Fur | 0 | 0 | 0 | 0 | 0 | 0 | 0 | 0 | 0 | 0 | 0 |
| | Roughened Fur | 1 | | | | | | | | | | |
| | Wet Fur | 2 | | | | | | | | | | |
| | Mucous eyes | 3 | | | | | | | | | | |
| Breathing | Normal | 0 | 0 | 0 | 0 | 0 | 0 | 0 | 0 | 0 | 0 | 0 |
| | Fast | 1 | | | | | | | | | | |
| | Slow | 2 | | | | | | | | | | |
| | Weak and intermittent | 3 | | | | | | | | | | |

TABLE 8-continued

Effect of $CeO_2$ nanoparticles on septic symptoms (physical behavior and morphological changes).

| | | | | | | | | | | | | |
|---|---|---|---|---|---|---|---|---|---|---|---|---|
| Weight changes | j 5% | 0 | 0 | | | | | | | | | |
| | j 15% | 1 | | 1 | | | | | | | | |
| | j 20% | 2 | | | 2 | 2 | 2 | 2 | 2 | 2 | 2 | 2 |
| | Greater than j 20% | 3 | | | | | | | | | | |
| Behavior | Normal, agile, prying | 0 | 0 | 0 | 0 | 0 | 0 | 0 | 0 | 0 | 0 | 0 |
| | Slow movement, sitting position | 1 | | | | | | | | | | |
| | Dull, Sloughed, tottering movements | 2 | | | | | | | | | | |
| | Lateral position | 3 | | | | | | | | | | |
| Provoked reaction | Escape reaction when cage is opened | 0 | 0 | 0 | 0 | 0 | 0 | 0 | 0 | 0 | 0 | 0 |
| | Fight when approached by hand | 1 | | | | | | | | | | |
| | Flight when touched | 2 | | | | | | | | | | |
| | No flight reaction at all | 3 | | | | | | | | | | |

| Physical behavior | External symptoms/sign | score | LPS | | | | | | | | | |
|---|---|---|---|---|---|---|---|---|---|---|---|---|
| | | | 0 h | 6 h | 22 h | 24 h | 48 h | 72 h | 96 h | 120 h | 144 h | 168 h |
| Appearance | Normal, Smooth Fur | 0 | 0 | | | | | 0 | 0 | 0 | 0 | 0 |
| | Roughened Fur | 1 | | 1 | 1 | 1 | 1 | | | | | |
| | Wet Fur | 2 | | | | | | | | | | |
| | Mucous eyes | 3 | | | | | | | | | | |
| Breathing | Normal | 0 | 0 | | | | | 0 | 0 | 0 | 0 | 0 |
| | Fast | 1 | | 1 | 1 | 1 | 1 | | | | | |
| | Slow | 2 | | | | | | | | | | |
| | Weak and intermittent | 3 | | | | | | | | | | |
| Weight changes | j 5% | 0 | 0 | | | | | | | | | |
| | j 15% | 1 | | | | | | | | | | |
| | j 20% | 2 | | 2 | 2 | 2 | 2 | 2 | 2 | 2 | 2 | 2 |
| | Greater than j 20% | 3 | | | | | | | | | | |
| Behavior | Normal, agile, prying | 0 | 0 | | | | | 0 | 0 | 0 | 0 | 0 |
| | Slow movement, sitting position | 1 | | 1 | 1 | 1 | 1 | | | | | |
| | Dull, Sloughed, tottering movements | 2 | | | | | | | | | | |
| | Lateral position | 3 | | | | | | | | | | |
| Provoked reaction | Escape reaction when cage is opened | 0 | 0 | | | | | | | 0 | 0 | 0 |
| | Fight when approached by hand | 1 | | | | | | | 1 | | | |
| | Flight when touched | 2 | | | | | | | | | | |
| | No flight reaction at all | 3 | | 3 | 3 | 3 | 3 | 3 | | | | |

| Physical behavior | External symptoms/sign | score | LPS + $CeO_2$ | | | | | | | | | |
|---|---|---|---|---|---|---|---|---|---|---|---|---|
| | | | 0 h | 6 h | 22 h | 24 h | 48 h | 72 h | 96 h | 120 h | 144 h | 168 h |
| Appearance | Normal, Smooth Fur | 0 | 0 | 1 | | | 0 | 0 | 0 | 0 | 0 | 0 |
| | Roughened Fur | 1 | | | 1 | 1 | | | | | | |
| | Wet Fur | 2 | | | | | | | | | | |
| | Mucous eyes | 3 | | | | | | | | | | |
| Breathing | Normal | 0 | 0 | 0 | | | 0 | 0 | 0 | 0 | 0 | 0 |
| | Fast | 1 | | | 1 | 1 | | | | | | |
| | Slow | 2 | | | | | | | | | | |
| | Weak and intermittent | 3 | | | | | | | | | | |
| Weight changes | j 5% | 0 | 0 | | | | | | | | | |
| | j 15% | 1 | | | | | | | | | | |
| | j 20% | 2 | | 2 | 2 | 2 | 2 | 2 | 2 | 2 | 2 | 2 |
| | Greater than j 20% | 3 | | | | | | | | | | |
| Behavior | Normal, agile, prying | 0 | 0 | | | | 0 | 0 | 0 | 0 | 0 | 0 |
| | Slow movement, sitting position | 1 | | 1 | 1 | 1 | | | | | | |
| | Dull, Sloughed, tottering movements | 2 | | | | | | | | | | |
| | Lateral position | 3 | | | | | | | | | | |
| Provoked reaction | Escape reaction when cage is opened | 0 | 0 | | | | 0 | 0 | 0 | 0 | 0 | 0 |
| | Fight when approached by hand | 1 | | 1 | 2 | 2 | | | | | | |
| | Flight when touched | 2 | | | | | | | | | | |
| | No flight reaction at all | 3 | | | | | | | | | | |

TABLE 9

Effect of CeO$_2$ nanoparticles on LPS induced changes in blood cells.

| | Whole blood cells counts | | | | | | | |
|---|---|---|---|---|---|---|---|---|
| | 6 h | | | | 24 h | | | |
| | Control | CeO$_2$ | Sepsis | Sepsis + CeO$_2$ | Control | CeO$_2$ | Sepsis | Sepsis + CeO$_2$ |
| WBC (10$^9$/L) | 3.03 ± 0.36 | 2.81 ± 0.38 | 1.39 ± 0.27* | 1.27 ± 0.44 | 3.4 ± 0.74 | 2.99 ± 0.46 | 2.106 ± 0.39 | 2.612 ± 0.45 |
| Lymphocytes (10$^9$/L) | 2.00 ± 0.20 | 0.82 ± 0.20* | 0.37 ± 0.05* | 0.82 ± 0.11*,# | 2.40 ± 0.55 | 1.96 ± 0.12 | 0.54 ± 0.54* | 0.43 ± 0.44 |
| Monocytes (10$^9$/L) | 0.08 ± 0.04 | 0.11 ± 0.06 | 0.07 ± 0.03 | 0.03 ± 0.00 | 0.18 ± 0.05 | 0.155 ± 0.04 | 0.17 ± 0.05 | 0.22 ± 0.05 |
| Granulocytes (10$^9$/L) | 1.03 ± 0.18 | 1.87 ± 0.32* | 0.946 ± 0.12 | 0.616 ± 0.34 | 0.815 ± 0.16 | 0.875 ± 0.34 | 2.13 ± 0.29* | 2.21 ± 0.38 |
| Lymphocytes (%) | 65.80 ± 4.11 | 37.51 ± 4.72 | 27.88 ± 2.07* | 67.10 ± 8.53*,# | 70.00 ± 3.79 | 68.75 ± 4.75 | 19.41 ± 1.79* | 15.80 ± 1.15 |
| Monocytes (%) | 2.55 ± 1.20 | 1.95 ± 1.71 | 5.166 ± 1.61 | 2.98 ± 0.75 | 5.18 ± 0.74 | 6.58 ± 2.01 | 6.41 ± 1.85 | 8.05 ± 1.72 |
| Granulocytes (%) | 31.56 ± 3.55 | 60.70 ± 6.13.# | 66.91 ± 1.19* | 29.9 ± 9.24*,# | 24.81 ± 4.16 | 24.64 ± 6.30 | 74.16 ± 1.81* | 76.18 ± 2.04 |

*P < 0.05 compared to control group, *,#.P < 0.05 compared to sepsis group. (n = 6/group).

Nanoparticle Treatment Decrease Sepsis Related Systemic Inflammation.

Figure 36:
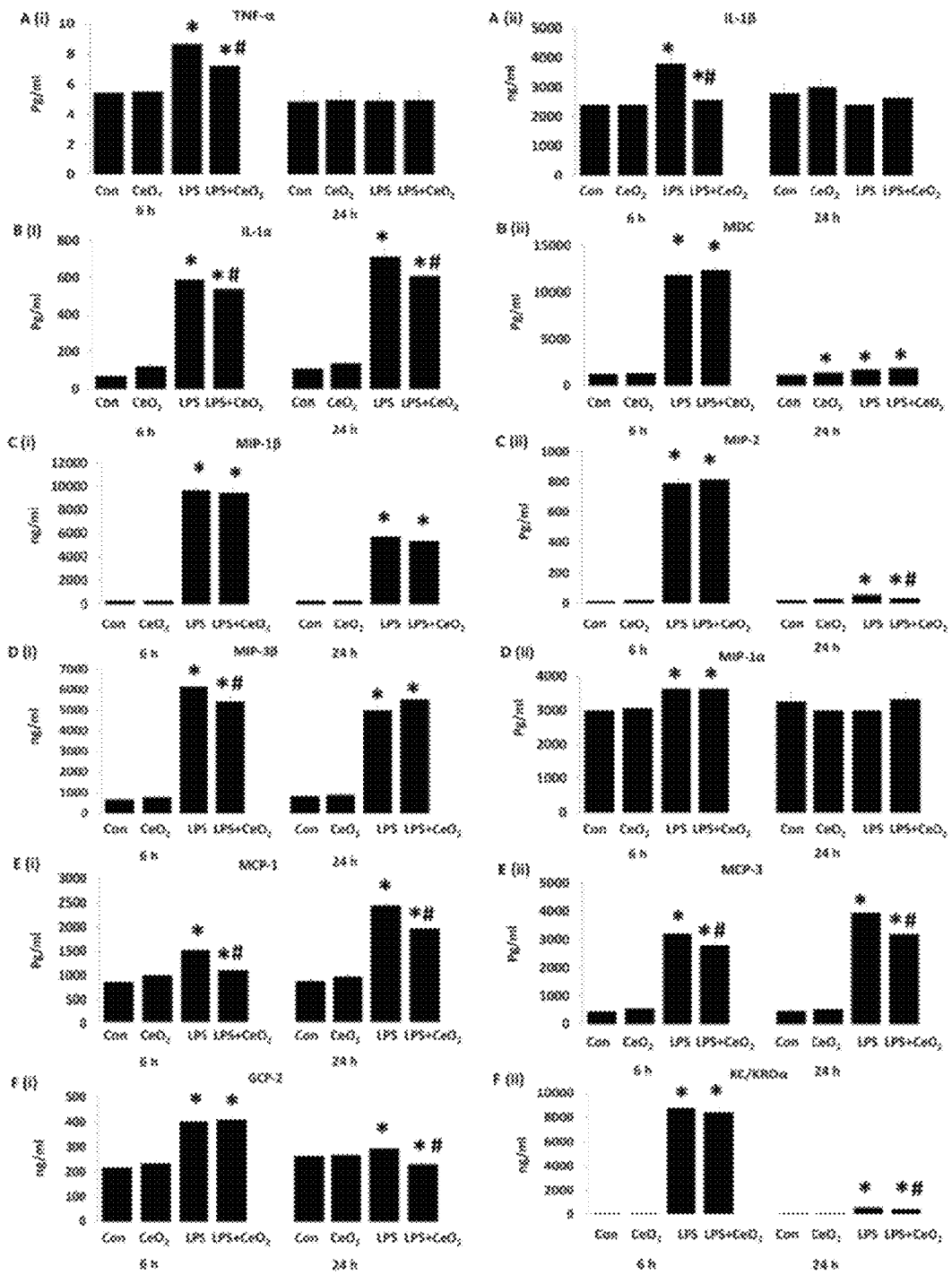
FIG. 36 includes graphs showing the effect of $CeO_2$ nanoparticles on LPS induced alteration of serum cytokines and chemokines, including: the cytokines A(i) tumor necrosis factor alpha (TNF-α), A(ii) interleukin 1 beta (IL-1β), B(i) interleukin 1 alpha (IL-1α); the chemokines B (ii) macrophage derived chemokines (MDC), C (i) macrophage inflammatory protein 1 beta (MIP-1β), C (ii) macrophage inflammatory protein-2 (MIP-2), D (i) macrophage inflammatory protein-3 beta (MIP-3β), D (ii) macrophage inflammatory protein-1 alpha (MIP-1α), E (i) monocyte chemotactic protein-1 (MCP-1), E (ii) monocyte chemotactic protein-3 (MCP-3), F (i) granulocytes chemotactic protein (GCP-2), and F (ii) growth regulated alpha protein (KC/GROα), where serum samples were pooled from control, $CeO_2$, sepsis, Sepsis+$CeO_2$ groups and analyzed in triplicate, where values are mean±SEM of 3 independent experiments performed in triplicate, and where statistical significance was determined by a one way ANOVA using Holm-Sidak test (*P<0.05 compared to control group, #P<0.05 compared to LPS group)

Compared to controls, LPS-induced sepsis was associated with increased serum cytokines, chemokines and acute phase proteins including tumor necrosis factor alpha (TNF-α), interleukin-1 beta (IL-1β), interleukin-1 alpha (IL-1α) at 6 h (P<0.05). Nanoparticle treatment decreased serum TNF-α, IL-1β levels at 6 h and IL-1α at both 6 and 24 h (FIG. 36, A(i,ii) and 2B(i), P<0.05). Compared to controls, LPS-induced sepsis appeared to increase the amount of macrophage derived chemokine (MDC), macrophage inflammatory protein-1 beta (MIP-1β), macrophage inflammatory protein-2 (MIP-2), macrophage inflammatory protein-3 beta (MIP-3β), macrophage inflammatory protein-1 alpha (MIP-1α), monocyte chemotactic protein-1 (MCP-1), monocyte chemotactic protein-3 (MCP-3), granulocyte chemotactic protein 2 (GCP-2), and growth regulated alpha protein (KC/GROα) at 6 and 24 h (FIG. 36, B(ii) to F(ii)). Nanoparticle administration decreased the levels of MIP-2, MIP-3β, MCP-1, MCP-3, GCP-2 and KC/GROα at both 6 and 24 h (P<0.05) (FIG. 36, C(ii) to F(ii)). The expression of several other acute phase and inflammatory proteins including stem cell factor, myoglobin, CD-40 ligand, fibrinogen, growth hormone, heptaglobin, leptin, and interferon gamma induced protein 10 (IF-10) were also altered with sepsis and with treatment (Table 10).

Nanoparticle Treatment Increase Liver Ceria Content and Protects the Liver Against Sepsis Induced Damage.

Figure 37A:
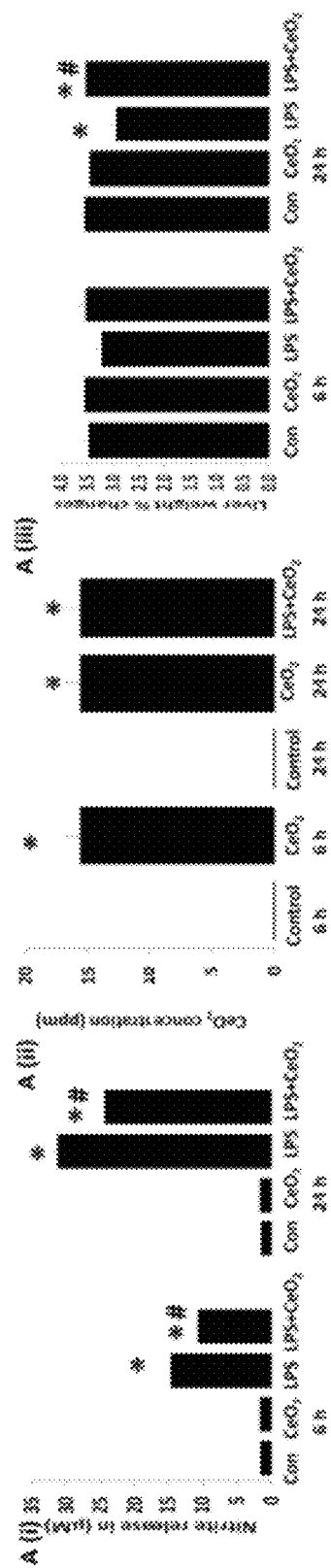
FIGS. 37A-37E include images and graphs showing the protective effect of $CeO_2$ nanoparticles on LPS induced liver failure in vivo via MyD dependent MAP kinase pathway, including: graphs (FIG. 37A) showing A (i) nitric oxide production in serum, A (ii) the presence of cerium in liver, and A (iii) liver weight change; images showing the histological change in the livers of the various groups of animals (H & E, Scale bars=100 µm); graphs showing C (i) total bilirubin (TBIL), C (ii) alanine aminotransferase (ALT), and C (iii) glutathione S transferase (GST-Mu); graphs showing D (i) glutathione S transferase (GST-α) levels of total and phosphorylated proteins as determined by western blotting and normalized to GAPDH respectively and D (ii) MyD 88 levels; and graphs showing E (i) P-p38, and E (ii) P-ERK 44/42 levels, where samples were pooled from control, $CeO_2$, sepsis, and sepsis+$CeO_2$ groups and were analyzed in triplicate, where statistical significance was determined by a one way ANOVA using Holm-Sidak test (*$P<0.05$ compared to control, #$P<0.05$ compared to sepsis group)
Figure 37B:
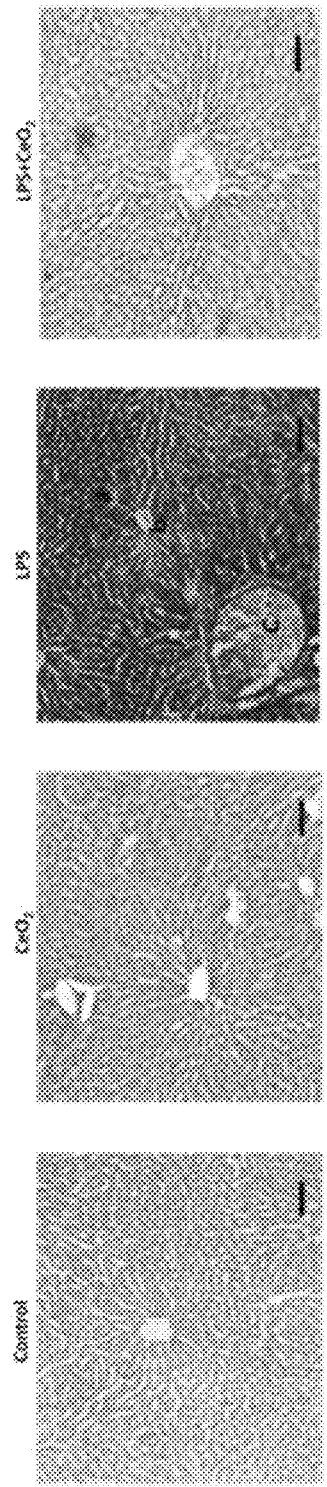
Figure 37C:
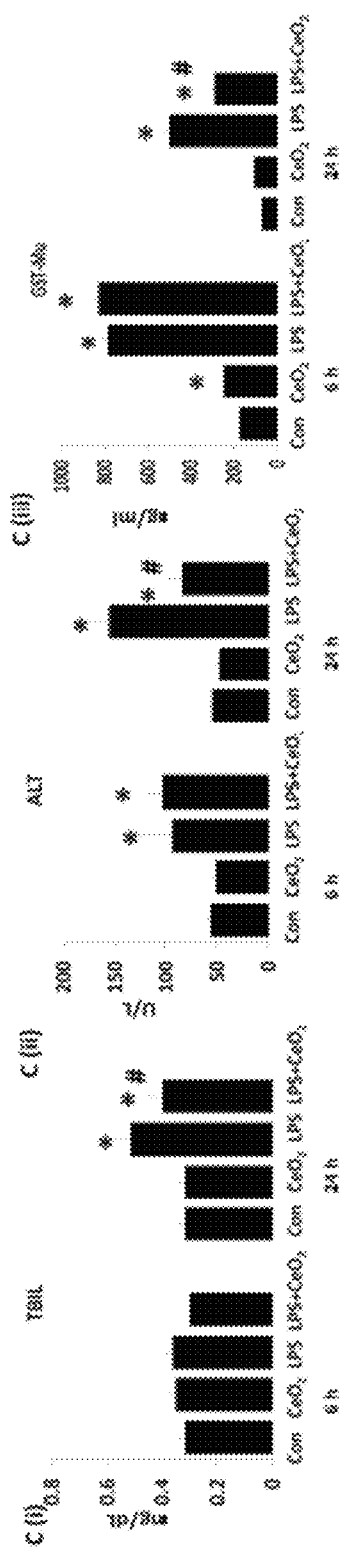

Compared to untreated animals, liver ceria content was increased in the nanoparticle injected animals (FIG. 37A, A(ii)). Sepsis associated decreases in liver weight were attenuated with nanoparticle treatment (FIG. 37A, A(iii), P<0.05). Histological analyses of the livers obtained from control animals were unremarkable. Sepsis was associated with changes in cell swelling, inflammation, necrosis, sinusoidal dilatation and the infiltration of cells in the portal area (FIG. 37B) which appeared to be diminished with nanoparticle treatment. Consistent with these changes in liver histology, sepsis was found to increase serum bilirubin (TBIL) at 24 h while serum alanine aminotransferase (ALT), glutathione S-transferase Mu (GST-Mu), and glutathione S-transferase alpha (GST-α) levels were elevated at 6 and 24 h. Nanoparticle treatment decreased serum bilirubin, ALT, GST-Mu, and GST-α (FIG. 37C, C (i to iii) and FIG. 37D, D(i), P<0.05).

Nanoparticle Treatment Decrease Sepsis Related Increase in MyD88, MAPK Activation, iNOS and HMGB1.

Figure 37D:
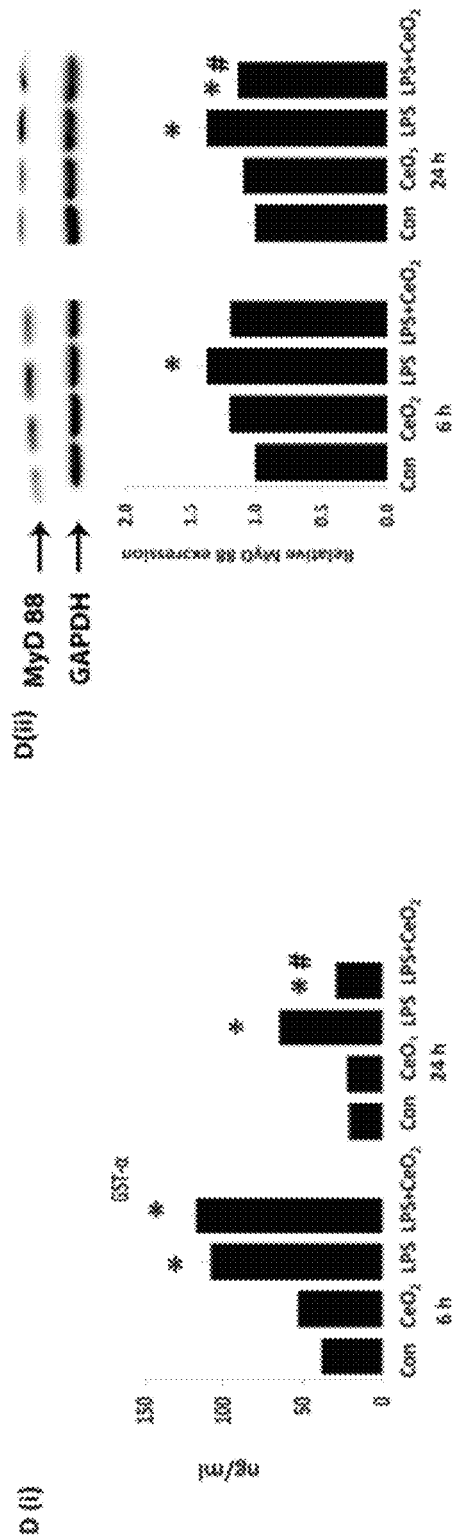

Compared to that seen in the control animals, sepsis increased the expression of MyD 88, and the phosphorylation of p38-MAPK and p44/42-MAPK which were decreased with nanoparticle treatment (FIG. 37D, D(ii) and E(i, ii), P<0.05). Sepsis increased serum nitrite levels at 6

TABLE 10

Effect of CeO$_2$ nanoparticles on LPS induced inflammatory proteins.

Figure 38A:
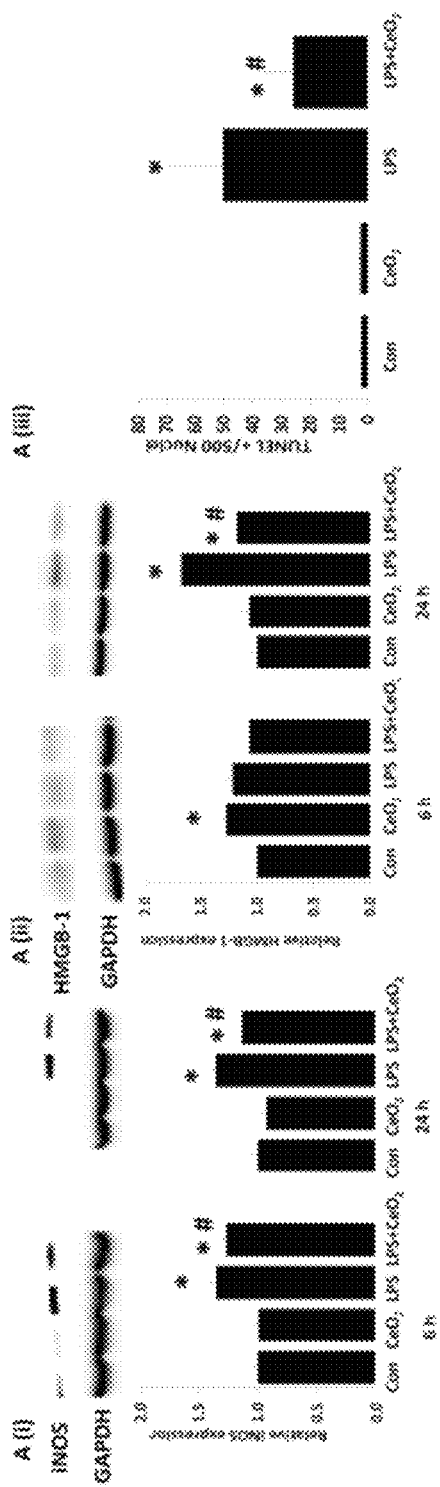
FIGS. 38A-38E include images and graphs showing the effect of $CeO_2$ nanoparticles on inflammatory mediators, apoptosis and Kupffer cell changes induced by LPS, including: graphs and images (FIGS. 38A-38B) showing levels of inflammatory mediator proteins as determined by western blotting and normalized to GAPDH and including A (i) iNOS, A (ii) HMGB1 and showing mitochondria dependent apoptosis as determined by TUNEL staining (Scale bar=100 µm) and quantification of TUNEL positive nuclei A (iii) and FIG. 38B; graphs and images showing C (i) total and cleaved caspase-3, and C (ii) Bax/Bcl-2 ratio; images showing morphological changes (FIG. 38D, scale bar=200 µm; and graphs showing C (iii) TNF-α, and E ROS production.

| | Serum | | | | | | | |
|---|---|---|---|---|---|---|---|---|
| | 6 h | | | | 24 h | | | |
| Analyte | Control | CeO2 | Sepsis | Sepsis + CeO$_2$ | Control | CeO2 | Sepsis | Sepsis + CeO$_2$ |
| Stem cell factor (pg/ml) | 545 ± 25 | 616 ± 38 | 1540 ± 150* | 1636 ± 131 | 655 ± 29 | 666 ± 11 | 1193 ± 37* | 878 ± 58*,# |
| Myoglobin (ng/ml) | 1540 ± 20 | 738 ± 43* | 42080 ± 141* | 1170 ± 45*,# | 702 ± 45 | 1710 ± 10* | 2370 ± 80* | 1816 ± 96*# |
| CD-40 ligand (pg/ml) | 428 ± 0 | 428 ± 0 | 964 ± 89* | 749 ± 80 | 431 ± 3 | 428 ± 0 | 1386 ± 96* | 1094 ± 95*,# |
| Fibrinogen (µg/ml) | 510 ± 0 | 510 ± 0 | 656 ± 47* | 540 ± 24 | 510 ± 0 | 510 ± 0 | 1223 ± 61* | 901 ± 19*,# |
| Growth hormone (ng/ml) | 55666 ± 2603 | 51000 ± 22143 | 64666 ± 1333 | 56000 ± 2516*,# | 5600 ± 1154 | 37333 ± 1452* | 19666 ± 666* | 56333 ± 881*,# |
| Heptaglobin (µg/ml) | 635 ± 21 | 203 ± 2* | 222 ± 2* | 259 ± 4*,# | 801 ± 21 | 607 ± 15* | 1093 ± 48* | 1326 ± 32 |
| Leptin (ng/ml) | 360 ± 26 | 446 ± 32 | 1366 ± 33* | 1300 ± 57 | 410 ± 8 | 406 ± 31 | 1400 ± 57* | 1433 ± 33 |
| IP 10 (pg/ml) | 91 ± 0 | 91 ± 0 | 1686 ± 18* | 1883 ± 69 | 91 ± 0 | 91 ± 0 | 337 ± 11* | 363 ± 10 | and 24 h. Nanoparticle treatment decreased LPS-induced nitrite production (FIG. 37A, A (i)) along with LPS associated increases in liver iNOS and HMBG-1 content (FIG. 38A, A(i, ii), P<0.05).

Nanoparticle Treatment Decrease Hepatic Apoptosis During Sepsis.

Figure 38B:
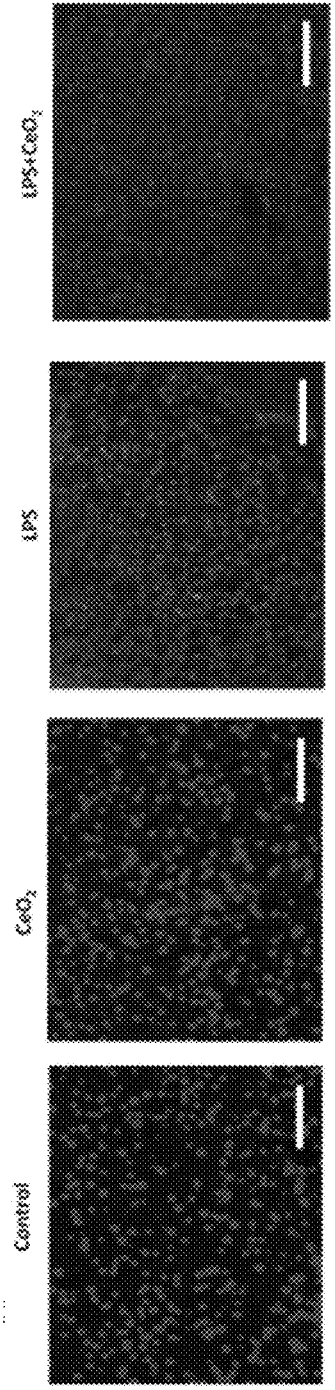
Figure 38C:
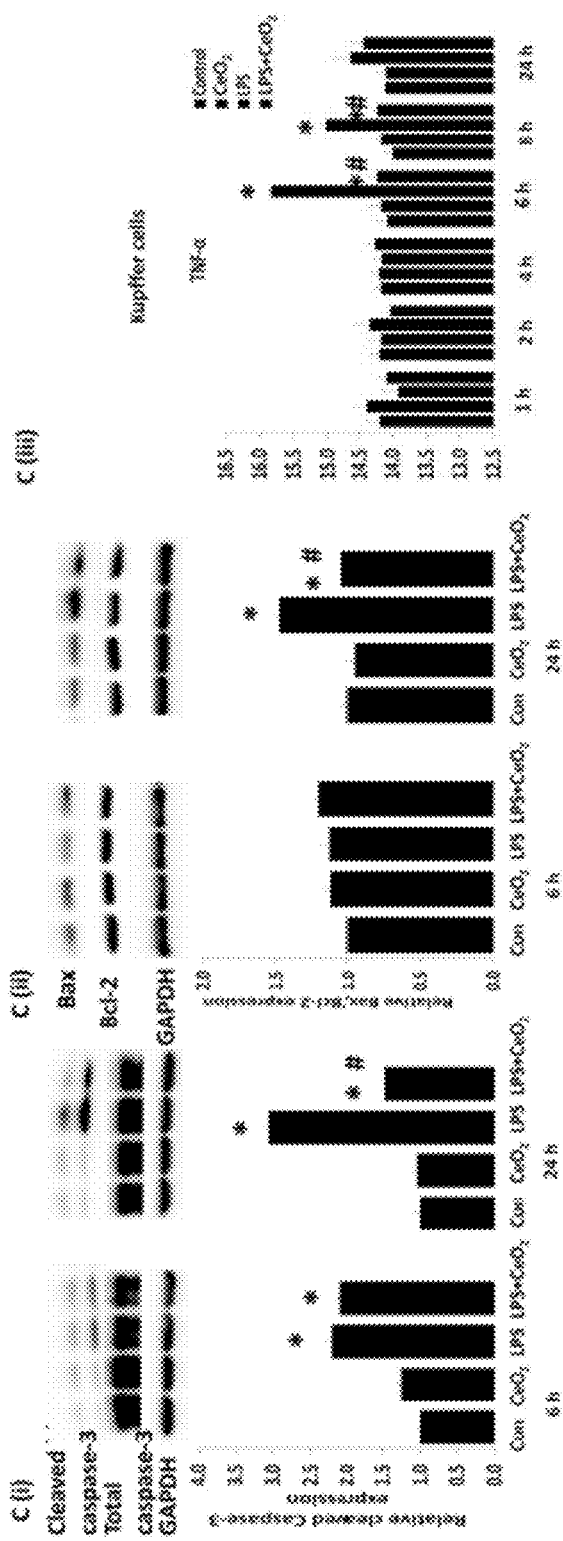

To investigate the possibility that changes in liver structure were associated with cellular apoptosis, it was determined the number of nuclei staining positively for DNA fragmentation by TUNEL staining. As expected, it was found that sepsis increased and that nanoparticle treatment decreased the number of TUNEL positive nuclei (FIG. 38A, A (iii), FIG. 38B, P<0.05). These decreases in cellular apoptosis with treatment were associated with decreased caspase-3 cleavage (19 and 17-kDa fragments) (FIG. 38C, C (i), P<0.05) and a decrease in the Bax/Bcl-2 ratio (FIG. 38C, C (ii), P<0.05).

Nanoparticle Treatment Decrease LPS-Induced Increase in Macrophage ROS Level and Cytokine Release.

Figure 38D:
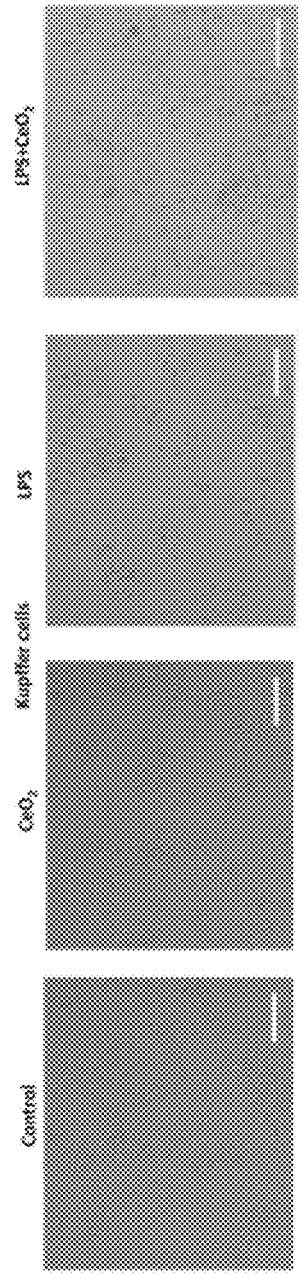
Figure 38E:
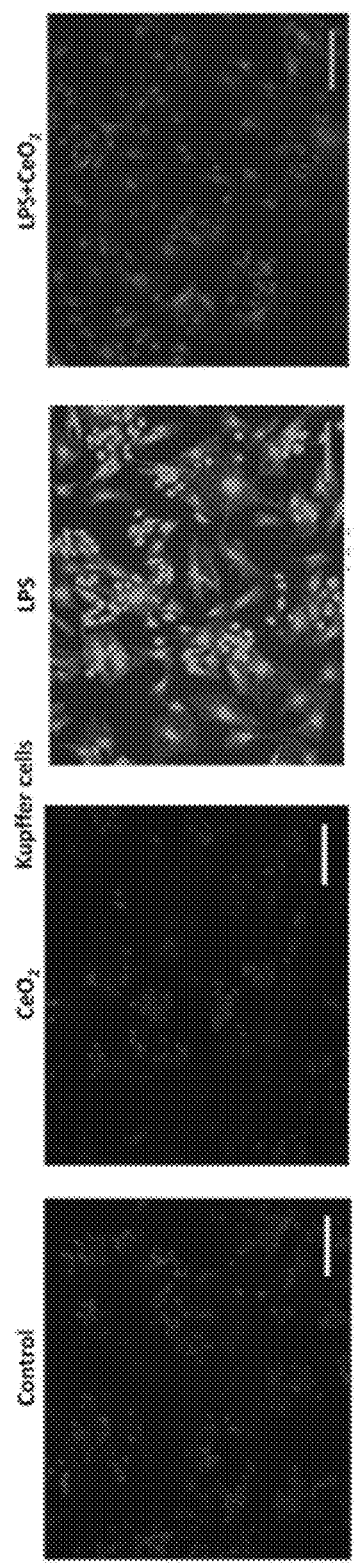

Based on the fact that many of the cytokines/chemokines and other inflammatory regulators observed during SIRS are likely derived from the liver Kupffer cells and from the serum profiling data (FIG. 36 and Table 10), the effect of LPS challenge on Kupffer cell function was next examined in the absence and presence of $CeO_2$ nanoparticles. Compared to control cells, LPS challenge was associated with alterations in cellular morphology, increased TNF-α production, and elevations in cellular ROS levels which appeared to be diminished with nanoparticle treatment (FIG. 38D, FIG. 38C, C(iii), and FIG. 38E).

Figure 39A:
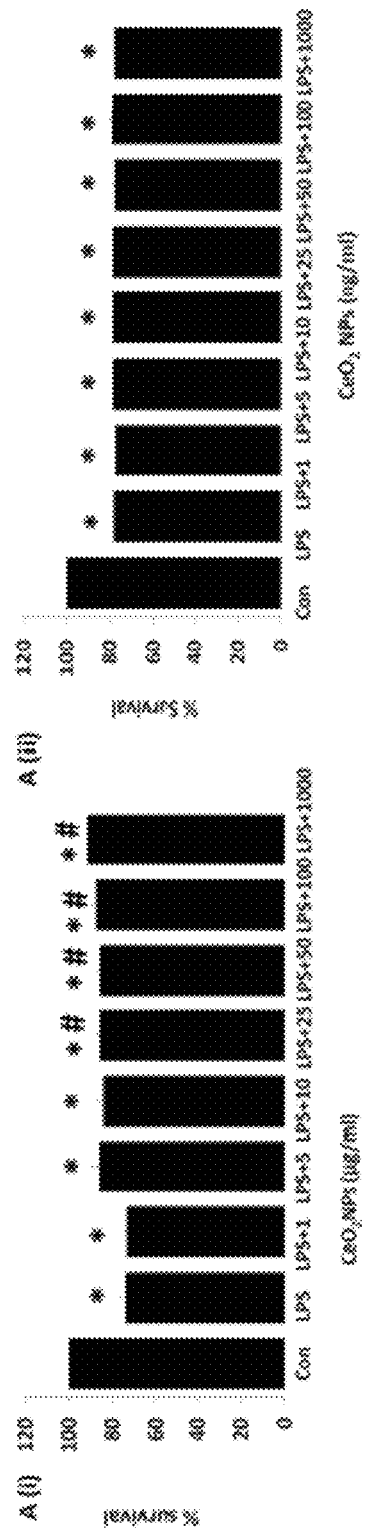
Figure 40A:
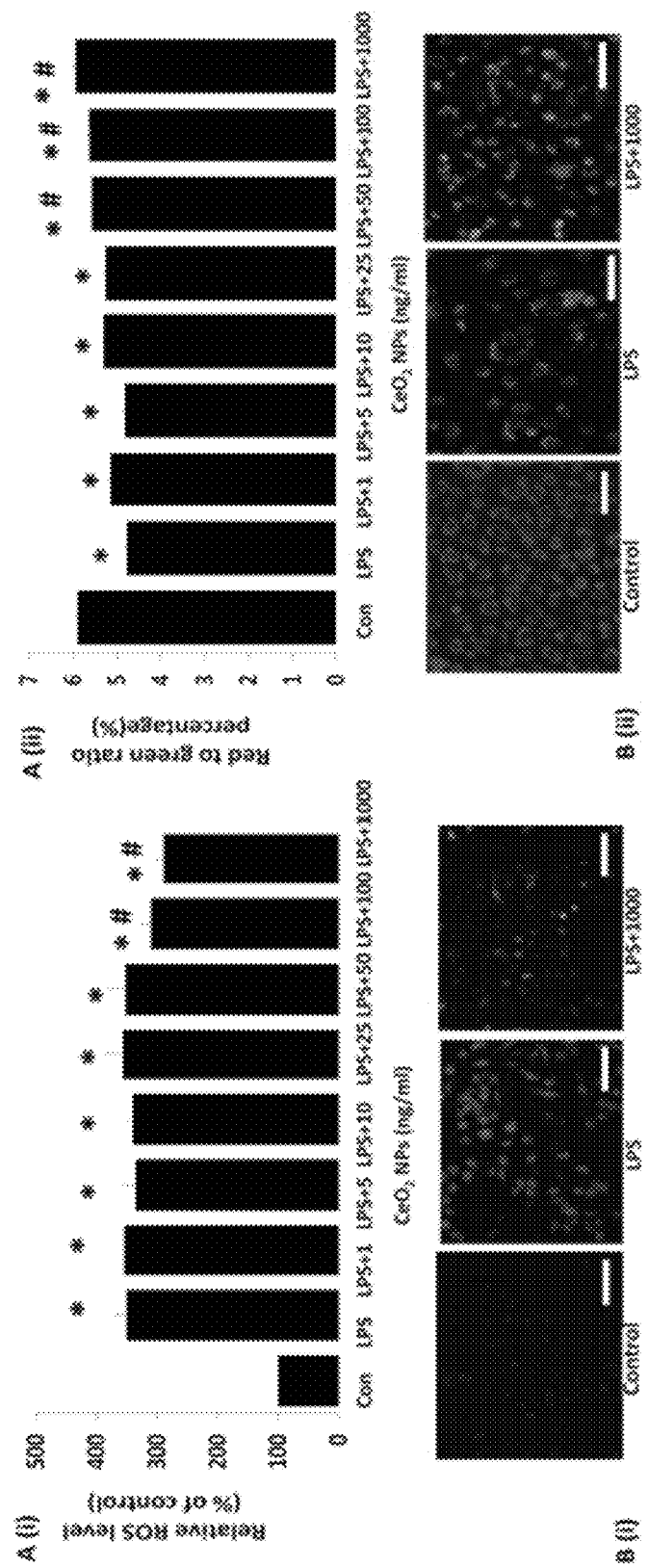
FIGS. 40A-40D include images and graphs showing the effect of $CeO_2$ nanoparticles on NO production and the expression of iNOS and COX-2 and translocation of NF-κB/p65 in RAW 264.7 cells where cells were exposed to LPS in the presence and absence of $CeO_2$ nanoparticles for 24 h, including: images and graphs (FIG. 40A) showing A (i) reactive oxygen species production (ROS) as determined by 2, 7-dichlorodihydrofluorescein diacetate (DCFH-DA) (Scale bar=50 µm) and A (ii) mitochondrial membrane potential (Δψm) as determined by JC-1 (Scale bar=50 µm); images and graphs (FIGS. 40B-40C) showing B (i) expression of IκB-α in whole cell lysate and B (ii) measurement of NF-κB in cytoplasmic and nuclear extracts C (i) by immunoblotting, and C (ii) a representative image of EMSA binding of NF-κB to DNA; and graphs showing quantification of EMSA by densitometry D (i) and D (ii) NF-κB luciferase activity by Luciferase reporter assay.

Because of the difficulties associated with the continued propagation of Kuppfer cells in culture, the effects of nanoparticle treatment was next examined in depth using cultured RAW 264.7 macrophages. Dose response toxicity experiments using the MTT assay suggested that nanoparticle dosages greater than 1 µg/ml appeared to be cytotoxic (FIG. 41, P<0.05). Consistent with the in vivo data, LPS-induced increases in cell death were diminished with nanoparticle treatment (25, 50, 100 or 1000 ng/ml) (FIG. 39A, A (i), P<0.05). To test if the improvements in cell survival were associated with the ability of the nanoparticles to bind to/sequester LPS or if exposure to the nanoparticles was able to neutralize LPS functionality, varying doses of $CeO_2$ nanoparticles (0, 1, 5, 10, 25, 50, 100, or 1000 ng/ml) were added to growth media containing LPS (2 µg/ml) and allowed to interact. After centrifugation to remove any suspended nanoparticles, the MTT assay was performed using the clarified media. Consistent with the possibility that the nanoparticles do not act to impair LPS functionality, no differences were observed in the amount of cell death caused between incubation of the cells with "native" and nanoparticle "exposed" LPS (FIG. 39A, A (ii). The uptake of $CeO_2$ nanoparticles by the RAW 264.7 cells in the presence or absence of LPS was confirmed using ICP-MS (FIG. 39B, B(i)).

To investigate whether changes in cell survival were associated with alterations in cellular ROS, RAW 264.7 cells were stained with DCFH-DA and JC-1 dyes to determine the effects of nanoparticle treatment on cellular superoxide levels and mitochondrial membrane potential (Atm) levels, respectively. Given the potential ROS scavenging ability of $CeO_2$ nanoparticles, nanoparticle treatment was found to decrease LPS-induced increases in cellular ROS and mitochondrial membrane potential (FIG. 40A, A(i, ii), P<0.05).

In addition to changes in cellular ROS, nanoparticle treatment also decreased the production of TNF-α, IL-6, IL-1β, and HMGB1 following LPS challenge (FIG. 39B, B(ii) to FIG. 39D, D(i), P<0.05). Similarly, nanoparticle treatment also decreased nitrite production, along with the upregulation of iNOS and COX-2 protein following LPS challenge (FIG. 39D, D(ii) to FIG. 39E, E(i, ii), (P<0.05)).

Nanoparticle Treatment Decrease NE-κB/p65 Transcriptional Activity.

Figure 40B:
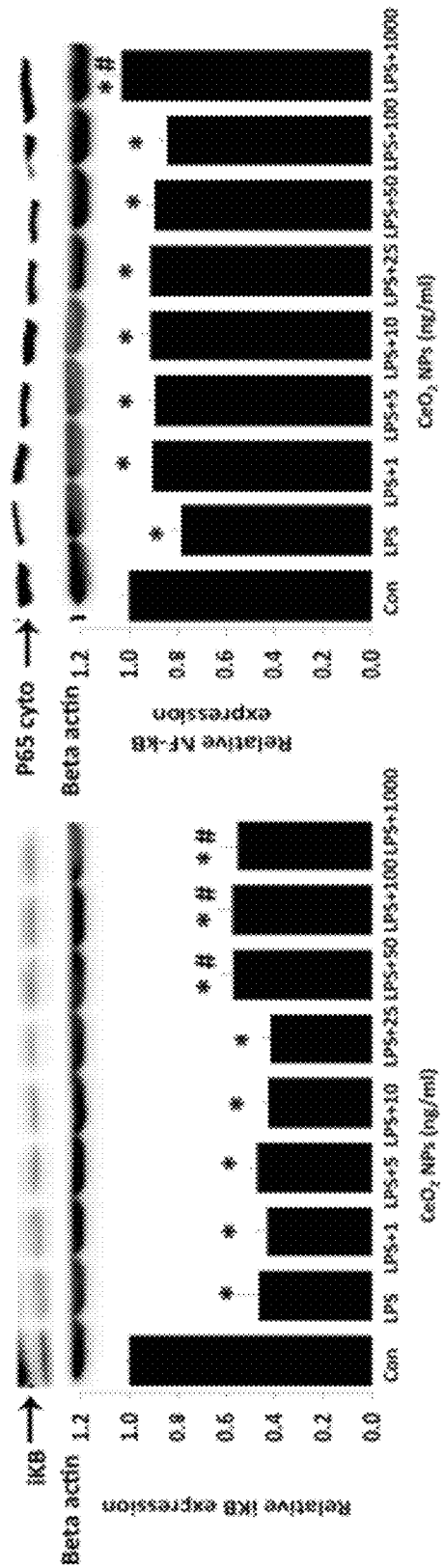
Figure 40C:
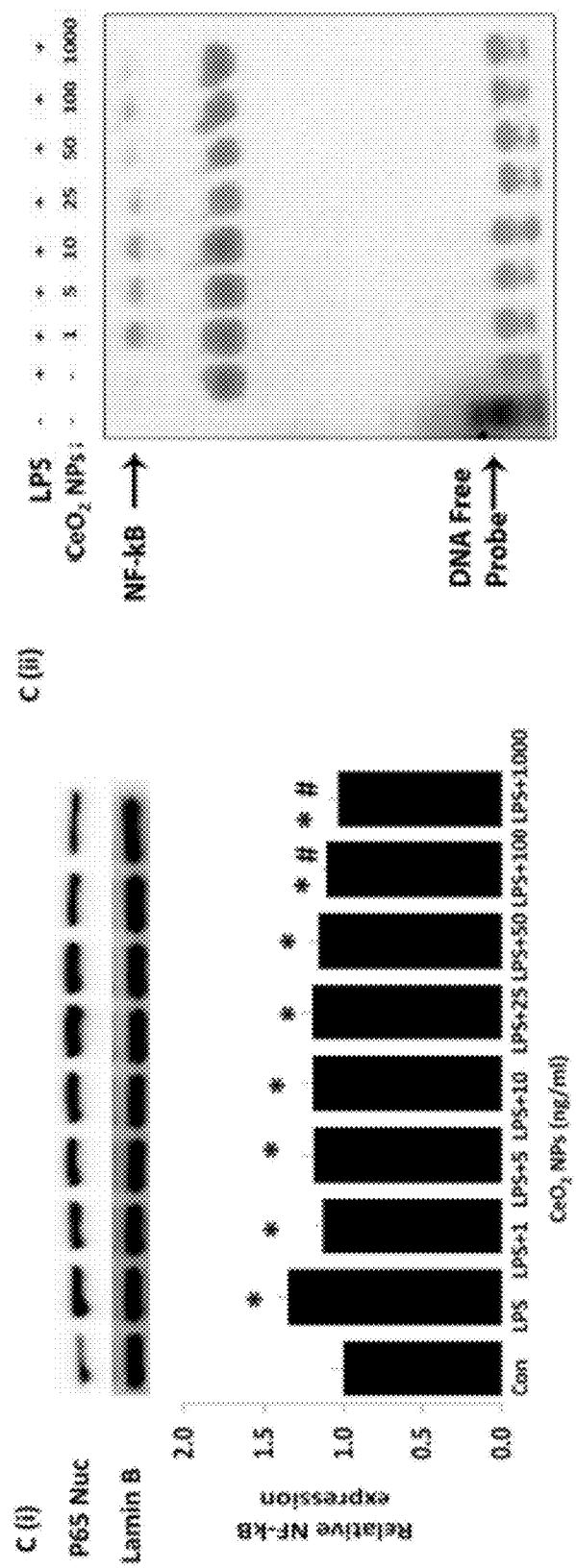
Figures 40D, 41:
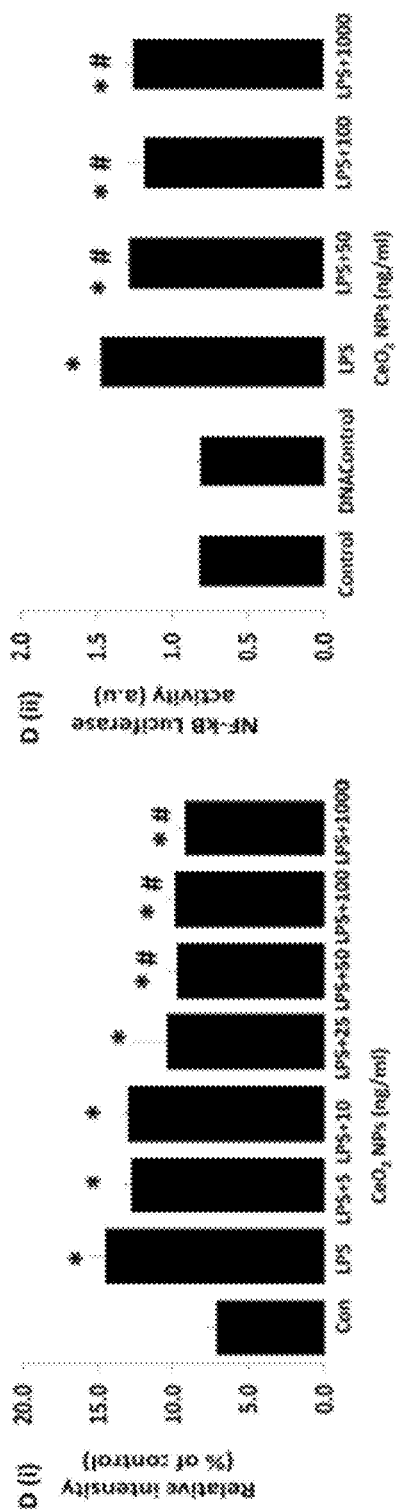
FIG. 41 is a graph showing the determination of cytotoxic and non-cytotoxic concentration of $CeO_2$ nanoparticles.

LPS-induced decreases in IκB-α protein were abrogated following nanoparticle treatment (FIG. 40B, B(i), P<0.05). Consistent with these data, nanoparticle treatment also decreased LPS-induced translocation of NF-κB/p65 to the nucleus (FIG. 40B, B(ii), FIG. 40C, C(i)), NF-κB/p65 binding to DNA (FIG. 40C, C(ii) and FIG. 40D, D(i)), and LPS-associated increases in NF-κB transcriptional activity (FIG. 40D, D (ii), P<0.05).

Discussion of Example 7

Despite decades of intensive investigation and significant advances in medical technology, the overall mortality rate in severe sepsis patients remains unacceptably high. An aim of the foregoing study was to evaluate whether $CeO_2$ nanoparticles were protective against LPS-induced sepsis in the Sprague Dawley rat. A finding of this study was that a single injection of $CeO_2$ nanoparticles, in the absence of antibiotic treatment, fluid resuscitation, or other pharmacological intervention, was able to increase animal survivability 200% following a severe septic insult (FIG. 35C, C (ii)).

Consistent with previous studies, it was found that severe sepsis was associated with changes in body temperature, respiratory rate, and blood pressure and blood cell counts. Nanoparticle treatment attenuated sepsis-induced changes in these variables (FIG. 35D, D (i,ii), and FIG. 35E)). Given that serum cytokine/chemokine levels are highly correlated with patient survival, it was next sought to determine if the nanoparticle treatment functioned to diminish SIRS development. It was found that sepsis was associated with the significant upregulation of a number of different cytokines, chemokine, acute phase proteins, and other inflammatory mediators and importantly, that the nanoparticle treatment appeared to significantly blunt many of these sepsis-induced changes (FIGS. 36A-36F and Table 10).

Figure 37E:
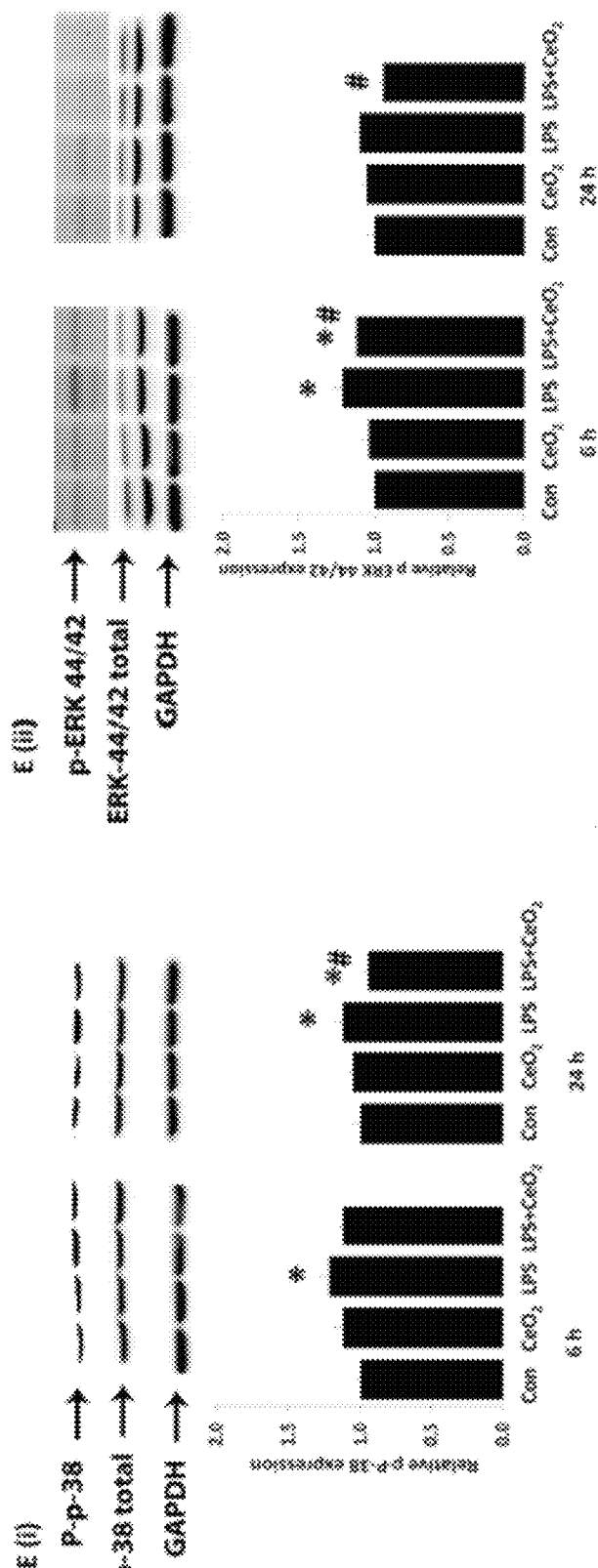

To explore the mechanistic basis of this finding, it was next determined where the injected $CeO_2$ nanoparticles may accumulate. ICPMS analysis demonstrated significantly higher amounts of ceria in the livers of the treated animals compared to that observed in the untreated animals (FIG. 37A, A (ii)). To examine if the $CeO_2$ nanoparticles were able to protect the liver injury against a septic insult, it was next examined if treatment was associated with improvement in liver structure and function. It was observed that sepsis was associated with alterations in liver morphology (FIG. 37B) and evidence of diminished function as suggested by increased serum bilirubin levels (FIG. 37C, C(i)). In addition, it was found that the LPS treated animals exhibited increased serum levels of the liver damage molecules alanine aminotransferase (ALT), glutathione S-transferase Mu (GST Mu), glutathione S-transferase alpha (GST-α), (FIG. 37C, C(ii, iii) and FIG. 37D, D(i)). Importantly, each of these measures were decreased significantly with nanoparticle treatment (FIG. 37C, C(i-iii) and FIG. 37D, D(i)). Supporting these data, it was also found that the nanoparticle treatment was associated with diminished hepatic MyD88 levels, p-p38 MAPK phosphorylation, p-ERK1/2, iNOS, and HMGB-1 suggesting that nanoparticle treatment was also associated with decreased liver inflammation (FIG. 37D, D (ii), FIG. 37E, E(i,ii) and FIG. 38A, A(i,ii)). To extend these finding, it was next examined if the nanoparticle treatment was also able to protect the liver from sepsis-induced apoptosis. It was found that the nanoparticle treatment was associated with a diminished number of TUNEL positive hepatic nuclei, decreased caspase-3 cleavage, and a reduction in the Bax/Bcl-2 ratio (FIG. 38A, A(iii), FIG. 38B, and FIG. 38C, C(i-ii)).

Given that many of cytokines and chemokines (e.g. TNF-α, IL-6, MDC, MIP-113, MIP-2, MIP-313, MCP-3, KC/GROα) that were found to be elevated with sepsis and that decreased with treatment were thought to be derived from the liver Kuppfer cells (macrophages), the function of these particles was next examined in isolated Kupffer cells. It was found that nanoparticle treatment was associated with decreased TNF-α release and cellular ROS levels after LPS challenge (FIG. 38C, C(iii) and FIG. 38E). Using cultured RAW 264.7 macrophages which could be propagated, the experimental approach was repeated and it was found that the nanoparticle treatment decreased LPS-induced increases in the secretion of TNF-α, IL-6, IL-1β and HMGB1 (FIG. 39B, B(ii) to FIG. 39D, D(i)). In addition to elevations in cytokine concentration, it has also been suggested that the large amount of nitric oxide (NO) produced during sepsis may play an important role in sepsis-induced mortality which has led some to postulate that decreasing NO levels may be beneficial. The foregoing in vivo and in vitro data show a significant decrease in the NO production in serum as well as cultured macrophages following nanoparticle treatment (FIG. 37A, A(i) and FIG. 39D, D (ii)). To confirm this finding, it was next examined how $CeO_2$ nanoparticle affected the expression of inducible nitric oxide synthase (iNOS) which is the enzyme thought to be responsible for much of the NO produced during the septic insult. Paralleling our findings of decreased serum nitrite (FIG. 37A, A(i)) and diminished iNOS levels (FIG. 38A, A (i)) in the livers of the nanoparticle treated animals, it was found that the nanoparticles also diminished LPS-induced expression of iNOS in cultured macrophages (FIG. 39E, E(i)).

The mechanism(s) regulating cytokine and NO production in macrophages following LPS stimulation are not yet fully understood; however, recent data has suggested that elevations in intracellular ROS levels may play an important role. To examine this possibility, it was next determined how nanoparticle treatment might affect cellular ROS and mitochondrial membrane potential levels by DCFH-DA and JC-1 staining. Consistent with previous reports using macrophages, it was found that $CeO_2$ nanoparticle treatment tended to decrease the induction of cellular ROS in RAW macrophage cells and mitochondrial membrane potential damage following LPS challenge (FIG. 40A, A (i, ii)).

It is thought that NF-κB and mitogen activated protein kinases (MAPK) are key regulators of inflammatory gene expression. Although the factors regulating NF-κB transcriptional activity are not fully understood, it is well known that nuclear localization of the redox sensitive NF-κB transcription factor is controlled by the phosphorylation and subsequent degradation of IκB-α. It has been reported that LPS challenge (2 μg/ml) can be used to induce the degradation of IκB-α and nuclear localization of NF-κB/p65 in cultured RAW 264.7 macrophages. Consistent with the previous data described herein, it was found that nanoparticle treatment functioned to attenuate LPS-induced IκB-α degradation and NF-κB/p65 translocation from the cytoplasm to the nucleus (FIG. 40B, B(i,ii) and FIG. 40C, C(i)). Importantly, we also noted that these decreases in NF-κB translocation were also associated with diminished NF-κB binding to DNA (FIG. 40C, C(ii) and FIG. 40D, D(i)) and reduced NF-κB transcriptional activation (FIG. 40D, D(ii) $P<0.05$).

Figure 42:
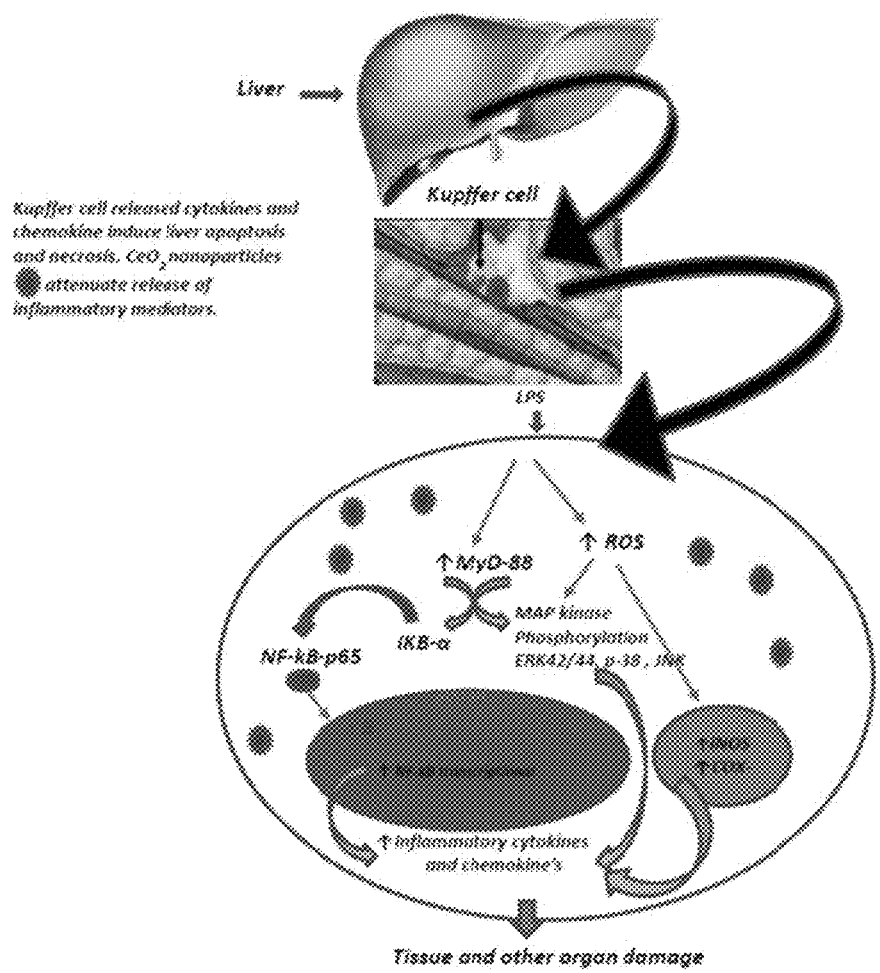
FIG. 42 is a schematic diagram showing the mechanistic insight of systemic inflammatory response syndrome (SIRS) of sepsis and the effect of $CeO_2$ nanoparticle treatment.

In summary, the foregoing data indicated that a single dose of $CeO_2$ nanoparticles was associated with improvements in animal survival, decreased hepatic damage, increased ceria deposition in the liver, and diminished evidence of systemic inflammation after a severe septic insult. In vitro experimentation using isolated Kupffer cells and cultured RAW 264.7 macrophages demonstrated that $CeO_2$ nanoparticle treatment decreased cytokine release (TNF-α, IL-1β, IL-6, HMGB1), the induction of iNOS, and NF-κB transcriptional activity following LPS challenge (FIG. 42). Given that the large scale manufacture of these particles is possible using existing technology and their likely stability under a wide range of environmental conditions, it was possible that these particles may have application for the treatment of sepsis in austere environments.

Example 8—Effect of Cerium Oxide Nanoparticles on Sepsis Induced Mortality and NF-κB Signaling in Cultured Macrophages To investigate whether cerium oxide ($CeO_2$) nanoparticles could be used for the treatment of severe sepsis, cecal peritonitis was induced in male Sprague-Dawley rats in the presence and absence of $CeO_2$ nanoparticles, cultured macrophages (RAW 264.7 cells) were challenged with lipopolysaccharide (LPS) in the absence and presence of $CeO_2$ nanoparticles, and the effect of nanoparticles on the growth of E. coli and S. aureus was determined in culture.

Materials and Methods for Example 8

$CeO_2$ Nanoparticle Preparation and Characterization.

Previously characterized NanoActive $CeO_2$ (99.9% purity as determined by ICP-MS; Lot #06-0118) was purchased from NanoScale corporation (Manhattan, Kans., USA). Stock suspensions (3.5 mg/ml) were prepared in dd$H_2$O by sonication (600 W for 2 min) using a Vibra Cell Sonicator (Sonics & Materials, Inc.) at room temperature and characterized.

Atomic Force Microscopy.

Particles were imaged in their native state on freshly pealed mica substrate using a MultiMode-8, Atomic Force Microscope (Bruker, Ewing, N.J.) in the tapping mode.

Transmission Electron Microscopy.

Particles were imaged using a Hitachi-H-7000 electron microscope at a magnification of 50,000×. ImageJ software was used to calculate particle size.

Dynamic Light Scattering.

The hydrodynamic size and size distribution of $CeO_2$ nanoparticles were evaluated in dd$H_2$O using a Particle Size Analyzer (HORIBA, Model-LB-550) equipped with a He—Ne laser (633 nm) using back scattered light. Experiments were performed in triplicate over three different days using freshly prepared samples.

Sepsis Model.

Male Sprague-Dawley rats weighing 300-350 g were obtained from Charles River laboratories and housed two per cage using a 12:12-h dark-light cycle at a temperature of 22±2° C. Animals were provided food and water ad libitum and allowed to acclimate for at least one week prior to any experimentation. All procedures were performed as outlined in the guide for the care and use of laboratory animals as approved by the council of the American physiological society and the institutional animal use review board of Marshall University. Polymicrobial sepsis was induced by the intraperitoneal injection of cecal material (400 mg/kg in 5 ml/kg of 5% sterile dextrose water) that was obtained from the cecal content of donor (uninfected) rats as outlined previously. Animals were randomly assigned to one of four groups: vehicle control group (n=6), $CeO_2$ nanoparticle treatment (3.5 mg/kg i.v.) group (n=6), cecal inoculate group (n=16), and cecal inoculate+$CeO_2$ nanoparticle (3.5 mg/kg) treatment group (n=16).

In other experiments, animals were randomly assigned to one of the four groups as detailed previously and then sacrificed at 6 or 24 h after study initiation for the collection of blood and tissues. Serum interleukin-6 (IL-6) levels were analyzed in triplicate by enzyme-linked immunosorbent assay (ELISA) (BD Bioscience, Franklin Lakes, N.J., USA) as outlined by the manufacturer. Serum samples from each of the different groups (n=6/group) were pooled and sent to Myriad RBM (Austin, Tex.) for the analysis of serum growth factors, cytokines and markers of inflammation using a Luminex MAP instrument [24, 25]. Each analyte was quantified using 4 and 5 parameter, weighted and non-weighted curve fitting algorithms using proprietary data analysis software developed at Rules-Based Medicine. Serum biochemical parameters were analyzed using an Abaxis VetScan® analyzer (Abaxis, Union City, Calif., USA). The liver, kidney, and lungs were fixed in formalin, paraffin embedded, sectioned, and stained with hematoxylin and eosin (H&E) for histopathological examination using an EVOS XL Core Imaging System (Fisher Scientific, Pittsburgh, Pa., USA).

Sepsis Induction.

Animals were anesthetized (45 mg/kg ketamine HCL/5 mg/kg xylazine i.p.) and a small 0.25 cm vertical midline abdominal incision was made. Animals in the sepsis group received an i.p. injection of freshly prepared cecal inoculum (400 mg cecal material/kg in 5 ml of dextrose $D_5W$ water) that was obtained from the cecal contents of donor rats. The sham-septic rats received sterile $D_5W$ (5 ml/kg, i.p.) only. All incisions were closed with interrupted silk sutures, and the abdomen gently massaged to distribute the injectate. After cecal material administration, animals received either 100 µl of sterile water or 3.5 mg/kg of $CeO_2$ nanoparticles in 100 µl of sterile water via a tail vein injection. All rats were given free access to food and water after recovery from anesthesia. Animal survival was assessed over 24 days.

Determination of Reactive Oxygen Species (ROS).

Briefly, experimentally treated cells were washed with cold PBS, harvested, and then centrifuged at 400×g for 10 min. The resulting pellets were re-suspended in PBS and the cell densities were separately adjusted or normalized to $1 \times 10^5$ cells/ml in PBS. Aliquots from each cell suspension (100 µl) were then gently mixed with a 1× solution of DCFH-DA reagent (100 µl) and incubated at 37° C. for 1 h. After incubation, cells were lysed and the fluorescence of each cell suspension was measured with a fluorometric plate reader (Spectramax, Gemini EM) at 530 nm. Observation of dye uptake by adherent cells was determined following imaging using an EVOSfl fluorescence (Fisher Scientific, Pittsburgh, Pa., USA) microscope equipped with a GFP filter. Cellular ROS levels were measured by monitoring the enzymatic cleavage of DCFH-DA to the fluorescent product DCF.

Effect of $CeO_2$ Nanoparticles on Bacterial Growth.

For the zone of inhibition, 5 ml of sterile Muller Hatton broth was prepared and inoculated with *E. coli* (ATCC#35150) or *Staphylococcus aureus* (ATCC#29213) for overnight growth at 37° C. Bacterial cultures were spread uniformly on the Muller Hatton agar plate by sterile swab and allowed to equilibrate for 5 min. Sterile Whatman filter paper discs of uniform size (6 mm) were impregnated with 100 µl of Sterile water (C: control, no cerium oxide nanoparticles), cerium oxide containing (C1: 1 mg of cerium oxide nanoparticles/L, C10: 10 mg/L, C50: 50 mg/L, C100: 100 mg/L), or ampicillin containing (A10: 10 mg) solution, allowed to dry for 1 h and then incubated on the plates for 6 h at 37° C. After 6 h, the zone clearance around the bacterial colony was observed and recorded.

For the measurement of dynamics of bacterial growth curve, *E. coli* and *S. aureus* were grown overnight in 5 ml LB broth or trypticase soy broth, respectively. On the subsequent day, 50 µl of the culture was transferred into 250 ml flasks containing 100 ml of LB broth or trypticase soy broth. Different concentrations of $CeO_2$ nanoparticles (1, 10, 50, or 100 mg/L) or 10 mg/L of ampicillin (positive control) was added to respective flasks. Flasks containing media with no nanoparticles were used as a negative control. Flasks were incubated on a shaker (200 rpm) at 37° C. and bacterial growth was monitored by the measurement of optical density (600 nm) every 60 min for 6 h. The determination of colony forming units (CFU) were determined by removing 1 ml of bacterial culture from each of the different flasks at the 3 h time point, serial dilution of the sample with sterile PBS, and transfer onto nutrient agar plates. CFU was determined after 24 h of incubation at 37° C.

Macrophage Culture and Determination of $CeO_2$ Nanoparticle Cytotoxicity and Protective Effect Against LPS.

RAW 264.7 cells from (ATCC #TIB71) were grown in 25 $cm^2$ cell culture flasks at 37° C. with 5% $CO_2$ in DMEM high glucose medium containing 1% Pen/Strep (10,000 U Penicillin and 10 mg Streptomycin/ml) and supplemented with 5% fetal bovine serum. The cytotoxicity of $CeO_2$ nanoparticles was determined using the MTT, LDH leakage and the trypan blue exclusion tests. The MTT assay utilizes the reduction of the soluble yellow MTT tetrazolium salt to a purple insoluble MTT formazan product by mitochondrial succinate-dependent dehydrogenase to measure the cell viability/proliferation. The lactate dehydrogenase (LDH) leakage assay was used to measure cell death due to cell membrane damage using a LDH assay kit (Biovision Research Products, USA) as detailed by the manufacturer. The trypan blue test was used to determine the number of viable and dead cells using a Cellometer™ Auto T4 from Nexcelon Bioscience (Lawrence, Mass., USA). To determine the protective effect of $CeO_2$ nanoparticles against LPS induced cell death, RAW 264.7 cells ($1.2 \times 10^5$/ml) were grown until 70-80% confluence and the media was replaced with the fresh medium containing different concentrations of $CeO_2$ nanoparticles (0, 0.72, 1.72, 4.3, or 8.6 µg/ml) in the presence or absence of LPS (2 µg/ml) for 24 h. MTT assays were performed as previously detailed.

Determination of Reactive Oxygen Species, Nitric Oxide and Cytokine Levels.

Reactive oxygen species (ROS) levels were determined following the addition of 2, 7-dichlorodihydrofluorescein diacetate (DCFH-DA), using the OxiSelect™ kit from Cell Bio Labs (San Diego, Calif., USA) as outlined by the manufacturer.

RAW 264.7 cells were treated with different concentrations of $CeO_2$ nanoparticles in the presence and absence of LPS (2 µg/ml) for 24 h. Nitrite production in the culture supernatants was assayed using the Griess reaction kit from Cayman Chemical Company (Ann Arbor, Mich., USA). One hundred microliters was removed from the medium and incubated with an equal volume of Griess reagent for 30 min at room temperature before measuring the absorbance at 540 nm in an ELISA reader (BioTek, Instrument, Inc., Winooski, Vt., USA). Nitrite concentration was calculated with reference to a standard curve obtained using $NaNO_2$.

Cytokine levels were assayed after culturing the cells for 24 h in the absence or presence of $CeO_2$ nanoparticles with and without LPS. Cell culture media was recovered by centrifugation at 400×g for 10 min. The concentration of TNF-α, IL-6, and IL-1β in the media was measured by ELISA kits (BD Bioscience, Franklin Lakes, N.J., USA) in triplicate as detailed by the manufacturer.

Immunoblotting and Electromobility Shift Assays.

Cells were washed with cold PBS, collected by scraping and centrifuged at 400×g for 10 min. Total cell lysates, cytoplasmic, and nuclear fractions were prepared by cell Lytic™ M cell lysis reagent (Sigma) and NE-PER cell lysis buffer (Thermo Scientific, Rockford, Ill., USA) as outlined by the manufacturer. Protein content was estimated in triplicate using the 660 nm protein assay (Pierce Biotechnology, Thermo Scientific, Rockford, Ill.) with bovine serum albumin as a standard. Protein separation using SDS-PAGE and immunoblotting were performed using fifty µg of total protein from each group as detailed previously. Membranes were incubated overnight at 4° C. with the appropriate primary iNOS, COX-2, IκB-α, or NF-κβ antibody (Cell Signaling, Danvers, Mass.), washed, and then incubated for 1 h at room temperature with a HRP labeled anti-rabbit before detection by ECL (Western Blotting Detection Reagent, GE Health Care Amersham, Piscataway, N.J.). Immunoreactive signals were quantified by densitometry using Alpha Innotech software (Santa Clara, Calif.). Beta actin immunoreactivity was used for normalization between samples.

The electromobility shift (EMSA) assay was performed using a commercially available kit (Pierce, Rockford, Ill., USA) as detailed by the manufacturer. Briefly, 5 µg of the nuclear protein extract was used in a binding reaction with 1× binding buffer, 2.5% glycerol, 5 mM $MgCl_2$, 50 ng/μl of poly (dI:dC), and 0.05% Nonidet P-40. A double stranded 5'-biotin-NF-κB oligonucleotide probe (consensus sequence 5'-AGTTGAGGGGACTTTCCCAGGC-3') was added to the reaction at a final concentration of 10 μM and the samples allowed to incubate on ice for 30 min. After incubation, 5 μl of 5× loading buffer was added to the reaction mix, and the samples were resolved on 6% polyacrylamide gels at 120 V for 55 min before transfer to nylon membrane at 10 V for 70 min using 0.5% TBE. After UV cross-linking of the protein-DNA complexes, NF-κB specific bands were detected by streptavidin-horseradish peroxidase conjugate using a chemiluminescence nucleic acid detection kit (Thermo scientific, Rockford, Ill., USA).

Effects of $CeO_2$ Nanoparticles on Bacterial Growth.

The effect of $CeO_2$ exposure on the gram negative *Escherichia coli* (ATCC#35150) and the gram positive *Staphylococcus aureus* (ATCC#29213) was studied by disc diffusion, the monitoring bacterial growth and by determination of colony forming units. The disc diffusion method was adopted as described previously. Growth dynamics and the number of colony forming units in the presence and absence of $CeO_2$ nanoparticles was determined as detailed in the supplementary methods.

Statistical Analysis.

Data is presented as mean±standard error of the mean (SEM). Dependent variables were analyzed by one way ANOVA using Holm-Sidak test in SigmaStat (Aspire Software International, Auburn Va.) and Newman Keuls post-hoc testing where appropriate. A P value <0.05 was considered as significant.

Results for Example 8

$CeO_2$ Nanoparticle Characterization.

Figure 43A:
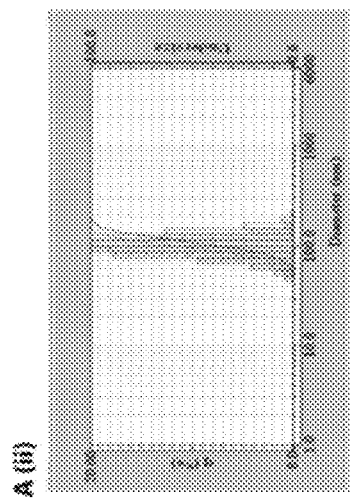
FIGS. 43A-43C include images and graphs showing the yet further characterization of $CeO_2$ nanoparticles, animal survivability and the effect of treatment on serum biomarker levels, including.
Figure 43A:
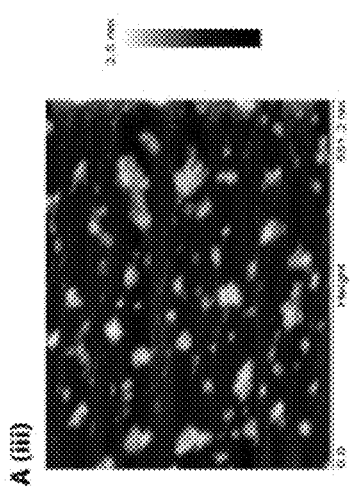
Figure 43A:
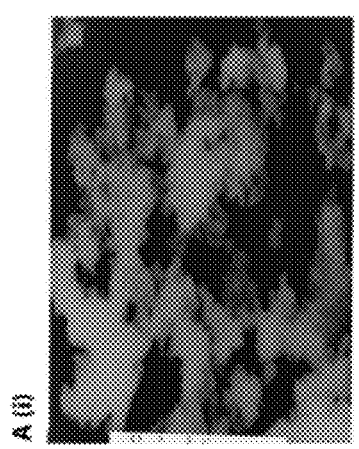

TEM and AFM analysis suggested that the $CeO_2$ nanoparticles were likely spherical in shape (FIG. 43A, A (i) and FIG. 43A, A (iii)). The mean hydrodynamic diameter of the $CeO_2$ nanoparticles as determined by dynamic light scattering (DLS) was 140±53 nm (FIG. 43A, A(ii)).

$CeO_2$ Nanoparticle Treatment Increases Animal Survivability and Decreases Sepsis-Induced Inflammation.

Figure 49:
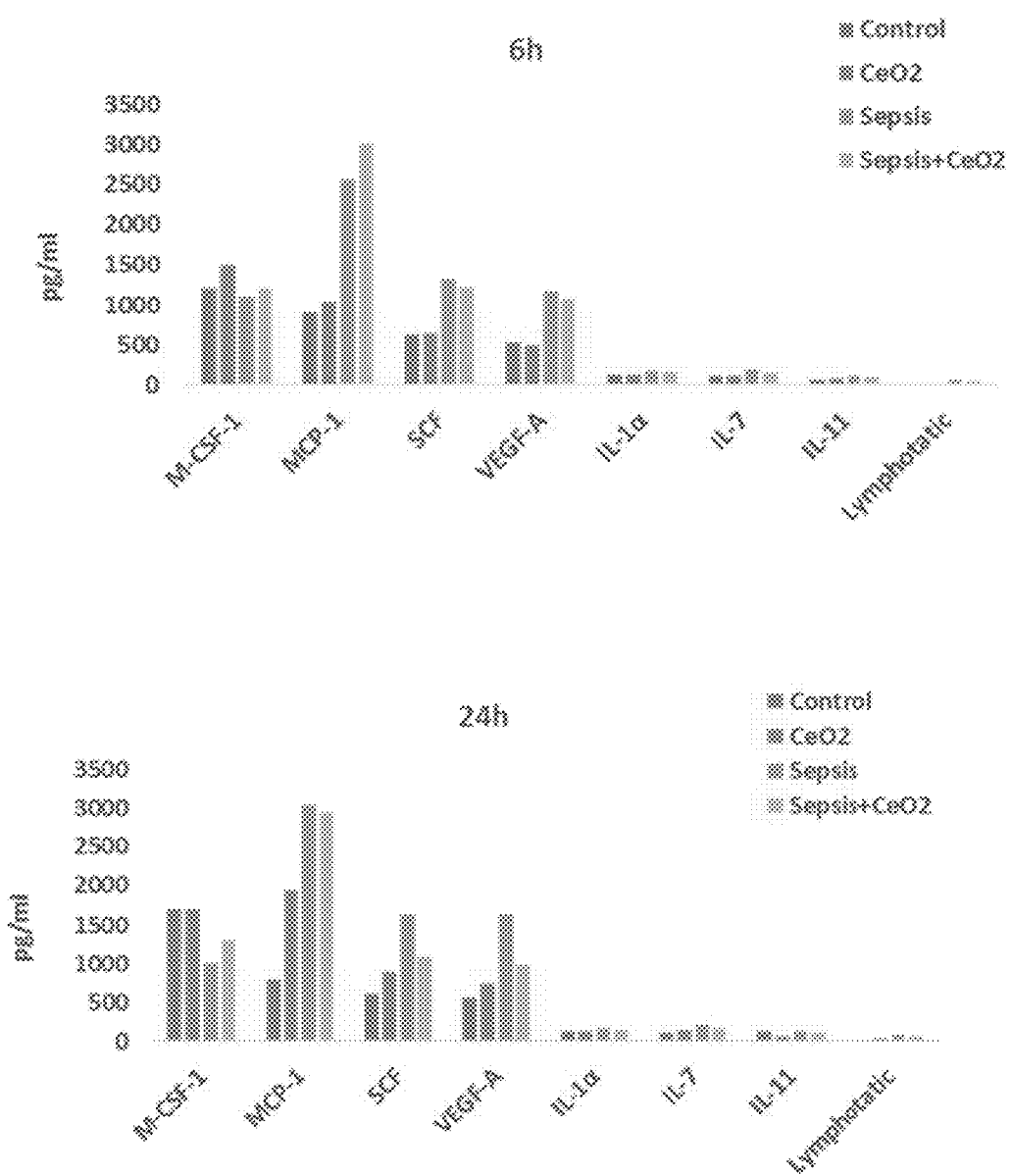
FIG. 49 includes graphs showing the effect of sepsis and cerium oxide nanoparticle treatment on serum biomarkers.

Compared to the Control Animals, the Animals Inoculated with the Cecal suspension exhibited several signs of septic shock including diarrhea, piloerection, and little or no spontaneous movement. Treatment of the septic animals with $CeO_2$ nanoparticles increased animal survivability from 20% to 90% at 48 h (FIG. 43B, B(i)). Animals subjected to the polymicrobial challenge exhibited increased serum IL-6 levels at 6 and 24 h (P<0.05) which were decreased with $CeO_2$ nanoparticle treatment at 6 h (FIG. 43B, B (ii), P<0.05). Although not statistically evaluated, sepsis appeared to increase the amount of growth regulated alpha protein (KC/GRO), macrophage inflammatory protein-1 beta (MIP-1β) macrophage derived chemokine (MDC), monocyte chemotactic protein-3 (MCP-3), myoglobin, macrophage inflammatory protein-3 beta (MIP-3β), eotaxin, leptin, macrophage inflammatory protein-2 (MIP-2), interferon gamma induced protein-10 (IP-10), tissue inhibitor of metalloproteinases-1 (TIMP-1) and plasminogen activator inhibitor-1 (PAI-1) at 6 and 24 h (FIG. 43B, B(iii), FIG. 43C, C (i), C(ii), and C(iii)). In contrast, nanoparticle administration also appeared to decrease the levels of KC/GRO, MIP-1β, MDC, MCP-3, myoglobin MIP-3β, eotaxin, leptin, MIP-2, IP-10, and TIMP-1. Likewise, sepsis appeared to increase and treatment tended to decrease the levels of macrophage colony stimulating factor-1 (M-CSF-1), monocyte chemotactic protein-1 (MCP-1), stem cell factor (SCF), and vascular endothelial growth factor A (VEGF-A) (FIG. 49).

$CeO_2$ Nanoparticle Treatment Decreases Sepsis-Induced Liver and Renal Dysfunction.

Compared to control animals, serum ALT was lower at 6 h and blood urea nitrogen (BUN) was higher at 6 h in the septic animals (P<0.05). The amount of ALB, ALP, amylase and glucose were lower at 24 h while BUN and globulin levels were higher at 24 h in septic animals (P<0.05; Table 11). $CeO_2$ nanoparticle treatment decreased BUN at 6 h significantly (Table 11).

TABLE 11

Effect of sepsis and $CeO_2$ nanoparticle treatment on blood chemistry.

| Analyte | 6 h Control | 6 h Ceo2 | 6 h Sepsis | 6 h Sepsis + Ceo2 | 24 h Control | 24 h Ceo2 | 24 h Sepsis | 24 h Sepsis + Ceo2 |
|---|---|---|---|---|---|---|---|---|
| ALB | 4.08 ± 0.06 | 4.16 ± 0.11 | 3.78 ± 0.12$ | 3.86 ± 0.04 | 3.46 ± 0.05 | 3.33 ± 0.11 | 2.80 ± 0.08*$ | 2.78 ± 0.08*$ |
| ALP | 195.00 ± 19.96 | 196.25 ± 20.78 | 160.88 ± 15.22 | 176.13 ± 25.47 | 265.88 ± 22.02 | 238.13 ± 36.40 | 91.29 ± 4.83*$ | 113.44 ± 6.05*$ |
| ALT | 77.63 ± 6.83 | 66.13 ± 4.85 | 54.38 ± 2.52* | 55.13 ± 3.96* | 86.00 ± 15.34 | 76.00 ± 6.12 | 69.14 ± 6.14 | 82.88 ± 11.45 |
| Amylase | 920.25 ± 30.64 | 874.50 ± 17.90 | 1003.50 ± 57.40 | 972.25 ± 32.65 | 863.63 ± 17.89 | 889.25 ± 66.22 | 561.71 ± 58.26*$ | 790.56 ± 108.41 |
| BUN | 25.00 ± 1.83 | 29.25 ± 2.86 | 39.13 ± 1.38*$ | 32.13 ± 1.13*‡ | 17.88 ± 0.90 | 18.88 ± 2.89 | 71.43 ± 13.40*$ | 41.22 ± 5.60*$ |
| Ca+ | 10.75 ± 0.26 | 10.60 ± 0.22 | 10.91 ± 0.22 | 10.478 ± 0.18 | 10.50 ± 0.14 | 10.50 ± 0.19 | 10.19 ± 0.08 | 10.11 ± 0.21 |
| Phos | 11.41 ± 0.79 | 10.70 ± 0.58 | 13.86 ± 0.73$ | 11.78 ± 0.89 | 9.89 ± 0.26 | 9.35 ± 0.21 | 10.77 ± 0.87 | 9.41 ± 0.40 |
| Glu | 376.88 ± 12.44 | 363.75 ± 16.26 | 312.88 ± 66.71 | 283.75 ± 40.21 | 341.63 ± 11.36 | 267.63 ± 22.30 | 101.86 ± 11.88*$ | 116.67 ± 6.08*$ |
| Na+ | 142.00 ± 0.82 | 144.25 ± 10.13 | 140.88 ± 1.39 | 138.50 ± 0.66$ | 143.75 ± 0.73 | 143.75 ± 1.01 | 145.00 ± 1.23 | 140.378 ± 1.15‡ |
| K+ | 7.16 ± 0.25 | 7.46 ± 0.23 | 6.98 ± 0.23 | 6.79 ± 0.16 | 7.59 ± 0.28 | 7.63 ± 0.21 | 8.29 ± 0.25 | 7.64 ± 0.23 |
| Glob | 1.35 ± 0.05 | 1.44 ± 0.07 | 1.50 ± 0.06 | 1.43 ± 0.05 | 1.80 ± 0.06 | 2.00 ± 0.09 | 2.39 ± 0.07*$ | 2.34 ± 0.07*$ |
| TP | 5.41 ± 0.04 | 5.60 ± 0.09 | 5.26 ± 0.08$ | 5.30 ± 0.06$ | 5.28 ± 0.05 | 5.31 ± 0.08 | 5.19 ± 0.13 | 5.13 ± 0.09 |

Figure 44A:
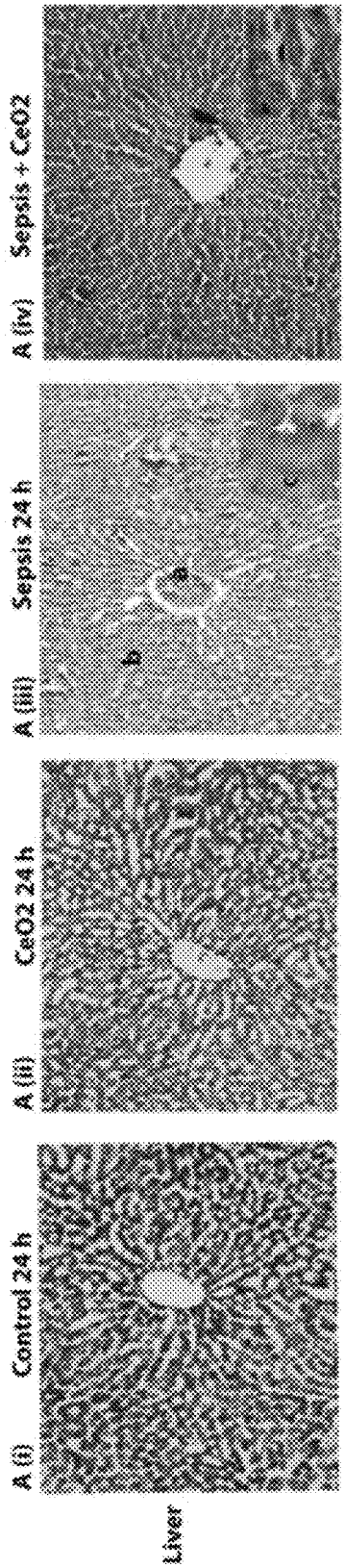
FIGS. 44A-44C are images and graphs showing the effect of $CeO_2$ nanoparticles on sepsis-induced organ damage, including representative micrographs of liver (FIG. 44A), kidney (FIG. 44B), and lung (FIG. 44C) 24 h after sepsis induction as visualized by light microscopy.

Compared to liver sections obtained from control animals (FIG. 44A, A(i)), sepsis was associated with changes in cell swelling, sinusoidal dilatation and the infiltration of cells in the peri-portal area (FIG. 44A, A(iii)). Light microscopic evaluation of the kidney demonstrated structural deterioration of the glomerulus, decreased Bowman's space, loss of brush border, and tubular cell sloughing (FIG. 44B, B(iii)). Similarly, examination of the lung showed evidence of a thickening of the alveolar septum and the infiltration of inflammatory cells within the alveolar tissue (FIG. 44C, C(iii)). $CeO_2$ nanoparticle treatment appeared to prevent the development of these histopathological features (FIG. 44A, A(iv), FIG. 44B, B(iv) and FIG. 44C, C(iv)). Hematoxylin and eosin staining of the liver from nanoparticle treated animals suggested $CeO_2$ nanoparticle uptake by the liver Kupffer cells (FIG. 45A, A(ii) and FIG. 45A, A (iii)).

$CeO_2$ Nanoparticle Treatment Decreases LPS-Induced Cell Death, Reactive Oxygen Species, Nitric Oxide Production and Cytokine Release.

Figure 45A:
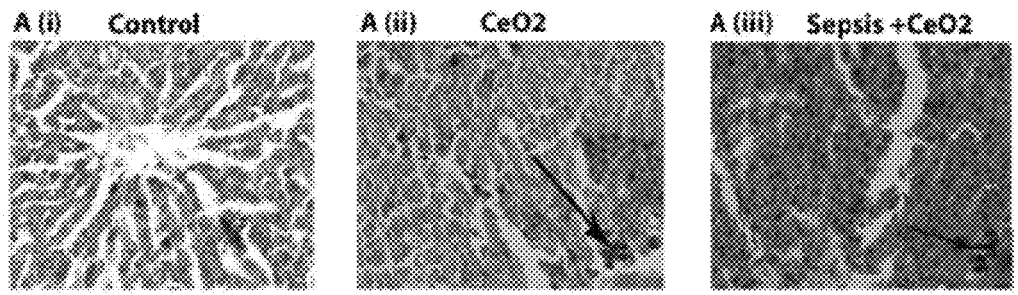
FIGS. 45A-45C include images and a graphs showing the uptake of $CeO_2$ nanoparticles and the effect of nanoparticle treatment on LPS-induced cell death, including: representative micrographs of liver sections obtained from animals that had been injected with $CeO_2$ nanoparticles (A (ii)) and treated septic animals (A (iii)) showing evidence of $CeO_2$ nanoparticle deposition (FIG. 45A); uptake of nanoparticles by cultured RAW 264.7 macrophage cells cultured in the presence (B (ii)) but not the absence of $CeO_2$ nanoparticles (B (i)) and in cells exposed to LPS and $CeO_2$ nanoparticles (B (iii)); and a graph showing the effect of $CeO_2$ nanoparticle treatment of LPS-induced cell death in cultured RAW 264.7 macrophages (FIG. 45C)
Figure 45B:
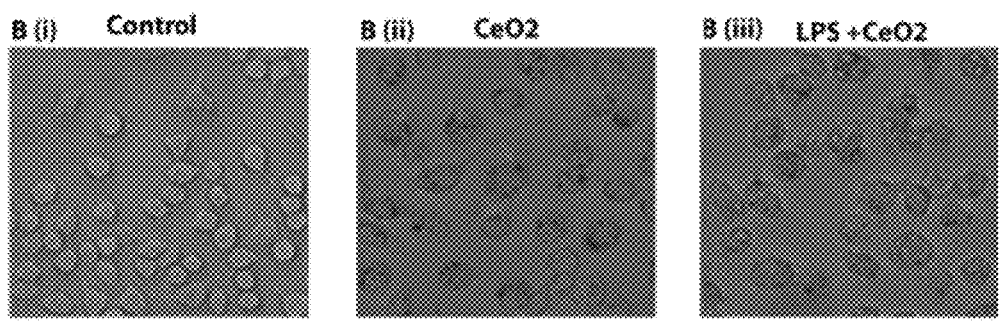
Figure 45C:
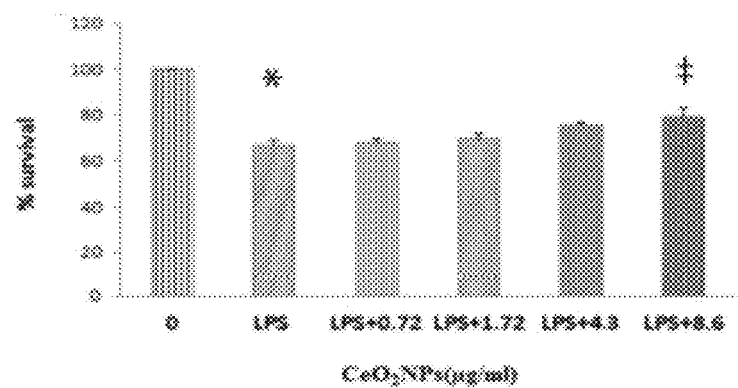
Figure 50A:
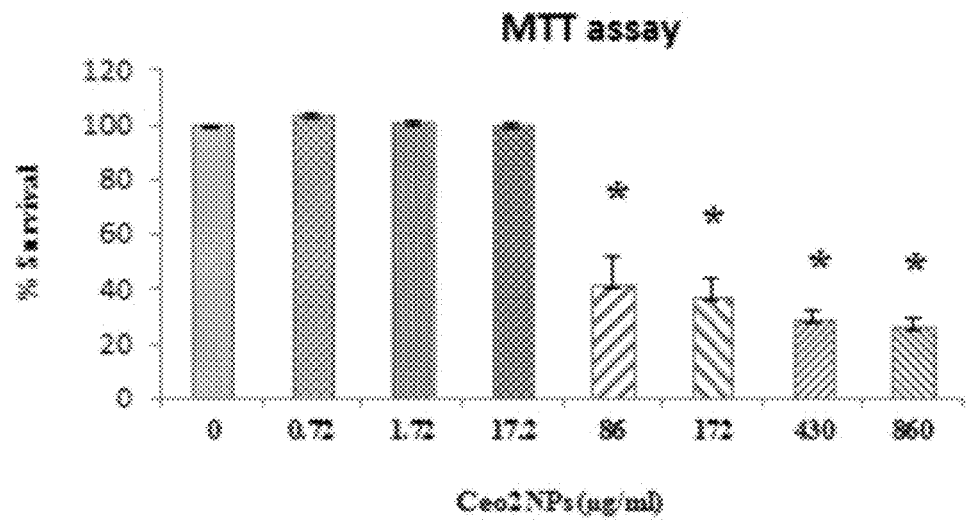
FIGS. 50A-50C include graphs showing the determination of cerium oxide nanoparticle cytotoxicity by MTT assay (FIG. 50A), trypan blue assay (FIG. 50B), and LDH leakage assay (FIG. 50C).
Figure 50B:
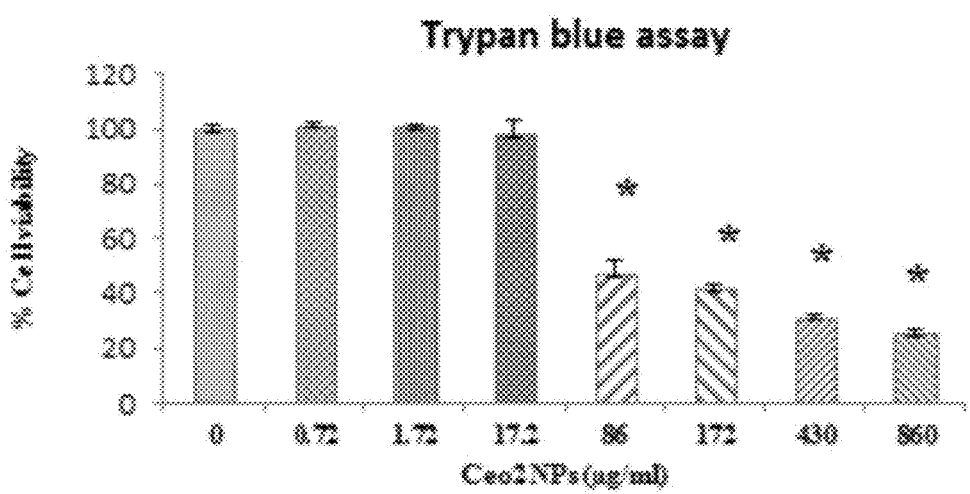
Figure 50C:
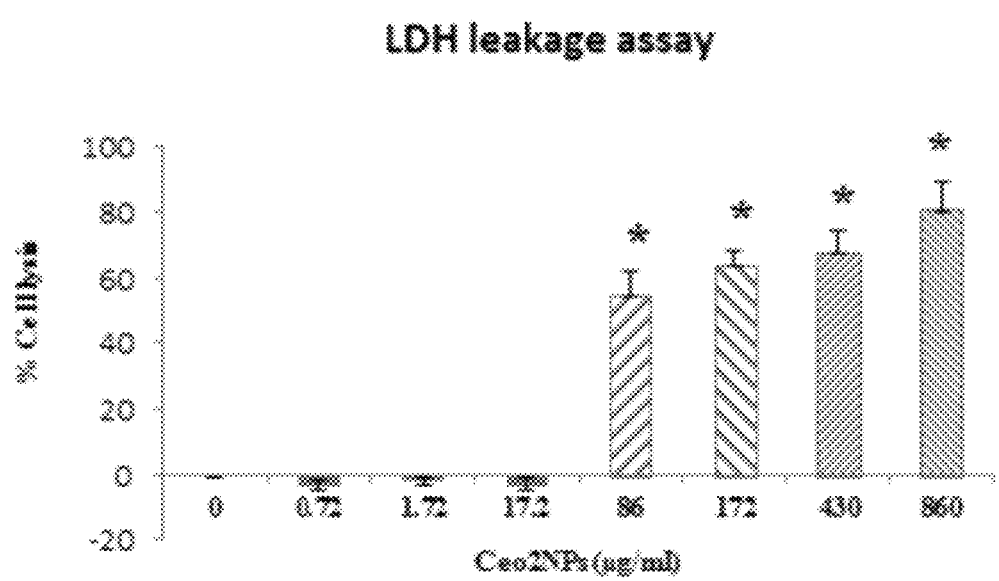

Microscopic examination of RAW cells that had been treated with $CeO_2$ nanoparticles in the presence and absence of LPS appeared to suggest that particle uptake by RAW cells (FIG. 45B, B(ii) and FIG. 45B, B(iii)). Concentrations of $CeO_2$ nanoparticles less than 17.2 μg/ml did not appear to significantly influence cell survival as determined by the MTT assay, trypan blue dye exclusion test and LDH leakage assay (FIGS. 50A-50C). To determine if exposure to $CeO_2$ nanoparticles was protective against LPS challenge, macrophage cells were treated with different concentrations of nanoparticles (0, 0.72, 1.72, 4.3 and 8.6 μg/ml) for 24 h in the absence and presence of LPS. As expected, exposure to LPS decreased cell survival/proliferation (FIG. 45C). Compared to LPS only treated cells, $CeO_2$ nanoparticle treatment Exposure to $CeO_2$ Nanoparticles Impairs the Growth of *E. coli*.

Figure 48A:
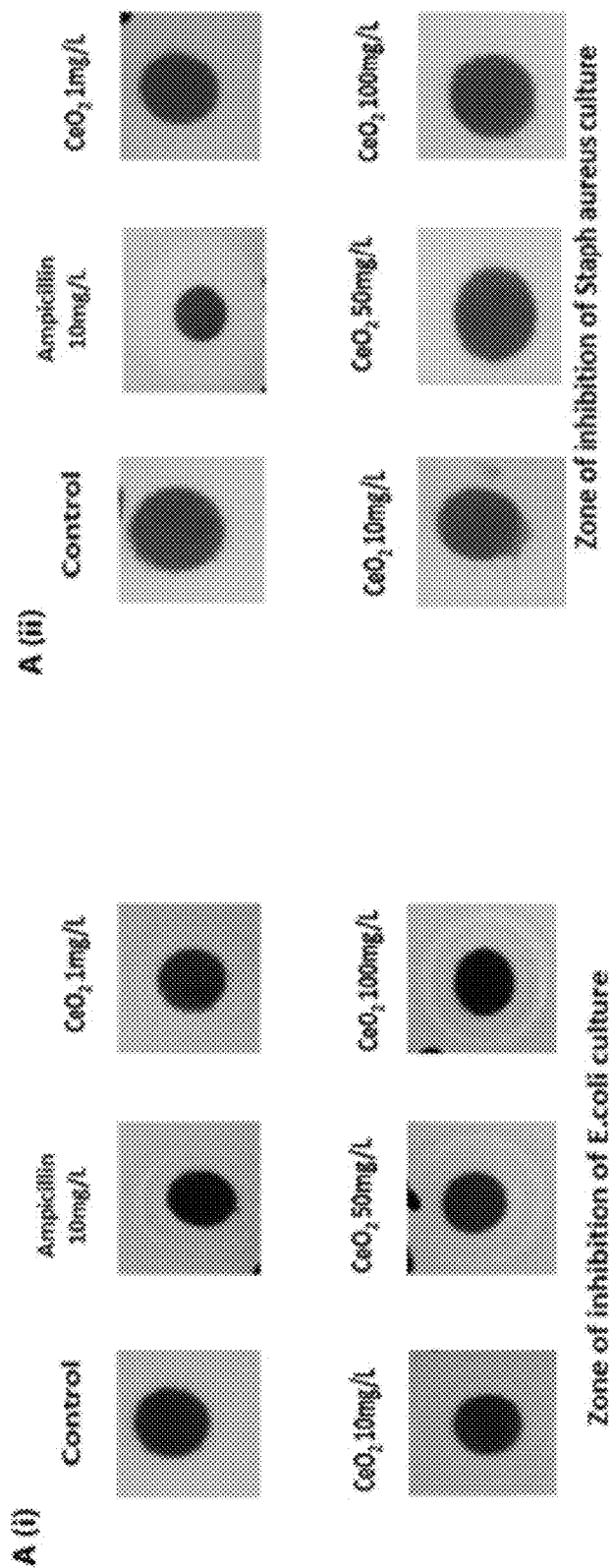

$CeO_2$ nanoparticles inhibit the growth of *Escherichia coli* (zone of inhibition) but not *S. aureus* (FIG. 48A, A(i), A(ii)). The bactericidal activity of $CeO_2$ nanoparticles was also demonstrated in liquid culture by measuring the optical density of the solution at 600 nm. Consistent with our zone of inhibition measurements, the addition of 50 or 100 mg/l of $CeO_2$ nanoparticles decreased *E. coli* but not *S. aureus* growth and CFU (FIG. 48B, B(i), FIG. 48C, C(i), Table 12).

TABLE 12

Dynamic growth curves for *E. coli* and *Staph aureus* following treatment with different concentrations of $CeO_2$ NPs.

| Concentration of cerium oxide (mg/l) | 0 h | 1 h | 2 h | 3 h | 4 h | 5 h | 6 h |
|---|---|---|---|---|---|---|---|
| | | | Optical density (OD) at 600 nm for *E. coli* | | | | |
| Control | 0.001 ± 0.00 | 0.002 ± 0.00 | 0.014 ± 0.00 | 0.133 ± 0.00 | 0.527 ± 0.02 | 1.085 ± 0.05 | 1.455 ± 0.05 |
| Ampicillin (10) | 0.001 ± 0.00 | 0.002 ± 0.00 | 0.008 ± 0.00* | 0.074 ± 0.00* | 0.340 ± 0.02* | 0.484 ± 0.03* | 1.147 ± 0.06* |
| 1 | 0.001 ± 0.00 | 0.001 ± 0.00 | 0.009 ± 0.00 | 0.110 ± 0.00 | 0.481 ± 0.00 | 1.095 ± 0.06 | 1.472 ± 0.05 |
| 10 | 0.001 ± 0.00 | 0.001 ± 0.00 | 0.009 ± 0.00 | 0.099 ± 0.00 | 0.458 ± 0.01 | 1.065 ± 0.06 | 1.500 ± 0.02 |
| 50 | 0.001 ± 0.00 | 0.001 ± 0.00 | 0.012 ± 0.00 | 0.096 ± 0.01* | 0.436 ± 0.02* | 1.084 ± 0.02 | 1.460 ± 0.04 |
| 100 | 0.001 ± 0.00 | 0.003 ± 0.00 | 0.013 ± 0.00 | 0.104 ± 0.01* | 0.448 ± 0.03* | 1.069 ± 0.05 | 1.473 ± 0.09 |
| | | | Optical density (OD) at 600 nm for *Staph aureus* | | | | |
| Control | 0.001 ± 0.00 | 0.002 ± 0.00 | 0.038 ± 0.01 | 0.239 ± 0.03 | 0.681 ± 0.06 | 0.777 ± 0.03 | 1.300 ± 0.32 |
| Ampicillin (10) | 0.001 ± 0.00 | 0.003 ± 0.00 | 0.005 ± 0.00* | 0.002 ± 0.00* | 0.005 ± 0.00* | 0.006 ± 0.00* | 0.006 ± 0.00* |
| 1 | 0.001 ± 0.00 | 0.004 ± 0.00 | 0.037 ± 0.02 | 0.216 ± 0.02 | 0.678 ± 0.06 | 0.778 ± 0.08 | 1.290 ± 0.38 |
| 10 | 0.001 ± 0.00 | 0.001 ± 0.00 | 0.046 ± 0.2 | 0.232 ± 0.03 | 0.661 ± 0.04 | 0.743 ± 0.05 | 1.265 ± 0.36 |
| 50 | 0.002 ± 0.00 | 0.003 ± 0.00 | 0.055 ± 0.01 | 0.226 ± 0.03 | 0.693 ± 0.05 | 0.772 ± 0.08 | 1.264 ± 0.38 |
| 100 | 0.004 ± 0.00 | 0.002 ± 0.02 | 0.052 ± 0.05 | 0.229 ± 0.04 | 0.694 ± 0.04 | 0.776 ± 0.05 | 1.267 ± 0.39 |

*Significantly different from control ($p < 0.050$).

(8.6 μg/ml) improved cell survival ($P<0.05$) (FIG. 45C). To determine if exposure to $CeO_2$ nanoparticles was associated with diminished cellular ROS levels following LPS challenge, the enzymatic cleavage of dichlorodihydrofluorescein diacetate (DCFH-DA) was examined. Cerium oxide nanoparticles decreased ROS levels in LPS-stimulated RAW cells (FIG. 46A, A(i) and A(ii)) and was similar to that seen following incubation with the known reducing agent n-acetyl cysteine (FIG. 46A, A(i) and A(ii)).

Figure 46A:
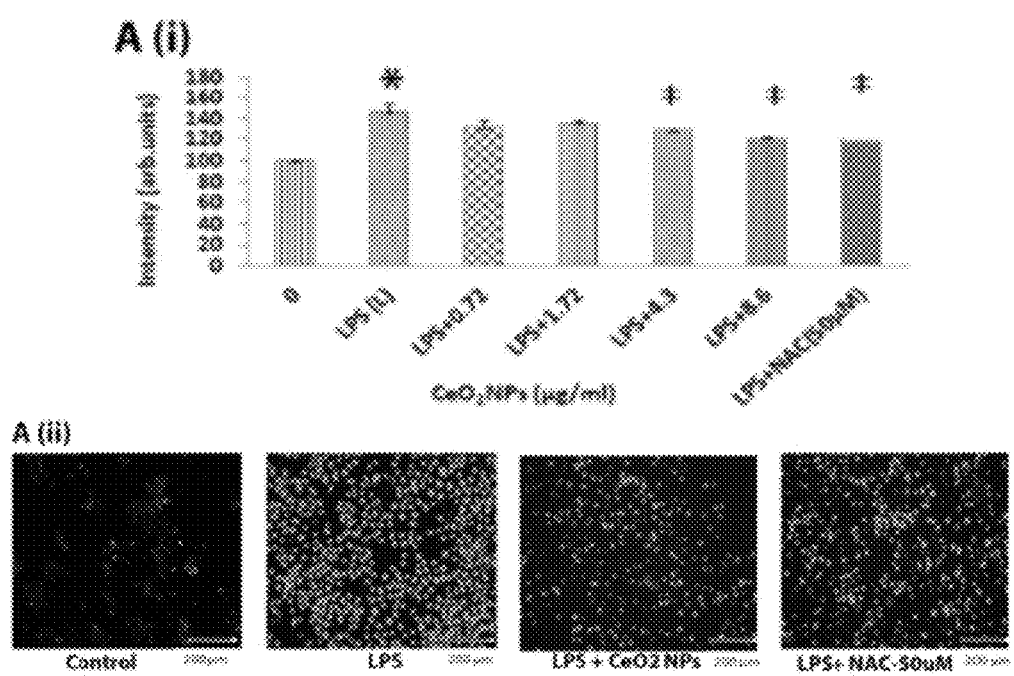
FIGS. 46A-46D include images and graphs showing the ability of $CeO_2$ nanoparticle treatment to decrease LPS-induced increases in cellular ROS, cytokine release, NO production and the expression of iNOS and COX-2 in RAW 264.7 cells, including: images and graphs (FIG. 46A) showing cells that were exposed to LPS in the presence and absence of $CeO_2$ nanoparticles for 24 h and cellular fluorescence was measured using a plate reader (A (i)) or imaged by fluorescence microscopy at 20× (A (ii)); images and graphs (FIG. 46B-46C) showing the concentration of TNF-α (B (i)), IL-6 (B (ii)), IL-1β (C (i)) and nitrites (C (ii)) determined in the cell free media by ELISA; and images and graphs (FIG. 46D) showing the effect of $CeO_2$ nanoparticle treatment on LPS-induced expression of iNOS (D (i)) and COX-2 (D (ii)) as determined by immunoblotting.
Figure 46B:
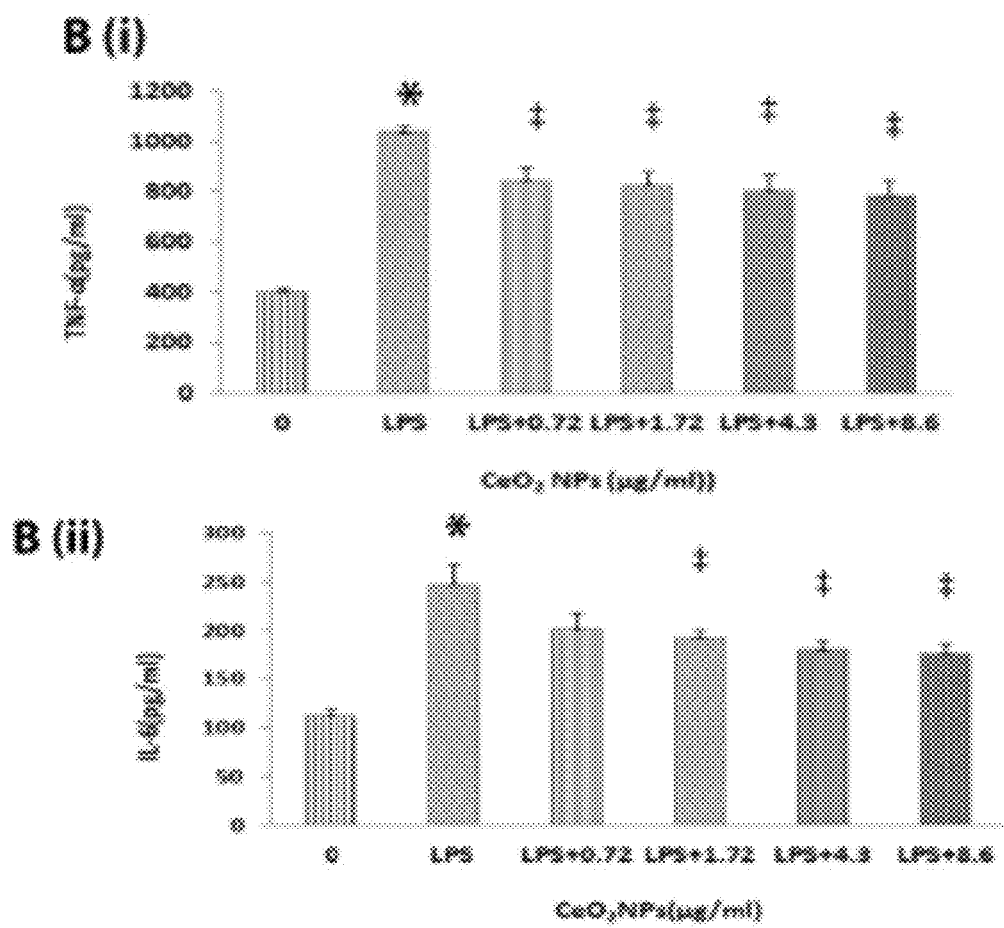

Compared to that seen in the control cells, LPS increased the production of TNF-α, IL-6, and IL-1β at 24 h (FIG. 46B, B(i), B(ii), and C(i), $P<0.05$). $CeO_2$ nanoparticle treatment significantly decreased LPS-induced increases in TNF-α, IL-6, and IL-1β ($P<0.05$). The ability of $CeO_2$ nanoparticles to reduce LPS-induced cytokine release appeared to vary between cytokines. The production of TNF-α was suppressed by $CeO_2$ nanoparticle treatment at concentrations of 0.72-8.6 μg/ml (FIG. 46B, B(i), $P<0.05$). Conversely, elevations in IL-6 were decreased when the concentration of $CeO_2$ nanoparticles was between 1.72-8.6 μg/ml (FIG. 46B, B(ii)), while IL-1β production was lower at higher concentrations (4.3-8.6 μg/ml) (FIG. 46C, C(i)).

Figure 46C:
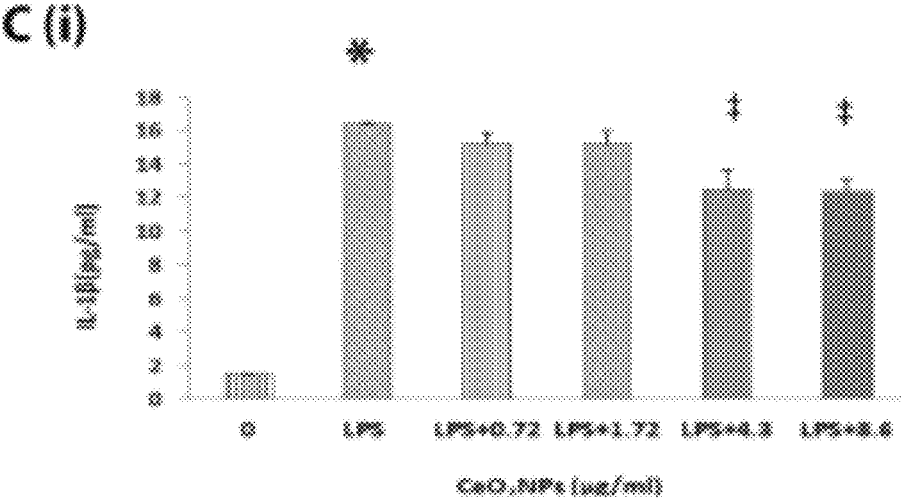
Figure 46C:
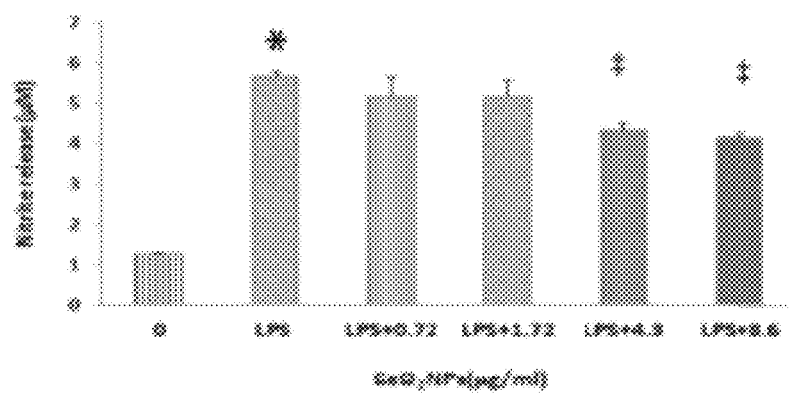

Compared to that observed in the control cells, LPS increased nitrite production ($P<0.05$, FIG. 46C, C(ii)). Treatment with $CeO_2$ nanoparticles (4.3-8.6 μg/ml) suppressed LPS-induced nitrite production ($P<0.05$), along with iNOS and COX-2 protein levels (FIG. 46D, D(i) and D(ii), $P<0.05$).

$CeO_2$ Nanoparticle Treatment Decreases NF-κB/p65 Translocation and DNA Binding.

Figure 47A:
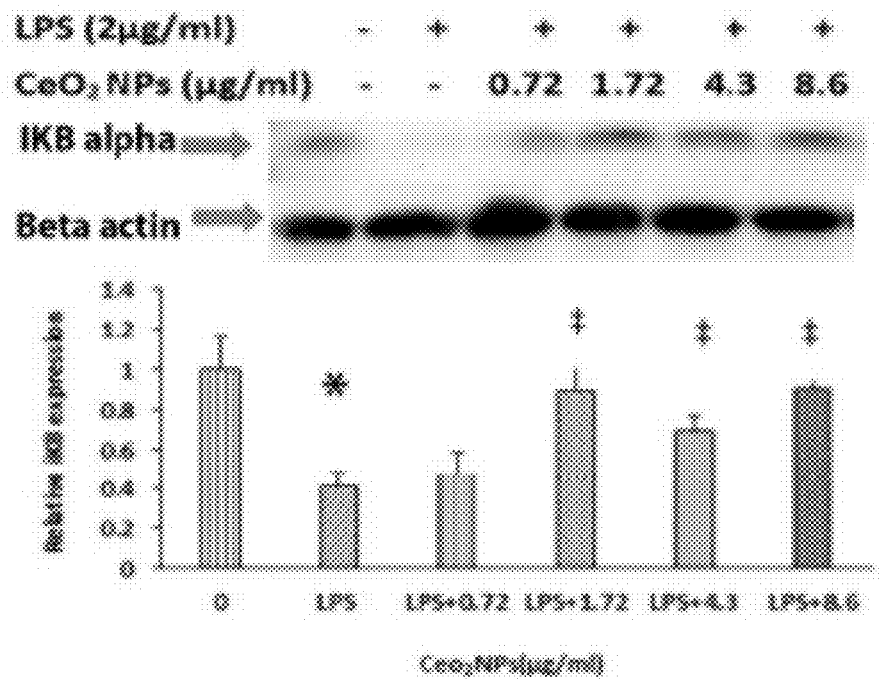
FIGS. 47A-47D includes images and graphs showing the ability of $CeO_2$ nanoparticle treatment to reduce LPS-induced translocation of NF-κB/p65, where cultured RAW 264.7 macrophage cells were exposed to LPS in the absence and presence of $CeO_2$ nanoparticles for 24 h, the amount of IκB-α in whole cell lysate (FIG. 47A), the protein levels of NF-κB in the cyotosol (FIG. 48B) and the NF-κB content of nuclear extracts (FIG. 48C) were determined by immunoblotting, and where the binding of NF-κB to DNA in the nuclear extract was determined by EMSA (FIG. 47D).
Figure 47B:
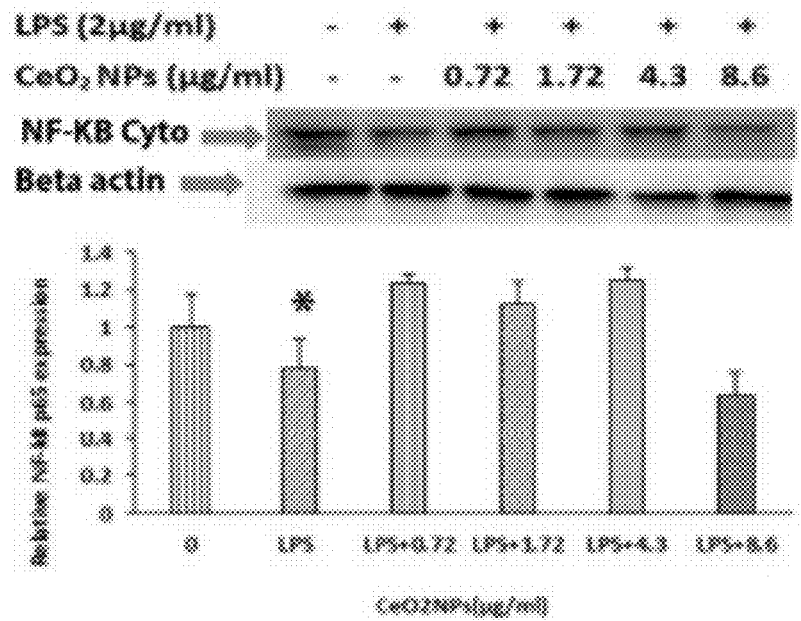
Figure 47C:
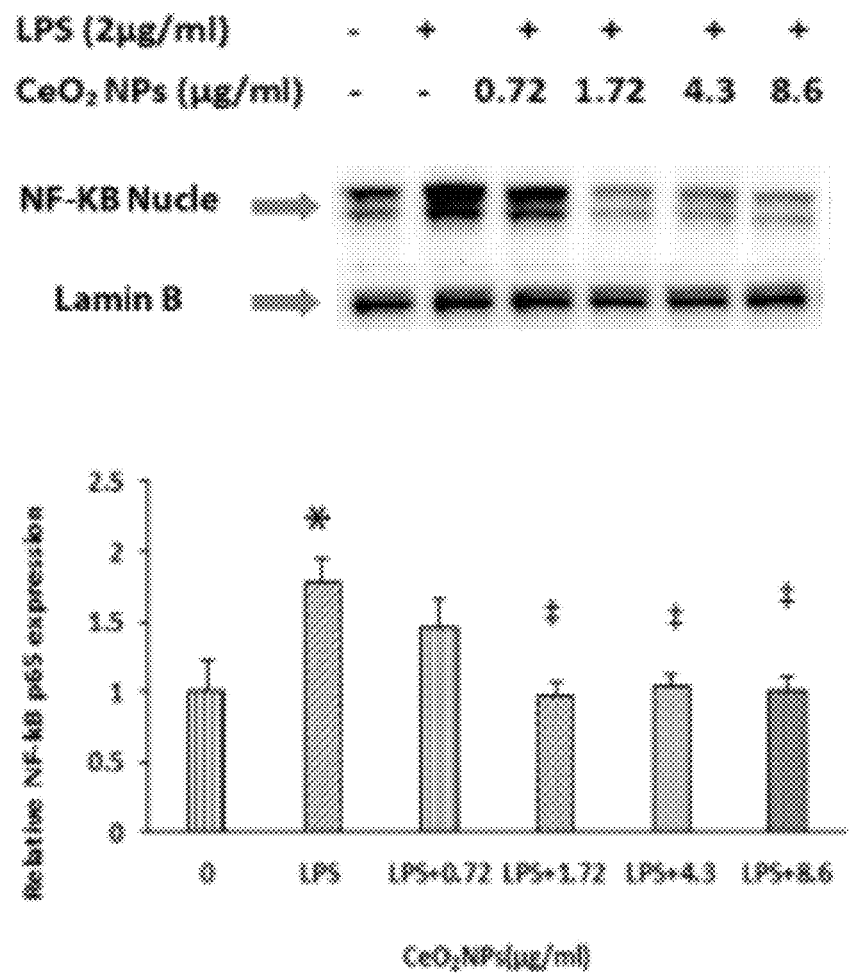
Figure 47D:
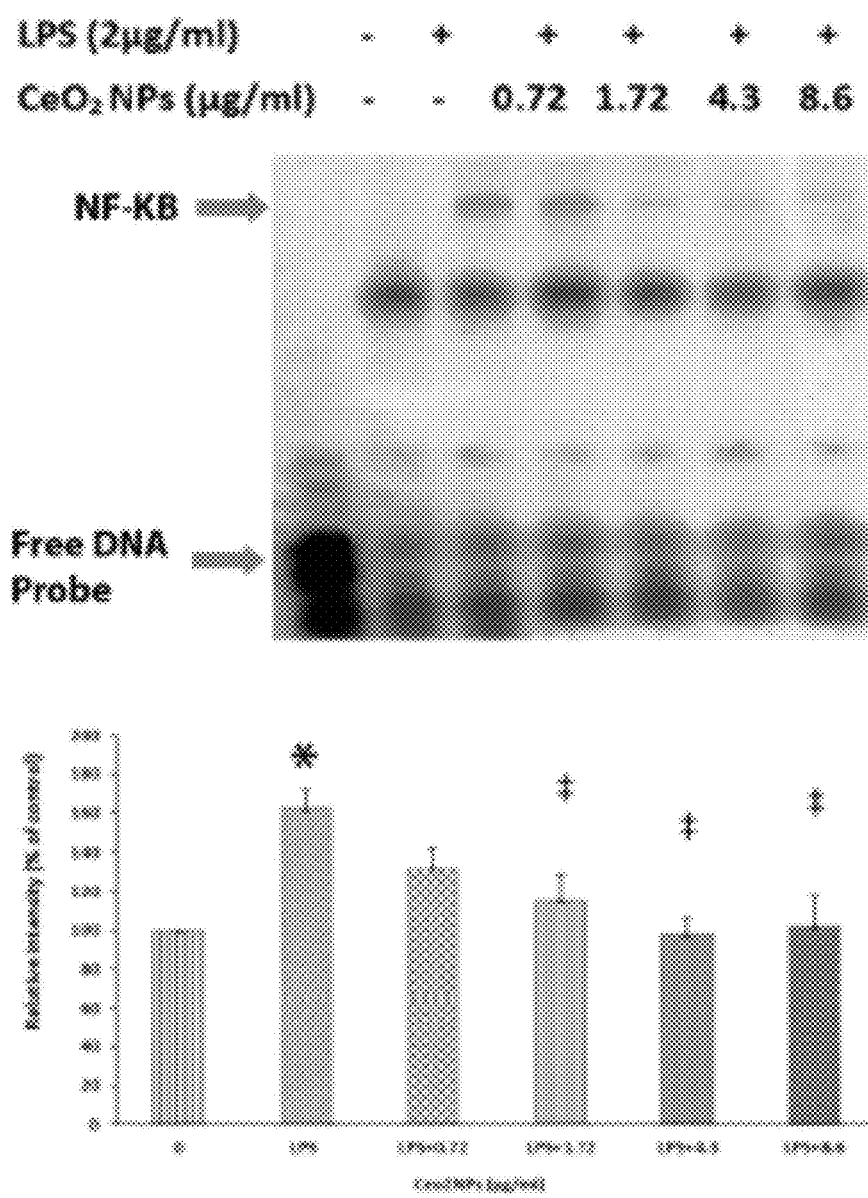

LPS-induced decreases in IκB-α protein in the whole cell lysate were abrogated following $CeO_2$ treatment (FIG. 47A, $P<0.05$). Consistent with these findings, LPS-induced translocation of NF-κB/p65 to the nucleus and binding of protein to an NF-κB oligonucleotide was attenuated by $CeO_2$ nanoparticle treatment (FIGS. 47C-47D, $P<0.05$).

Discussion of Example 8

Figure 43B:
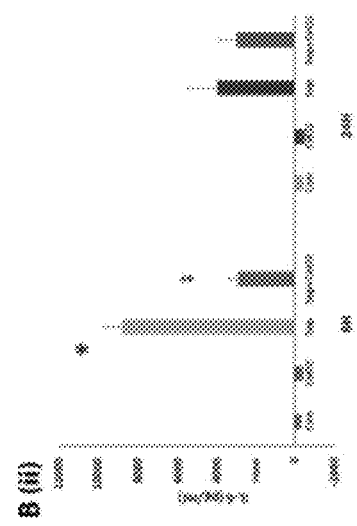
Figure 43B:
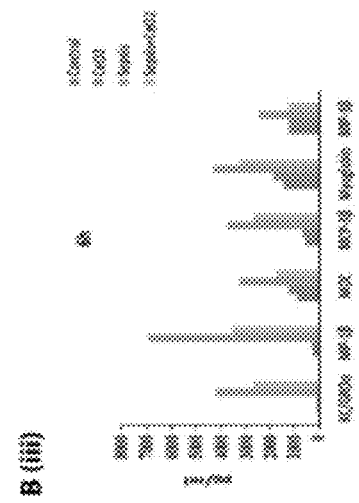
Figure 43B:
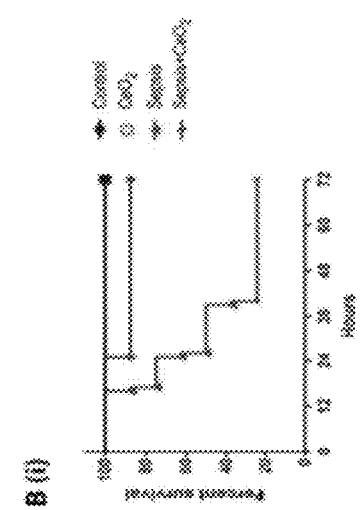

Despite decades of intensive investigation and significant advances in medical technology, the management of patient care and antimicrobial therapy the overall mortality rate in severe sepsis still remains unacceptably high. A finding of the foregoing study was the observation that a single injection of $CeO_2$ nanoparticles, in the absence of antibiotic treatment, fluid resuscitation, or other pharmacological intervention, was associated with an approximately 70% increase in animal survivability in the cecal inoculum model of severe sepsis (FIG. 43B).

Figure 44B:
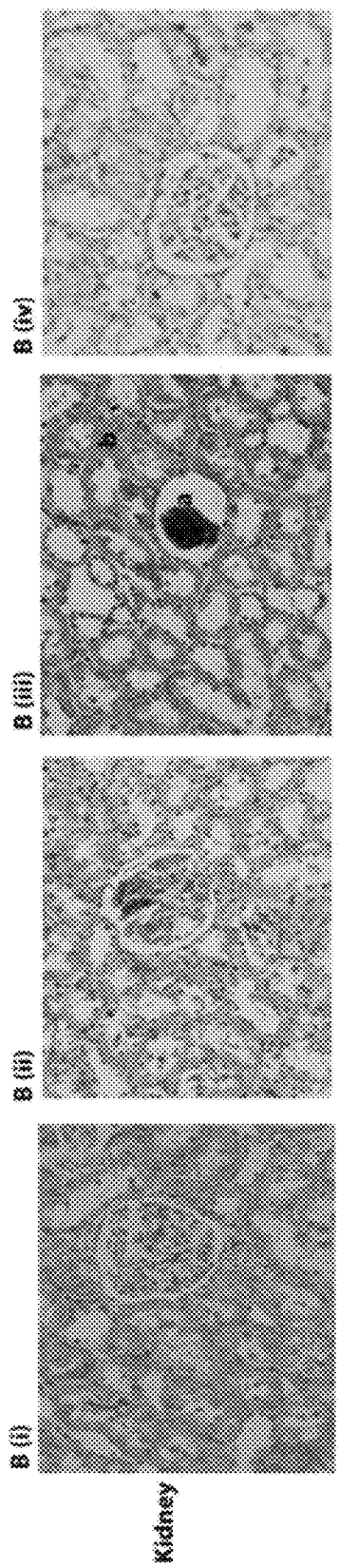
Figure 44C:
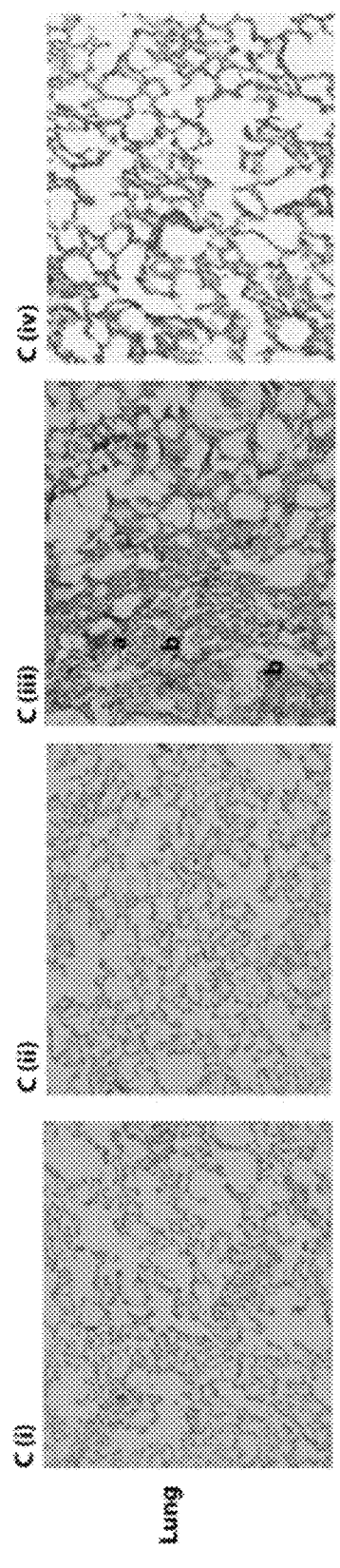

Consistent with previous work, it was found that sepsis was associated with increased blood urea nitrogen (BUN), and decreased in alkaline aminotransferase (ALT) and alkaline phosphatase (ALP) levels, which are suggestive of kidney and liver dysfunction. Histological examination of liver and kidney structure confirmed this possibility (FIG. 44B). Whether these improvements in liver kidney function and structure, by themselves, can explain the increase in animal survivability we see with nanoparticle treatment, is currently unclear.

Figure 43C:
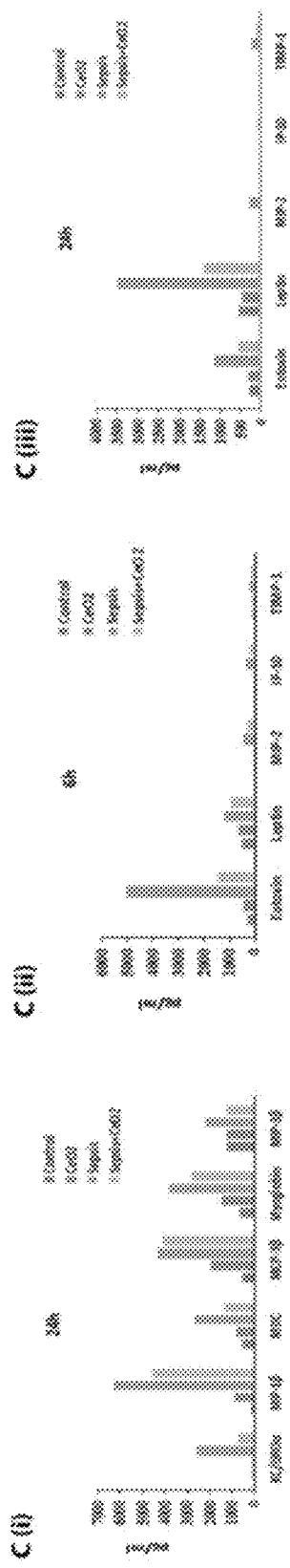

It is thought that elevations in serum IL-6 levels are highly correlated with the survival of the septic patient. Similar to other reports, the above-described in vivo studies showed that sepsis was associated with increased serum IL-6 levels and importantly, that the nanoparticle based treatment significantly attenuated this increase (FIG. 43B). In addition to IL-6, it was also found that sepsis was associated with what appeared to be increases in a number of different serum cytokines, chemokines, growth factors and inflammatory proteins which appeared to be less in the nanoparticle treated animals (FIGS. 43B-43C). Given that many of the chemokines (KC/GROα, MIP1β, MDC, MIP-3β) that appeared to be elevated with sepsis and decreased with treatment are thought to be synthesized in the liver Kupffer cells, these data suggested that the nanoparticle intervention was also capable of affecting macrophage function. Consistent with the in vivo data, cell culture experiments using the RAW 264.7 macrophage cell line and exposure to LPS to mimic a gram negative bacterial challenge suggested that incubation with the $CeO_2$ nanoparticles appeared to significantly decrease the amount of secreted TNF-α, IL-6 and IL-1β into the media (FIGS. 46B and 46C).

Although the mechanism(s) regulating cytokine production in macrophages following bacterial or LPS stimulation are not yet fully understood, recent data has suggested that elevations in intracellular ROS levels may play an important role. To examine this possibility, it was next determined how nanoparticle treatment might affect cellular superoxide levels by DCFH-DA staining. It was found that $CeO_2$ nanoparticle treatment tended to decrease the induction of cellular ROS following LPS challenge (FIG. 46A).

Figure 46D:
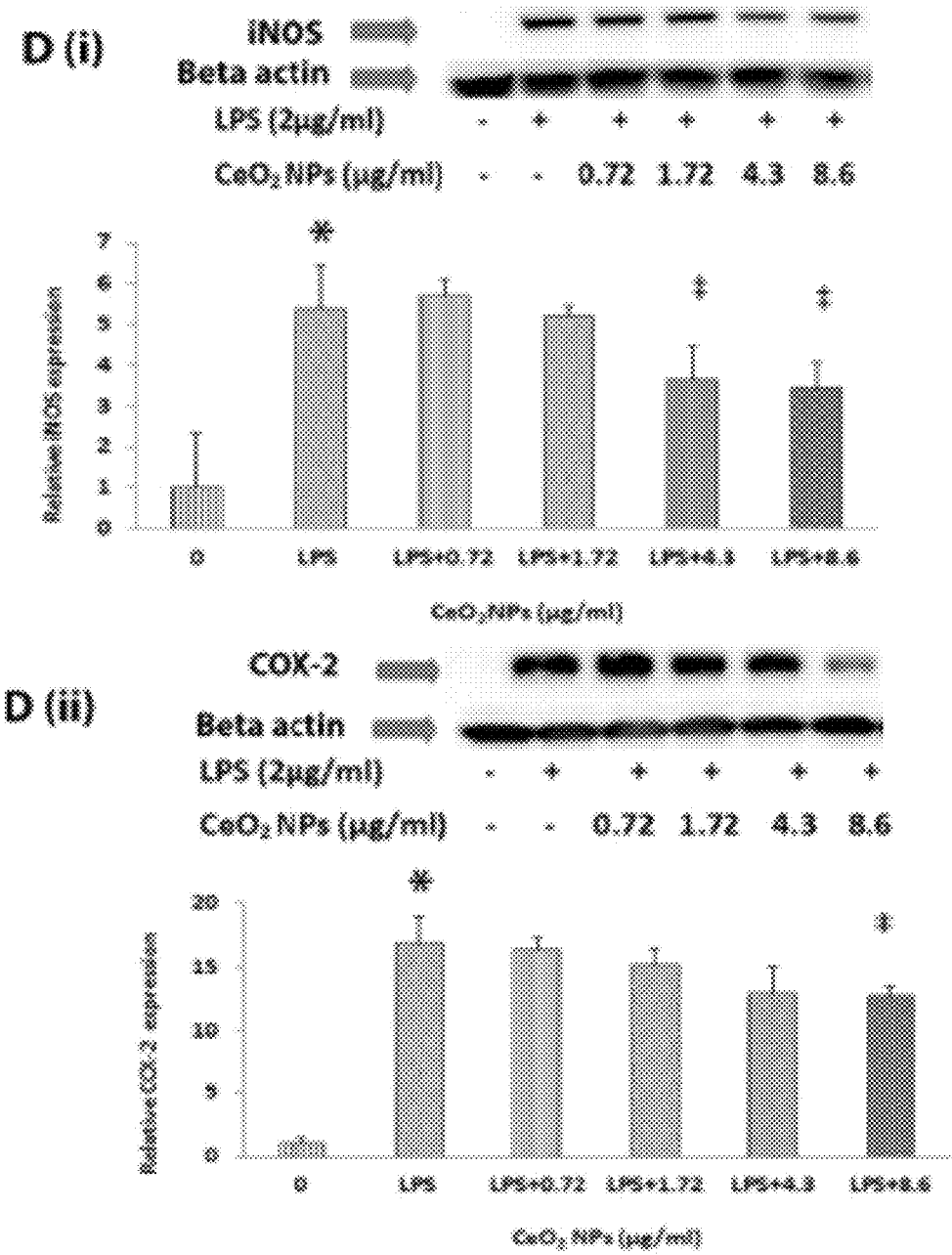

In addition to elevations in cytokine concentration, it has also been suggested that the large amount of nitric oxide (NO) produced during sepsis may play an important role in sepsis-induced mortality which has led some to postulate that decreasing NO levels may be beneficial. The above data showed a significant concentration-dependent decrease in the nitrite production and iNOS expression in LPS-challenged macrophages following nanoparticle treatment (FIGS. 46C-46D). It is thought that NF-κB is a key regulator of the inflammatory mediators TNF-α, IL-1β, IL-6, and iNOS. The activity of NF-κB is increased with elevations in cellular ROS which causes the phosphorylation and subsequent degradation of IκB-α thereby allowing NF-κB p65 to translocate to the nucleus where it functions as a transcription factor. It has been reported that LPS exposure (2 μg/ml) can be used to induce the degradation of IκB-α and nuclear localization of NF-κB/p65 in cultured RAW 264.7 macrophages. Consistent with our cytokine and NO data, it was found that nanoparticle treatment functioned to attenuate LPS-induced IκB-α degradation, NF-κB/p65 translocation into the nucleus and NF-κB/p65 binding to DNA (FIG. 47).

Although the production of inflammatory cytokines has long been considered the primary mediator of sepsis induced damage, it is also possible that some portion of the beneficial effects observed with $CeO_2$ nanoparticle treatment could be due to the effects of the particles on the bacteria itself. To investigate this possibility, it was examined how exposure to $CeO_2$ nanoparticles might affect bacterial growth using a disc diffusion assay, the measurement of optical density at 600 nm, and after determination of colony forming unit (CFU). It was found that incubation with $CeO_2$ nanoparticles appeared to inhibit the growth of E. coli but not S. aureus (FIG. 48). These data were consistent with previous reports demonstrating that exposure to $CeO_2$ nanoparticles does not inhibit the growth of S. aureus when tested with concentrations up to 172 mg/L.

In summary, the foregoing data indicated that a single dose of nanoparticles was associated with improvements in animal survival, decreased organ damage, and diminished evidence of systemic inflammation. Using cultured macrophages, it was shown that $CeO_2$ nanoparticle treatment diminishes LPS-induced increases in cellular ROS, iNOS, and NO. These in vitro findings appear to be associated with the ability of the $CeO_2$ nanoparticles to decrease cellular ROS levels which functions to attenuate IκB-α degradation, decreased NF-κB/p65 translocation into the nucleus and diminished NF-κB/p65 binding to DNA. Other work, using bacterial cultures suggest that $CeO_2$ nanoparticles may negatively affect the reproduction of E. coli. Whether these changes seen in vitro are responsible for the improvements in animal survival observed following insult will require further investigation. Given that these particles can be easily synthesized at a large scale using existing technology, their stability under a wide range of environmental conditions, and their potentially nearly infinite shelf life may allow for the possible application of these particles for medical purposes in underdeveloped countries.

Throughout this document, various references are mentioned. All such references are incorporated herein by reference, including the references set forth in the following list:

REFERENCES

1. Reed, H. L., S. D. Renton, and M. D. Hines, Dependence of All-Cause Standardized In-Hospital Mortality on Sepsis Mortality Between 2005 and 2010. Am J Med Qual, 2013.
2. Yang, C., et al., Protective effect of curcumin against cardiac dysfunction in sepsis rats. Pharm Biol, 2013. 51(4): p. 482-7.
3. Holthoff, J. H., et al., Resveratrol improves renal microcirculation, protects the tubular epithelium, and prolongs survival in a mouse model of sepsis-induced acute kidney injury. Kidney Int, 2012. 81(4): p. 370-8.
4. U.S. Pat. No. 8,337,898, entitled "Functionalized nanoceria composition for ophthalmic treatment."
5. U.S. Pat. No. 7,534,453, entitled "Cerium oxide nanoparticles and use in enhancing cell survivability."
6. U.S. Pat. No. 7,504,356, entitled "Nanoparticles of cerium oxide having superoxide dismutase activity."
7. U.S. Pat. No. 7,727,559, entitled "Inhibition of reactive oxygen species and protection of mammalian cells."
8. U.S. Pat. No. 7,347,987, entitled "Inhibition of reactive oxygen species and protection of mammalian cells."
9. Mayr F B, Yende S, Angus D C. Epidemiology of severe sepsis. Virulence. 2014; 5:4-11.
10. Connor A J, Chen L C, Joseph L B, Laskin J D, Laskin D L. Distinct responses of lung and liver macrophages to acute endotoxemia: role of toll-like receptor 4. Experimental and molecular pathology. 2013; 94:216-27.
11. Kishta O A, Goldberg P, Husain S N. Gadolinium chloride attenuates sepsis-induced pulmonary apoptosis and acute lung injury. ISRN inflammation. 2012; 2012: 393481.
12. Fisher J E, McKenzie T J, Lillegard J B, Yu Y, Juskewitch J E, Nedredal G I, et al. Role of Kupffer cells and tolllike receptor 4 in acetaminophen-induced acute liver failure. J Surg Res. 2013; 180:147-55.
13. Kono H, Fujii H, Tsuchiya M, Hirai Y, Ishii K, Hosomura N, et al Inhibition of the Kupffer cell and neutralization of IL-10 increase the expression of chemokines in the lung in a rat peritonitis model. J Surg Res. 2008; 150:169-82.
14. Kono H, Fujii H, Hirai Y, Tsuchiya M, Amemiya H, Asakawa M, et al. The Kupffer cell protects against acute lung injury in a rat peritonitis model: role of IL-10. J Leukoc Biol. 2006; 79:809-17.
15. Weiss S L, Fitzgerald J C, Faustino E V, Festa M S, Fink E L, Jouvet P, et al. Understanding the global epidemiology of pediatric critical illness: the power, pitfalls, and practicalities of point prevalence studies. Pediatric critical care medicine: a journal of the Society of Critical Care Medicine and the World Federation of Pediatric Intensive and Critical Care Societies. 2014; 15:660-6.
16. Wunsch H. Untangling the healthcare use patterns of severe sepsis survivors. American journal of respiratory and critical care medicine. 2014; 190:7-8.
17. Hofhuis J G, Spronk P E, van Stel H F, Schrijvers A J, Rommes J H, Bakker J. The impact of severe sepsis on health-related quality of life: a long-term follow-up study. Anesthesia and analgesia. 2008; 107:1957-64.
18. Fujitani S, Sun H Y, Yu V L, Weingarten J A. Pneumonia due to *Pseudomonas aeruginosa*: part I: epidemiology, clinical diagnosis, and source. Chest. 2011; 139:909-19.
19. Gruson D, Hilbert G, Bebear C, Allery A, Boiron J M, Pigneux A, et al. Early infectious complications after bone marrow transplantation requiring medical ICU admission. Hematology and cell therapy. 1998; 40:269-74.

20. Morrison A J, Jr., Wenzel R P. Epidemiology of infections due to *Pseudomonas aeruginosa*. Reviews of infectious diseases. 1984; 6 Suppl 3:S627-42.
21. Hirst S M, Karakoti A S, Tyler R D, Sriranganathan N, Seal S, Reilly C M. Anti-inflammatory properties of cerium oxide nanoparticles. Small. 2009; 5:2848-56.
22. Wason M S, Colon J, Das S, Seal S, Turkson J, Zhao J, et al. Sensitization of pancreatic cancer cells to radiation by cerium oxide nanoparticle-induced ROS production. Nanomedicine. 2013; 9:558-69.
23. Heckert E G, Karakoti A S, Seal S, Self W T. The role of cerium redox state in the SOD mimetic activity of nanoceria. Biomaterials. 2008; 29:2705-9.
24. Dowding J M, Dosani T, Kumar A, Seal S, Self W T. Cerium oxide nanoparticles scavenge nitric oxide radical (NO). Chemical communications. 2012; 48:4896-8.
25. Chen S, Hou Y, Cheng G, Zhang C, Wang S, Zhang J. Cerium oxide nanoparticles protect endothelial cells from apoptosis induced by oxidative stress. Biological trace element research. 2013; 154:156-66.
26. Niu J, Wang K, Kolattukudy P E. Cerium oxide nanoparticles inhibit oxidative stress and nuclear factorkappaB activation in H9c2 cardiomyocytes exposed to cigarette smoke extract. The Journal of pharmacology and experimental therapeutics. 2011; 338:53-61.
27. Niu J, Azfer A, Rogers L M, Wang X, Kolattukudy P E. Cardioprotective effects of cerium oxide nanoparticles in a transgenic murine model of cardiomyopathy. Cardiovascular research. 2007; 73:549-59.
28. Hirst S M, Karakoti A, Singh S, Self W, Tyler R, Seal S, et al. Bio-distribution and in vivo antioxidant effects of cerium oxide nanoparticles in mice. Environmental toxicology. 2013; 28:107-18.
29. Amin K A, Hassan M S, Awad el S T, Hashem K S. The protective effects of cerium oxide nanoparticles against hepatic oxidative damage induced by monocrotaline. International journal of nanomedicine. 2011; 6:143-9.
30. Kolli M B, Manne N D, Para R, Nalabotu S K, Nandyala G, Shokuhfar T, et al. Cerium oxide nanoparticles attenuate monocrotaline induced right ventricular hypertrophy following pulmonary arterial hypertension. Biomaterials. 2014.
31. Dejager L, Pinheiro I, Dejonckheere E, Libert C. Cecal ligation and puncture: the gold standard model for polymicrobial sepsis? Trends in microbiology. 2011; 19:198-208.
32. Lee S C, Hua C C, Yu T J, Shieh W B, See L C. Risk factors of mortality for nosocomial pneumonia: importance of initial anti-microbial therapy. International journal of clinical practice. 2005; 59:39-45.
33. Li N, Hu X, Liu Y, Wang Y, Wang Y, Liu J, et al. Systemic inflammatory responses and multiple organ dysfunction syndrome following skin burn wound and *Pseudomonas aeruginosa* infection in mice. Shock. 2013; 40:152-9.
34. Wilson K R, Napper J M, Denvir J, Sollars V E, Yu H D. Defect in early lung defence against *Pseudomonas aeruginosa* in DBA/2 mice is associated with acute inflammatory lung injury and reduced bactericidal activity in naive macrophages. Microbiology. 2007; 153:968-79.
35. Stotland P K, Radzioch D, Stevenson M M. Mouse models of chronic lung infection with *Pseudomonas aeruginosa*: models for the study of cystic fibrosis. Pediatric pulmonology. 2000; 30:413-24.
36. Niesler U, Palmer A, Froba J S, Braumuller S T, Zhou S, Gebhard F, et al. Role of alveolar macrophages in the regulation of local and systemic inflammation after lung contusion. The journal of trauma and acute care surgery. 2014; 76:386-93.
37. Neunaber C, Oestern S, Andruszkow H, Zeckey C, Mommsen P, Kutter D, et al. Cytokine productive capacity of alveolar macrophages and Kupffer cells after femoral fracture and blunt chest trauma in a murine trauma model. Immunology letters. 2013; 152:159-66.
38. Seitz D H, Perl M, Liener U C, Tauchmann B, Braumuller S T, Bruckner U B, et al. Inflammatory alterations in a novel combination model of blunt chest trauma and hemorrhagic shock. The Journal of trauma. 2011; 70:189-96.
39. Lee S H, Clemens M G, Lee S M. Role of Kupffer cells in vascular stress genes during trauma and sepsis. The Journal of surgical research. 2010; 158:104-11.
40. Campbell S J, Zahid I, Losey P, Law S, Jiang Y, Bilgen M, et al. Liver Kupffer cells control the magnitude of the inflammatory response in the injured brain and spinal cord. Neuropharmacology. 2008; 55:780-7.
41. Gong J P, Wu C X, Liu C A, Li S W, Shi Y J, Yang K, et al. Intestinal damage mediated by Kupffer cells in rats with endotoxemia. World journal of gastroenterology: WJG. 2002; 8:923-7.
42. Koo D J, Chaudry I H, Wang P. Kupffer cells are responsible for producing inflammatory cytokines and hepatocellular dysfunction during early sepsis. The Journal of surgical research. 1999; 83:151-7.
43. Kim T H, Yoon S J, Lee S M. Genipin attenuates sepsis by inhibiting Toll-like receptor signaling. Molecular medicine. 2012; 18:455-65.
44. Chopra M, Golden H B, Mullapudi S, Dowhan W, Dostal D E, Sharma A C. Modulation of myocardial mitochondrial mechanisms during severe polymicrobial sepsis in the rat. PloS one. 2011; 6:e21285.
45. Dowding J M, Das S, Kumar A, Dosani T, McCormack R, Gupta A, et al. Cellular interaction and toxicity depend on physicochemical properties and surface modification of redox-active nanomaterials. ACS nano. 2013; 7:4855-68.
46. Nalabotu S K, Kolli M B, Triest W E, Ma J Y, Manne N D, Katta A, et al. Intratracheal instillation of cerium oxide nanoparticles induces hepatic toxicity in male Sprague-Dawley rats. International journal of nanomedicine. 2011; 6:2327-35.
47. Celardo I, Pedersen J Z, Traversa E, Ghibelli L. Pharmacological potential of cerium oxide nanoparticles. Nanoscale. 2011; 3:1411-20.
48. Das S, Dowding J M, Klump K E, McGinnis J F, Self W, Seal S. Cerium oxide nanoparticles: applications and prospects in nanomedicine. Nanomedicine. 2013; 8:1483-508.
49. Assaly R A, Habib R H, Azizi M, Shapiro J I, Dignam J D. Use of multiple fluorophores for evaluating microvascular permeability in control rats and rats with sepsis. Clinical science. 2008; 114:123-30.
50. Assaly R A, Azizi M, Kennedy D J, Amauro C, Zaher A, Houts F W, et al. Plasma expansion by polyethyleneglycol-modified albumin. Clinical science. 2004; 107:263-72.
51. Montravers P, Mohler J, Saint Julien L, Carbon C. Evidence of the proinflammatory role of *Enterococcus faecalis* in polymicrobial peritonitis in rats. Infection and immunity. 1997; 65:144-9.
52. Hu M D, Yang Y, Zhou C X, Li Q, Yi W, Qian G S, et al. Pretreatment with anti-flagellin serum delays acute lung injury in rats with sepsis. Inflammation research: official journal of the European Histamine Research Society [et al]. 2012; 61:837-44.
53. Pulli B, Ali M, Forghani R, Schob S, Hsieh K L, Wojtkiewicz G, et al. Measuring myeloperoxidase activity in biological samples. PloS one. 2013; 8:e67976.
54. Weber G F, Schlautkotter S, Kaiser-Moore S, Altmayr F, Holzmann B, Weighardt H. Inhibition of interleukin-22 attenuates bacterial load and organ failure during acute polymicrobial sepsis. Infection and immunity. 2007; 75:1690-7.

55. Kern E F, Erhard P, Sun W, Genuth S, Weiss M F. Early urinary markers of diabetic kidney disease: a nested case-control study from the Diabetes Control and Complications Trial (DCCT). Am J Kidney Dis. 2010; 55:824-34.
56. Wu M, Desai D H, Kakarla S K, Katta A, Paturi S, Gutta A K, et al. Acetaminophen prevents aging associated hyperglycemia in aged rats: effect of aging-associated hyperactivation of p38-MAPK and ERK1/2. Diabetes Metab Res Rev. 2009; 25:279-86.
57. Coimbra T M, Janssen U, Grone H J, Ostendorf T, Kunter U, Schmidt H, et al. Early events leading to renal injury in obese Zucker (fatty) rats with type II diabetes. Kidney Int. 2000; 57:167-82.
58. Shih W, Hines W H, Neilson E G. Effects of cyclosporin A on the development of immune-mediated interstitial nephritis. Kidney Int. 1988; 33:1113-8.
59. Parra G, Hernandez S, Moreno P, Rodriguez-Iturbe B. Participation of the interstitium in acute immunecomplex nephritis: interstitial antigen accumulation, cellular infiltrate, and MHC class II expression. Clin Exp Immunol. 2003; 133:44-9.
60. Kakarla S K, Fannin J C, Keshavarzian S, Katta A, Paturi S, Nalabotu S K, et al. Chronic acetaminophen attenuates age-associated increases in cardiac ROS and apoptosis in the Fischer Brown Norway rat. Basic Res Cardiol. 2010; 105:535-44.
61. Wu M, Katta A, Gadde M K, Liu H, Kakarla S K, Fannin J, et al. Aging-associated dysfunction of Akt/protein kinase B: S-nitrosylation and acetaminophen intervention. PLoS One. 2009; 4:e6430.
62. Wang Y, Wu M, Al-Rousan R, Liu H, Fannin J, Paturi S, et al. Iron-induced cardiac damage: role of apoptosis and deferasirox intervention. J Pharmacol Exp Ther. 2011; 336:1-8.
63. Wu M, Liu H, Fannin J, Katta A, Wang Y, Arvapalli R K, et al. Acetaminophen improves protein translational signaling in aged skeletal muscle. Rejuvenation Res. 2010; 13:571-9.
64. Grisham M B, Johnson G G, Lancaster J R, Jr. Quantitation of nitrate and nitrite in extracellular fluids. Methods in enzymology. 1996; 268:237-46.
65. Gloire G, Legrand-Poels S, Piette J. NF-kappaB activation by reactive oxygen species: fifteen years later. Biochemical pharmacology. 2006; 72:1493-505.
66. Faulkner K M, Liochev S I, Fridovich I. Stable Mn(III) porphyrins mimic superoxide dismutase in vitro and substitute for it in vivo. The Journal of biological chemistry. 1994; 269:23471-6.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for treating sepsis, comprising administering to a subject in need thereof an effective amount of agglomerated cerium oxide nanoparticles having a nanoparticle agglomerate size of between 80 and 200 nm.
2. The method of claim 1, wherein administering an effective amount of cerium oxide nanoparticles comprises administering about 0.1 mg/kg to about 1.0 mg/kg of the cerium oxide nanoparticles.
3. The method of claim 1, wherein administering the cerium oxide nanoparticles normalizes a body temperature of the subject, reduces an amount of blood urea nitrogen in the subject, increases arterial oxygen levels in the subject, improves diaphragm contractility in the subject, or a combination thereof.
4. The method of claim 1, wherein administering the cerium oxide nanoparticles decreases an amount of mitogen activated protein kinase (MAPK) signaling in a cell of the subject, decreases an amount of signal transducer and activation of transcription (stat) signaling in a cell of the subject, decreases an amount of NF-κB activation in a cell of the subject, or a combination thereof.
5. The method of claim 1, wherein administering the cerium oxide nanoparticles reduces an amount of an inflammatory marker in the subject.
6. The method of claim 5, wherein the inflammatory marker is selected from the group consisting of glutathione S-transferase, myeloperoxidase, leukemia inhibitory factor, interferon gamma, interleukin 6, macrophage inflammatory protein, monocyte chemotactic protein, and tumor necrosis factor alpha.
7. The method of claim 1, wherein the sepsis is polymicrobial sepsis.
8. The method of claim 1, wherein administering the nanoparticles increases an amount of P-selectin and/or vascular cell adhesion molecule (VCAM) expression in a cell of the subject.
9. A method for treating an inflammatory disorder, comprising administering to a subject in need thereof an effective amount of agglomerated cerium oxide nanoparticles having a nanoparticle agglomerate size of between 80 and 200 nm.
10. The method of claim 9, wherein the inflammatory disorder is selected from the group consisting of acute kidney injury, acute lung injury, systemic inflammatory response syndrome, multiple organ dysfunction syndrome, and polymicrobial sepsis.
11. The method of claim 9, wherein administering an effective amount of cerium oxide nanoparticles comprises administering about 0.1 mg/kg to about 1.0 mg/kg of the cerium oxide nanoparticles.
12. The method of claim 9, wherein administering the cerium oxide nanoparticles normalizes a body temperature of the subject, reduces an amount of blood urea nitrogen in the subject, increases arterial oxygen levels in the subject, improves diaphragm contractility in the subject, or a combination thereof.
13. The method of claim 9, wherein administering the cerium oxide nanoparticles decreases an amount of mitogen activated protein kinase (MAPK) signaling in a cell of the subject, decreases an amount of signal transducer and activation of transcription (stat) signaling in a cell of the subject, decreases an amount of NF-κB activation in a cell of the subject, or a combination thereof.
14. The method of claim 9, wherein administering the cerium oxide nanoparticles reduces an amount of an inflammatory marker in the subject.
15. The method of claim 14, wherein the inflammatory marker is selected from the group consisting of glutathione S-transferase, myeloperoxidase, and leukemia inhibitory factor.
16. The method of claim 14, wherein the inflammatory marker is an inflammatory cytokine.
17. The method of claim 16, wherein the inflammatory cytokine is selected from the group consisting of tumor necrosis factor α, interleukin 6, and interferon gamma.
18. The method of claim 9, wherein administering the nanoparticles increases an amount of P-selectin and/or vascular cell adhesion molecule (VCAM) expression in a cell of the subject.
19. The method of claim 1, wherein the cerium oxide nanoparticles include an increased amount of cerium in a +3 state during initial and middle stages of sepsis and a decreased amount of cerium in the +3 state during latter stages of sepsis.

20. A method for attenuating release of cytokines and chemokines from liver macrophage cells, the method comprising administering an effective amount of agglomerated cerium oxide nanoparticles to a subject in need thereof, the agglomerated cerium oxide nanoparticles having a nanoparticle agglomerate size of between 80 and 200 nm.

* * * * *

UNITED STATES PATENT AND TRADEMARK OFFICE
CERTIFICATE OF CORRECTION

PATENT NO. : 9,669,055 B1
APPLICATION NO. : 14/685426
DATED : June 6, 2017
INVENTOR(S) : Eric Blough, Nandini Manne and Selvaraj Vellaisamy It is certified that error appears in the above-identified patent and that said Letters Patent is hereby corrected as shown below:

In the Specification

Column 1, Line 16, add:
Government Support
This invention was made with government support under contract number DE-SC0005162 awarded by the Department of Energy. The government has certain rights in the invention.

Signed and Sealed this
Twelfth Day of December, 2023

Katherine Kelly Vidal
*Director of the United States Patent and Trademark Office*